US012570680B2

(12) United States Patent
Barnes et al.

(10) Patent No.: US 12,570,680 B2
(45) Date of Patent: Mar. 10, 2026

(54) COMPOSITIONS OF MECHANICALLY INTERLOCKED, TOPOLOGICALLY COMPLEX CROSSLINKERS AND POLYMERS AND METHODS OF MAKING AND USING SAME

(71) Applicant: Washington University, St. Louis, MO (US)

(72) Inventors: Jonathan Barnes, St. Louis, MO (US); Nathan Colley, St. Louis, MO (US); Mark Nosiglia, St. Louis, MO (US); Sheila Tran, St. Louis, MO (US); Gray Harlan, St. Louis, MO (US)

(73) Assignee: Washington University, St. Louis, MO (US)

( * ) Notice: Subject to any disclaimer, the term of this patent is extended or adjusted under 35 U.S.C. 154(b) by 995 days.

(21) Appl. No.: 17/505,533

(22) Filed: Oct. 19, 2021

(65) Prior Publication Data

US 2022/0119435 A1 Apr. 21, 2022

Related U.S. Application Data

(60) Provisional application No. 63/093,467, filed on Oct. 19, 2020.

(51) Int. Cl.

| | |
|---|---|
| ***C07F 15/02*** | (2006.01) |
| ***C07D 519/00*** | (2006.01) |
| ***C08F 20/14*** | (2006.01) |
| ***C08G 65/332*** | (2006.01) |

(52) U.S. Cl.

CPC .......... *C07F 15/025* (2013.01); *C07D 519/00* (2013.01); *C08F 20/14* (2013.01)

(58) Field of Classification Search

CPC ...... C07D 519/00; C07F 15/025; C08F 20/14; C08G 65/3322

See application file for complete search history.

(56) References Cited

PUBLICATIONS

Amabilino, D. B., et al., "Olympiadane," Jun. 6, 1994, Angew Chem, Int Ed Engl, 1994, 33/12:1286-1290, 5 pages.
Bunha, A., et al., "Polymer Catenanes via a Supramolecularly Templated ATRP Initiator," 2011, Chem Commun, 47/32:9173-9175, 3 pages.
Chambron, J. C., et al., "Synthesis, Characterization, and a Proton NMR Study of Topologically Chiral Copper(I) [2]-Catenates and Achiral Analogs," Jun. 1, 1992, J Am Chem Soc, 11412:4625-463, 7 pages.
Colley, N. D. , et al. One-Pot Synthesis of a Linear [4]Catenate Using Orthogonal Metal Templation and Ring-Closing Metathesis, 2020, Inorg Chem, 59(15):10450-10460, with Supplementary Information, s1-s82, 93 pages.
Dietrich-Buchecker, et al., "Templated Synthesis of Interlocked Macrocyclic Ligands, the Catenands. Preparation and Characterization of the Prototypical bis-30 Membered Ring System," 1990, Tetrahedron, 46/2:503-512, 10 pages.
Forgan, R. S., et al., The Topological and Chemical Implications of Introducing Oriented Rings to [3]Catenanes, 2014, Supramol Chem, 26/3-4:192-201, 11 pages.
(Continued)

*Primary Examiner* — Renee Claytor
*Assistant Examiner* — Elena Vladimirovna Vishnyakova
(74) *Attorney, Agent, or Firm* — Stinson LLP

(57) ABSTRACT

Among the various aspects of the present disclosure is the provision of compositions of mechanically interlocked, topologically complex crosslinkers and polymers and methods of making and using same.

20 Claims, 45 Drawing Sheets

(56) References Cited

PUBLICATIONS

Iwamoto, H., et al., "Synthesis of Linear [5]Catenanes via Olefin Metathesis Dimerization of Pseudorotaxanes Composed of a [2]Catenane and a Secondary Ammonium Salt," 2016, Chem Commun, 52/2:319-322, 4 pages.
Lam, R.T.S., et al., Amplification of Acetylcholine-Binding Catenanes from Dynamic Combinatorial Libraries, 2005, Science, 308 (5722), 667-669, 5 pages.
Liu, Y., et al., "The Geometry of Periodic Knots, Polycatenanes and Weaving from a Chemical Perspecitve: A Library for Reticular Chemistry," 2017, Chem Soc Rev, Royal Soc Chem, downloaded May 5, 2018, 16:40:35, 23 pages.
Mitchell, D. K., et al., A Topologically Chiral [2]Catenand, Jul. 1988, Angew Chem, Int Ed Engl, 27/7:930-931, 2 pages.
Patiny, L., et al., "ChemCalc: A Building Block for Tomorrow's Chemical Infrastructure," 2013, J Chem Inf Model, 53/5:1223-1228, 6 pages.
Product Brochure, Spartan'18 Parallel Suite, Wavefunction, Inc. Irvine, CA, 8 pages, document not dated.
Veliks, J., et al., "Towards the Molecular Borromean Link with Three Unequal Rings: Double-Threaded Ruthenium(II) Ring-in-RingComplexest," 2016, Org Chem Front, 3:667-672, 7 pages.
Veliks, J., et al., "Linear Bilateral Extended 2,2':6',2"-Terpyridine Ligands, Their Coordination Complexes and Heterometallic Supramolecular Networks," 2014, Chem Sci, 5/11: 4317-4327, 12 pages.
Wu, Q, et al., "Poly[n]catenanes: Synthesis of Molecular Interlocked Chains," Dec. 15, 2017, Science, 358:1434-1439, 7 pages.
Xing, H., et al., "Catenane Crosslinked Mechanically Adaptive Polymer Gel," 2018, Macromol Rapid Commun, 39:1700361, 6 pages.
Xing, H., et al., Mechanochemistry of an Interlocked Poly[2]catenane: From Single Molecule to Bulk Gel, 2019, CCS Chem, 1:513-523, 11 pages.
Yee, C-C., et al., "Control Over the Macrocyclisation Pathway and Product Topology in a cVopper-Templated Catenane Synthesis," 2019, Chem Commun, 55/44:6169-6172, 5 pages.

OTPM

Fe-(OTPM)$_2$

[2]C-M

[4]C-M

[4]C

7

7

8

6

9

8

12

13

13

14

14

15

14

16

12

9

[4]C

15

9

[6]C (9) (10) (11) (12) (14)

(13)

(14)

(15)

(15)

COMPOSITIONS OF MECHANICALLY INTERLOCKED, TOPOLOGICALLY COMPLEX CROSSLINKERS AND POLYMERS AND METHODS OF MAKING AND USING SAME

CROSS-REFERENCE TO RELATED APPLICATIONS

This application claims benefit of U.S. Provisional Application Ser. No. 63/093,467 filed Oct. 19, 2020, the entire disclosure of which is incorporated herein by reference.

FIELD OF THE INVENTION

The present disclosure generally relates to compositions and methods of making and using mechanically linked macrocycles.

BACKGROUND OF THE INVENTION

In comparison to the most well-studied types of chemical bonds—covalent, ionic, and metallic—the mechanical bond remains relatively underexplored. Mechanical bonding occurs when two or more molecular species are interlocked via a physical entanglement in space, such that they cannot be separated without breaking covalent bonds. The two main classes of mechanically interlocked molecules (MIMs) are rotaxanes and catenanes, the former consisting of a molecularly-shaped dumbbell threaded through one or more macrocycles, and the latter being constructed from two or more linearly or radially interlocked macrocycles. Of the two types of MIMs, catenanes are generally more challenging to synthesize because the ring-closing reactions required to establish the mechanical bond are notorious for generating non-interlocked byproducts and so-called figure-of-eight topologies.

MIMs are of interest for their potential in applications such as molecular machines, catalysis, drug delivery, and improved materials. For example, catenanes have been suggested as switches, sensors, and rotary motors in molecular machines. Poly[n]catenanes can also act as strong, flexible molecular chains thought to have potential as energy damping materials and tough elastomers with stimuli-responsive mechanical properties. They can be incorporated into polymers and metal-organic frameworks.

Higher molecular weight MIMs possessing multiple mechanical bonds have received attention in the past 25 years, and although oligo- and poly[n]rotaxanes are generally more straightforward to synthesize, discrete catenane-based oligomers and disperse polymers have proved much more difficult. Linear catenanes, which provide the maximum degrees of freedom through rotation, rocking, and elongation, are especially difficult to synthesize because the desired ring-closing step directly competes with unwanted oligomerization processes that can lead to complex mixtures. Accordingly, although [2]- and [3]-catenanes have been reported previously, there are only a handful of reports on the successful synthesis of well-defined linear oligocatenanes consisting of four (Yee et al., 2019) or five (Amabilino et al., 1994; Iwamoto et al., 2016) interlocked rings. Moreover, there have been no reports of well-defined linear oligocatenanes beyond five interlocked rings. To date, a [5]catenane has stood as the record for total number of interlocked macrocycles in a linear, unimolecular oligo[n] catenane. A metallo-supramolecular approach has been reported to template the synthesis of disperse poly[n]catenanes that were purified using selective metalation and size-exclusion methods (Wu et al., 2017); however, the resulting product was a mix of branched, cyclic, and linear architectures rather than only linear product.

One of the key limitations moving forward in developing different and/or higher order linear oligocatenanes of precise molecular weight is the fact that each mechanical bond forming step is typically low yielding and often performed one at a time. In order to overcome this challenge, synthetic methods are needed that can form [n]catenane architectures containing multiple mechanical bonds in as few, high-yielding steps as possible. Poly[n]catenane syntheses may require fewer synthetic steps (i.e., one-pot reactions) and result in higher molecular weight polymers; yet their syntheses lack topological control and generate product mixtures that are often difficult to purify.

SUMMARY OF THE INVENTION

Among the various aspects of the present disclosure is the provision of compositions of mechanically interlocked, topologically complex crosslinkers and polymers and methods of making and using same.

An aspect of the present disclosure provides for a composition comprising a mechanically interlocked, topologically complex crosslinker. In some embodiments the composition comprises a macrocycle having an [n]catenane-based architecture, wherein n=2 or 3 or 4 or 5 or 6 or more. In some embodiments, the at least one of the interlocked molecular macrocycles are functionalized with at least one polymerizable group, such as a group comprising a monomer. In some embodiments, the macrocycles are difunctionalized with at least one polymerizable group. In some embodiments, the macrocycles are difunctionalized at its termini or side groups. In some embodiments, the at least one polymerizable group comprises a styrene, acrylate, acrylamide, cycloalkene, amine, alcohol, thiol, or combinations thereof. In some embodiments, at least one macrocycle is loaded with a metal ion (e.g., one per molecular ring via metal-ligand coordination). In some embodiments, at least one macrocycle is loaded with a metal ion (e.g., one per molecular ring via metal-ligand coordination) selected from iron (Fe), copper (Cu), ruthenium (Ru), nickel (Ni), manganese (Mn), zinc (Zn), or combinations thereof.

Another aspect of the present disclosure provides for a composition comprising a material comprising a mechanically interlocked, topologically complex crosslinker, optionally, with and/or without metal ions. In some embodiments, the composition comprises at least one or more monomers in an amount sufficient to form a solvated polymer network (e.g., hydrogel or organogel, depending on whether water or an organic solvent is used to swell the gel). In some embodiments, the mechanically interlocked, topologically complex crosslinkers are cross-linked resulting in a polymer network.

In some embodiments, the one or more monomers are selected from at least one di-, tri-, or tetra-functional monomer in an amount sufficient to form a thermoset polymer network void of solvents, wherein the monomer is capable of cross-linking the mechanically interlocked, topologically complex crosslinker and resulting in a polymer network.

In some embodiments, the di-, tri-, or tetra-functional crosslinkers are selected from epoxy, acyl chloride, activated esters (like N-hydroxysuccinimide), ring-strained cycloalkenes/alkynes, or combinations thereof.

In some embodiments, the mechanically interlocked, topologically complex crosslinker is a rigid difunctional covalent linker arranged in a linear fashion to form poly[3]catenane/ate, poly[4]catenane/ate, poly[5]catenane/ate, or poly[6]catenane/ate, etc.; optionally, with and/or without metal ions; and/or the composition is a thermoplastic.

Yet another aspect of the present disclosure provides for a method of producing polymeric materials containing well-defined mechanically interlocked structures. In some embodiments, the method comprises providing the mechanically interlocked, topologically complex crosslinker material of any one of the preceding claims; and/or providing polymerizable groups; and/or optionally, providing metal ions. In some embodiments, the polymerizable groups can comprise monomers selected from the group consisting of: vinyl-containing monomers such as acrylates, acrylamides, styrenes, vinyl ethers, or using ring-strained cycloalkenes and cycloalkynes, as well as di, tri, or tetra-amino, -hydroxy, -thiol based monomers that can be used to make step-growth polymers, or combinations thereof. In some embodiments, at least one macrocycle is loaded with a metal ion (e.g., one per molecular ring via metal-ligand coordination) selected from iron (Fe), copper (Cu), ruthenium (Ru), nickel (Ni), manganese (Mn), zinc (Zn), or combinations thereof. In some embodiments, the method comprises functionalizing the material comprising a mechanically interlocked, topologically complex crosslinker, optionally with and/or without metal ion(s), with at least one or more monomers; forming a solvated polymer network (e.g., hydrogel or organogel, depending on whether water or an organic solvent is used to swell the gel); and/or cross-linking the mechanically interlocked, topologically complex crosslinker and resulting polymer network.

In some embodiments, the method further comprises cross-linking the mechanically interlocked, topologically complex crosslinker and resulting polymer network. In some embodiments, the material comprising a mechanically interlocked, topologically complex crosslinker optionally comprises at least one metal ion. In some embodiments, the at least one monomer comprises di-, tri-, or tetra-functional monomers, or combination thereof, capable of forming a thermoset polymer network void of solvents. In some embodiments, the di-, tri-, and tetra-functional crosslinkers are selected from epoxy, acyl chloride, activated esters (like N-hydroxysuccinimide), ring-strained cycloalkenes/alkynes, and combinations thereof. In some embodiments, a thermoplastic is generated; and/or the thermoplastic comprises the mechanically interlocked, topologically complex crosslinkers and forms a rigid difunctional covalent linker is arranged in a linear fashion to form poly[3]catenane/ate, poly[4]catenane/ate, poly[5]catenane/ate, and poly[6]catenane/ate, etc.; optionally with and/or without metal ions.

In some embodiments, method for the synthesis of poly[n]catenane/ate thermoplastics are composed exclusively of mechanically interlocked molecular macrocycles arranged in a linear fashion, optionally with metal ions.

In some embodiments, the composition contains mechanical bonding topology; the composition is flexible; the composition is tough; or the composition is responsive to the addition or removal of metal ions, or a change in the oxidation state of the metals.

In some embodiments, the mechanically interlocked, topologically complex crosslinker is used in a step-growth polymerization method.

In some embodiments, the mechanically interlocked, topologically complex crosslinker is used in a chain-growth polymerization method.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

The present disclosure is based, at least in part, on the discovery of a synthetic method to mechanically link two or more macrocycles, such as catenate, to form oligocatenanes which can be functionalized to polymerize.

Figure 1:
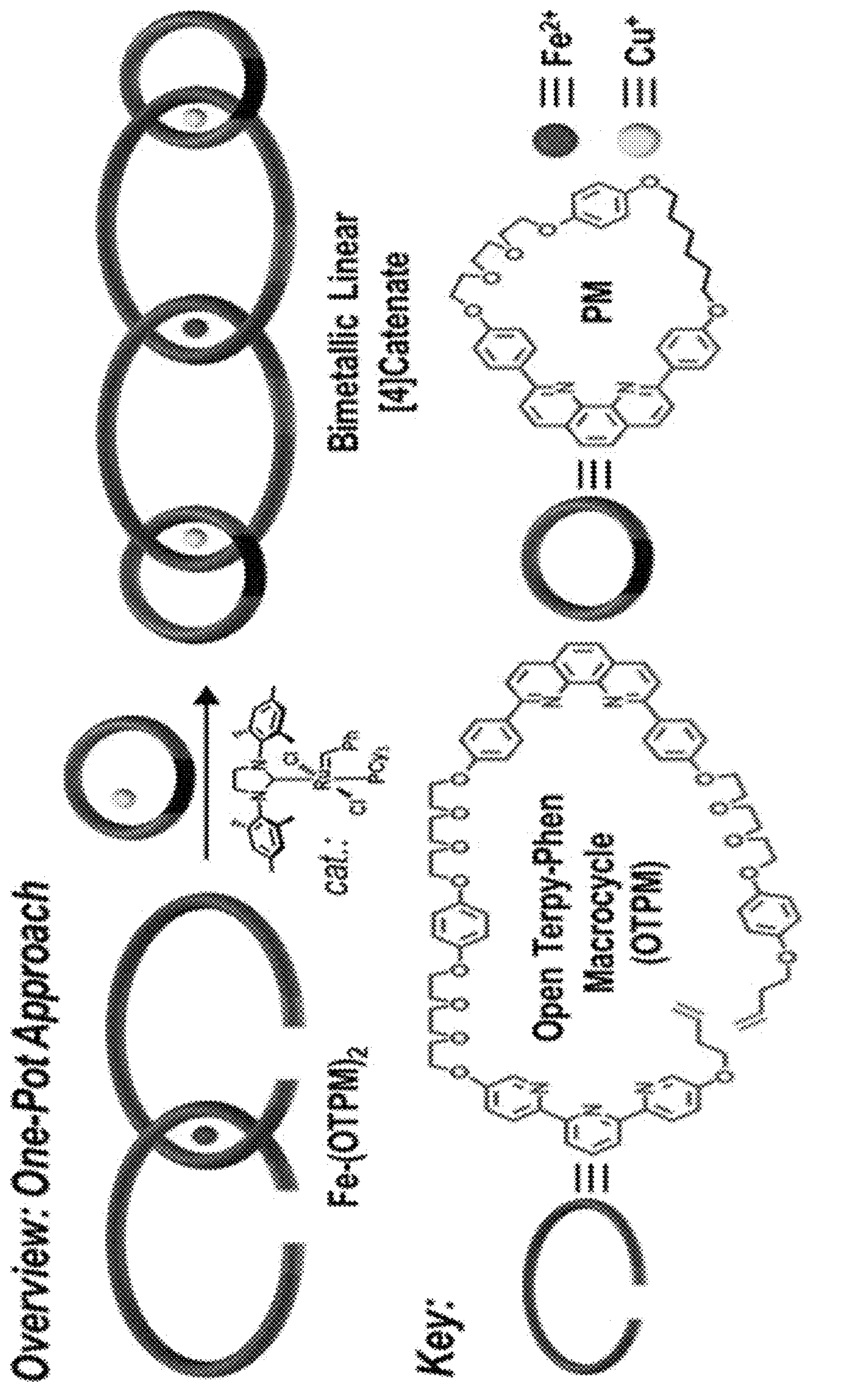
FIG. 1 depicts an overview of a one-pot approach to form three mechanical bonds in one step. This strategy requires a dual-ligand containing open terpy-phen macrocycle precursor (OTPM), a closed molecular ring (PM) bearing a phenanthroline ligand, and two metals with mono- and bivalent oxidation states ($Cu^+$ and $Fe^{2+}$) for orthogonal metal temptation steps.

Using orthogonal metal templation to synthesize catenanes, rotaxanes, and figure-of-eights, the present disclosure describes a strategy (FIG. 1) that allows for three mechanical bonds to be formed in a single, one-pot reaction. This strategy is made possible by implementing an open terpy-phen macrocycle precursor (OTPM) consisting of flexible linkers and two metal-coordinating ligands, namely, terpyridine (terpy) and phenan-throline (phen), which allows for orthogonal metal templation that begins with the formation of a ternary iron-OTPM complex ($Fe-(OTPM)_2$) that can be obtained in high yield and without chromatography. Next, a monometalated ($Cu^+$) phenanthroline-based macrocycle (PM) is added to $Fe-(OTPM)_2$ to form two more metal complexes, and isolation of a [4]catenate is possible after two simultaneous ring-closing metathesis (RCM) reactions are completed.

As shown herein, the advantages of the topologically elastic linker (TEL) design are 1) it uses catenanes that are responsive to specific metal ions to cause changes in the properties of the bulk material, 2) it will be the first example of higher order well-defined catenane crosslinkers for the synthesis of polymeric materials, and 3) its versatile monomer compatibility allows the introduction of well-defined mechanical bonds into hydrogels, organogels, elastomers, and thermosets.

The pursuit of improved polymers has increased rapidly in the past few decades as the demand for durable and lightweight materials with a wide range of chemical and physical properties has grown in nearly every economic sector. Although these properties can be tuned via monomer modification, the greatest enhancements would be realized if it were also possible to have precise control over the topological features, specifically spatial control over the linkages in polymer backbones and crosslinking junctions in polymer networks. The technology disclosed herein provides a synthetic route to introduce well-defined topologies via the mechanical bonds present in catenanes into a vast array of polymeric materials including hydrogels, organogels, elastomers, thermosets, and thermoplastics. These bulk materials will contain a high concentration of mechanical bonds, which will afford strength and flexibility relative to topologically trivial materials of the same chemical composition that are only connected via covalent linkages. Additionally, since our platforms are based on catenanes that contain ligands, the properties of the aforementioned materials can be reversibly modified via the addition and removal of specific metal ions, potentially allowing for the same material to be utilized for different applications.

Monomers and cross-linkers are well known in the art. For example, a monomer can be a di-, tri-, or tetra-functional monomer. A di-, tri-, or tetra-functional crosslinkers can be epoxy, acyl chloride, activated esters (like N-hydroxysuccinimide), ring-strained cycloalkenes/alkynes, etc. A monomer can be a vinyl containing monomer such as acrylates, acrylamides, styrenes, vinyl ethers, or using ring-strained cycloalkenes and cycloalkynes, as well as di, tri, or tetra-amino, -hydroxy, -thiol based monomers, etc. Monomers can be carbohydrates such as monosaccharides, lipids such as glycerol or fatty acids, nucleic acids such as nucleotides, or proteins or amino acids.

One aspect of the present disclosure is a [n]catenane-based product comprising a polymer building block represented by formula (II-A), (II-B), (III-A), or (III-B):

(II-A)

A1||||||M1||||||C1||||||D1||||||C2||||||M2||||||A2

(II-B)

A1||||||D2||||||C3||||||M1||||||C1||||||D1||||||C2||||||M2||||||C4||||||D3||||||A2

(A1)(C1)(C2)(A2) (III-A)

(A1)(C3)(C1)(C2)(C4)(A2) (III-B)

where: A1 and A2 each independently comprise a closed ring macrocyclic compound comprising a monovalent or divalent ligand or a [n]catenane/ate; C1, C2, C3, and C4 each independently comprise a closed ring macrocycle molecule comprising a monovalent ligand and a divalent ligand; D1, D2, and D3 are each a divalent metal ion; M1 and M2 are each the monovalent metal ion; and wherein "||||||" represents one or more bonds between a metal ion and a ligand, wherein A1 and C1, C1 and C2, and C2 and A2 are mechanically interlocked or A1 and C3, C3 and C1, C1 and C2, C2 and C4, and C4 and A2 are mechanically interlocked.

In certain embodiments, A1 and A2 each independently comprise a compound represented by formula (VI-A), (VI-B), or an ion thereof:

(VI-A)

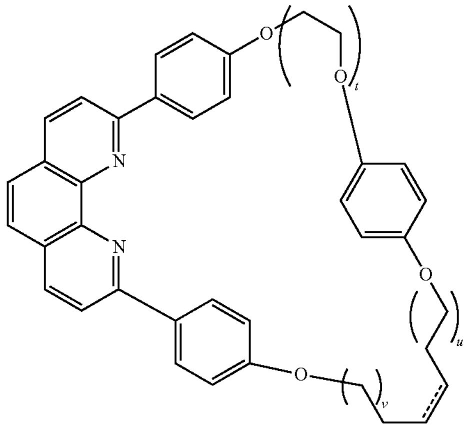

(VI-B)

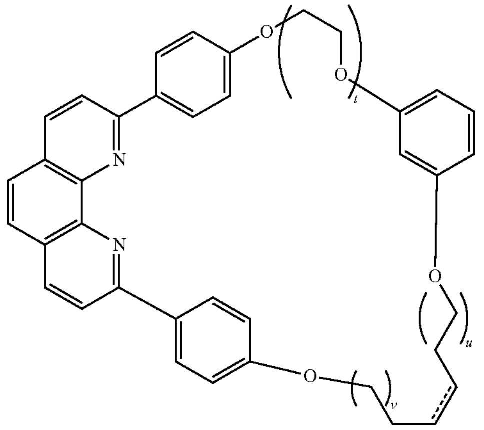

where: t is an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and u and v are each independently an integer of from 0 to 20, 0 to 15, 0 to 10, 0 to 5, 0 to 4, to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

In certain embodiments, A1 and A2 each independently comprise a compound of the following structure, or an ion thereof:

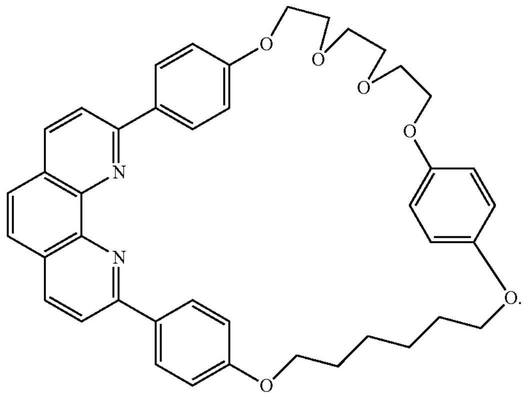 [SMILES: c1cc2ccc1OCCCCCCOc1ccc(cc1)-c1ccc3ccc4ccc(nc4c3n1)-c1ccc(cc1)OCCOCCOCCO2]

In certain embodiments, C1, C2, C3, and C4 each independently comprise a compound represented by formula (V), or an ion thereof:

(V)

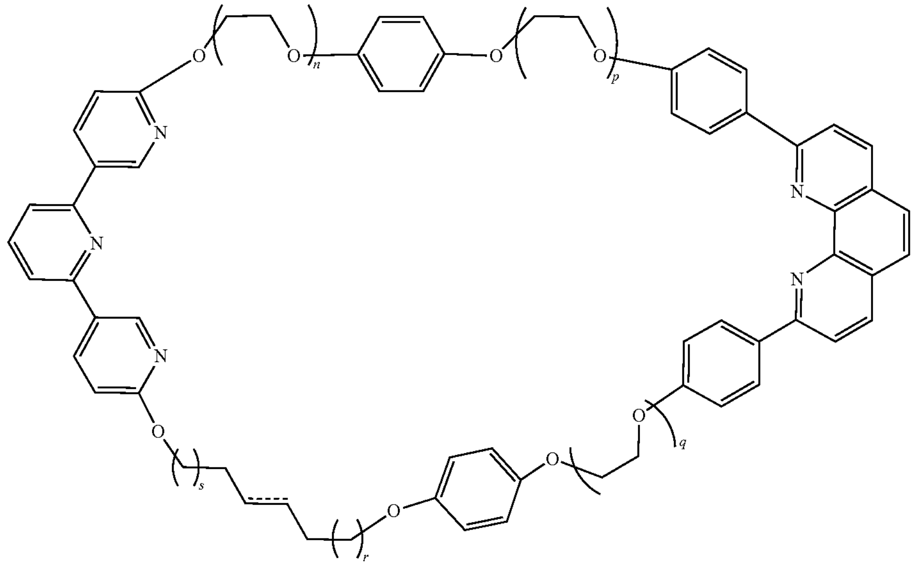

where: n, p, and q are each independently an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and r and s are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

In certain embodiments, C1, C2, C3, and C4 each independently comprise a compound of the following structure, or an ion thereof:

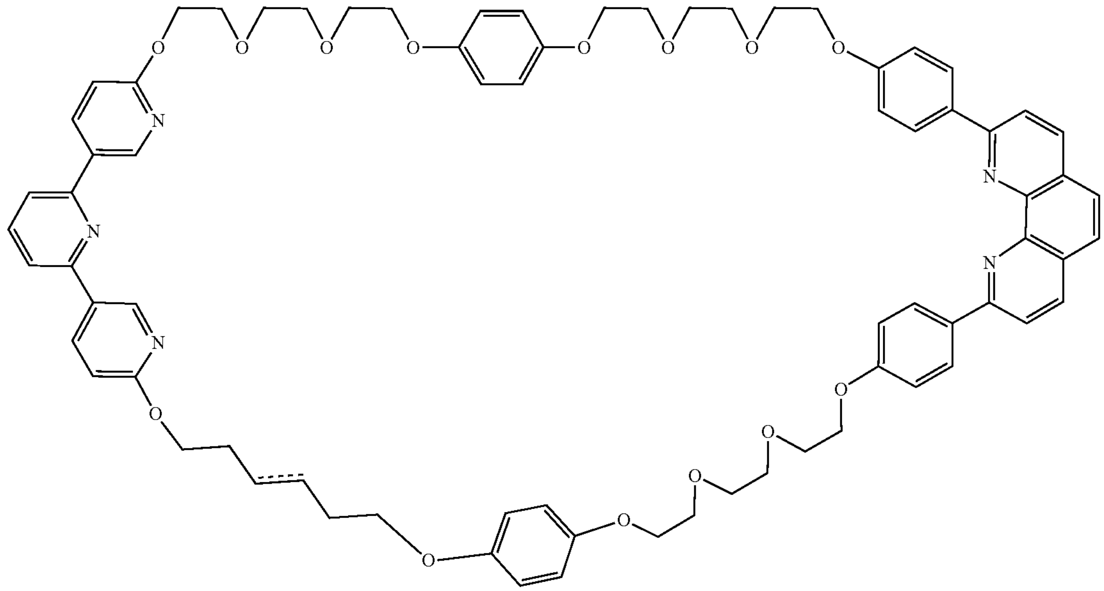

In certain embodiments, D1, D2, and D3 are each $Fe^{2+}$. In certain embodiments, M1 and M2 are each $Cu^{+}$.

In certain embodiments, the polymer building block of formula (II-A) comprises the following structure:

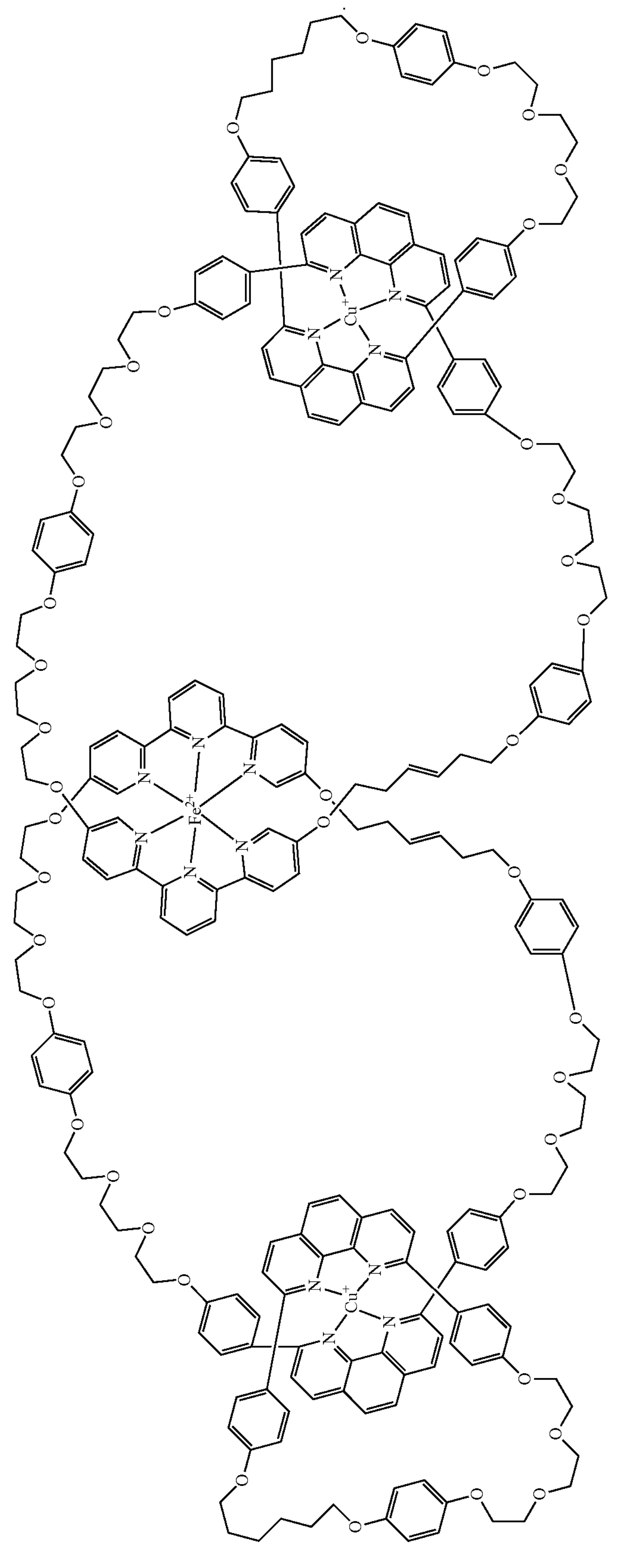

In certain embodiments, the polymer building block of formula (III-A) comprises the following structure, or an ion thereof:

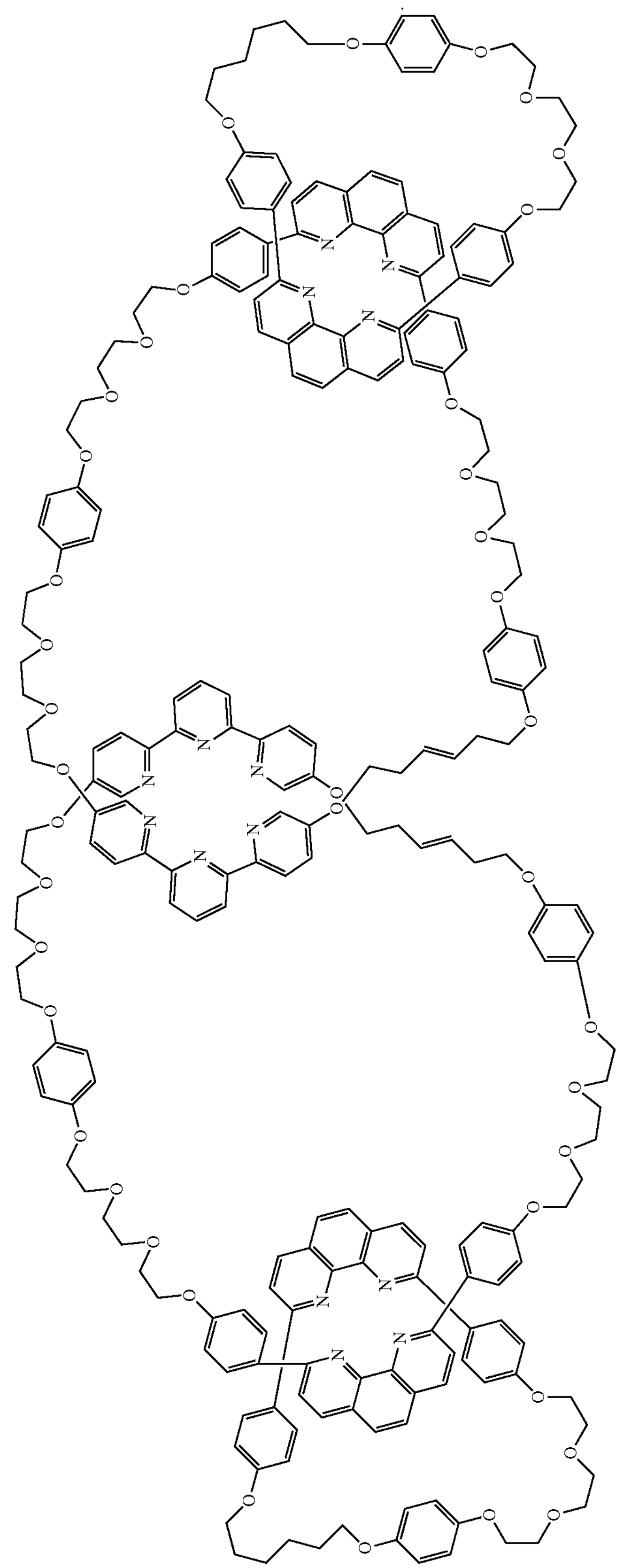

In certain embodiments, at least one or at least two of A1, A2, C1, C2, C3, and C4 is functionalized with at least one polymerizable group.

In certain embodiments, A1 and/or A2 is functionalized with at least one polymerizable group and independently comprises a compound represented by formula (VI-B), (VI-C), or an ion thereof:

(VI-C)

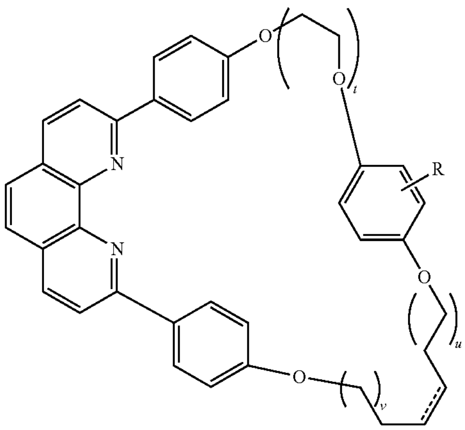

-continued (VI-D)

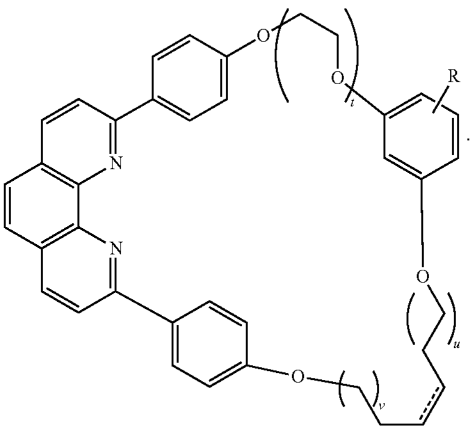

.

where: R is a polymerizable group (e.g., an amine containing group); t is an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and u and v are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

1. In certain embodiments, A1 and/or A2 each independently comprises a compound of the following structure, or ion or salt thereof:

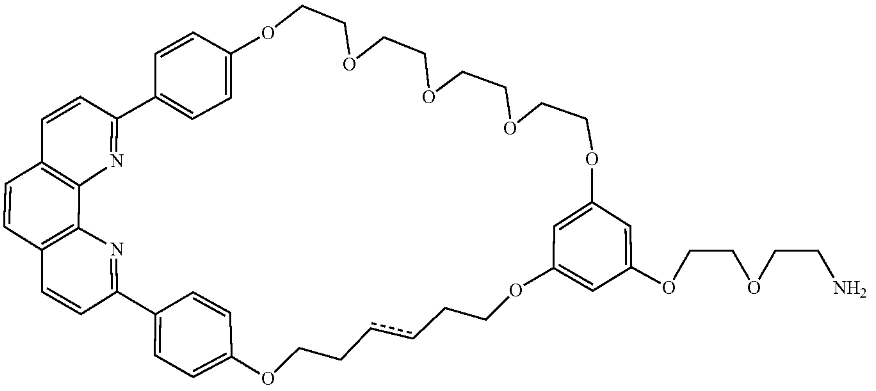

or

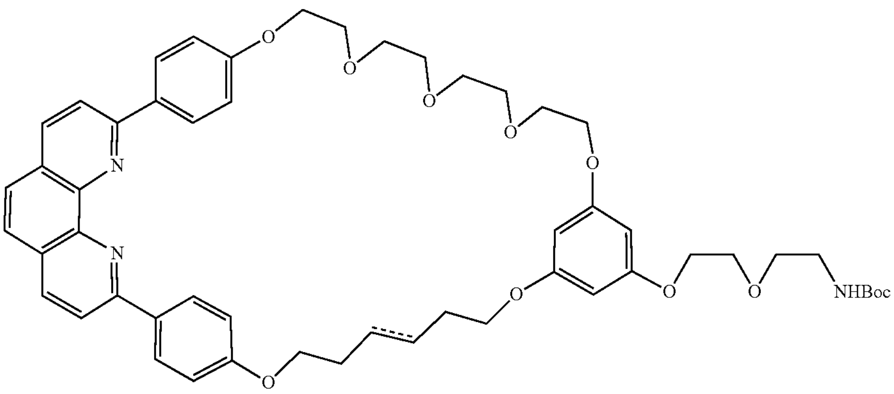

In certain embodiments, at least one polymerizable group comprises a styrene, acrylate, acrylamide, cycloalkene, amine, alcohol, thiol, or combinations thereof.

Another aspect of the present disclosure is a polymeric composition comprising: a plurality of the [n]catenane-based product comprising the polymer building block as described herein, wherein the at least one polymerizable group of the plurality of [n]catenane-based product are polymerized into a polymer network.

Another aspect of the present disclosure is a polymeric composition comprising: a plurality of the [n]catenane-based product comprising the polymer building block as described herein; and at least one or more monomers in an amount sufficient to form a polymer network; wherein the [n]catenane-based product are cross-linked with the monomers of the polymer network.

Certain embodiments disclose one ore more monomers, wherein the one or more monomers are selected from at least one di-, tri-, or tetra-functional monomer in an amount sufficient to form a thermoset polymer network void of solvents. In certain embodiments, the di-, tri-, or tetra-functional crosslinkers are selected from the group consisting of epoxy, acyl chloride, activated esters, ring-strained cycloalkenes/alkynes, and combinations thereof.

Another aspect of the present disclosure is a method of preparing a metal-loaded [n]catenane-based product, the method comprising: contacting in a reaction mixture: (i) a metal loaded-catenane precursor complex represented by formula (I):

(I)

P1||||||D1||||||P2 where: P1 and P2 are each an open ring macrocycle precursor molecule, wherein P1 and P2 each independently comprise a monovalent ligand and a divalent ligand; D1 is a divalent metal ion; and (ii) a closed ring macrocyclic compound comprising a monovalent or divalent ligand and/or a metal-loaded [2]catenane comprising two mechanically interlocked macrocycles and a divalent ligand; and, (iii) a monovalent metal compound comprising a monovalent metal ion, to form the metal loaded-[n]catenane-based product, wherein the metal loaded-[n]catenane-based product is represented by formula (II-A) or (II-B):

(II-A)

A1||||||M1||||||C1||||||D1||||||C2||||||M2||||||A2

(II-B)

A1||||||D2||||||C3||||||M1||||||C1||||||D1||||||C2||||||M2||||||C4||||||D3||||||A2 where: C1 is a closed ring form of P1; C2 is a closed ring form of P2; A1 and A2 each independently comprise a closed ring macrocyclic compound comprising a monovalent or divalent ligand or a [n]catenane/ate; C3 and C4 each independently comprise a closed ring macrocycle molecule comprising a monovalent ligand and a divalent ligand; D2 and D3 are each a divalent metal ion; M1 and M2 are each a monovalent metal ion; and wherein "||||||" represents one or more bonds between a metal ion and a ligand, wherein A1 and C1, C1 and C2, and C2 and A2 are mechanically interlocked or A1 and C3, C3 and C1, C1 and C2, C2 and C4, and C4 and A2 are mechanically interlocked. In certain embodiments, the reaction mixture further comprises a Grubbs catalyst. In certain embodiments, the Grubbs catalyst comprises a second generation Grubbs catalyst. In certain embodiments, the reaction mixture further comprises a solvent. In certain embodiments, the method further comprises contacting the open ring macrocycle precursor with a divalent metal compound comprising the divalent metal ion to form the metal loaded-catenane precursor complex.

In certain embodiments, P1 and P2 each independently comprise a compound represented by formula (IV), or an ion thereof:

(IV)

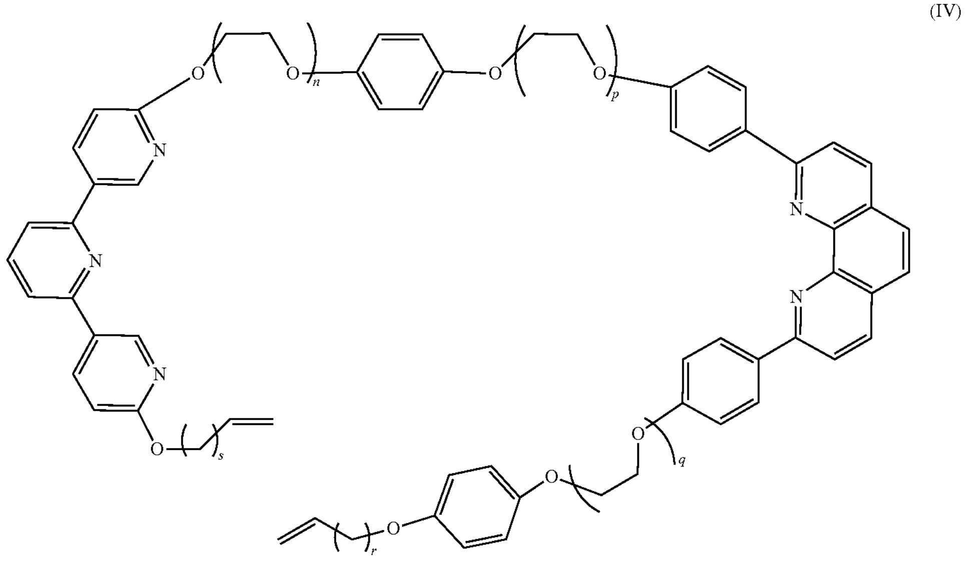

where: n, p, and q are each independently an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and r and s are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

In certain embodiments, P1 and P2 each independently comprise a compound of the following structure:

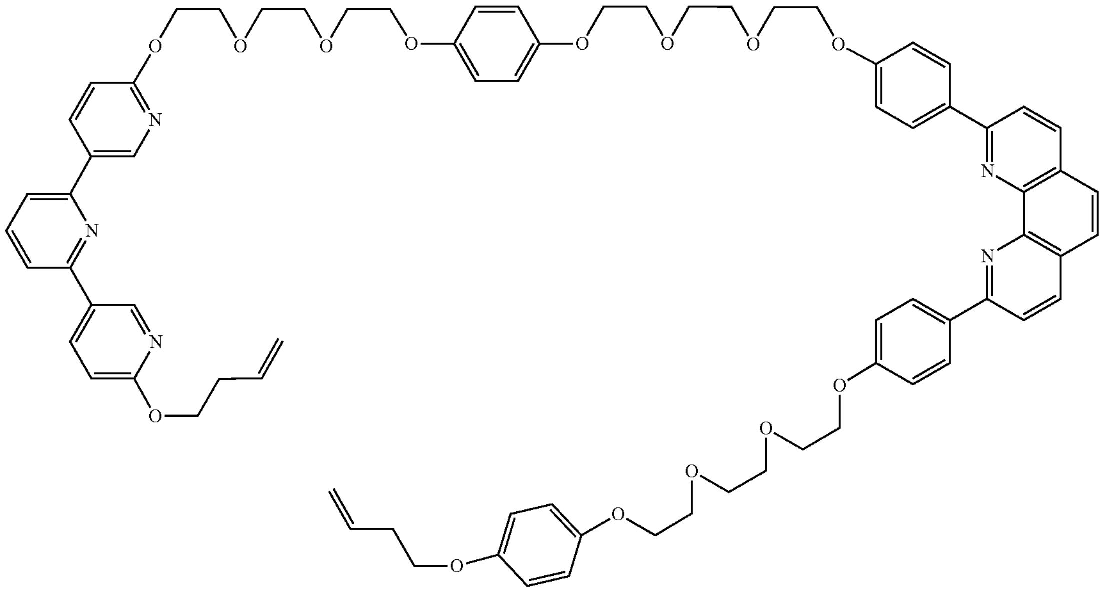 [SMILES: C=CCCOc1ccc(OCCOCCOCCOc2ccc(-c3ccc4ccc5ccc(-c6ccc(OCCOCCOCCOc7ccc(OCCOCCOCCOc8ccc(-c9cccc(-c%10ccc(OCCC=C)nc%10)n9)cn8)cc7)cc6)nc5c4n3)cc2)cc1]

In certain embodiments, D1, D2, and D3 are each $Fe^{2+}$. In certain embodiments, M1 and M2 are each $Cu^{+}$.

In certain embodiments, C1, C2, C3, and C4 each independently comprise a compound represented by formula (V), or an ion thereof:

(V)

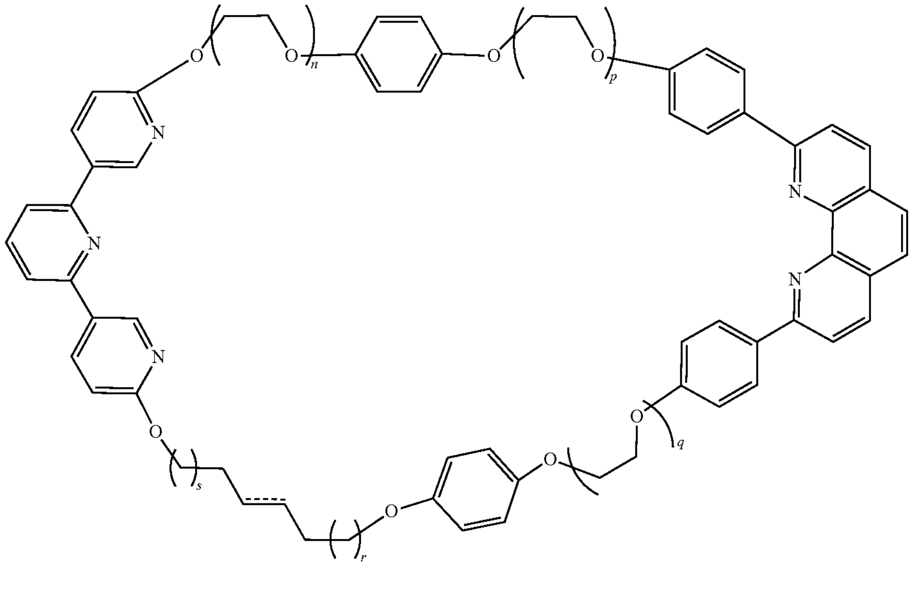

where: n, p, and q are each independently an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and r and s are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

In certain embodiments, C1, C2, C3, and C4 each independently comprise a compound of the following structure, or an ion thereof:

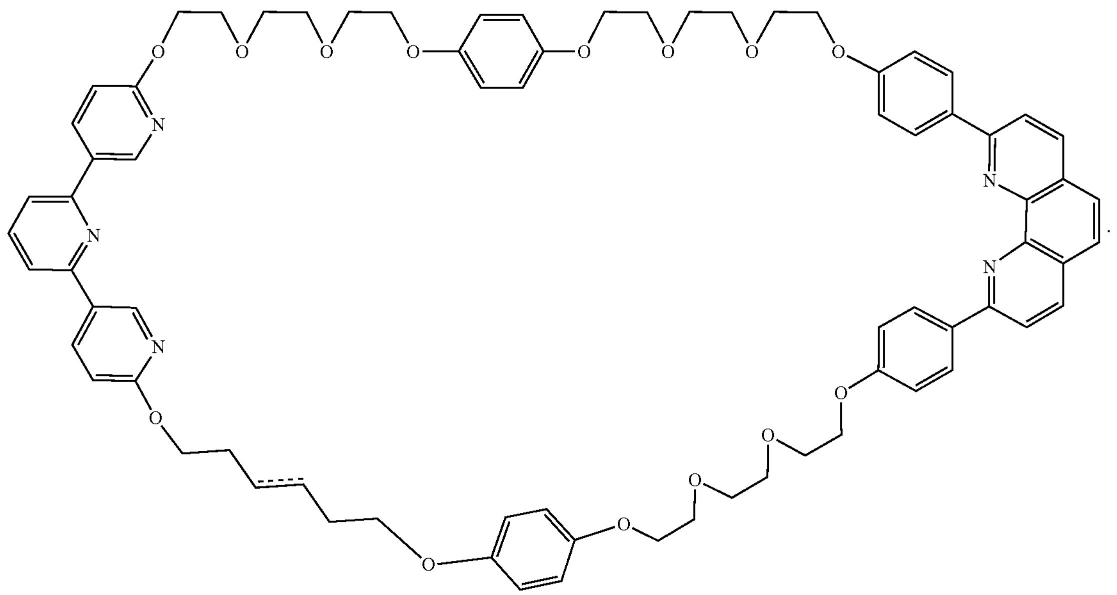

In certain embodiments, A1 and A2 each independently comprise a compound represented by formula (VI-A), (VI-B), or an ion thereof:

(VI-A)

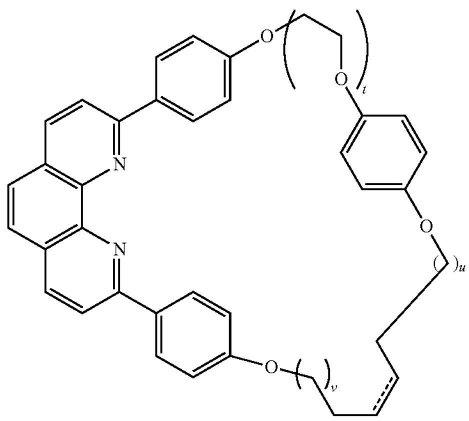

(VI-B)

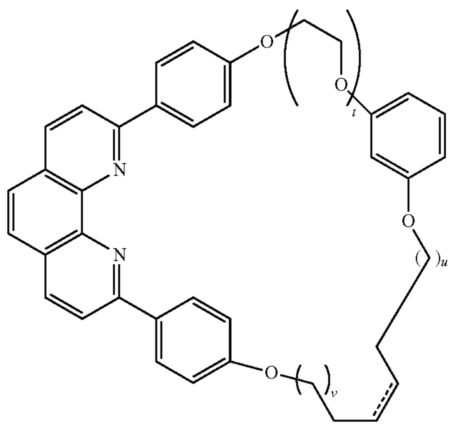

where: t is an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and u and v are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

In certain embodiments, A1 and A2 are each a compound of the following structure, or an ion thereof:

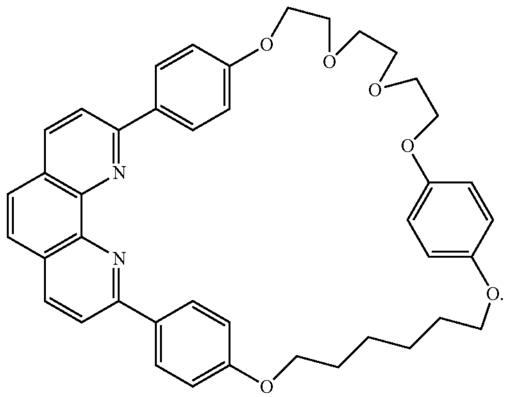 [SMILES: c1cc2ccc1OCCCCCCOc1ccc(cc1)-c1ccc3ccc4ccc(nc4c3n1)-c1ccc(cc1)OCCOCCOCCO2]

In certain embodiments, the metal loaded-catenane precursor complex is a compound of the following structure, or an ion thereof:

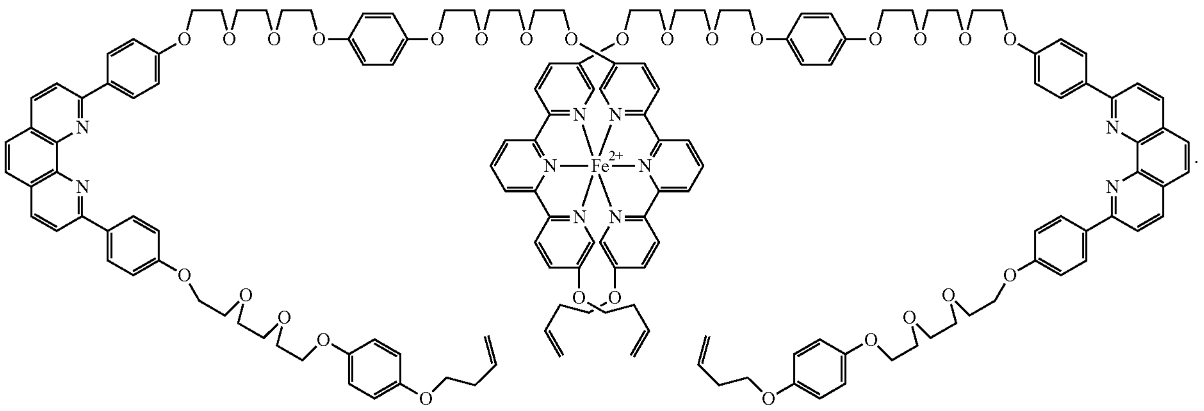
In certain embodiments, the polymer building block comprises a compound of the following structure:

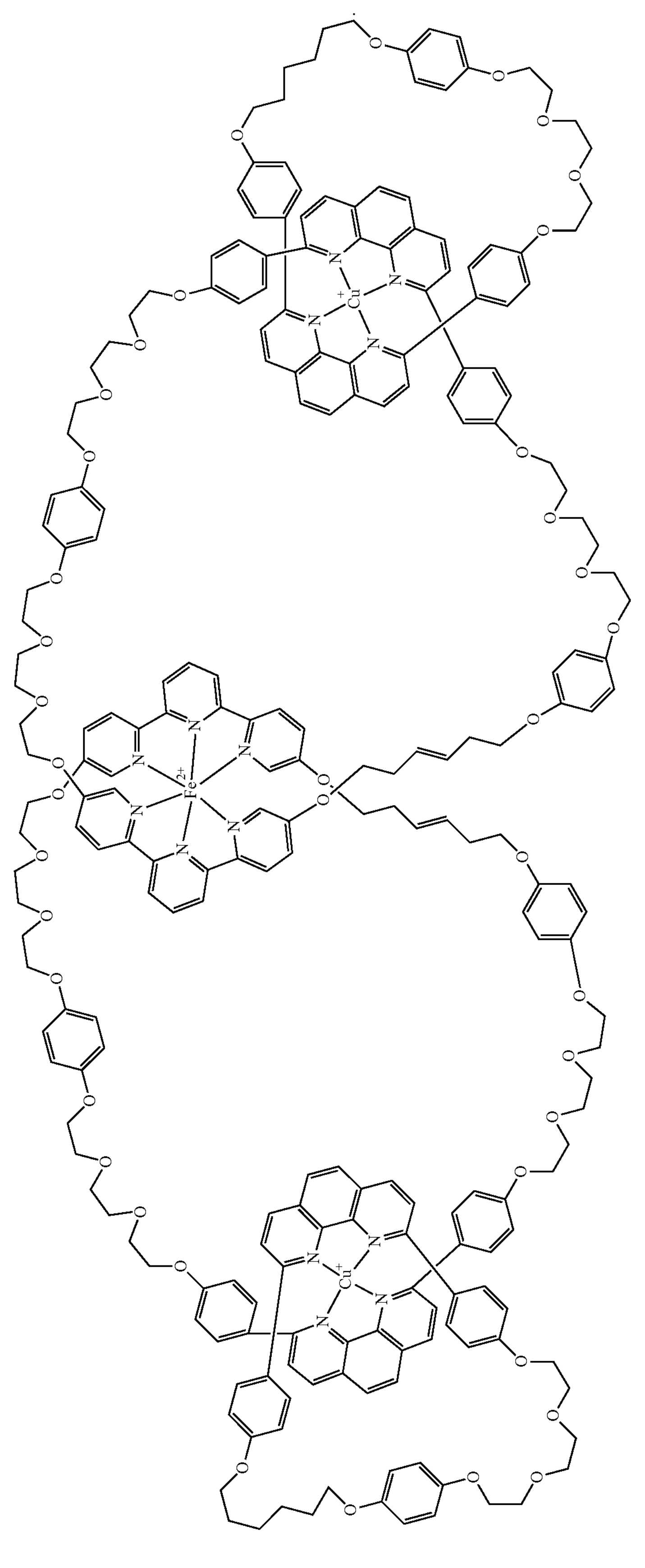

In certain embodiments, the polymer building block comprises a compound of the following structure:

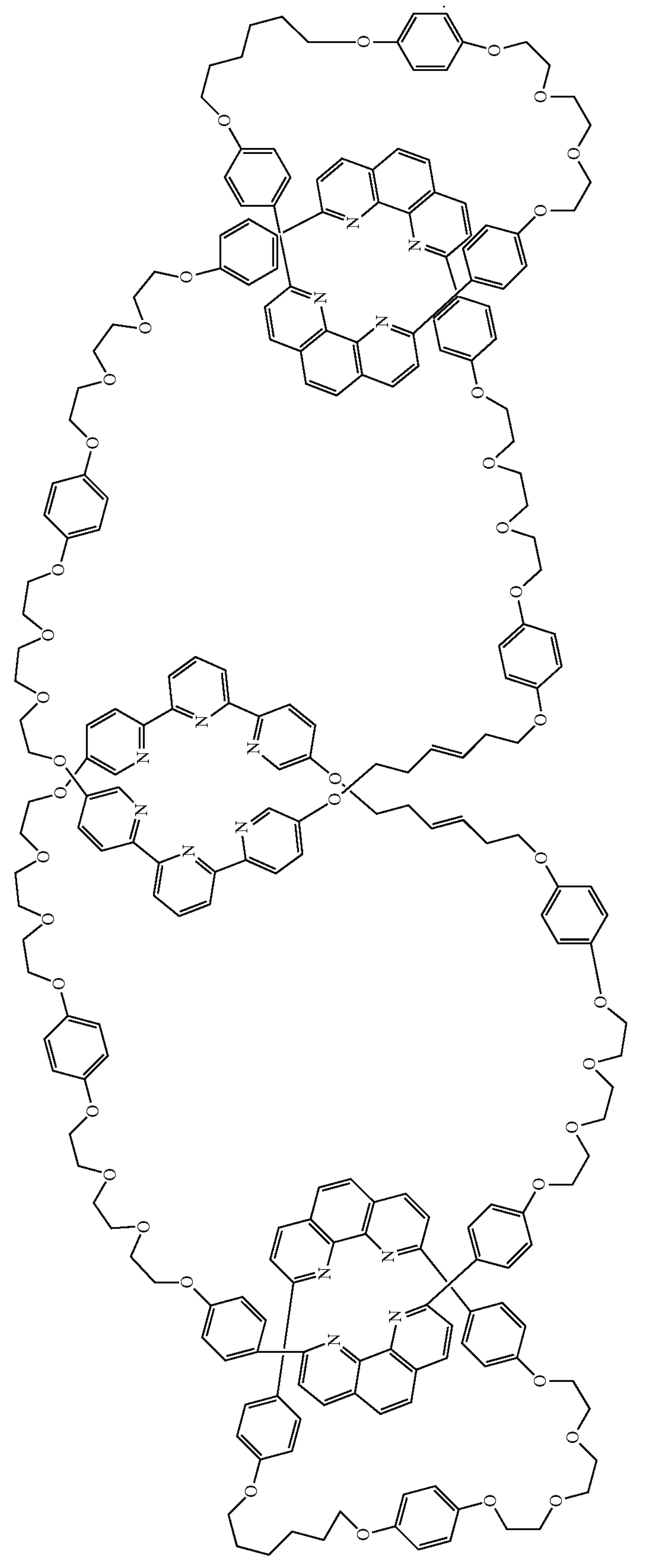

In certain embodiments, the method further comprises functionalizing at least one of A1, A2, C1, C2, C3, and C4 with at least one polymerizable group. In certain embodiments, A1 and/or A2 is functionalized with at least one polymerizable group and independently comprises a compound represented by formula (VI-B), (VI-C), or an ion thereof:

(VI-C)

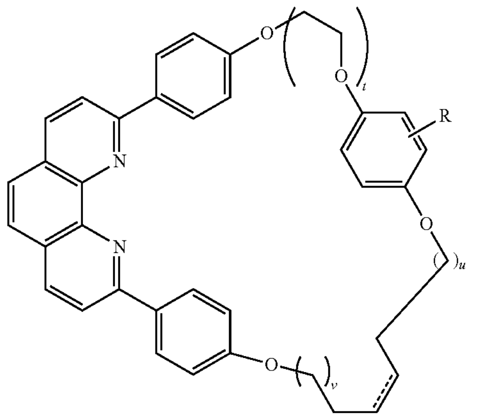

-continued (VI-D)

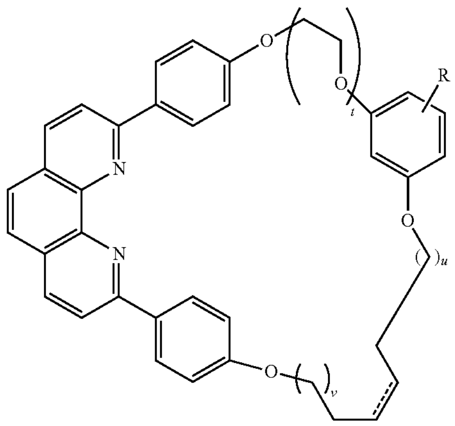

where: R is a polymerizable group; t is an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and u and v are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

In certain embodiments, A1 and/or A2 each independently comprises a compound of the following structure, or ion or salt thereof:

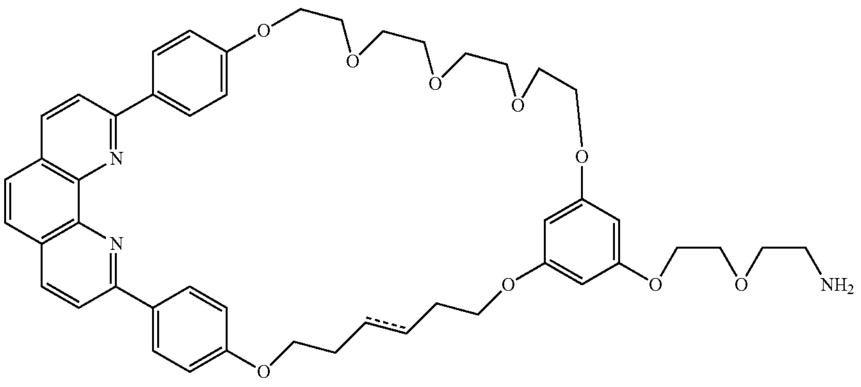

or

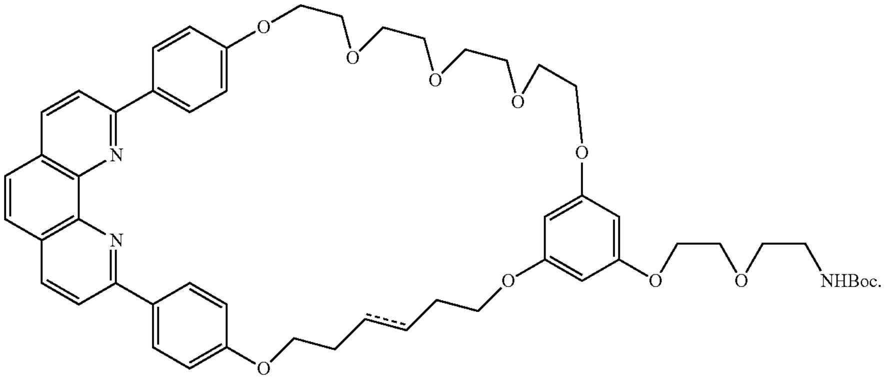

In certain embodiments, the at least one polymerizable group comprises a styrene, acrylate, acrylamide, cycloalkene, amine, alcohol, thiol, or combinations thereof.

Another aspect of the present disclosure is a method of producing a polymeric material containing mechanically interlocked structures comprising: reacting a plurality of the [n]catenane-based products with polymer precursors comprising polymerizable groups. In certain embodiments, the polymerizable groups comprises a plurality of monomers selected from the group consisting of acrylates, acrylamides, styrenes, vinyl ethers, ring-strained cycloalkenes and cycloalkynes, di, tri, or tetra-amino, -hydroxy, -thiol based monomers, and combinations thereof. In certain embodiments, at least one macrocycle of each [n]catenane-based product is loaded with a metal ion selected from the group consisting of iron (Fe), copper (Cu), ruthenium (Ru), nickel (Ni), manganese (Mn), zinc (Zn), and combinations thereof.

Another aspect of the present disclosure is a method of preparing a polymeric material, the method comprising: forming a solvated polymer network; and cross-linking a plurality of the [n]catenane-based products of claim 1 and the solvated polymer network. In certain embodiments, the solvated polymer network is hydrogel or organogel. In certain embodiments, the material comprising a plurality of [n]catenane-based products optionally comprises at least one metal ion; and the at least one polymerizable group of the [n]catenane-based products comprises a di-, tri-, or tetra-functional monomer, or combination thereof, capable of forming a thermoset polymer network void of solvents. In certain embodiments, the di-, tri-, and tetra-functional monomers are selected from the group consisting of epoxy, acyl chloride, activated esters, ring-strained cycloalkenes/alkynes, and combinations thereof.

In certain embodiments, a thermoplastic is generated; and the thermoplastic comprises mechanically interlocked, topologically complex crosslinkers and forms a rigid difunctional covalent linker is arranged in a linear fashion to form a [n]catenane/ate thermoplastic selected from the group consisting of [3]catenane/ate, [4]catenane/ate, [5]catenane/ate, and [6]catenane/ate.

In certain embodiments, the method is a step-growth polymerization method or a chain-growth polymerization method.

Another aspect of the present disclosure is a method of preparing a [n]catenane-based product, the method comprising: contacting a metal loaded-[n]catenane-based product with a chelating agent to remove the monovalent and divalent metal ions from the product and form the [n]catenane-based product.

Another aspect of the present disclosure is a compound comprising the structure of formula (IV) or (V):

(IV)

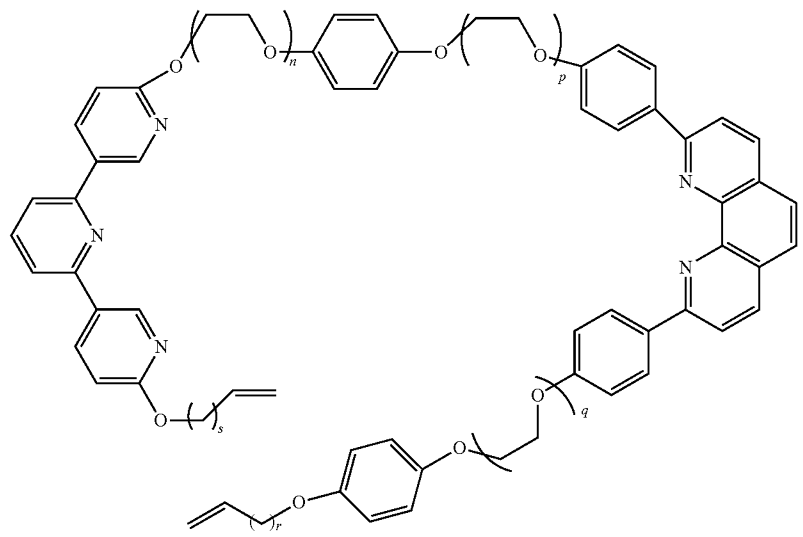

(V)

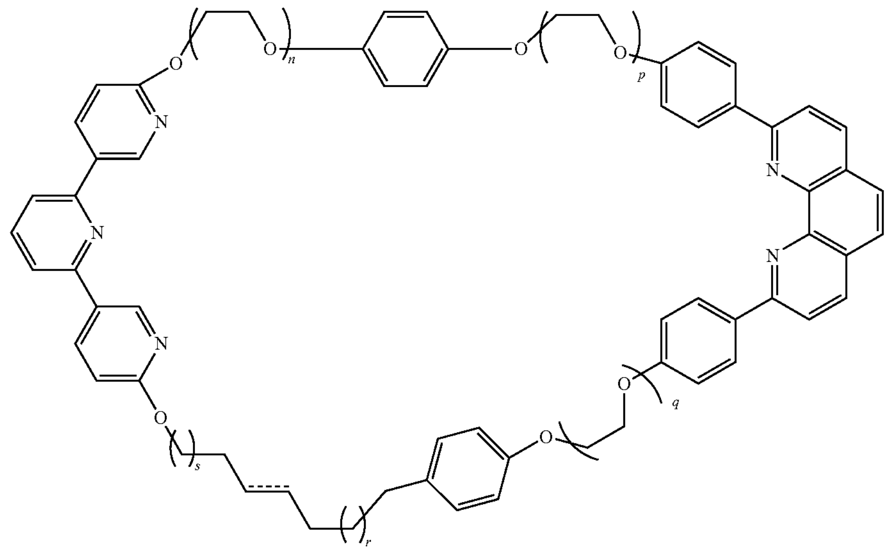

where: n, p, and q are each independently an integer of from 1 to 20, 1 to 15, 1 to 10, 1 to 5, 1 to 4, 1 to 3, 2 to 20, 2 to 15, 2 to 10, 2 to 5, 2 to 4, or 2, 3, 4, 5, or 6; and r and s are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.
In certain embodiments, the compound comprises the following structure:
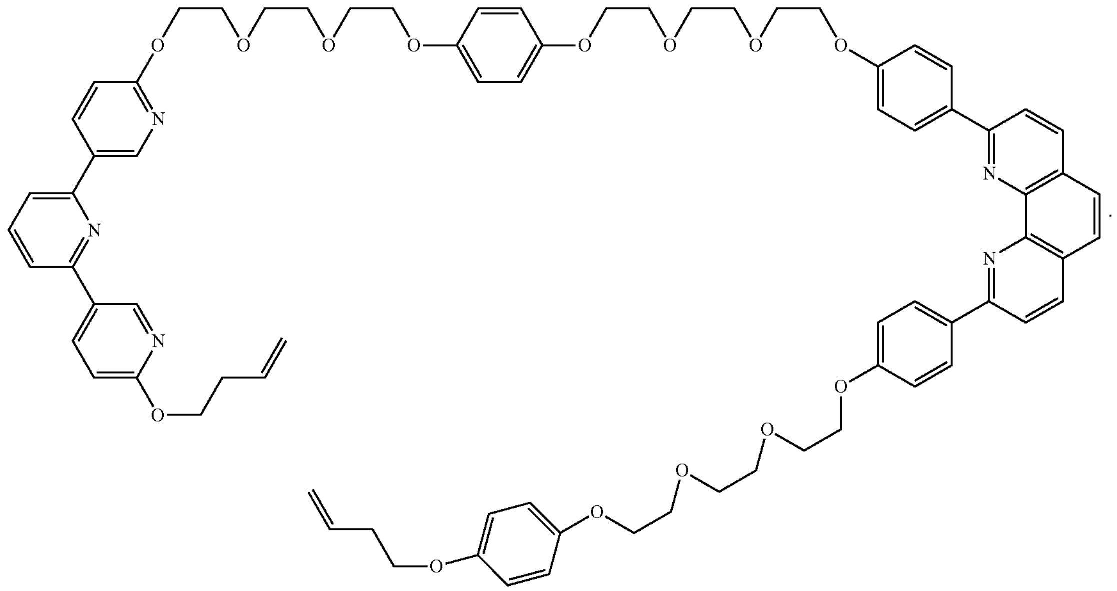 [SMILES: C=CCCOc1ccc(OCCOCCOCCOc2ccc(-c3ccc4ccc5ccc(-c6ccc(OCCOCCOCCOc7ccc(OCCOCCOCCOc8ccc(-c9cccc(-c%10ccc(OCCC=C)nc%10)n9)cn8)cc7)cc6)nc5c4n3)cc2)cc1]
In certain embodiments, the compound comprises the following structure:
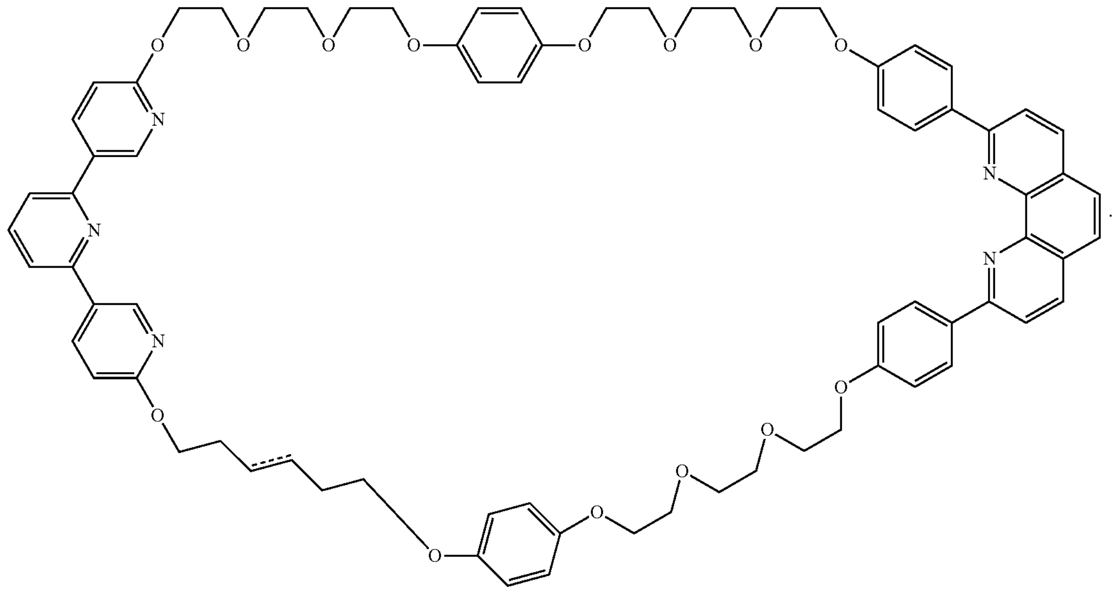

Another aspect of the present disclosure is a composition comprising a mechanically interlocked, topologically complex crosslinker comprising: a macrocycle having an [n]catenane-based architecture, wherein n=2 or 3 or 4 or 5 or 6 or more, wherein at least one of the interlocked molecular macrocycles are functionalized with at least one polymerizable group, such as a group comprising a monomer. In certain embodiments, the macrocycles are difunctionalized with at least one polymerizable group. In certain embodiments, the macrocycles are difunctionalized at its termini or side groups. In certain embodiments, the at least one polymerizable group comprises a styrene, acrylate, acrylamide, cycloalkene, amine, alcohol, thiol, or combinations thereof. In certain embodiments, least one macrocycle is loaded with a metal ion (e.g., one per molecular ring via metal-ligand coordination). In certain embodiments, at least one macrocycle is loaded with a metal ion (e.g., one per molecular ring via metal-ligand coordination) selected from iron (Fe), copper (Cu), ruthenium (Ru), nickel (Ni), manganese (Mn), zinc (Zn), or combinations thereof.

Another aspect of the present disclosure is a composition comprising a material comprising: a mechanically interlocked, topologically complex crosslinker, optionally, with and/or without metal ions; and/or at least one or more monomers in an amount sufficient to form a solvated polymer network (e.g., hydrogel or organogel, depending on whether water or an organic solvent is used to swell the gel); wherein the mechanically interlocked, topologically complex crosslinkers are cross-linked resulting in a polymer network. In certain embodiments, the one or more monomers are selected from at least one di-, tri-, or tetra-functional monomer in an amount sufficient to form a thermoset polymer network void of solvents, wherein the monomer is capable of cross-linking the mechanically interlocked, topologically complex crosslinker and resulting in a polymer network. In certain embodiments, the di-, tri-, or tetra-functional crosslinkers are selected from epoxy, acyl chloride, activated esters (like N-hydroxysuccinimide), ring-strained cycloalkenes/alkynes, or combinations thereof.

In certain embodiments, the mechanically interlocked, topologically complex crosslinker is a rigid difunctional covalent linker arranged in a linear fashion to form poly[3]catenane/ate, poly[4]catenane/ate, poly[5]catenane/ate, or poly[6]catenane/ate, etc.; optionally, with and/or without metal ions; and the composition is a thermoplastic.

Another aspect of the present disclosure is a method of producing polymeric materials containing well-defined mechanically interlocked structures comprising: providing the mechanically interlocked, topologically complex crosslinker material of any one of the preceding claims; providing polymerizable groups; and optionally, providing metal ions. In certain embodiments, the polymerizable groups can comprise monomers selected from the group consisting of: vinyl-containing monomers such as acrylates, acrylamides, styrenes, vinyl ethers, or using ring-strained cycloalkenes and cycloalkynes, as well as di, tri, or tetra-amino, -hydroxy, -thiol based monomers that can be used to make step-growth polymers, or combinations thereof. In certain embodiments, at least one macrocycle is loaded with a metal ion (e.g., one per molecular ring via metal-ligand coordination) selected from iron (Fe), copper (Cu), ruthenium (Ru), nickel (Ni), manganese (Mn), zinc (Zn), or combinations thereof.

In certain embodiments, the method further comprises functionalizing the material comprising a mechanically interlocked, topologically complex crosslinker, optionally with and/or without metal ion(s), with at least one or more monomers; forming a solvated polymer network (e.g., hydrogel or organogel, depending on whether water or an organic solvent is used to swell the gel); and cross-linking the mechanically interlocked, topologically complex crosslinker and resulting polymer network. In certain embodiments, the method further comprises cross-linking the mechanically interlocked, topologically complex crosslinker and resulting polymer network, wherein, the material comprising a mechanically interlocked, topologically complex crosslinker optionally comprises at least one metal ion; and/or the at least one monomer comprises di-, tri-, or tetra-functional monomers, or combination thereof, capable of forming a thermoset polymer network void of solvents. In certain embodiments, the di-, tri-, and tetra-functional crosslinkers are selected from epoxy, acyl chloride, activated esters (like N-hydroxysuccinimide), ring-strained cycloalkenes/alkynes, and combinations thereof.

In certain embodiments, a thermoplastic is generated; and/or the thermoplastic comprises the mechanically interlocked, topologically complex crosslinkers and forms a rigid difunctional covalent linker is arranged in a linear fashion to form poly[3]catenane/ate, poly[4]catenane/ate, poly[5]catenane/ate, and poly[6]catenane/ate, etc.; optionally with and/or without metal ions. In certain embodiments, the method for the synthesis of poly[n]catenane/ate thermoplastics are composed exclusively of mechanically interlocked molecular macrocycles arranged in a linear fashion, optionally with metal ions. In certain embodiments, the composition contains mechanical bonding topology; the composition is flexible; the composition is tough; and/or the composition is responsive to the addition or removal of metal ions, or a change in the oxidation state of the metals. In certain embodiments, the mechanically interlocked, topologically complex crosslinker is used in a step-growth polymerization method. In certain embodiments, the mechanically interlocked, topologically complex crosslinker is used in a chain-growth polymerization method.

In certain embodiments, macrocycles A1, A2, C1, C2, C3, and/or C4 are substituted at least once. The at least one substitution can be at various positions on the macrocycles. Substitutions can include, for example, various moieties to link monomers or polymers to the polymer building blocks.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

For labeling of chemical compounds by number, the numbering system restarts at Example 11 and Example 16. Examples 1-10 use one chemical numbering system. Examples 11-15 use a second chemical numbering system, and Examples 16-21 use a third chemical numbering system.

Example 1. Materials and Methods [4]Catenane/ate

The materials and methods of this Example were used in Examples 2-10.

All reagents were purchased from commercial suppliers and used without further purification unless stated otherwise. Metal sources $Fe(BF_4)_2 \cdot 6\ H_2O$ and $Cu(MeCN)_4PF_6$ were purchased from Sigma-Aldrich. Modified literature procedures were employed in the synthesis of compounds 1-4 (Veliks et al., 2016) and 10-11 (Dietrich-Buchecker et al., 1990). All reactions were performed under $N_2$ using common Schlenk techniques.

Column chromatography was carried with silica gel (Sorbtech, 0.040-0.063 mm) or neutral alumnia (Sorbtech, Act. 1, 0.050-0.2 mm) or basic alumnia (Sorbtech, Act. 1, 0.050-0.2 mm). All ring closing reactions were done using Grubb's $2^{nd}$ generation catalyst (Asta Tech). Preparative gel permeation chromatography (GPC) was performed on a Japan Analytical Industry LaboACE instrument with one JAIGEL-2HR column and one JIAGEL-2.5HR column in sequence, running with either dimethylformamide (DMF) at 8 $mL \cdot min^{-1}$ or chloroform ($CHCl_3$) at 10 $mL \cdot min^{-1}$ as the mobile phase. Preparative high-pressure liquid chromatography (HPLC) was performed on an Agilent 1260 Infinity instrument with a Zorbax 300SB-C18 column (21.2×250 mm) with a gradient mobile phase of water ($H_2O$) with 0.1% acetic acid ($CH_3COOH$) and acetonitrile (MeCN) with 0.1% $CH_3COOH$ or methanol (MeOH) with 0.1% formic acid (HCOOH).

All nuclear magnetic resonance (NMR) spectra were recorded on a Varian Inova-500 spectrometer at 25° C., with working frequencies of 500 ($^1H$), 471 ($^{19}F$), and 125 ($^{13}C$) MHz or a Varian Unity Inova-600 spectrophotometer at 25° C., with working frequencies of 600 ($^1H$) and 150 ($^{13}C$) MHz. Chemical shifts are reported in ppm relative to the signals corresponding to the residual non-deuterated solvents: $CDCl_3$: $\delta_H$=7.26 ppm and $\delta_C$=77.16 ppm; $(CD_3)_2SO$: $\delta_H$=2.50 ppm and $\delta_C$=39.52 ppm.

Ultraviolet-Visible (UV-Vis) absorbance spectra were recorded on an Agilent Cary 5000 spectrophotometer with a quartz cuvette (0.2 cm pathlength). Analytical GPC analyses were performed on an Agilent 1260 Infinity setup with two Shodex GPC KD-806M columns in sequence in DMF mobile phase (0.025 M LiBr) running at 60° C. at 1.0 $mL \cdot min^{-1}$. The differential refractive index (dRI) of each compound was monitored using a Wyatt Optilab T-rEX detector. Analytical HPLC analyses were performed on an Avant 2000 HPLC with a Shodex Asahipak ODP-50-2D reverse phase column with a gradient mobile phase of $H_2O$ with 0.1% HCOOH and MeOH with 0.1% HCOOH at running at 40° C. at 0.2 $mL \cdot min^{-1}$, which was in series with an Advion Expression-L Compact Mass Spectrometer; UV-vis absorbance was recorded at 254 nm.

Low-res mass spectrometry electrospray ionization (LRMS-ESI) was recorded on an Advion Expression-L Compact Mass Spectrometer. High-res mass spectrometry electrospray ionization (HRMS-ESI) was recorded on a Waters Synapt G2 HDMS or a Bruker maXis 4G UHR-TOF mass spectrometer. Matrix assisted laser desorption/ionization time-of-flight mass spectrometry (MALDI-TOF-MS) was recorded on a Bruker Solaris 12T FT-MS; samples were prepared using 2,5-dihydroxybenzoic or α-Cyano-4-hydroxycinnamic acid matrices. MALDI-TOF-MS data was simulated using the free online calculator ChemCalc (Patiny et al., 2013). Molecular models were generated to calculate the equilibrium geometry in the gas phase with molecular mechanics and the MMFF force field (Spartan'18); anions were omitted from the simulation for simplicity.

Example 2. Methods Summary [4]Catenane/ate

Synthesis of Fe-$(OTPM)_2$.

All reagents were purchased from commercial suppliers and were used without further purification. Metal sources $Fe(BF_4)_2 \cdot 6H_2O$ and $Cu(MeCN)_4PF_6$ were purchased from Sigma-Aldrich. Precursor OTPM (0.0105 g, 0.0081 mmol, 1 equiv) was dissolved in 5 mL of tetrahydrofuran (THF) in a 25 mL RB flask and was heated to 60° C. for 15 min. A solution of $Fe(BF_4)_2 \cdot 6H_2O$ (0.0035 g, 0.0105 mmol, 1.3 equiv) in 0.5 mL of DI $H_2O$ was added via syringe, and the red solution was heated for an additional 1 h at 60° C. The solution was allowed to cool to room temperature and was diluted with 100 mL of chloroform ($CHCl_3$). The red solution was washed with 3×25 mL of DI $H_2O$. The organic layer was collected and was dried over $Na_2SO_4$. The solution was filtered and the solvent was removed to afford the product as a red film (0.0101 g, 89%).

$^1H$ NMR (500 MHz, $CDCl_3$): $\delta_H$ 8.61 (d, J=7.2 Hz, 2H), 8.53-8.32 (m, 12H), 8.32-8.21 (m, 6H), 8.07 (dt, J=15.8, 6.4 Hz, 4H), 7.75 (s, 4H), 7.10 (t, J=8.5 Hz, 8H), 6.9-6.72 (m, 14H), 6.47 (dd, J=33.2, 1.8 Hz, 4H), 5.88 (m, 2H), 5.65 (m, 2H), 5.20-4.95 (m, 8H), 4.24 (d, J=4.5 Hz, 7H); 4.09 (s, 6H), 3.98-3.84 (m, 22H), 3.80 (d, J=8.1 Hz, 16H), 3.71-3.63 (m, 6H), 3.55 (d, J=7.3 Hz, 6H), 2.49 (d, J=6.5 Hz, 4H), 2.34 (d, J=4H). $^{13}C$ NMR (125 MHz, $CDCl_3$): $\delta_H$ 160.3, 160.3, 159.7, 159.5, 157.6, 157.6, 156.5, 156.4, 156.3, 153.4, 153.3, 153.2, 153.1, 149.8, 149.7, 146.1, 142.1, 141.6, 137.0, 137.0, 134.7, 133.2, 132.4, 129.1, 127.7, 125.8, 125.3, 125.0, 122.5, 122.3, 121.5, 121.3, 119.5, 118.1, 117.0, 115.8, 115.7, 115.7, 115.1, 115.0, 71.1, 71.0, 70.7, 70.6, 70.1, 70.0, 69.9, 69.1, 68.9, 68.7, 68.3, 68.1, 68.0, 67.7, 67.1, 33.9, 33.0, 30.1. HRMS-ESI calcd for $C_{154}H_{162}FeN_{10}O_{28}$: m/z=885.7002 $[M+H]^{3+}$; found 885.7024 $[M+H]^{3+}$.

Synthesis of [2]C-M.

A solution of precursor Fe-$(OTPM)_2$ (0.062 g, 0.0219 mmol, 1 equiv) and Grubbs' second-generation catalyst (0.0038 g, 0.0046 mmol, 0.2 equiv) was prepared in 75 mL of $CHCl_3$ in a RB flask fitted with a reflux condenser, and the solution was heated to 45° C. for 16 h while stirring under $N_2$. An additional 0.2 equiv of Grubbs' second-generation catalyst was added, and the solution was heated for an additional 4 h. The solvent was then removed via a rotary evaporator to afford the crude product, which was purified via column chromatography with basic alumnia ($CHCl_3$ to 5% MeOH/$CHCl_3$) to afford the product as a deep red solid (0.019 g, 31%).

$^1H$ NMR (500 MHz, $CDCl_3$): $\delta_H$ 8.63 (s, 2H), 8.42 (dd, J=33.8, 25.1 Hz, 12H), 8.31-8.19 (m, 6H), 8.03 (dd, J=24.5, 8.3 Hz, 5H), 7.74 (d, J=5.7 Hz, 4H), 7.20 (d, J=20.6 Hz, 4H), 7.07 (dd, J=17.3, 8.8 Hz, 8H), 6.97 (d, J=14.7 Hz, 2H), 6.89-6.62 (m, 16H), 6.41 (d, J=39.6 Hz, 6H), 5.35 (d, J=53.7 Hz, 8H), 4.22 (s, 6H), 4.15-3.42 (m, 67H), 2.32-2.21 (m, 8H). $^{13}C$ NMR (125 MHz, $CDCl_3$): $\delta_C$ 160.3, 159.5, 157.4, 156.4, 153.3, 149.9, 146.1, 137.1, 135.1, 132.4, 130.3, 129.1, 127.7, 125.8, 122.1, 119.5, 115.7, 115.1, 71.1, 70.7, 70.1, 69.9, 68.3, 68.2, 67.7, 29.8. HRMS-ESI calcd for $C_{154}H_{154}FeN_{10}O_{28}$: m/z=1300.0160 $[M]^{2+}$, 867.0132 $[M+H]^{3+}$; found 1300.0459 $[M]^{2+}$, 867.0344 $[M+H]^{3+}$.

Synthesis of [4]C-M.

Figure 3A:
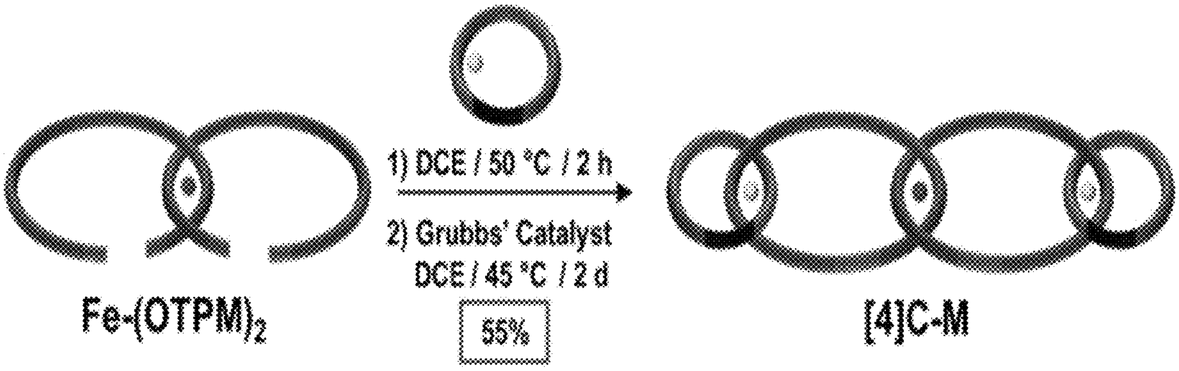
FIG. 3A depicts synthesis of [4]C-M using a one-pot approach.
Figure 3B:
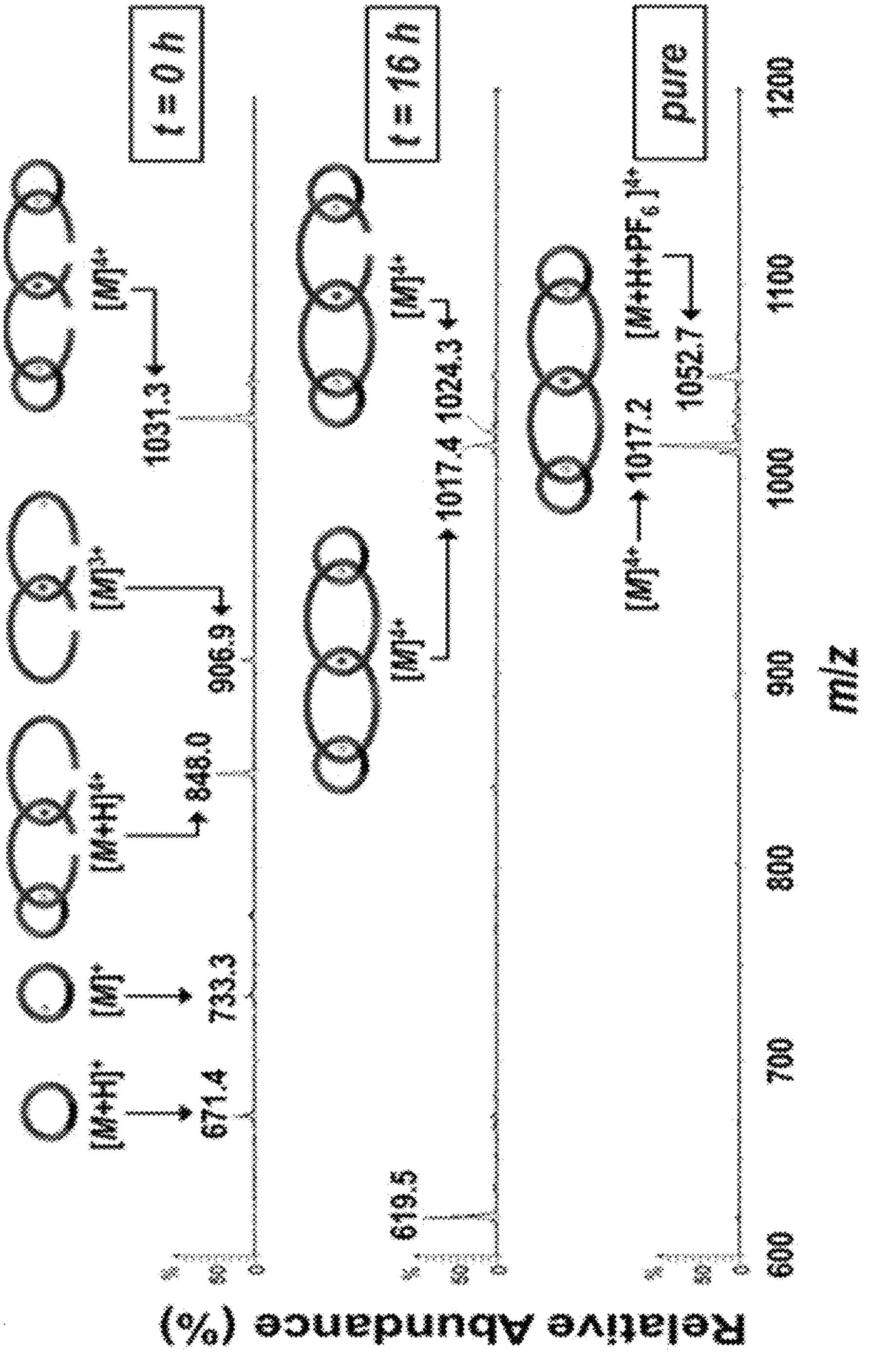
FIG. 3B depicts a kinetic LRMS study to monitor catenation reactions starting from Fe-$(OTPM)_2$ and PM to the final catenated product, [4]C-M.

A solution of precursor PM (0.0177 g, 0.02639 mmol, 5.0 equiv) was prepared in 5 mL of $N_2$-purged dichloroethane (DCE) in an oven-dried 25 mL round-bottom (RB) flask under $N_2$. To this was added a solution of $Cu(MeCN)_4PF_6$ (0.0098 g, 0.02639 mmol, 5.0 equiv) in 1 mL of $N_2$-purged anhydrous MeCN, which instantaneously resulted in a color change of the solution from light yellow to orange. The solution was kept under intense $N_2$ air flow while stirring for 15 min before adding a solution of precursor Fe-$(OTPM)_2$ (0.0176 g, 0.00622 mmol, 1.0 equiv) in 5 mL of $N_2$-purged DCE via syringe. The dark red solution was then heated to 50° C. for 2 h. The solvent was removed via a rotary evaporator to afford the crude precatenate complex mixture as a dark red solid. The crude mixture was redissolved in 10 mL of DCE and Grubbs' second-generation catalyst (0.0016 g, 0.00018 mmol, 0.3 equiv) in 1 mL of DCE was added via syringe. The reaction mixture was then heated to 45° C., and the reaction progress was monitored via LRMS-ESI (FIG. 3B). After 24 h, an additional 0.3 equiv of Grubbs' second-generation catalyst was added, and the solution was heated for an additional 24 h. The reaction was then quenched with 1 mL of ethyl vinyl ether (EVE) and 5 mL of MeCN. The solvent was then removed via rotary evaporator, and the crude red solid was redissolved in a minimal amount of $CH_2CO_2$. The solution was then precipitated with $Et_2O$ and was followed by centrifugation to afford a red solid; this process was repeated twice.

The crude red solid was purified via preparatory HPLC with 20-100% MeOH in $H_2O$/0.1% HCOOH in 15 min and then 100% MeOH up to 25 min at 15 mL $min^1$. The purified fractions were redissolved in 5 mL of MeCN and 5 mL of saturated aqueous $KPF_6$ was added. The solution was stirred at room temperature for 0.5 h. The precipitated red solid was then collected via vacuum filtration on Celite, which was washed with 50 mL of DI water and 50 mL of $Et_2O$. The solid was then redissolved in MeCN, and the solvent was removed to afford the product as a deep red solid (0.0161 g, 55%). The average yield for three reactions at this scale purified via HPLC is 50%.

$^1H$ NMR (500 MHz, DMSO-$d_6$): $\delta_H$ 8.94-8.83 (m, 4H), 8.63 (bs, 4H), 8.49 (d, J=5.3 Hz, 8H), 8.31 (bs, 2H), 8.11 (m, 4H), 8.01-7.89 (m, 8H), 7.76 (s, 4H), 7.58 (m, 4H), 7.50-7.33 (m, 16H), 7.04 (dd, J=24.2, 8.9 Hz), 6.96-6.43 (m), 6.12-5.93 (m, 16H), 5.35 (m, 4H), 4.28-3.12 (m), 2.18 (bs), 2.09 (s), 1.86-1.39 (m), 1.34 (m). $^{13}C$ NMR (125 MHz, DMSO-$d_6$): $\delta_C$ 159.5, 159.3, 156.1, 153.3, 153.2, 153.1, 152.9, 143.2, 137.6, 131.4, 129.1; 128.1, 127.9, 126.2, 124.6, 116.1, 116.0, 115.8, 115.7, 115.6, 115.2, 113.1, 113.0, 70.8, 70.6, 70.5, 70.4, 70.2, 70.1, 69.68, 69.65, 69.58, 69.4, 69.3, 69.2, 69.1, 68.7, 68.5, 68.1, 68.0, 67.8, 67.7, 67.6, 67.64, 67.57, 67.4, 30.9, 30.2, 29.0, 28.63, 28.58, 28.52, 25.7, 25.6, 25.5, 25.3. $^{19}F$ NMR (471 MHz, DMSO-$d_6$): $\delta_F$ −69.4, −70.9. LRMS-ESI calcd for $C_{234}H_{238}Cu_2FeN_{14}O_{40}$: m/z=1016.4 $[M]^{4+}$, 1052.9 $[M+H+PF_6]^{4+}$; found 1017.2 $[M]^{4+}$, 1052.7 $[M+H+PF_6]^{4+}$. MALDI-TOF calcd for $C_{234}H_{239}Cu_2FeN_{14}O_{40}$: m/z=3950.7 $[M–Fe–Cu]^+$, 2006.8 $[M–Fe]^{2+}$; found 3950.2 $[M–Fe–Cu]^+$, 2006.3 $[M–Fe]^{2+}$.

Synthesis of [4]C.

A solution of [4]C-M (0.0051 g, 0.00113 mmol, 1 equiv) was prepared in 10 mL of MeCN. To this was added 10 mL of saturated sodium ethylenediaminetetraacetic acid (EDTA) dibasic in $H_2O$, 2 mL of saturated $NH_4OH$, and 2 mL of 30% $H_2O_2$. The reaction mixture was heated to 80° C. for 15 min, at which point the color of the solution changed from red to colorless. The mixture was diluted with 50 mL of $H_2O$ and extracted with 3×25 mL of $CHCl_3$. The organic layer was dried over $Na_2SO_4$ and was filtered. The solvent was removed via a rotary evaporator to afford an orange film, which was washed with 50 mL of MeOH and 50 mL of MeCN to remove any remaining metalated species, leaving the product behind as a faint orange-pink film (0.0013 g, 30%).

$^1$H NMR (500 MHz, DMSO-$d_6$): $\delta_H$ 8.55-8.34 (m), 8.31 (s), 8.27-8.12 (in), 8.04-7.77 (m), 7.57-7.28 (m), 7.15 (d, J=8.5 Hz), 7.04 (bs), 7.01 (d, J=7.9 Hz), 6.93-6.57 (m), 6.08-4.40 (m), 4.31-3.33 (m), 1.35 (s), 1.24 (s). $^{13}$C NMR (125 MHz, DMSO-$d_6$): $\delta_C$ 167.0, 160.1, 159.8, 159.7, 159.5, 154.9, 154.8, 154.5, 152.6, 152.5, 152.4, 147.8, 147.7, 145.3, 137.1, 137.0, 136.9, 131.7, 131.6, 131.4, 131.3, 131.2, 131.1, 128.7, 128.5, 127.3, 125.7, 121.3, 119.1, 118.9, 115.6, 115.3, 115.2, 115.1, 114.8, 114.7, 114.6, 114.5, 114.3, 69.9, 69.0, 68.8, 67.4, 38.1, $^3$1.3, 29.8, 29.0, 28.7, 28.5, 28.4, 28.1, 25.1, 25.0, 23.2, 22.4, 14.9, 10.8. LRMS-ESI calcd for $C_{234}H_{238}N_{14}O_{40}$: m/z=649.1 $[M+6H]^{6+}$, 660.5 $[M+Na(HCOO)+6H]^{6+}$, 778.8 $[M+5H]^{5+}$, 792.4 $[M+Na(HCOO)+5H]^{5+}$, 972.9 $[M+4H]^{4+}$, 989.9 $[M+Na(HCOO)+4H]^{4+}$, 1006.9 $[M+2Na(HCOO)+4H]^{4+}$; found m/z=648.4 $[M+6H]^{6+}$, 659.3 $[M+Na(HCOO)+6H]^{6+}$, 778.0 $[M+5H]^{5+}$, 790.5 $[M+Na(HCOO)+5H]^{5+}$, 972.4 $[M+4H]^{4+}$, 987.4 $[M+Na(HCOO)+4H]^{4-}$, 1003.7 $[M+2Na(HCOO)+4H]^{4+}$. MALDI-TOF calcd for $C_{234}H_{238}N_{14}O_{40}$: m/z=3885.7 $[M+H]^+$, 1942.9 $[M+2H]^{2-}$, 1964.8 $[M+2Na]^{2+}$; found 3885.7 $[M+H]^+$, 1944.2 $[M+2H]^{2+}$, 1966.2 $[M+2Na]^{2+}$.

Example 3. [2]C-M Synthesis and Characterization

To test the feasibility of the one-pot strategy, the preparation of OTPM was carried out first via the convergent synthesis of asymmetric terpy- and phen-containing halves that were coupled together using a standard nucleophilic substitution reaction under high pressure. The terpy ligand was chosen due to its selectivity toward the formation of hexacoordinate complexes with bivalent ($M^{2+}$) metals such as $Fe^{2+}$ and $Ru^{2+}$. Conversely, the phen ligand favors a tetracoordinate geometry when complexed with monovalent ($M^+$) metals such as $Cu^+$. The synthesis of the larger macrocycle precursor OTPM has been demonstrated for the purpose of synthesizing a [4]catenate.

To form the first metal complex (Fe-$(OTPM)_2$), OTPM was dissolved in tetrahydrofuran (THF) and heated to 60° C., followed by the addition of 1.3 equiv of $Fe(BF_4)_2 \cdot 6H_2O$ in deionized (DI) $H_2O$, resulting in a red-colored solution. The reaction mixture was heated for 1 h before being cooled to room temperature and extracted in $CHCl_3$ against three DI $H_2O$ washes. After the organic layer was dried with $Na_2SO_4$, Fe-$(OTPM)_2$ was obtained in 89% yield.

Figure 2A:
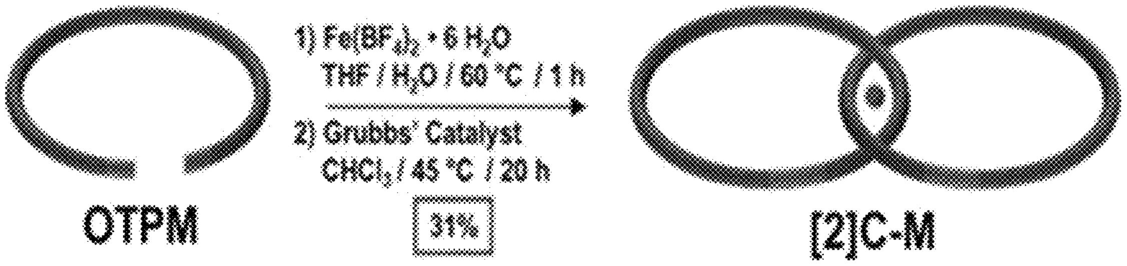
FIG. 2A depicts synthesis of a [2]catenate ([2]C-M) via two ring-closing metathesis (RCM) reactions on Fe-$(OTPM)_2$.

To demonstrate that two simultaneous RCM steps were possible on the ternary complex to afford a [2]catenate ([2]C-M), Fe-$(OTPM)_2$ was dissolved in $CHCl_3$ with 0.2 equiv of second-generation Grubbs' catalyst, and the mixture was heated at 45° C. for 16 h while stirring under $N_2$ (FIG. 2A). Proton nuclear magnetic resonance ($^1$H NMR) analysis of an aliquot revealed some starting material remained, so an additional 0.2 equiv of the catalyst was added, and the reaction mixture stirred for another 4 h. To obtain pure [2]C-M, column chromatography was performed on basic alumina using a gradient mobile phase ($CHCl_3$ to 5% MeOH/$CHCl_3$).

Figure 2B:
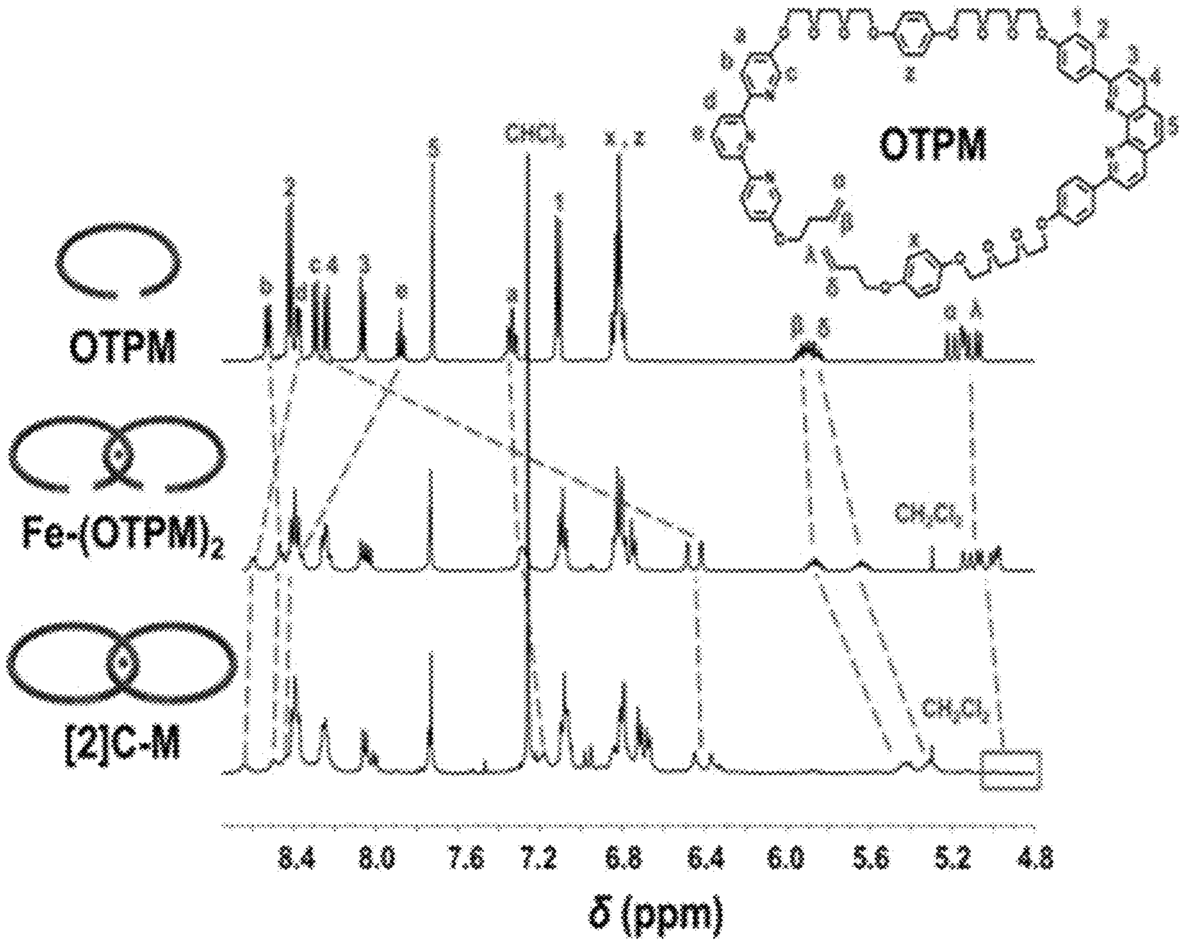
FIG. 2B depicts $^1H$ NMR (500 MHz, $CDCl_3$) spectra of OTPM, Fe-$(OTPM)_2$, and [2]C-M.
Figure 2C:
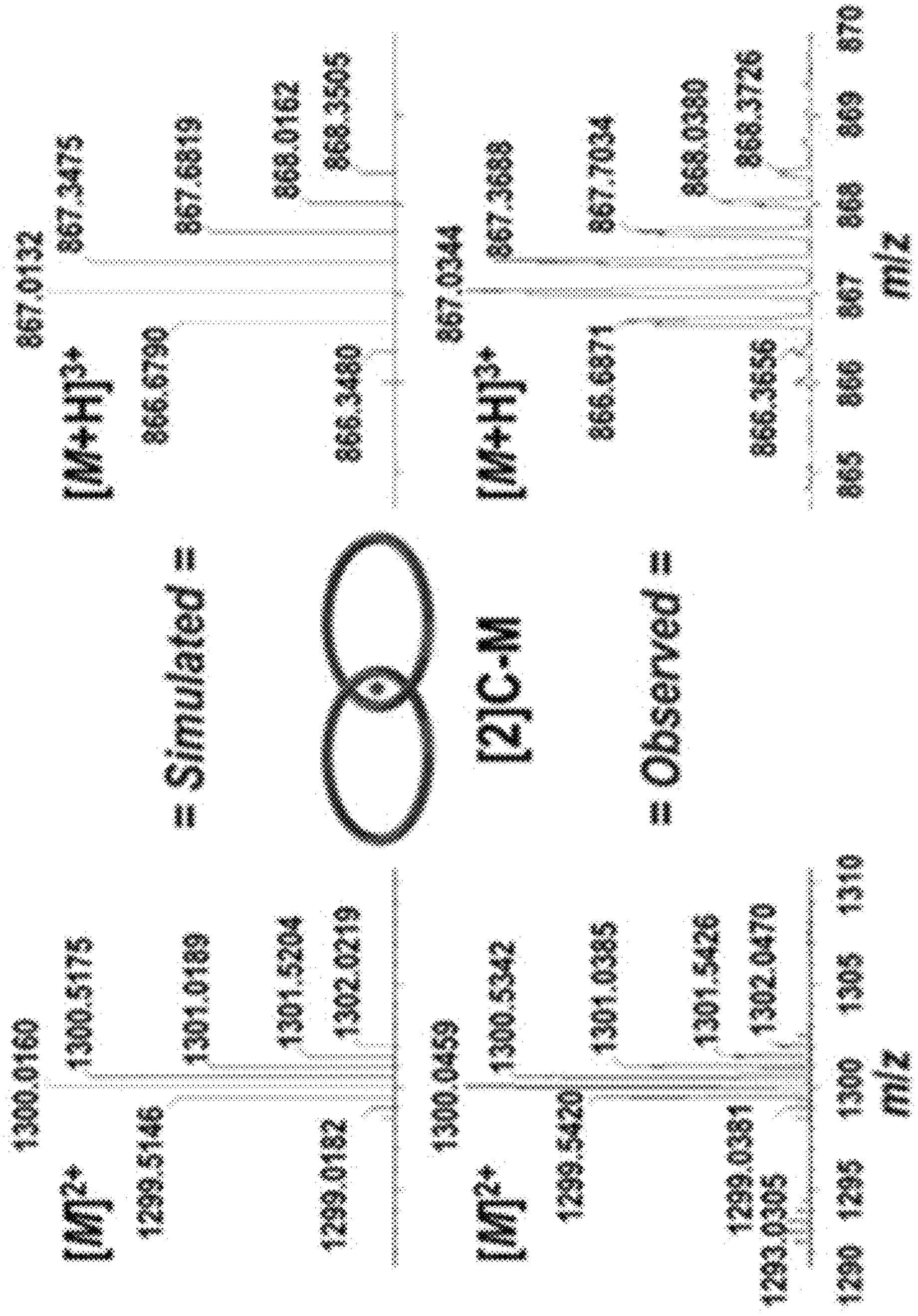
FIG. 2C depicts simulated and observed high-resolution mass spectrometry via electrospray ionization (HRMS-ESI) data for [2]C-M.

Comparison of the $^1$H NMR spectra of OTPM, Fe-$(OTPM)_2$, and [2]C-M (FIG. 2B) revealed changes in key diagnostic proton resonances associated with the terpy ligand and the terminal olefin of OTPM. Specifically, metalation of OTPM with $Fe^{2+}$ to form Fe-$(OTPM)_2$ resulted in significant shifting of the terpy proton resonances (a-e), while the chemical shifts of the phen proton resonances (1-5) remained relatively unchanged (FIG. 2B), supporting the suggestion of orthogonal metal ion selectivity of OTPM. However, peak broadening and new splitting patterns were observed for the phen protons, which could be attributed to a slight change in chemical environment afforded by the rigidification of the ligands in the dimeric complex Fe-$(OTPM)_2$, relative to free OTPM. It is also possible that, in solution, the unbound phen ligands in Fe-$(OTPM)_2$ are in close proximity to one another further differentiating their chemical environment, resulting in peak broadening and new splitting patterns. Similarly, the olefin proton resonances are no longer in the same chemical environment, likely due to the difference in rigidity of the metalated terpy half of the macrocycle compared to the unmetalated phen half. After RCM to form [2]C-M, some broadening was observed, and new splitting patterns emerged that can be attributed to the shielding and deshielding commonly observed in MIMs. Additionally, the terminal olefin proton resonances α and λ were consumed, suggesting the successful conversion to internal olefins of the catenate product. The product identity was further corroborated by high-resolution mass spectrometry via electrospray ionization (HRMS-ESI) (FIG. 2C). Data for the parent molecular ion $[M]^{2+}$ showed mass peaks centered around m/z=1300, which closely matched the simulated spectrum. Similarly, the $[M+H]^{3+}$ ion was also determined and matched the calculated spectrum.

Figure 2D:
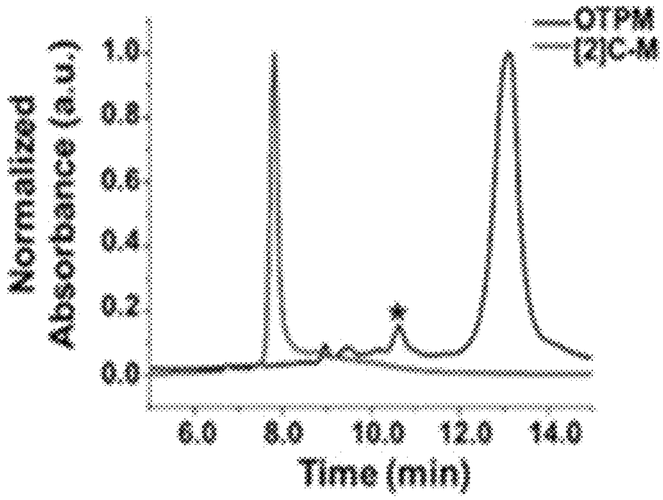
FIG. 2D depicts an overlay of analytical high-pressure liquid chromatography (HPLC) traces (normalized UV 254 nm) for OTPM and [2]C-M with a gradient mobile phase of $MeOH/H_2O$ (0.1% HCOOH): 5-100% in 7 min at 40° C. * indicates a minor peak identified as a OTPM-MeOH adduct using LC-MS-ESI.
Figure 2E:
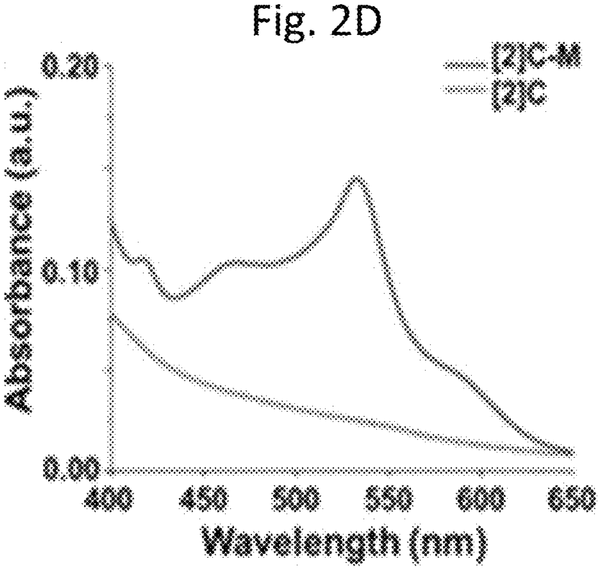
FIG. 2E depicts a UV-vis absorption spectrum of [2]C-M and demetalated catenate ([2]C).

Analytical high-pressure liquid chromatography (HPLC) was performed (FIG. 2D) on OTPM and [2]C-M to assess product purity. Although $^1$H NMR (FIG. 2B) indicates that the OTPM precursor is very pure, the HPLC trace displayed a small subpopulation of peaks at shorter retention times. These peaks were identified as OTPM-MeOH complexes using LC-MS-ESI, which is likely the result of hydrogen bonding with the nonmetalated pyridine rings. The purity of OTPM was further demonstrated using analytical GPC in DMF and by preparative GPC in $CHCl_3$. The purity of [2]C-M was also evaluated using analytical HPLC, and the resultant trace revealed a narrow, unimodal peak supporting that it was isolated cleanly. Additionally, retention of $Fe^{2+}$ in [2]C-M during purification was confirmed by UV-vis absorption spectroscopy (FIG. 2E). The resultant stability of the metal complex in [2]C-M is important in order for a one-pot synthetic strategy to be successful.

Example 4. [4]C-M Synthesis and Characterization

Demonstration of the one-pot synthesis of a [4]catenate ([4]C-M) (FIG. 3A) began with the monometalation of PM in dichloroethane (DCE) by adding 1.0 equiv of $Cu(MeCN)_4PF_6$ in MeCN under $N_2$. Addition of $Cu^+$ to the solution containing PM immediately changed the color of the solution from light yellow to orange, which is indicative of formation of the air-sensitive monometalated intermediate. After 15 min of stirring under $N_2$, a solution containing 1 equiv of Fe-$(OTPM)_2$ was added in DCE (i.e., 1.0:5.0 Fe-$(OTPM)_2$/Cu-PM). The dark red solution was then heated to 50° C. for 2 h, followed by the removal of the solvent to prevent solvent coordination of the ruthenium catalyst, which is added in the next step. The crude reaction mixture was redissolved in DCE and 0.3 equiv of Grubbs' second-generation catalyst was added (also in DCE), followed by heating at 45° C. The RCM reaction was done under high dilution (0.5 mM, based on Fe-$(OTPM)_2$), and the reaction progress was monitored by LRMS-ESI (FIG. 3B), where at t=0 h (i.e., no catalyst added); a mixture of metal complexes and precursors was visible, presumably the result of some of the components from the ternary metal complex falling apart during the MS experiment. After catalyst addition, the reaction mixture was assessed again at t=16 h using LRMS-ESI. Most of the mass peaks associated with the precursors and intermediate metal complexes were no longer visible. Instead, only the product [4]C-M and its precursor intermediate with one RCM reaction completed was visible (FIG. 3B, middle spectrum). To push the reaction forward, an additional 0.3 equiv of catalyst was added at t=24 h, and the reaction was heated at 45° C. for an additional 24 h, at which point the reaction was quenched with ethyl vinyl ether and excess MeCN. The solvent was then removed via rotary evaporator, and the crude product was purified via preparative HPLC to afford [4]C-M as a dark red solid in 55% yield. The higher yield of [4]C-M compared to [2]C-M is likely a result of the preorganization of the olefins afforded by the rigidification of the precatenate complex, which is not present in the [2]catenate.

Analysis of the LRMS data for the purified product (FIG. 3B, bottom spectrum) showed two major mass peaks at m/z=1017.2 and 1052.7, which correspond to the parent molecular ion $[M]^4$ and the molecular ion plus a hydrogen and $PF_6$ anion $[M+H+PF_6]^{4+}$ of [4]C-M, respectively. A less intense lower molecular weight peak at m/z=1013.6 was also observed for [4]C-M (FIG. 3B), which corresponds to a small population of ring-contracted [4]catenate. The ring contraction, which occurred during the RCM steps, has been previously reported and is likely due to isomerization of the alkene, which results in the loss of propene instead of ethene, accounting for the loss of a methylene group. A similar occurrence of ring contraction was also observed in the case of [2]C-M.

Figure 4:
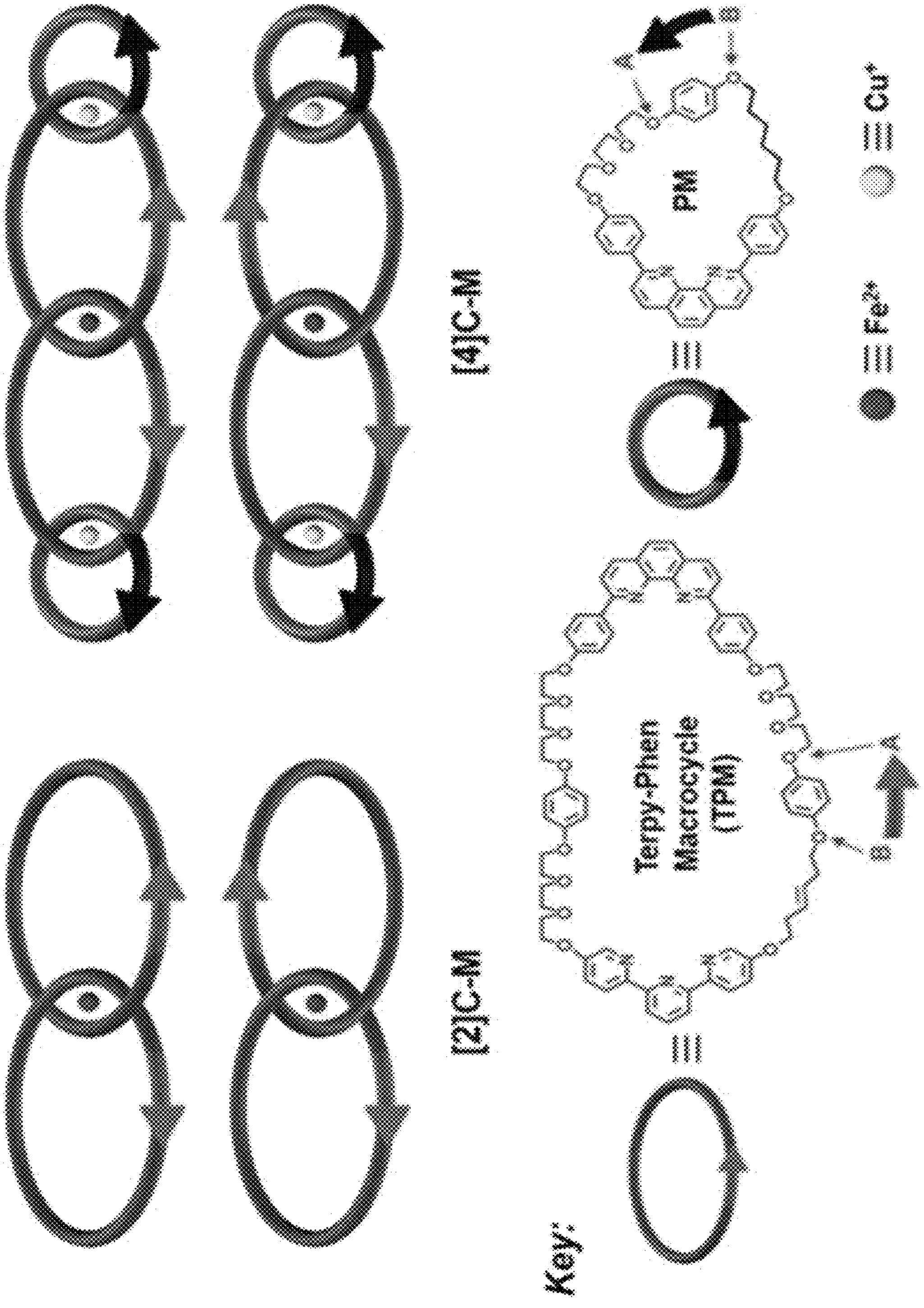
FIG. 4 depicts a cartoon representation of both enantiomers of [2]C-M (top left) and a cartoon representation of two of the six possible diastereomers of [4]C-M (top right).
Figure 8A:
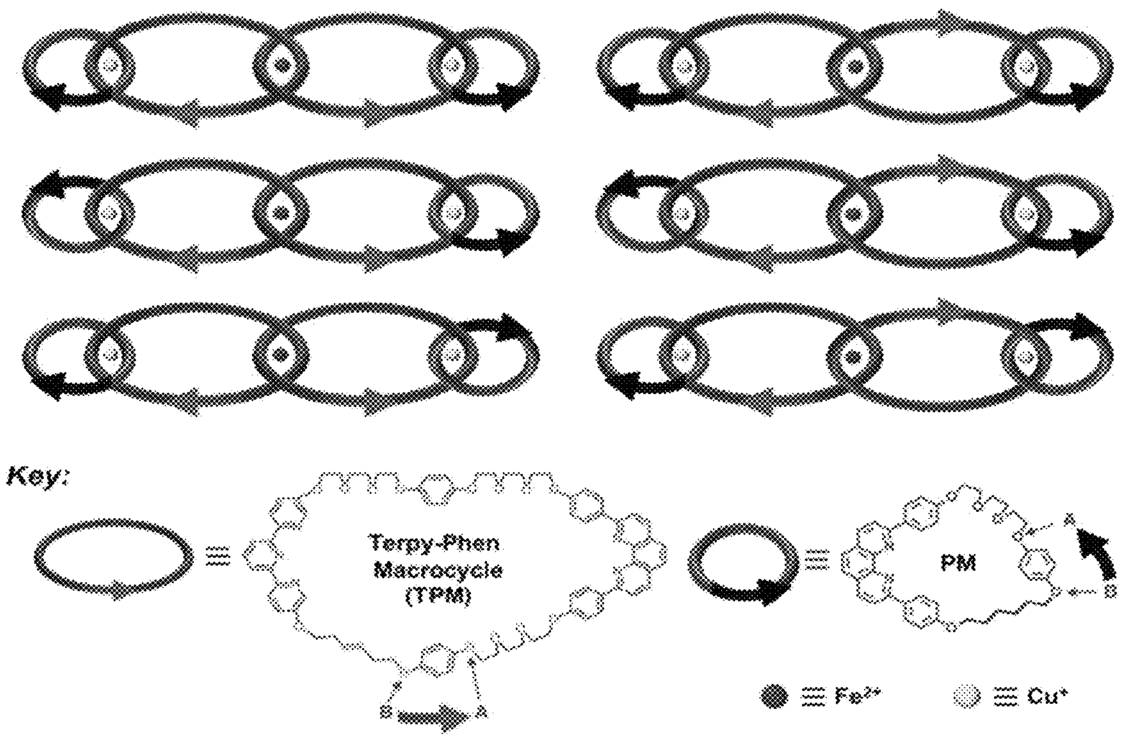
FIG. 8A depicts a cartoon representation of the six possible diastereomers of [4]C-M.
Figure 8B:
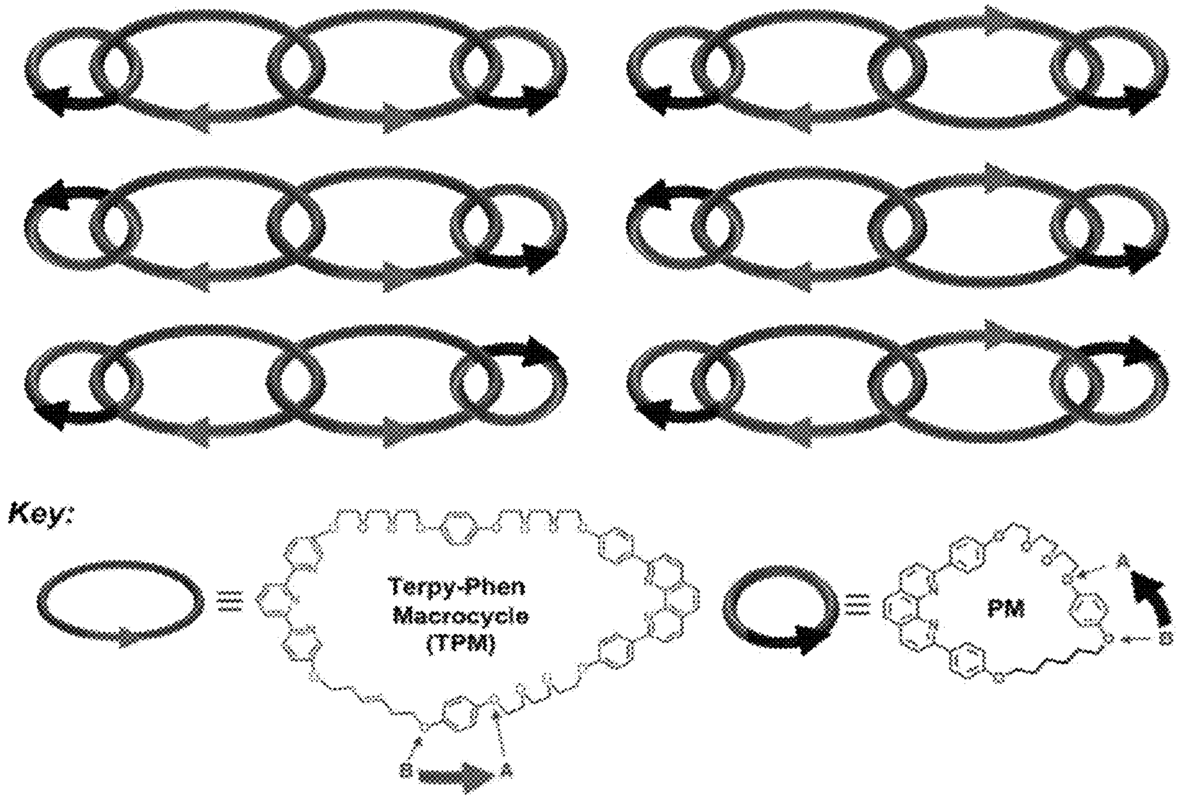
FIG. 8B depicts a cartoon representation of the six possible diastereomers of [4]C-M after removal of the metal ion templates.

A consequence of utilizing asymmetric macrocycles to assemble catenanes is that the resulting MIM products possess topological chirality, where, for example, topologically chiral [2]catenanes (Lam et al., 2005) and [3]catenanes (Forgan et al., 2014) have been reported previously. Since OTPM is asymmetric, the resulting macro-cycle afforded from RCM is said to be "oriented" (i.e., possessing directionality toward the atom of highest priority). The interlocking of two oriented macrocycles to form a [2]catenate/[2]catenane such as [2]C-M results in a pair of topologically chiral enantiomers (FIG. 4). The directionality of TPM was defined by comparing oxygen atoms in the hydroquinone linker labeled "A" and "B" in FIG. 4, following a similar method used previously in the assignment of topologically chiral $(Cu^+)$ phenanthroline-based [2]catenates (Mitchell et al., 1988; Chambron et al., 1992). The threading of two additional oriented PM macrocycles to produce [4]C-M results in a mixture of six possible topologically chiral catenate diastereomers, two of which are shown in FIG. 4 (see FIG. 8A-8B for more details of the possible diastereomers of [4]C-M and 4C).

Figure 5A:
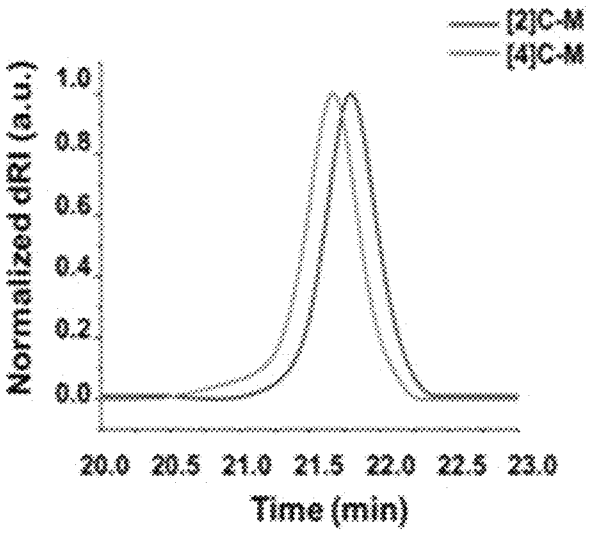
FIG. 5A depicts an overlay of GPC traces (normalized dRI) of [2]C-M and [4]C-M in DMF with 0.025 LiBr and heated to 60° C.
Figure 5B:
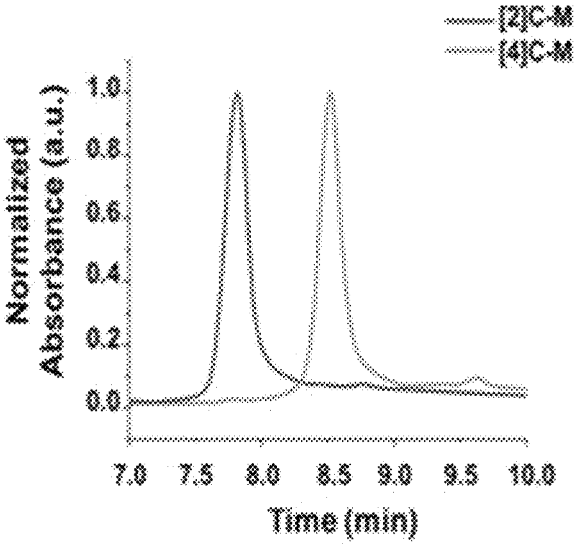
FIG. 5B depicts an overlay of analytical HPLC traces (normalized UV 254 nm) for [2]C-M and [4]C-M with a gradient mobile phase of $MeOH/H_2O$ (0.1% HCOOH): 5-100% in 7 min at 40° C.

The GPC traces for [2]C-M and [4]C-M (FIG. 5A) contain narrow and unimodal peaks for each, indicating that each MIM was isolated cleanly. As expected, the higher molecular weight MIM, [4]C-M, displayed a shorter retention time than [2]C-M. The purity of both MIMs was further corroborated by analytical HPLC (FIG. 5B), which again showed narrow peaks for both compounds.

Figure 5C:
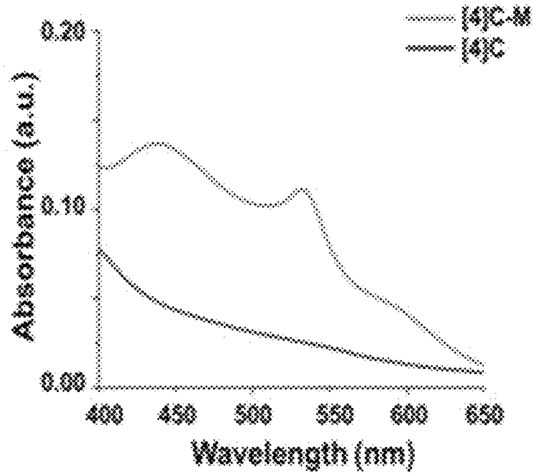
FIG. 5C depicts UV-vis absorption spectra of [4]C-M and [4]C.
Figure 5D:
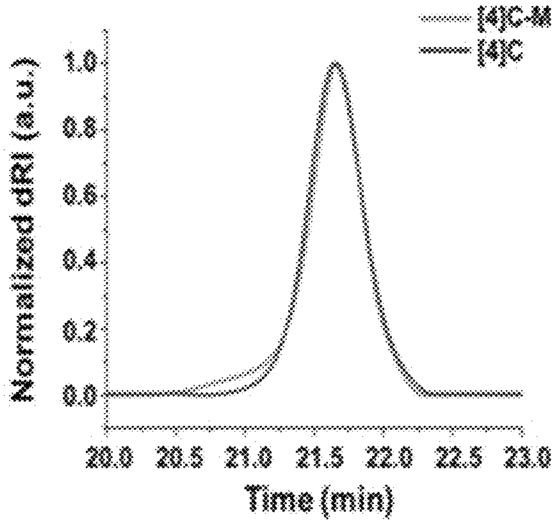
FIG. 5D depicts an overlay of GPC traces (normalized dRI) of [4]C-M and [4]C in DMF with 0.025 LiBr and heated to 60° C.

Demetalation of [4]C-M to obtain the [4]catenane was carried out by dissolving it in MeCN and adding sat. sodium ethylenediaminetetraacetic acid (EDTA) and sat. $NH_4OH$ with 30% $H_2O_2$ and heating at 80° C. for 15 min. After an aqueous workup and washing multiple times with MeOH and MeCN, the final product was obtained as an orange/pink film in 30% yield. The success of demetalation of [4]C-M to [4]C was confirmed by UV-vis (FIG. 5C), where the MLCT (metal-to-ligand charge transfer) band for the Cu-phen complexes at 450 nm and MLCT band for the Fe-terpy complexes at 530 nm were no longer present after demetalation. Analysis of the GPC traces for [4]C-M and [4]C (FIG. 5D) revealed little to no shifting upon demetalation and confirmed that [4]C was isolated cleanly, as evidenced by the narrow and unimodal peak. This result provides further evidence for the isolation of the correct MIM product.

Figure 7A:
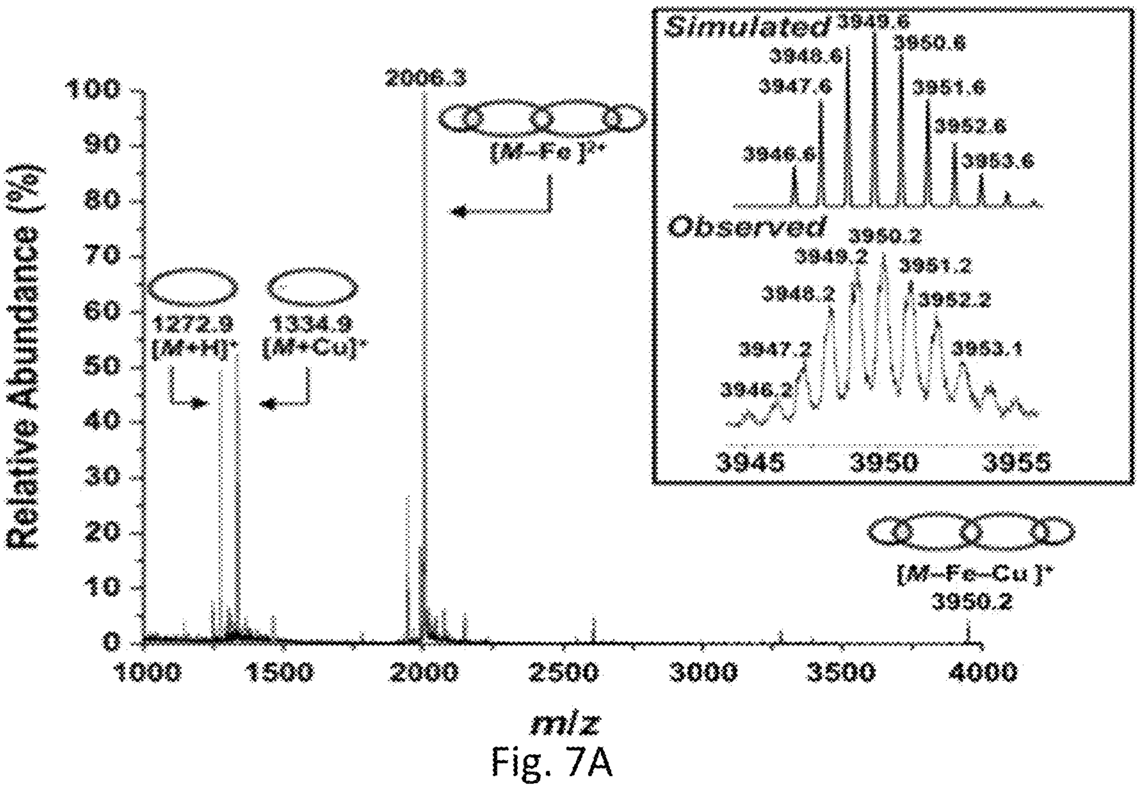
FIG. 7A depicts MALDI-TOF-MS of [4]C-M with α-cyano-4-hydroxycinnamic acid matrix.
Figure 7B:
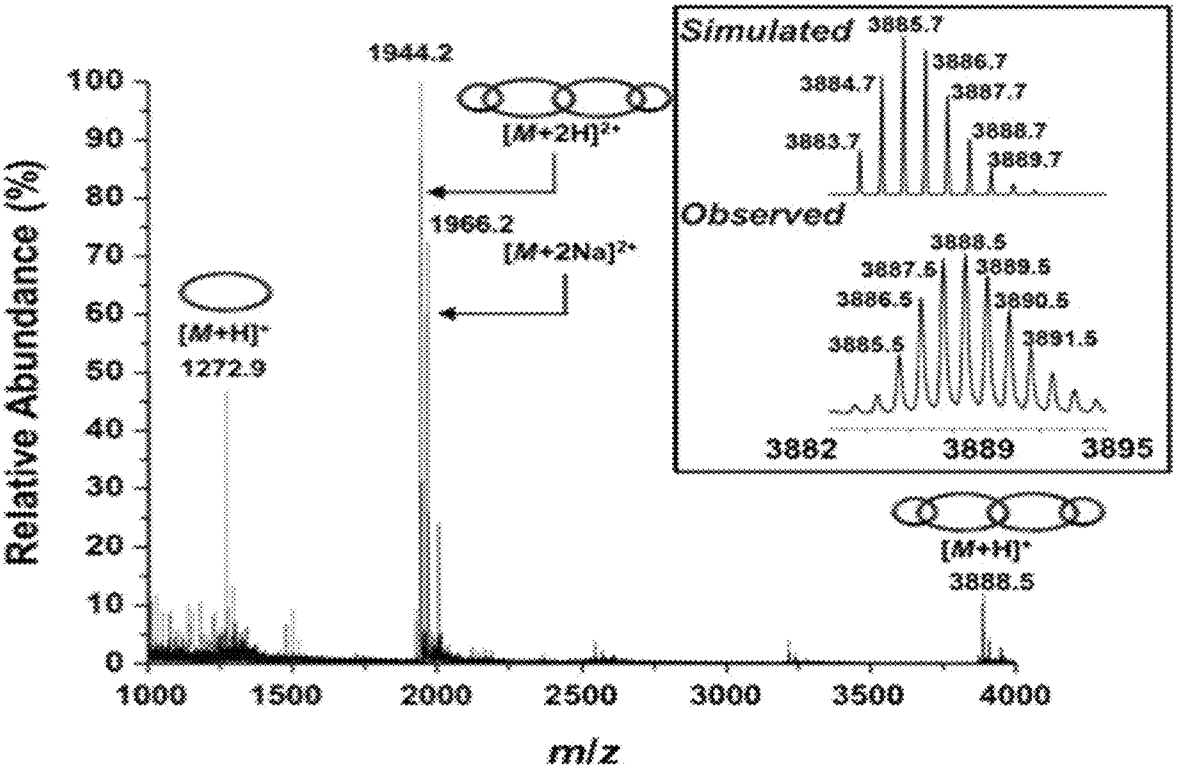
FIG. 7B depicts MALDI-TOF-MS of [4]C with 2,5-dihydroxybenzoic acid matrix.

By comparison, it has previously been reported that upon demetalation of a $(Cu^+)$ phenanthroline-based [2]catenate polymer, the corresponding GPC trace revealed a small population of lower molecular weight non-MIM polymer that appeared at longer retention times, even though the peak was unimodal prior to demetalation (Bunha et al., 2011). If [4]C was not mechanically interlocked, then the system would also disassemble into its lower molecular weight macrocyclic components and the expected GPC trace would be shifted toward significantly longer retention times. The lack of a significant shift in retention time between the GPC traces [4]C-M and [4]C strongly suggests that the species are four mechanically interlocked rings, a result which is consistent with MALDI-TOF-MS (FIG. 7A-7B).

Figure 9A:
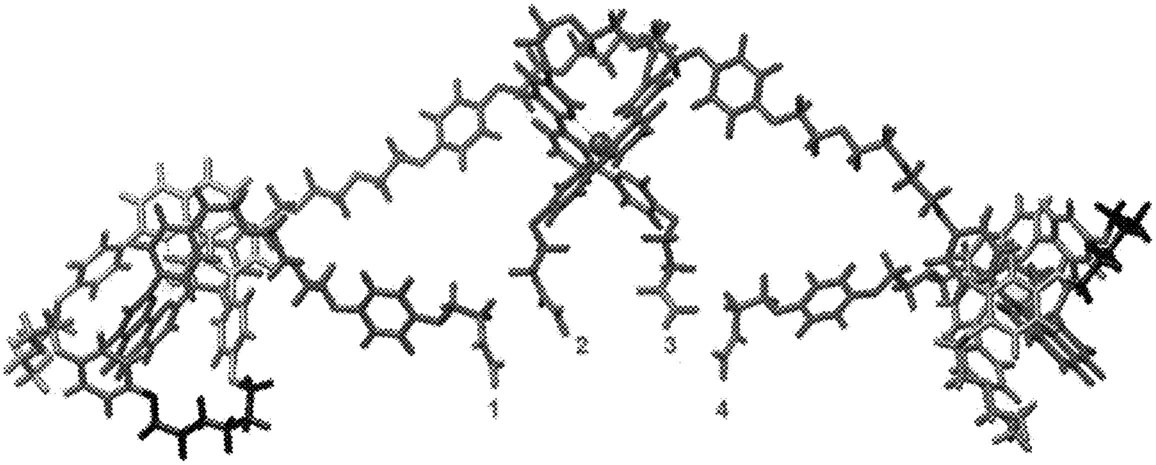
FIG. 9A depicts a molecular model (Spartan'18, MMFF) of the pre-catenate complex of [4]C-M.
Figure 9B:
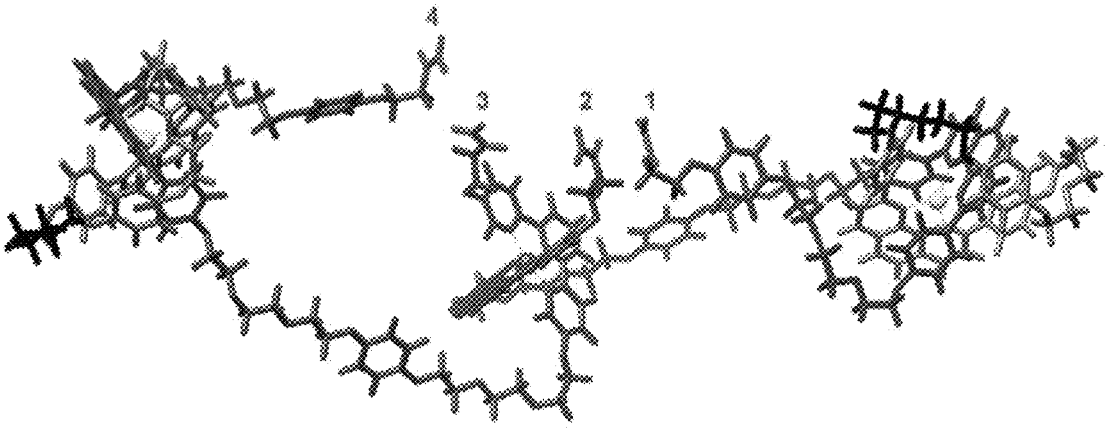
FIG. 9B depicts a rotated molecular model (Spartan'18, MMFF) of the pre-catenate complex of [4]C-M.

Additionally, molecular mechanics simulations (Spartan'18, MMFF) were performed on the precatenate complex of [4]C-M (FIG. 9A-9B). These results indicate a sterically preferred arrangement of olefins that favors formation of the linear [4]catenate product versus that of a potential figure-of-eight byproduct.

Analysis of [4]C-M by $^1H$ NMR spectroscopy (FIG. 6) proved more difficult given the interlocked nature of the product and the fact that six possible diastereomers (FIGS. 4 and 8A) can form during the one-pot synthesis that stitches together four asymmetric macrocycles. Due to the unique spatial arrangement of the macrocycles, these diastereomers have inequivalent chemical environments, leading to very complex $^1H$ NMR spectra. However, the combination of 1D $^1H$ NMR of Fe-$(OTPM)_2$ and [2]C-M (FIG. 2B) and 2D $^1H$ NMR of [4]C-M allowed for reasonable proton assignments of [4]C-M. Using $^1H$-$^1H$ COSY NMR, through-bond correlations were observed between phen protons 1 to 2 and 3 to 4. Assessment of through-space correlations (NOESY NMR) proved to be more informative in establishing the interlocked nature of [4]C-M. Specifically, correlations between proton b of the TPM terpy ligand and protons 3' and 5' of the PM phen ligand were observed. The correlation between protons b and 5' is attributed to the end-cap macrocycle PM since metal templation places its phen ligand within the cavity of the TPM macrocycle. Similarly, an nuclear Overhauser effect (NOE) correlation between protons b and 3' also results from interactions between the terpy of TPM and the phen of PM. Moreover, the NOEs observed between phen protons could either be intramolecular or intermolecular between adjacent phen ligands within the mechanically interlocked complex.

Figure 6:
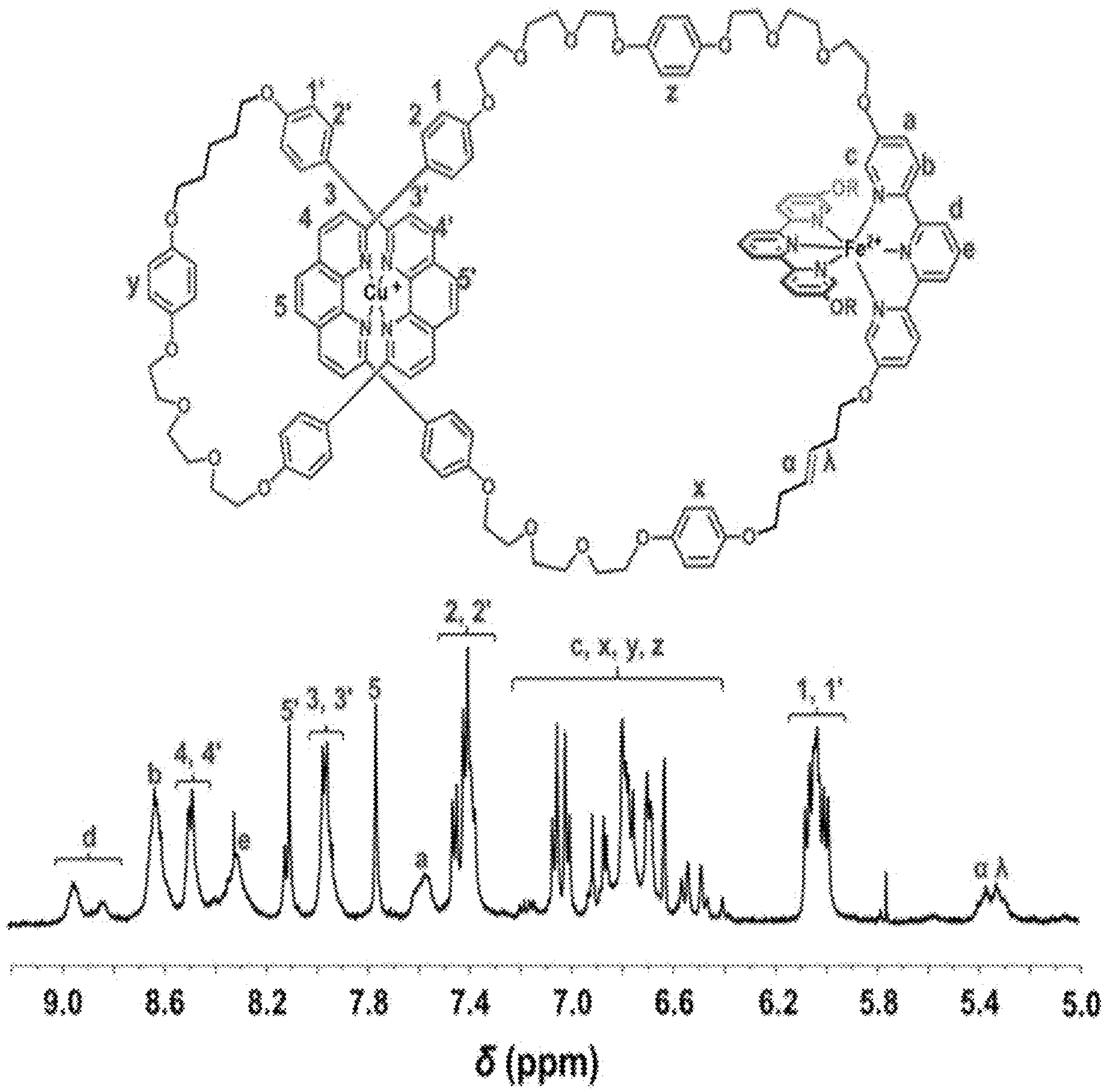
FIG. 6 depicts a $^1H$ NMR (500 MHz, DMSO-d6) spectrum of [4]C-M. Only two macrocycles are shown for clarity in the structure.

The culmination of the 1D and 2D NMR analyses allowed for the assignment of the aromatic region of [4]C-M's $^{1}H$ NMR spectrum (FIG. 6). Due to the different shielding and deshielding effects caused by the three mechanical bonds, the chemical environment of the central TPM phen ligand and end-cap PM phen ligand are different, leading to inequivalent chemical shifts. This effect is very prominent for the resonances associated with phen protons 5 and 5', which are separated by almost 0.4 ppm. Also, as was observed for the RCM steps for [2]C-M, the resonances associated with the terminal olefin protons of the complexed OTPM were absent at approximately 5.0 ppm in the $^{1}H$ NMR spectra of [4]C-M.

Additional 1D $^{1}H$ NMR analysis was carried out on [4]C, resulting in complex spectra, where removal of the metals led to a coalescence of the previously distinct aromatic peaks. Moreover, 2D $^{1}H$-$^{1}H$ NMR was employed again to investigate through-bond (COSY) and through-space (NOESY) correlations of [4]C. Unlike [4]C-M, no obvious NOE correlations were observed for the demetalated species. This may be explained by the increased degrees of freedom possessed by the [4]catenane at 298 K, which allows for faster molecular motions, making it difficult to observe through-space correlations and ultimately assign protons.

Matrix-assisted laser desorption/ionization time-of-flight (MALDI-TOF) MS was also performed on [4]C-M (FIG. 7A) and [4]C (FIG. 7B). In each case, very clean spectra were obtained. For example, a prominent peak corresponding to the parent molecular ion plus a hydrogen $[M+H]^{+}$ was found (FIG. 7B) for [4]C centered about m/z=3888.5, and little to no mass peaks associated with unwanted fragments or impurities were observed. It is also important to note that the closed TPM macrocycle was observed for [4]C-M and [4]C, which could only occur through fragmentation of the product consisting of four interlocked rings and not three.

In order to further demonstrate that the dual ligand design of [4]C-M is selective toward $Fe^{2+}$ and $Cu^{+}$, [4]C was remetalated iteratively by adding aliquots of $Fe(BF_4)_2 \cdot 6H_2O$ (0.5 equiv relative to [4]C), which resulted in an instant color change of the sample from yellow to pink. The upfield and downfield shifts associated with terpy protons were also observed. After 1.25 equiv of $Fe^{2+}$ had been added, the shifts belonging to the metalated phen protons had not yet appeared. However, the initial addition of 1.0 equiv of $Cu(MeCN)_4PF_6$ caused dramatic shifting of proton resonances to occur and the metalated phen protons became visible. Once saturated with $Fe^{2+}$ and $Cu^{+}$, the NMR spectra nicely resembles that of the as-synthesized [4]C-M, confirming the selectivity afforded by TPM.

In conclusion, a high-yielding, one-pot synthesis of a [4]catenate (and its corresponding demetalated [4]catenane) is reported. The use of orthogonal metal binding sites built into the macrocycle precursor allowed for two different types of metal complexes to be formed in the presence of a smaller macrocycle prior to two RCM steps. This strategy produced three mechanical bonds in one reaction and with only one purification step in high yield (55%), as a mixture of topological diastereomeric MIMs. This general synthetic strategy provides a faster and more efficient methodology that may be applied toward the synthesis of higher order and precise linear oligocatenates/catenanes consisting of four or more interlocking molecular rings.

Example 5. Detailed Syntheses of Open and Closed Macrocyclic Ligands a) Distannyl Pyridine (1)

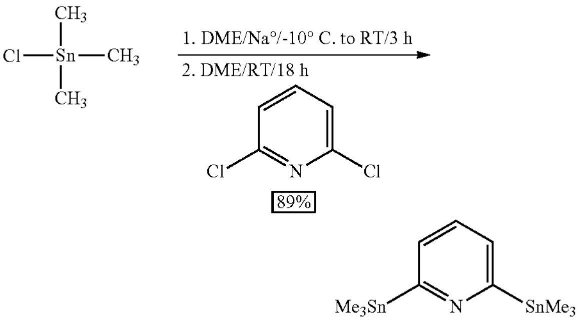

1

Compound 1 was prepared following a modified prep from Veliks et al., 2014. A suspension of freshly chopped sodium (8.6 g, 373.9 mmol, 9.2 eq.) in 100 mL anhydrous dimethoxyethane (DME) was prepared in a dry 500 mL 2-neck Schlenk flask under $N_2$. The suspension was cooled on an ice bath for 30 min before adding a solution of trimethyltin chloride (20.6 g, 103.4 mmol, 2.5 eq.) in 50 mL anhydrous DME via cannulation. The solution was cooled on an ice bath for 1 h before warming up to room temperature over an additional 2 h. The dark green solution was then transferred via cannulation to a solution of 2,6-dichloropyridine (6.00 g, 40.5 mmol, 1.0 eq.) in 50 mL DME on an ice bath. The resulting dark red solution was allowed to warm up to room temperature while stirring under $N_2$ for 16 h. The solution was then filtered over celite to remove insoluble salts and the cake was washed with 250 mL diethyl ether ($Et_2O$). The solvent was then removed under reduced pressure to afford the crude product as a brown oil (14.62 g, 89% crude), which was used without further purification.

$^{1}H$ NMR (500 MHz, $CD_2Cl_2$): $\delta_H$ 7.40-7.29 (m, 3H), 0.36-0.20 (m, 18H). $^{13}C$ NMR (125 MHz, $CD_2Cl_2$): $\delta_C$ 174.4, 131.5, 130.4, −9.5. HRMS-ESI: calculated for $C_{11}H_{21}NSn_2$: m/z=405.9790 $[M+H]^{+}$; Found: 405.9826.

b) Bpin-Bromo-Pyridine (2)

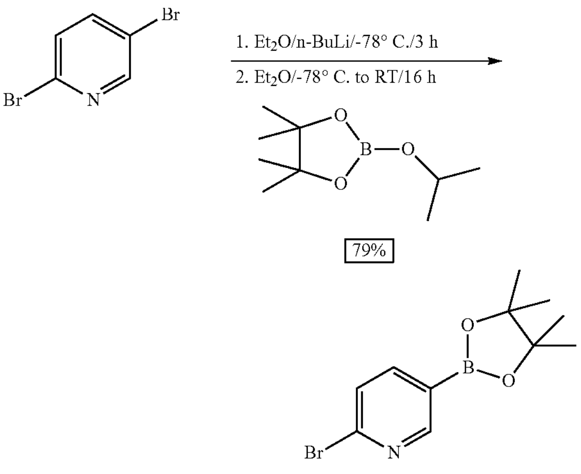

2

Compound 2 was prepared following a modified prep from Veliks et al., 2014. A solution of 2,5-dibromopyridine (13.50 g, 57.07 mmol, 1.0 eq.) in 350 mL $Et_2O$ was cooled to −78° C. using an acetone ($Me_2CO$)/dry ice bath. Then, 23.9 mL of n-BuLi (2.5 M hexanes, 59.75 mmol, 1.05 eq.) was added via slow addition funnel. The solution was kept at −78° C. for 3 h before adding a solution of 2-isopropoxy-4,4,5,5-tetramethyl-1,3,2-dioxaborolane (12.46 g, 59.08 mmol, 1.05 eq.) in 40 mL $Et_2O$ via syringe. The reaction mixture was allowed to warm up to room temperature overnight. The solvent was then removed under reduced pressure. To the crude orange oil was added a solution of 1.0 g NaOH in 250 mL deionized water. The solution was stirred at room temperature for 2 h. The aqueous layer was then washed with 3×100 mL dichloromethane ($CH_2Cl_2$). The pH of the water layer was then adjusted using 1 M HCl to pH 1-2 (approximately 100 mL 1M HCl), as confirmed by pH paper. The water was then extracted with 3×100 mL $CH_2Cl_2$. The solvent was then removed from the organic layer to afford the product as an off-white solid (12.73 g, 79%).

$^1$H NMR (500 MHz, $CDCl_3$): $\delta_H$ 8.67 (d, J=0.6 Hz, 1H), 7.88 (dd, J=7.9, 2.0 Hz, 1H), 7.48 (dd, J=7.9, 0.7 Hz, 1H), 1.34 (s, 12H). $^{13}$C NMR (125 MHz, $CDCl_3$): $\delta_C$ 156.2, 145.6, 144.5, 127.8, 84.7, 25.0. HRMS-ESI: calculated for $C_{11}H_{15}BBrNO_2$: m/z=284.0454, 286.0434 $[M+H]^+$; Found: 284.0469, 286.0449.

c) (Bpin)2 Terpy (3)

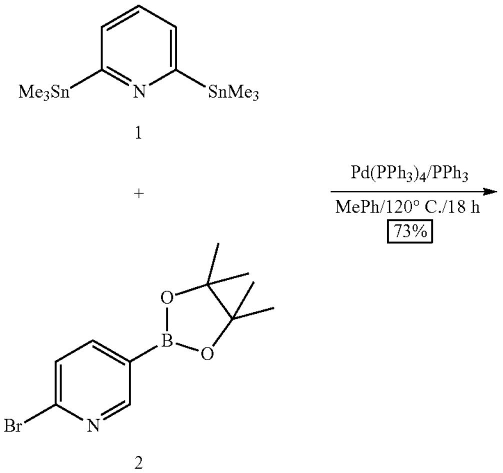

1

+

2

-continued

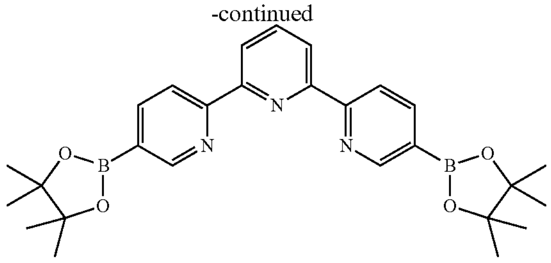

3

Compound 3 was prepared following a modified prep from Veliks et al., 2014. A solution of 1 (10.49 g, 25.92 mmol, 1.0 eq.) and 2 (19.88 g, 70.00 mmol, 2.7 eq.) was prepared in 150 mL $N_2$-purged toluene (PhMe) in a 500 mL RB flask. To this solution was added $Pd(PPh_3)_4$ (3.06 g, 2.65 mmol, 0.1 eq.) and $PPh_3$ (3.66 g, 13.95 mmol, 0.5 eq.). The reaction mixture was then refluxed at 120° C. while stirring under $N_2$ for 18 h. The reaction was then allowed to cool to room temperature before placing the RB flask in a freezer at −40° C. for 1 d. The solid precipitate was then collected via vacuum filtration with a Buchner funnel. The solid was washed with 500 mL MeCN, until the filtrate was colorless. The off-white solid was then collected. The filtrate was concentrated and additional product was precipitated by adding MeCN. The white solid was collected again and was washed with 500 mL MeCN, until the filtrate was colorless. The collected white solids were combined and were dissolved in 300 mL $CH_2Cl_2$. The solution was filtered over celite to remove any solid Pd catalyst. The filtrate was then concentrated via rotary evaporator to afford the product as a white solid (9.20 g, 73%).

$^1$H NMR (500 MHz, $CDCl_3$): $\delta_H$ 9.03 (s, 2H), 8.59 (d, J=7.9 Hz, 2H), 8.50 (d, J=7.8 Hz, 2H), 8.23 (dd, J=7.9, 1.7 Hz, 2H), 7.96 (t, J=7.8 Hz, 1H), 1.38 (s, 24H). $^{13}$C NMR (125 MHz, $CDCl_3$): $\delta_C$ 158.2, 155.5, 155.2, 143.3, 138.0, 121.9, 120.5, 84.4, 25.0. HRMS-ESI: calculated for $C_{27}H_{33}B_2N_3O_4$: m/z=508.2559 $[M+Na]^+$; Found: 508.2553 $[M+Na]^+$.

d) Terpy Diol (4)

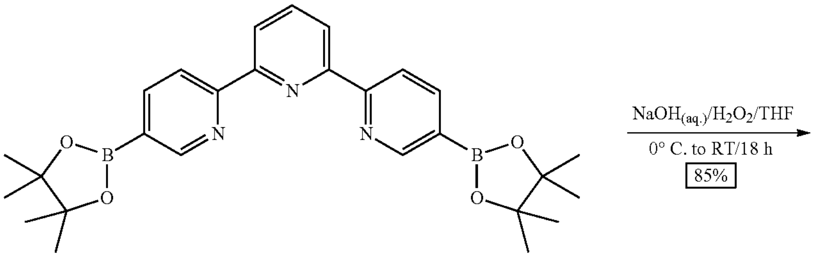

3

-continued

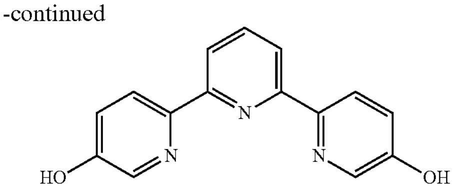

4

Compound 4 was prepared following a modified prep from Veliks et. al.[1] A solution of 3 (16.05 g, 33.06 mmol, 1 eq.) in 250 mL tetrahydrofuran (THF) was prepared. A solution of NaOH (5.3 g, 132.3 mmol, 4 eq.) in 25 mL DI $H_2O$ was then added. The light brown solution was stirred at room temperature for 30 min under $N_2$. At this point, white precipitate began to form on the glass. The suspension was then cooled using an ice bath before adding a solution of 30% $H_2O_2$ (13.6 mL, 132.3 mmol, 4.0 eq.) via syringe. The reaction was allowed to warm up to room temperature overnight. The reaction was then quenched by adding 100 mL of 10% (w/v) $Na_2S_2O_3$ aqueous solution and stirring for 30 min. The volatile organics were then removed via rotary evaporator and the pH of the orange solution was adjusted to pH 6-7 with 1 M HCl, as confirmed by pH paper. The yellow precipitate was collected via vacuum filtration and dried using lyophilization overnight to afford 4 as a yellow orange solid (7.48 g, 85%).

$^1$H NMR (500 MHz, DMSO-$d_6$): $\delta_H$ 10.24 (s, 2H), 8.44 (d, J=8.6 Hz, 2H), 8.25 (d, J=7.8 Hz, 2H), 8.20 (d, J=7.8 Hz, 2H), 7.94 (t, J=7.8 Hz, 1H), 7.34 (dd, J=8.6, 2.9 Hz, 2H). $^{13}$C NMR (125 MHz, DMSO-$d_6$): $\delta_C$ 154.8, 154.4, 146.6, 137.9, 137.4, 123.0, 121.6, 118.4. HRMS-ESI: calculated for $C_{15}H_{11}N_3O_2$: m/z=288.0743 $[M+Na]^+$; Found: 288.0742 $[M+Na]^-$.

e) Bis-(Oligoethylene Glycol) Hydroquinone (HQ) (5)

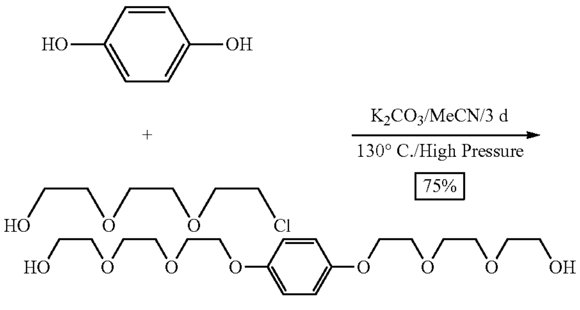

5

To a 350 mL high-pressure vessel (Kemtech) with Teflon screw cap and a stir bar was added hydroquinone (5.00 g, 45.41 mmol, 1.0 eq.), 2-(2-(2-chloroethoxy)ethoxy)ethan-1-ol (19.14 g, 113.51 mmol, 2.5 eq.), and $K_2CO_3$ (15.68 g, 113.53 mmol, 2.5 eq.) was added, followed by 130 mL of MeCN. The vessel was then sealed and the reaction mixture was heated to 130° C. while stirring for 3 d. The reaction mixture was then allowed to cool to room temperature over 2 h. The insoluble salts were removed via vacuum filtration over celite. The solvent was removed via rotary evaporator to afford the crude as a dark brown oil. Silica column chromatography (EtOAc to 8% MeOH/EtOAc) of the crude material afforded the product as a white solid (12.8 g, 75%).

$^1$H NMR (500 MHz, $CDCl_3$): $\delta_H$ 6.85 (s, 4H), 4.10-4.07 (m, 4H), 3.86-3.82 (m, 4H), 3.75-3.68 (m, 12H), 3.64-3.60 (m, 4H). $^{13}$C NMR (125 MHz, $CDCl_3$): $\delta_C$ 153.2, 115.8, 72.6, 71.0, 70.6, 70.0, 68.2, 62.0. HRMS-ESI: calculated for $C_{11}H_{30}O_8$: m/z=397.1833 $[M+Na]^-$; Found: 397.1969 $[M+Na]^+$.

f) Mono-Tos-HQ (6)

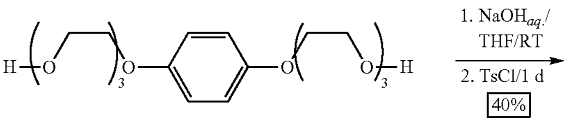

5

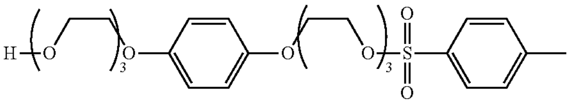

6

To a solution of 5 (10.03 g, 26.79 mmol, 1 eq.) in 50 mL THF was added an aqueous solution of NaOH (1.4 g, 35 mmol, 1.3 eq.) in 20 mL DI $H_2O$. The solution was stirred at room temperature before adding tosyl chloride (TsCl) (5.10 g, 26.75 mmol, 1 eq.) in 200 mL THF via slow addition funnel over 2 h. After stirring at room temperature for 1 d, the reaction was quenched with 200 mL DI $H_2O$. The solution was extracted with 3×150 mL $CH_2Cl_2$ washes. The combined organic layers were dried over $Na_2SO_4$ and filtered. The solvent was removed via rotary evaporator to afford the crude as a light yellow oil. Silica column chromatography (EtOAc to 2.5% MeOH/EtOAc) of the crude material afforded the product as a colorless oil (5.6 g, 40%).

$^1$H NMR (500 MHz, $CDCl_3$): $\delta_H$ 7.79 (d, J=8.3 Hz, 2H), 7.32 (d, J=8.3 Hz, 2H), 6.86-6.80 (m, 4H), 4.17-4.14 (m, 2H), 4.10-4.06 (m, 2H), 4.06-4.03 (m, 2H), 3.83 (dd, J=5.5, 4.1 Hz, 2H), 3.78 (dd, J=5.5, 4.2 Hz, 2H), 3.72 (dd, J=6.2, 3.0 Hz, 4H), 3.71-3.67 (m, 4H), 3.66-3.63 (m, 2H), 3.63-3.58 (m, 4H), 2.42 (s, 3H). $^{13}$C NMR (125 MHz, $CDCl_3$): $\delta_C$ 153.2, 145.0, 133.2, 123.0, 128.1, 115.7, 72.6, 70.9, 70.5, 70.0, 69.4, 68.9, 68.2, 62.0, 21.8. HRMS-ESI: calculated for $C_{25}H_{36}O_{10}S$: m/z=551.1921 $[M+Na]^+$; Found: 551.2058 $[M+Na]^-$.

g) Terpy HQ Phenol (7)

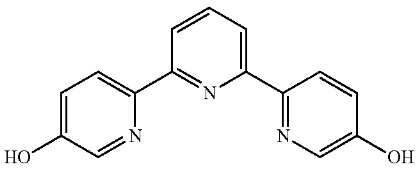

4

+

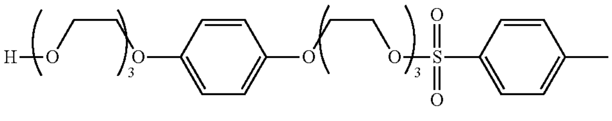

6

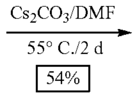

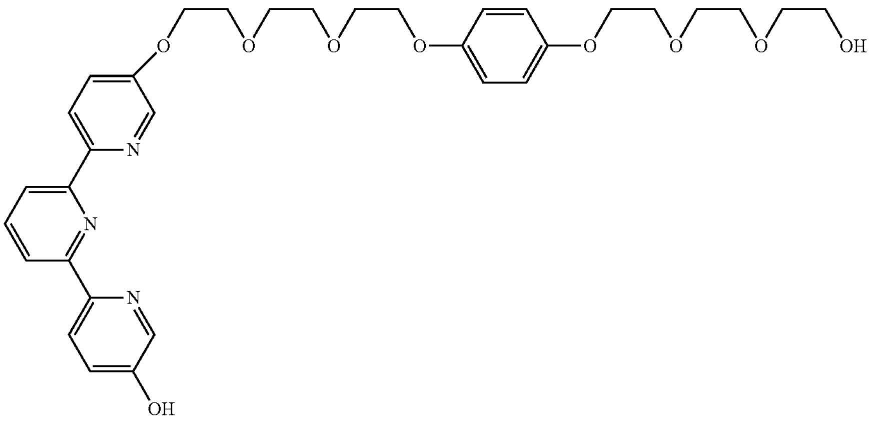

7

A suspension of 4 (1.00 g, 3.77 mmol, 2.5 eq.) and $Cs_2CO_3$ (4.91 g, 15.19 mmol, 10 eq.) in 200 mL anhydrous DMF was heated to 55° C. for 30 min while stirring under $N_2$. A solution of 6 (0.79 g, 1.49 mmol, 1 eq.) in 50 mL anhydrous DMF was added via syringe pump at 1.5 mL/h. The reaction was heated at 55° C. for a total of 2 d. The solvent was then removed via rotary evaporator. The crude was re-dissolved in 150 mL 15% MeOH/$CHCl_3$ and was washed with 100 mL brine. The aqueous layer was back extracted with 2×100 mL $CHCl_3$. The combined organics were then dried over $Na_2SO_4$ and filtered. The solvent was removed to afford the crude as a sticky brown oil, which was re-dissolved in 20 mL HPLC grade DMF. The crude was then purified via recycling prep GPC with DMF and the pure product was collected as a dark orange oil (0.50 g, 54%).

$^1$H NMR (500 MHz, $CDCl_3$): $\delta_H$ 8.44 (d, J=8.8 Hz, 1H), 8.37-8.34 (m, 2H), 8.31 (d, J=2.8 Hz, 1H), 8.21 (d, J=7.8 Hz, 1H), 8.18 (d, J=7.3 Hz, 1H), 7.83 (t, J=7.8 Hz, 1H), 7.34 (dd, J=8.8, 2.9 Hz, 1H), 7.28 (dd, J=8.6, 2.8 Hz, 1H), 6.79-6.73 (m, 4H), 4.26-4.22 (m, 2H), 4.01-3.97 (m, 4H), 3.89 (dd, J=5.3, 3.9 Hz, 2H), 3.81-3.68 (m, 14H), 3.65-3.61 (m, 2H). $^{13}$C NMR (125 MHz, $CDCl_3$): $\delta_C$ 155, 155.1, 155.0, 153.3, 153.0, 149.3, 138.0, 137.5, 137.5, 124.0, 122.4, 122.3, 122.0, 119.5, 115.7, 115.6, 72.6, 71.2, 71.0 70.9, 70.5, 70.1, 70.0, 69.9, 68.2, 68.1, 67.9, 61.9. HRMS-ESI: calculated for $C_{33}H_{39}N_3O_9$: m/z=622.2759 $[M+H]^+$; Found 622.2787 $[M+H]^+$: m/z=644.2579 $[M+Na]^+$; Found: 644.2607 $[M+Na]^+$.

h) Terpy HQ Olefin (8)

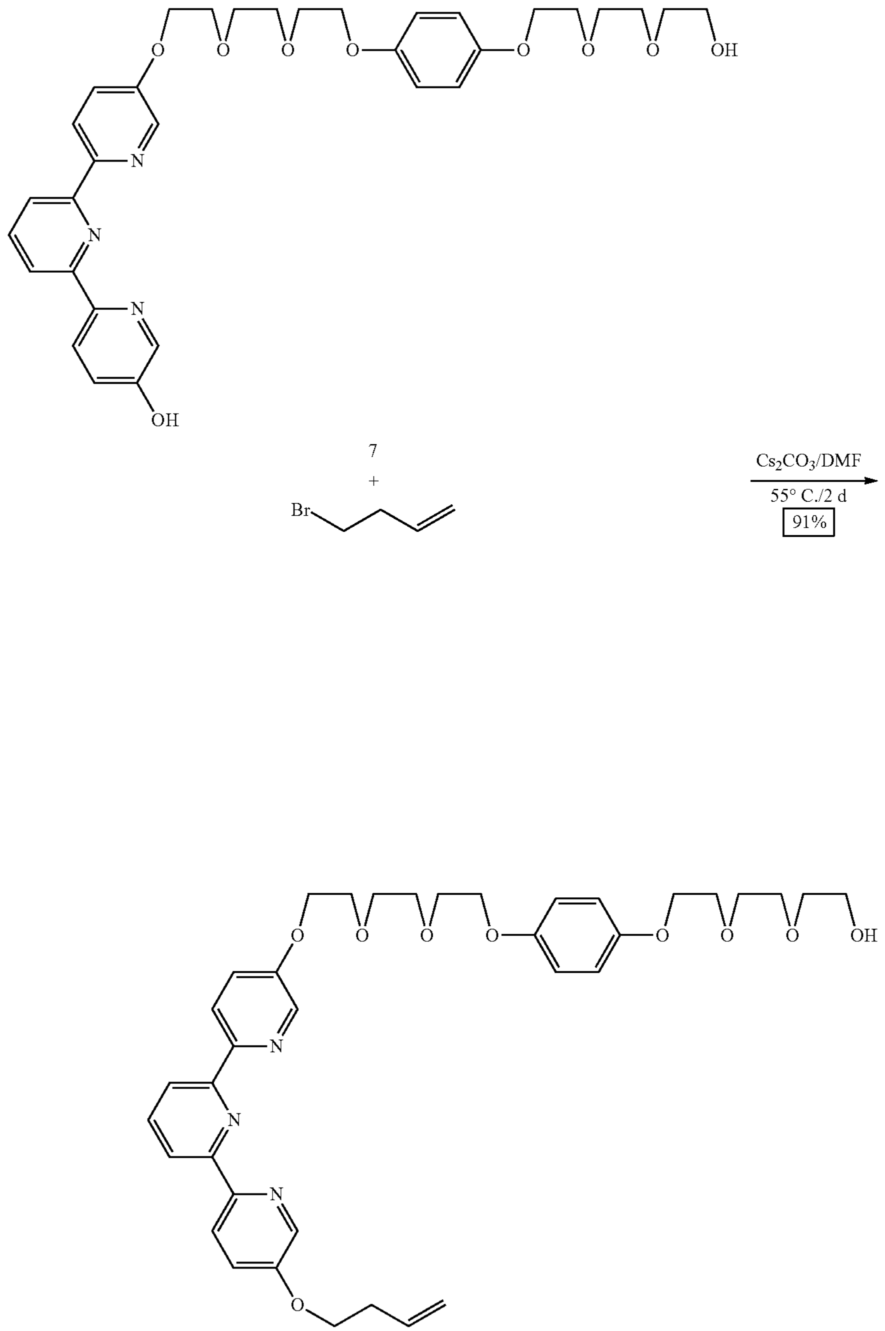

7

8

A suspension of 7 (0.54 g, 0.88 mmol, 1 eq.), 1-bromobutene (0.36 g, 2.63 mmol, 3 eq.), and $Cs_2CO_3$ (0.68 g, 2.63 mmol, 3 eq.) in 25 mL anhydrous DMF was heated to 55° C. for 2 d while stirring under $N_2$. The solvent was then removed and the crude was re-dissolved in 200 mL $CHCl_3$ and was washed with 3×100 mL brine. The organic layer was dried over $Na_2SO_4$ and was filtered. The solvent was then removed to afford the product as a light brown solid (0.54 g, 91%).

$^1H$ NMR (500 MHz, $CDCl_3$): $\delta_H$ 8.53 (d, J=8.8 Hz, 2H), 8.38 (dd, J=9.7, 2.8 Hz, 2H), 8.29 (d, J=7.8 Hz, 2H), 7.88 (t, J=7.8, 1H), 7.38-7.32 (m, 2H), 6.85-6.80 (m, 4H), 5.98-5.88 (m, 1H), 5.25-5.12 (m, 2H), 4.28-4.22 (m, 4H), 4.14 (t, J=6.7 Hz, 2H), 4.09-4.03 (m, 4H), 3.95-3.90 (m, 2H), 3.86-3.66 (m, 15H), 3.64-3.58 (m, 2H), 2.61 (q, J=6.7 Hz, 2H). $^{13}C$ NMR (125 MHz, $CDCl_3$): $\delta_C$ 155.6, 155.5, 155.2, 155.1, 153.3, 153.2, 149.5, 149.4, 137.9, 137.3, 137.2, 134.1, 122.1, 122.0, 121.9, 121.8, 119.7, 117.6, 115.7, 115.7, 72.6, 71.1, 71.0, 70.9, 70.5, 70.1, 70.0, 69.8, 68.2, 68.1, 68.1, 67.9, 62.0, 33.7. HRMS-ESI: calculated for $C_{37}H_{45}N_3O_9$: m/z=676.3228 $[M+H]^-$; Found: 676.3244 $[M+H]^+$.

i) Terpy HQ Olefin Mesyl (9)

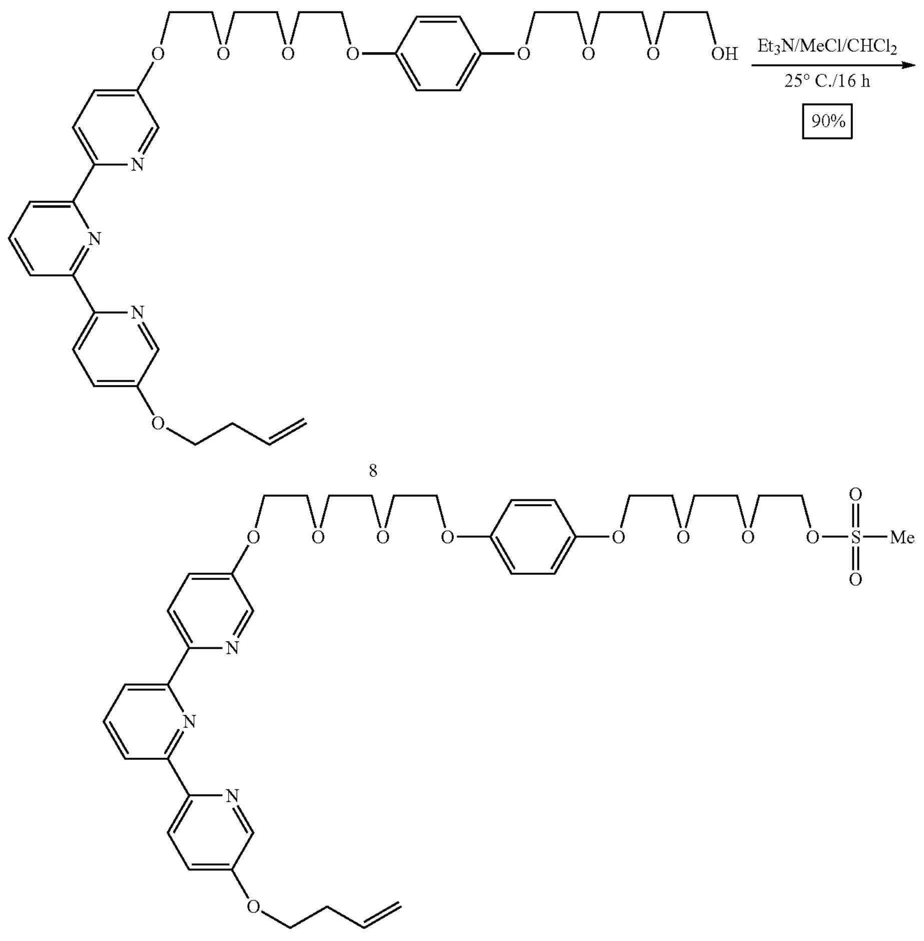

8

9

A solution of 8 (0.52 g, 0.77 mmol, 1 eq.) and $Et_3N$ (0.39 g, 3.83 mmol, 5 eq.) was prepared in 25 mL $CHCl_3$. While stirring under $N_2$, a solution of mesyl chloride (MsCl) (0.26 g, 2.3 mmol, 3 eq.) in 10 mL $CHCl_3$ was added via syringe. After stirring at room temperature for 16 h, the reaction mixture was diluted with 100 mL $CHCl_3$ and was washed with 3×100 mL 1 M $CH_3COOH$, 2×100 mL aqueous saturated $NaHCO_3$, and 2×100 mL brine. The organic layer was dried over $Na_2SO_4$ and filtered. The solvent was removed via rotary evaporator to afford the product as a light brown oil (0.52 g, 90%).

$^1$H NMR (500 MHz, $CDCl_3$): $\delta_H$ 8.53 (d, J=8.7 Hz, 2H), 8.38 (dd, J=10.0, 2.8 Hz, 2H), 8.29 (d, J=7.9 Hz, 2H), 7.88 (t, J=7.8 Hz, 1H), 7.40-7.31 (m, 2H), 6.87-6.76 (m, 4H), 5.99-5.87 (m, 1H), 5.24-5.12 (m, 2H), 4.38-4.33 (m, 2H), 4.29-4.22 (m, 2H), 4.14 (t, J=6.7 Hz, 2H), 4.10-4.05 (m, 2H), 3.94-3.90 (m, 2H), 3.86-3.82 (m, 2H), 3.80-3.73 (m, 8H), 3.71-3.65 (m, 4H), 3.03 (s, 3H), 2.60 (q, J=6.7 Hz, 2H). $^{13}$C NMR (125 MHz, $CDCl_3$): $\delta_C$ 155.6, 155.5, 155.2, 155.10, 153.3, 153.1, 137.9, 137.2, 137.1, 134.1, 122.1, 122.0, 121.9, 121.8, 119.7, 117.6, 115.8, 115.6, 71.1, 71.0, 70.8, 70.8, 70.0, 70.0, 69.8, 69.4, 69.2, 68.2, 68.1, 68.1, 67.9, 37.8, 33.7. HRMS-ESI: calculated for $C_{38}H_{47}N_3O_{11}S$: m/z=776.28235 $[M+Na]^+$; Found: 776.29847 $[M+Na]^+$.

j) Methoxy Phen (10)

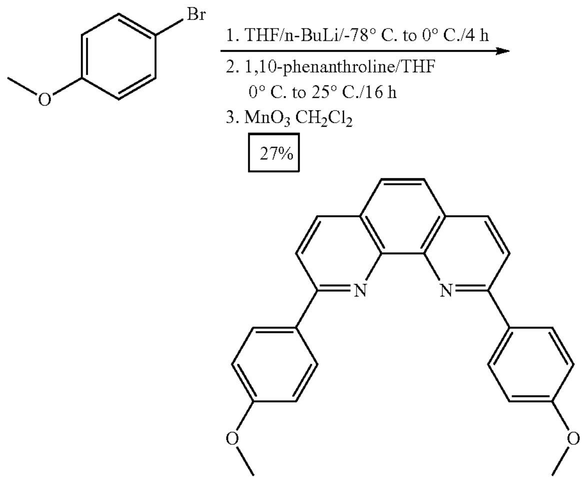

10

Compound 10 was prepared following a modified prep from Dietrich-Buchecker et al., 1990. To an oven-dried 250 mL RB flask was added 4-bromoanisole (9.9 g, 53 mmol, 4.0 eq.) and 70 mL anhydrous THF. The solution was cooled on $Me_2CO$/dry ice bath and 45 mL n-BuLi (2.5 M hexanes, 113 mmol, 8.5 eq.) was added dropwise via syringe while stirring under $N_2$. The solution was stirred at −78° C. for 2 h and was then transferred to ice bath for an additional 2 h while stirring. The resulting yellow solution was transferred via syringe to an oven-dried 300 mL RB flask containing a solution of 1,10-phenanthroline (2.4 g, 13 mmol, 1.0 eq.) in 45 mL anhydrous THE cooled on an ice bath. The resulting dark red solution was stirred in ice bath for 1 h and was then allowed to warm up to room temperature while stirring over 16 h. The reaction was quenched by adding 40 mL $H_2O$ that had been cooled on an ice bath and the solvent was removed via rotary evaporator. The aqueous residue was extracted with 3×100 mL $CH_2Cl_2$. The organic layer was dried over $Na_2SO_4$ and was filtered. The filtrate was evaporated under reduced vacuum and the residue was re-dissolved in 200 mL $CH_2Cl_2$. To this solution was added $MnO_2$ (24 g, 280 mmol, 5.2 eq.) and the suspension was stirred at room temperature for 12 h. The solid was filtered off and the filtrate was evaporated. The residue was then purified by silica column chromatography ($CH_2Cl_2$ to 2% MeOH/$CH_2Cl_2$). The yellow oil was then washed in hexanes/$Et_2O$ (50/50 v/v, 60 mL) and was allowed to sit at 4° C. overnight. The solid was filtered and dried under vacuum to afford the product as a white solid (1.4 g, 27%).

$^1H$ NMR (500 MHz, $CDCl_3$): $\delta_H$ 8.44 (d, J=8.8 Hz, 4H), 8.26 (d, J=8.4 Hz, 2H), 8.09 (d, J=8.4 Hz, 2H), 7.74 (s, 2H), 7.12 (d, J=8.8 Hz, 4H), 3.93 (s, 6H). $^{13}C$ NMR (125 MHz, $CDCl_3$): $\delta_C$ 161.1, 156.5, 146.2, 136.9, 132.4, 129.1, 127.7, 125.8, 119.5, 114.3, 55.5. LRMS-ESI: calculated for $C_{26}H_{20}N_2O_2$: m/z=393.2 $[M+H]^+$; Found: 393.2 $[M+H]^+$.

k) Phen Diol (11)

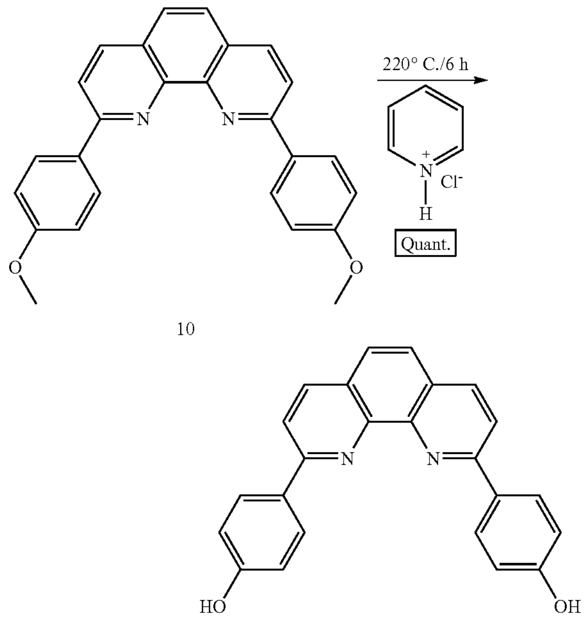

10

11

Compound 11 was prepared following a modified prep from Dietrich-Buchecker et al., 1990. To a 500 mL RB flask was added 10 (2.9 g, 7.4 mmol, 1.0 eq.) and pyridine hydrochloride (55 g, 480 mmol, 65 eq.). The mixture was stirred at 220° C. for 6 h. After cooling to 180° C., 120 mL hot $H_2O$ was added slowly. A mixed solvent of 250 mL $EtOH/H_2O$ (40/60 v/v) was added at room temperature. The suspension was stirred for 1 h and was allowed to sit at 4° C. for overnight. The suspension was neutralized to pH=7.4 with 1 M NaOH solution in $H_2O$ (approximately 450 mL). The solid was filtered and dried under vacuum to afford the product as a dark brown solid with a quantitative yield (2.7 g).

$^1H$ NMR (500 MHz, DMSO-$d_6$): $\delta_H$ 10.20 (s, 2H), 8.72 (d, J=7.7 Hz, 2H), 8.42 (d, J=8.4 Hz, 2H), 8.35 (d, J=8.4 Hz, 4H), 8.08 (s, 2H), 7.06 (d, J=8.5 Hz, 4H). $^{13}C$ NMR (125 MHz, DMSO-$d_6$): $\delta_C$ 159.9, 155.2, 138.7, 129.9, 129.5, 127.3, 125.8, 120.4, 115.9, 115.8. HRMS-ESI: calculated for $C_{24}H_{16}N_2O_2$: m/z=365.1285 $[M+H]^+$; Found: 365.1319 $[M+H]^+$.

l) Mono HQ (12)

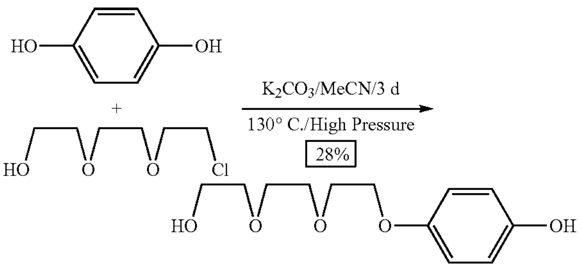

12

100 mL of MeCN was added to a 350 mL high pressure vessel (Kemtech) with Teflon screw cap and was stirred vigorously. While stirring, solid $K_2CO_3$ (12.3 g, 88.96 mmol, 5 eq.) and hydroquinone (4.9 g, 44.48 mmol, 2.5 eq.) were added. Then a solution of 2-(2-(2-chloroethoxy) ethoxy)ethan-1-ol (3.0 g, 17.79 mmol, 2.5 eq.) was added and the vessel was sealed. The suspension was heated at 130° C. for 3 d. Then, the reaction mixture was allowed to cool to room temperature over 2 h. The insoluble salts were removed via vacuum filtration over celite. The celite pad was rinsed with 1 L of MeCN and the combined organics were concentrated via rotary evaporator. The brown solid was taken up in 250 mL 1 M HCl and 500 mL 5% MeOH/$CH_2Cl_2$. The aqueous layer was further extracted with 2×500 mL mL 5% MeOH/$CH_2Cl_2$. The combined organics were dried over $Na_2SO_4$ and were concentrated via rotary evaporator. Silica column chromatography (EtOAC to 5% MeOH/EtOAc) of the crude material afforded the pure product as a light brown oil (1.2 g, 28%).

$^1H$ NMR (500 MHz, $CDCl_3$): $\delta_H$ 6.71 (s, 4H), 4.01-4.03 (m, 2H), 3.83-3.82 (m, 2H), 3.74-3.70 (m, 6H), 3.63-3.62 (m, 2H). $^{13}C$ NMR (125 MHz, $CDCl_3$): $\delta_C$ 152.7, 150.2, 116.2, 115.9, 72.7, 70.9, 70.5, 70.1, 68.0, 61.9. HRMS-ESI: calculated for $Cl_2H_{18}O_5$: m/z=265.1046 $[M+Na]^+$; Found: 265.1079 $[M+Na]^+$.

m) Mono HQ Olefin (13)

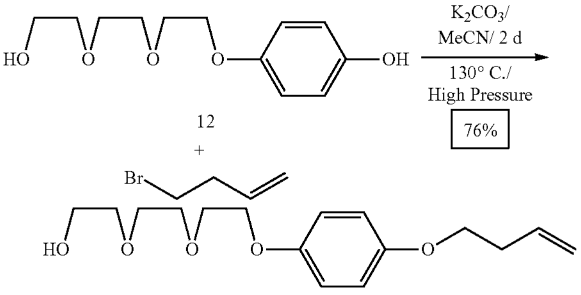

12

+

13

A suspension of 12 (0.98 g, 4.05 mmol, 1.0 eq.), 1-bromobutene (2.18 g, 16.21 mmol, 4.0 eq.) and $K_2CO_3$ (2.24 g, 16.21 mmol, 4 eq.) in 50 mL MeCN was prepared in a 100 mL high-pressure vessel (Kemtech) with Teflon screw cap and was stirred vigorously. The vessel was sealed, and the suspension was heated at 130° C. for 2 d. The reaction was then allowed to cool to room temperature and the crude slurry was transferred to a RB flask. The solvent was removed via rotary evaporator and the resulting solid was re-dissolved in 100 mL 1 M HCl and 100 mL $CHCl_3$. The aqueous layer was extracted with 2×100 mL $CHCl_3$ and the organics were combined and washed with 100 mL brine. The organic layer was dried over $Na_2SO_4$ and filtered. The solvent was removed aging to afford the product as a brown oil (0.92 g, 76%).

$^1H$ NMR (500 MHz, $CDCl_3$): $\delta_H$ 6.86-6.81 (m, 4H), 5.94-5.86 (m, 1H), 5.17-5.08 (m, 2H), 4.09-4.07 (m, 21H), 3.97-3.95 (t, J=6.5 Hz, 2H), 3.85-3.83 (m, 2H), 3.74-3.69 (m, 6H), 3.63-3.61 (m, 2H), 2.53-2.49 (q, J=11.5, 1.0 Hz, 2H). $^{13}C$ NMR (125 MHz, $CDCl_3$): $\delta_H$ 153.3, 152.9, 116.9, 115.6, 115.5, 72.5, 70.8, 70.4, 69.9, 68.1, 67.9, 61.8, 33.8. HRMS-ESI: calculated for $C_{16}H_{24}O_5$: m/z=319.1516 $[M+Na]^+$; Found: 319.1542 $[M+Na]^+$.

n) Mono HQ Olefin Mesyl (14)

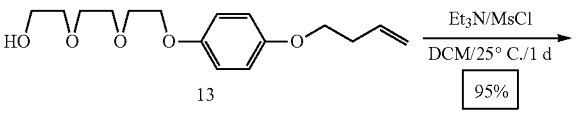

13

-continued

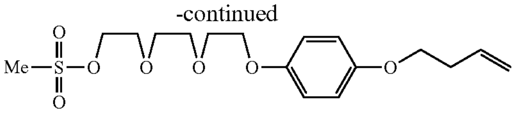

14

A solution of 13 (0.72 g, 2.43 mmol, 1 eq.) and $Et_3N$ (1.7 mL, 12.2 mmol, 5 eq.) was prepared in 5 mL anhydrous $CH_2Cl_2$ in a 20 mL scintillation vial. Then, neat MsCl (0.5 mL, 6.1 mmol, 2.5 eq.) was added dropwise over several minutes via syringe. The vial was then capped and the solution was stirred at 25° C. for 1 d. The reaction mixture was then diluted with 50 mL $CH_2Cl_2$ and was washed with 2×50 mL 1% (w/v) citric acid, followed by 30 mL 10% (w/v) $NaHCO_3$. The organic layer was then dried over $Na_2SO_4$ and was filtered. The solvent was removed via rotary evaporator to afford the product as a dark orange oil (0.86 g, 95%).

$^1H$ NMR (500 MHz, $CDCl_3$): $\delta_H$ 6.82 (s, 4H), 5.93-5.85 (m, 1H), 5.17-5.08 (m, 2H), 4.38-4.36 (m, 2H), 4.07-4.09 (m, 2H), 3.97-3.94 (t, J=6.5 Hz, 2H), 3.82-3.80 (m, 2H), 3.77-3.75 (m, 2H), 3.73-3.68 (m, 4H), 3.04 (s, 3H), 2.53-2.49 (q, J=6.5 Hz, 2H). $^{13}C$ NMR (125 MHz, $CDCl_3$): $\delta_H$ 153.4, 153.0, 134.6, 117.0, 115.7, 70.8, 70.7, 70.0, 69.4, 69.2, 68.2, 68.0, 37.8, 33.9. HRMS-ESI: calculated for $C_{17}H_{26}O_7S$: m/z=375.1472 $[M+H]^+$; Found: 375.1500 $[M+H]^-$.

o) Phen HQ Olefin (15)

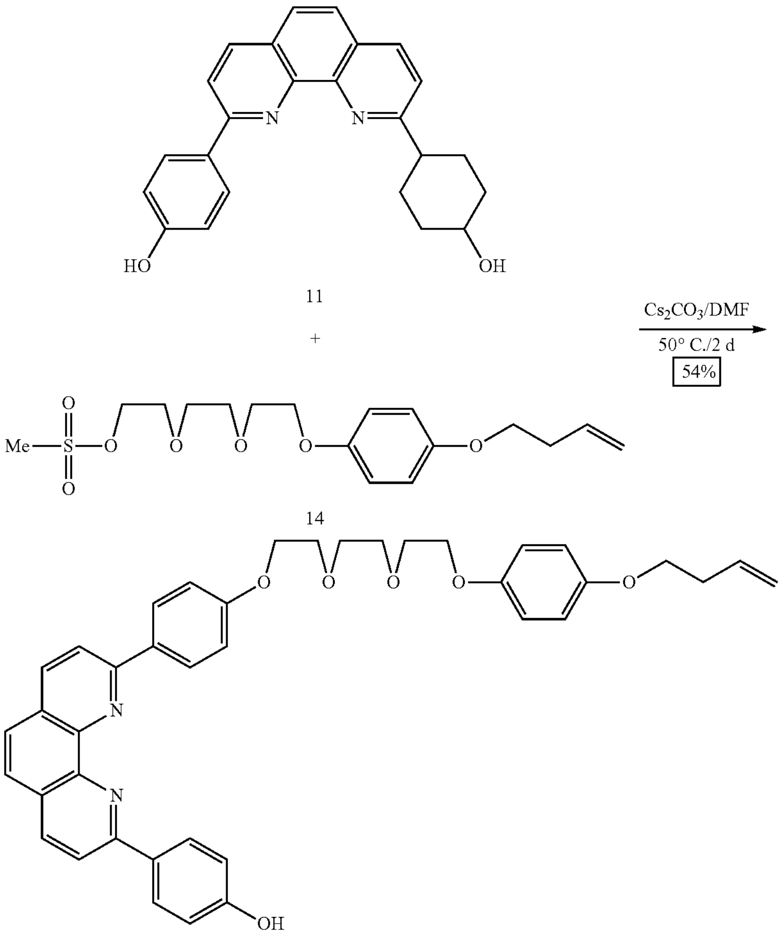

15

A suspension of 11 (0.51 g, 1.40 nmol, 3 eq.) and $Cs_2CO_3$ (0.91 g, 2.80 mmol, 6 eq.) was prepared in 100 mL anhydrous DMF and was heated to 50° C. while stirring under $N_2$. To this was added a solution of 14 (0.17 g, 0.45 mmol, 1 eq.) in 50 mL anhydrous DMF via syringe pump at 1.5 mL/h. After heating at 50° C. for 2 d total, the solvent was removed via rotary evaporator and the crude was re-dissolved in $H_2O$ and $CHCl_3$. 100 mL of brine was added and the aqueous layer was extracted with 3×100 mL $CHCl_3$. The combined organics were filtered via vacuum filtration and the filtrate was dried over $Na_2SO_4$. The organics were filtered again and the solvent was removed via rotary evaporator to afford the crude as an orange oil. The crude oil was dissolved in 20 mL HPLC grade DMF and was purified via recycling prep GPC with DMF to afford the pure asymmetric product as a sticky orange solid (0.16 g, 54%).

$^1H$ NMR (500 MHz, $CDCl_3$): $\delta_H$ 8.38 (d, J=8.8 Hz, 2H), 8.30 (d, J=8.6 Hz, 2H), 8.24 (dd, J=8.4, 0.6 Hz, 2H), 8.04 (dd, J=8.4, 5.7 Hz, 2H), 7.73 (s, 2H), 7.10 (d, J=8.8 Hz, 2H), 7.00 (d, J=8.6 Hz, 2H), 6.86-6.79 (m, 4H), 5.87 (m, 1H), 5.16-5.05 (m, 2H), 4.26-4.22 (m, 2H), 4.08 (dd, J=9.6, 4.5 Hz, 2H), 3.93 (dt, J=7.9, 5.7 Hz, 4H), 3.88-3.84 (m, 2H), 3.80-3.74 (m, 5H), 2.49 (qd, J=6.7, 5.5 Hz, 2H). $^{13}C$ NMR (150 MHz, $CDCl_3$): $\delta_C$ 162.1, 158.4, 157.1, 156.6, 153.2, 153.1, 145.9, 136.9, 134.6, 132.3, 131.3, 129.3, 129.2, 127.6, 127.5, 125.8, 125.5, 119.9, 119.8, 117.0, 116.2, 115.7, 115.7, 115.0, 71.0, 70.9, 70.0, 69.9, 68.1, 68.0, 67.5, 50.8, 33.8. HRMS-ESI: calculated for $C_{40}H_{38}N_2O_6$: m/z=643.28026 $[M+H]^+$; Found: 643.27794 [M+H].

p) Open Terpy Phen Macrocycle (OTPM)

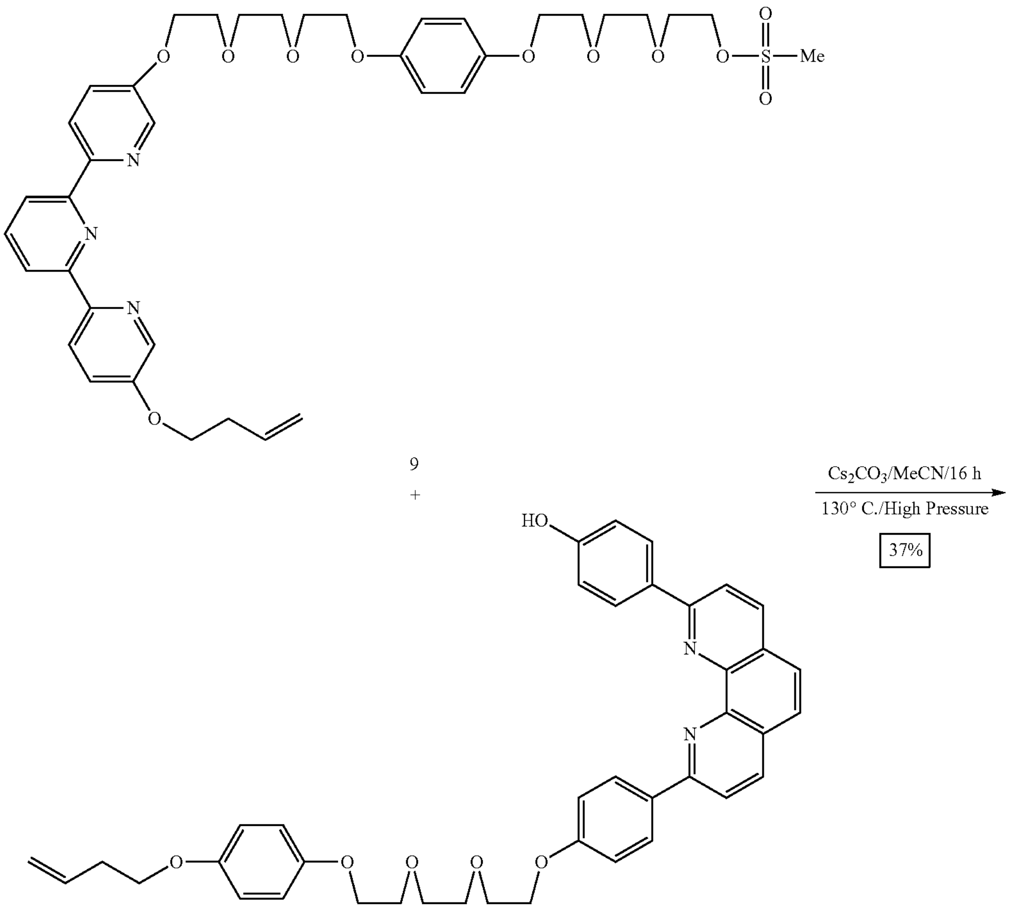

9

+

15

-continued

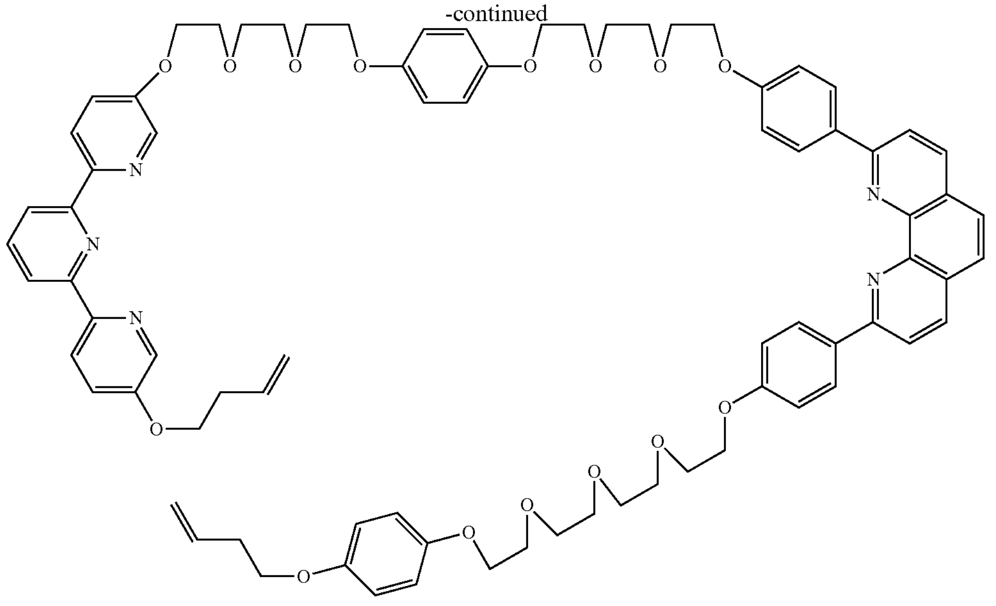

OTPM

A suspension of 9 (0.082 g, 0.109 mmol, 1.0 eq.), 15 (0.074 g, 0.116 mmol, 1.05 eq.), and $Cs_2CO_3$ (0.107 g, 0.327 mmol, 3.0 eq.) was prepared in 5 mL anhydrous MeCN in a 38 mL high-pressure vessel (Kemtech) a stir bar. The reaction was sealed and was heated to 130° C. for 16 h. The reaction was allowed to cool to room temperature and was diluted with 100 mL $CHCl_3$. The solution was washed with 3×50 mL brine. The organic layer was dried over $Na_2SO_4$ and was filtered. The solvent was then removed via rotary evaporator to afford the crude as an orange film, which was purified via HPLC with MeCN/$H_2O$/0.1% $CH_3COOH$: 5 to 40% in 9 min/40 to 95% in 17 min/95 to 100% in 25 min at 20 mL·min$^{-1}$. The product was isolated as a sticky orange solid (0.054 g, 37%).

$^1$H NMR (500 MHz, $CDCl_3$): $\delta_H$ 8.54 (t, J=8.3 Hz, 2H), 8.48-8.37 (m, 6H), 8.33-8.28 (m, 2H), 8.25 (d, J=8.1 Hz, 2H), 8.08 (t, J=9.7 Hz, 2H), 7.89 (t, J=7.8 Hz, 1H), 7.73 (s, 2H), 7.41-7.34 (m, 2H), 7.11 (d, J=8.2 Hz, 4H), 6.88-6.76 (m, 8H), 5.97-5.83 (m, 2H), 5.25-5.03 (m, 4H), 4.24 (s, 6H), 4.14 (t, J=6.5 Hz, 2H), 4.11-4.02 (m, 6H), 3.96-3.72 (m, 26H), 2.60 (dd, J=12.4, 6.0 Hz, 2H), 2.48 (dd, J=13.0, 6.4 Hz, 2H). $^{13}$C NMR (125 MHz, $CDCl_3$): $\delta_C$ 160.3, 156.4, 155.7, 155.7, 153.4, 153.3, 153.2, 146.1, 138.0, 137.0, 134.7, 134.0, 132.4, 129.1, 127.7, 125.8, 122.1, 119.9, 119.5, 117.7, 117.0, 71.1, 71.0, 71.0, 70.1, 70.0, 69.9, 69.80, 68.2, 68.2, 68.0, 67.9, 67.7, 33.9, 33.7. HRMS-ESI: calculated for $C_{77}H_{81}N_5O_{14}$: m/z=1322.5677 [M+Na]$^+$; Found: 1322.5718 [M+Na]$^+$.

q) Phen HQ Diolefin (16)

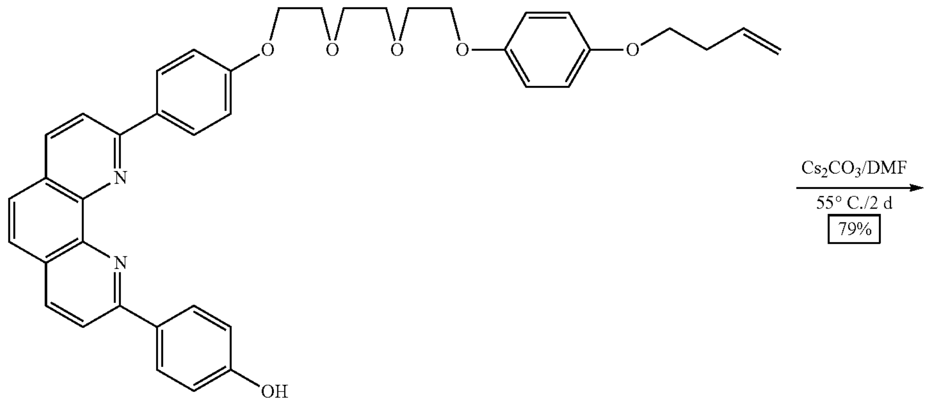

15

+

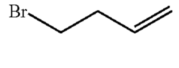

-continued

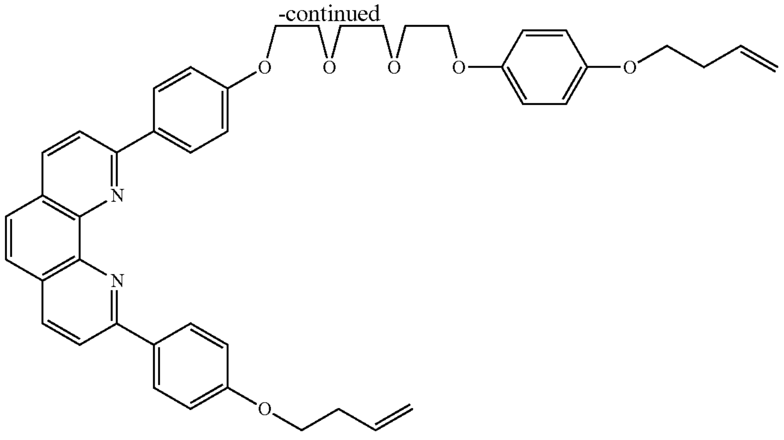

16

A suspension of 15 (0.10 g, 0.16 mmol, 1 eq.) and $Cs_2CO_3$ (0.15 g, 0.47 mmol, 3 eq.) was prepared in 5 mL anhydrous DMF. The reaction mixture was heated at to 55° C. for 30 min while stirring under $N_2$, followed by the addition of neat 1-bromo-butene (0.05 mL, 0.47 mmol, 3 eq.). After heating for 16 h, the solvent was removed via rotary evaporator. The crude mixture was dissolved in 50 mL $CHCl_3$ and 50 mL 1 M HCl. The organic layer was then washed with 3×30 mL brine. The organic layer was dried over $Na_2SO_4$ and was filtered. The solvent was removed to afford the product as an orange oil (0.086 g, 79%).

$^1$H NMR (500 MHz, $CDCl_3$): $\delta_H$ 8.42 (d, J=7.1 Hz, 4H), 8.26 (d, J=8.4, 2H), 8.08 (dd, J=8.4, 4.6 Hz, 2H), 7.74 (s, 2H), 7.11 (dd, J=8.4, 6.6 Hz, 4H), 6.83 (dd, J=21.4, 9.1 Hz, 4H), 6.03-5.82 (m, 2H), 5.28-5.03 (m, 4H), 4.29-4.23 (m, 2H), 4.14 (t, J=6.7 Hz, 2H), 4.11-4.07 (m, 2H), 3.93 (dd, J=8.4, 3.7 Hz, 4H), 3.89-3.84 (m, 2H), 3.78 (t, J=4.8 Hz, 4H), 2.61 (q, J=6.7 Hz, 2H), 2.49 (q, J=6.7 Hz, 2H). $^{13}$C NMR (125 MHz, $CDCl_3$): $\delta_C$ 160.1, 160.3, 156.5, 156.4, 153.4, 153.2, 146.1, 137.0, 134.7, 134.6, 132.4, 129.1, 129.1, 127.7, 125.8, 119.5, 117.3, 117.0, 115.8, 115.7, 115.1, 115.0, 71.1, 71.0, 70.0, 68.3, 68.0, 67.7, 67.5, 33.9, 33.8. HRMS-ESI: calculated for $C_{44}H_{44}N_2O_6$: m/z=697.32721 $[M+H]^+$; Found: 697.32447 $[M+H]^+$.

r) Phen Macrocycle Unsaturated (PM-U)

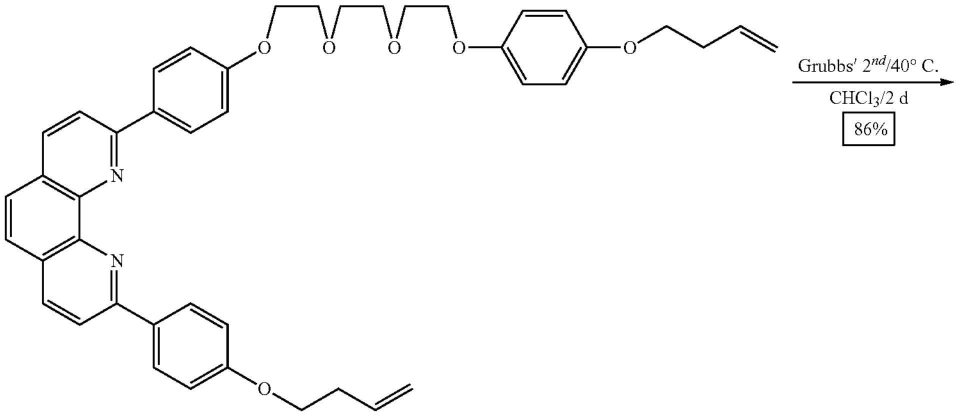

16

-continued

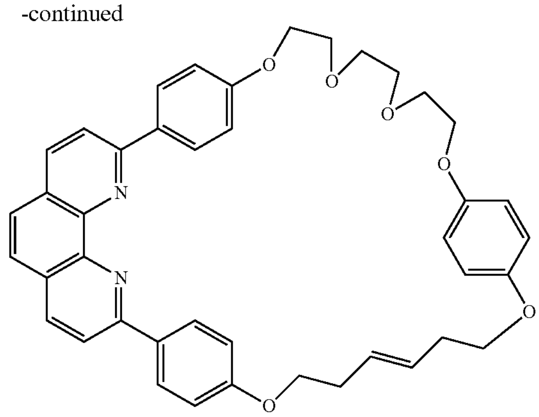

PM-U

A solution of 16 (0.044 g, 0.063 mmol, 1 eq.) was prepared in 40 mL $CHCl_3$ while stirring under $N_2$. To this was added a solution of Grubbs' 2nd generation catalyst (0.011 g, 0.013 mmol, 0.2 eq.) in 10 mL $CHCl_3$ via syringe. The solution was then heated to 40° C. while stirring under $N_2$. The reaction was periodically checked via low-res ESI for the consumption of the starting material. After 2 d, the reaction was quenched with 1 mL ethyl vinyl ether (EVE) and was allowed to cool to RT for 1 h. The solvent was removed via rotovap and the crude was then purified via column chromatography with neutral alumnia ($CH2Cl_2$ to 5% $MeOH/CH_2Cl_2$) to afford the product as a sticky orange oil (0.037 g, 86%).

$^1$H NMR (500 MHz, $CDCl_3$): $\delta_H$ 8.43 (dd, J=8.7, 2.0 Hz, 4 Hz), 8.26 (d, J=8.4, 2H), 8.09 (d, J=8.4 Hz, 2H), 7.74 (s, 2H), 7.11 (dd, J=12.0, 8.8 Hz, 4H), 6.96-6.87 (m, 4H), 5.80-5.60 (m, 2H), 4.27-4.20 (m, 2H), 4.09 (t, J=6.9 Hz, 2H), 4.03 (t, J=6.4 Hz, 2H), 3.97-3.92 (m, 2H), 3.87 (dd, J=9.0, 4.3H, 2H), 3.78 (s, 4H), 2.61-2.46 (m, 4H). $^{13}$C NMR (125 MHz, $CDCl_3$): $\delta_C$ 160.5, 160.3, 156.5, 156.4, 153.4, 153.2, 146.1, 137.0, 132.3, 132.1, 129.1, 128.2, 128.1, 127.7, 125.8, 119.5, 116.1, 115.9, 115.9, 114.9, 71.2, 71.1, 69.9, 69.9, 68.6, 68.6, 67.6, 67.6, 32.7, 32.5. HRMS-ESI: calculated for $C_{42}H_{40}N_2O_6$: m/z=669.2959 $[M+H]^+$; Found: 669.3002 $[M+H]^+$.

s) Phen Macrocycle (PM)

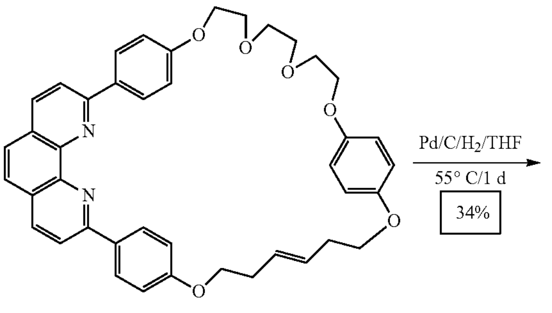

PM-U

-continued

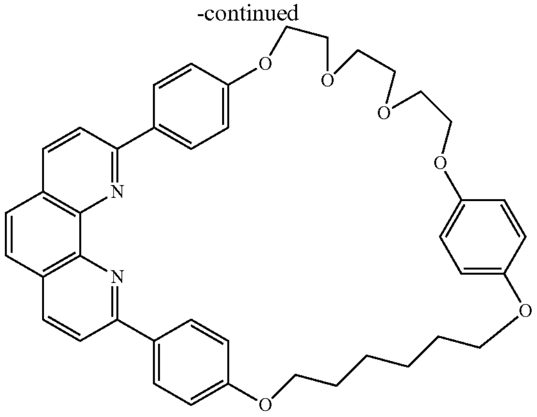

PM

A solution of PM-U (0.033 g, 0.049 mmol, 1 eq.) was prepared in 3 mL anhydrous THF. To this was added 10% (w/w) palladium on carbon (0.034 g, 10% (w/w)). The flask was flushed with $N_2$, followed by flushing with $H_2$. Under constant $H_2$, the reaction was mixture was heated to 55° C. for 1 d. The crude was filtered over a celite pad, which was washed with 100 mL $CHCl_3$. The solvent was removed and the crude yellow film was purified via HPLC with MeCN/$H_2O$/0.1% $CH_3COOH$: 10 to 30% in 10 min/30 to 100% in 30 min at 20 mL·min$^1$. The product was isolated as a sticky yellow solid (0.012 g, 34%).

$^1$H NMR (500 MHz, $CDCl_3$): $\delta_H$ 8.47-8.40 (m, 4H), 8.29-8.23 (m, 2H), 8.08 (d, J=8.5 Hz, 2H), 7.74 (s, 2H), 7.11 (dd, J=14.2, 8.8 Hz, 4H), 6.97-6.87 (m, 4H), 4.27-4.21 (m, 2H), 4.17-4.13 (m, 2H), 4.08 (q, J=6.3 Hz, 2H), 4.02 (dd, J=13.4, 7.2 Hz, 2H), 3.98-3.92 (m, 2H), 3.90-3.85 (m, 2H), 3.82-3.75 (m, 4H), 2.01 (s, 4H), 1.91-1.79 (m, 4H). $^{13}$C NMR (125 MHz, $CDCl_3$): $\delta_C$ 160.6, 160.3, 156.5, 156.4, 153.5, 153.1, 146.2, 136.9, 132.4, 132.1, 129.0, 127.7, 127.6, 125.7, 125.7, 119.3, 119.3, 115.9, 115.9, 114.9, 114.9, 91.9, 71.2, 71.1, 69.9, 69.88, 68.5, 68.1, 67.5, 30.1, 29.2, 25.7, 25.7. HRMS-ESI: calculated for $C_{42}H_{42}N_2O_6$: m/z=671.3116 $[M+H]^+$; Found: 671.3152 $[M+H]^+$.

Example 6. Detailed Synthesis of [2]Catenate a) Fe-$(OTPM)_2$

Figure 10:
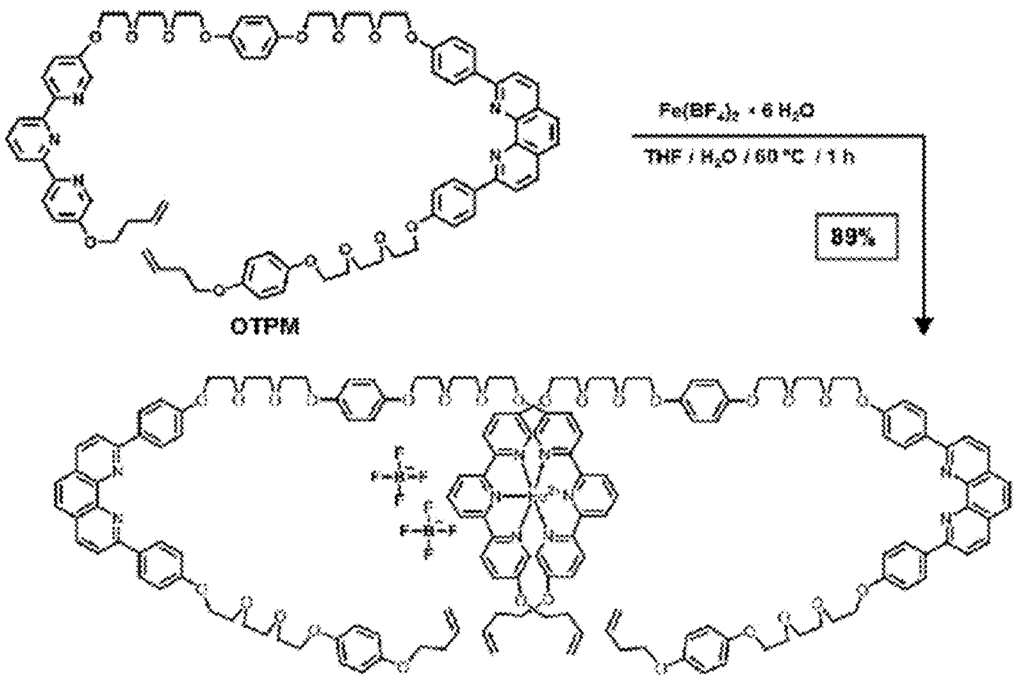
FIG. 10 depicts a detailed scheme for the synthesis of Fe-$(OTPM)_2$.

A scheme of this synthesis is shown in FIG. 10. A solution of OTPM (0.0105 g, 0.0081 mmol, 1 eq.) in 5 mL THE was prepared in a 25 mL RB flask and was heated to 60° C. for 15 min. A solution of $Fe(BF_4)_2 \cdot 6\ H_2O$ (0.0035 g, 0.0105 mmol, 1.3 eq.) in 0.5 mL DT $H_2O$ was added via syringe. The red solution was continually heated at 60° C. for 1 h. The solution was then allowed to cool to room temperature before diluting with 100 mL $CHCl_3$ and washing with 3×25 mL DI $H_2O$. The organic layer was dried over $Na_2SO_4$ and was filtered. The solvent was removed to afford the product as a red film (0.0101 g, 89%). Note the overall expected integrations were lower than expected (due to metalation) and the observed integrations are reported.

$^1H$ NMR (500 MHz, $CDCl_3$): $\delta_H$ 8.61 (d, J=7.2 Hz, 2H), 8.53-8.32 (m, 12H), 8.32-8.21 (m, 6H), 8.07 (dt, J=15.8, 6.4 Hz, 4H), 7.75 (s, 4H), 7.10 (t, J=8.5 Hz, 8H), 6.9-6.72 (m, 14H), 6.47 (dd, J=33.2, 1.8 Hz, 4H), 5.88 (m, 2H), 5.65 (m, 2H), 5.20-4.95 (m, 8H), 4.24 (d, J=4.5 Hz, 7H), 4.09 (s, 6H), 3.98-3.84 (m, 22H), 3.80 (d, J=8.1 Hz, 16H), 3.71-3.63 (m, 6H), 3.55 (d, J=7.3 Hz, 6H), 2.49 (d, J=6.5 Hz, 4H), 2.34 (d, J=4H). $^{13}C$ NMR (125 MHz, $CDCl_3$): 5c 160.3, 160.3, 159.7, 159.5, 157.6, 157.6, 156.5, 156.4, 156.3, 153.4, 153.3, 153.2, 153.1, 149.8, 149.7, 146.1, 142.1, 141.6, 137.0, 137.0, 134.7, 133.2, 132.4, 129.1, 127.7, 125.8, 125.3, 125.0, 122.5, 122.3, 121.5, 121.3, 119.5, 119.5, 118.1, 117.0, 115.8, 115.7, 115.7, 115.1, 115.0, 71.1, 71.0, 70.7, 70.6, 70.1, 70.0, 69.9, 69.1, 68.9, 68.7, 68.3, 68.1, 68.0, 67.7, 67.1, 33.9, 33.0, 30.1. HRMS-ESI: calculated for $C_{154}H_{162}FeN_{10}O_{29}$: m/z=885.7002 $[M+H]^{3-}$; Found: 885.7024 $[M+H]^{3+}$.

b) [2]Catenate ([2]C-M)

Figure 11:
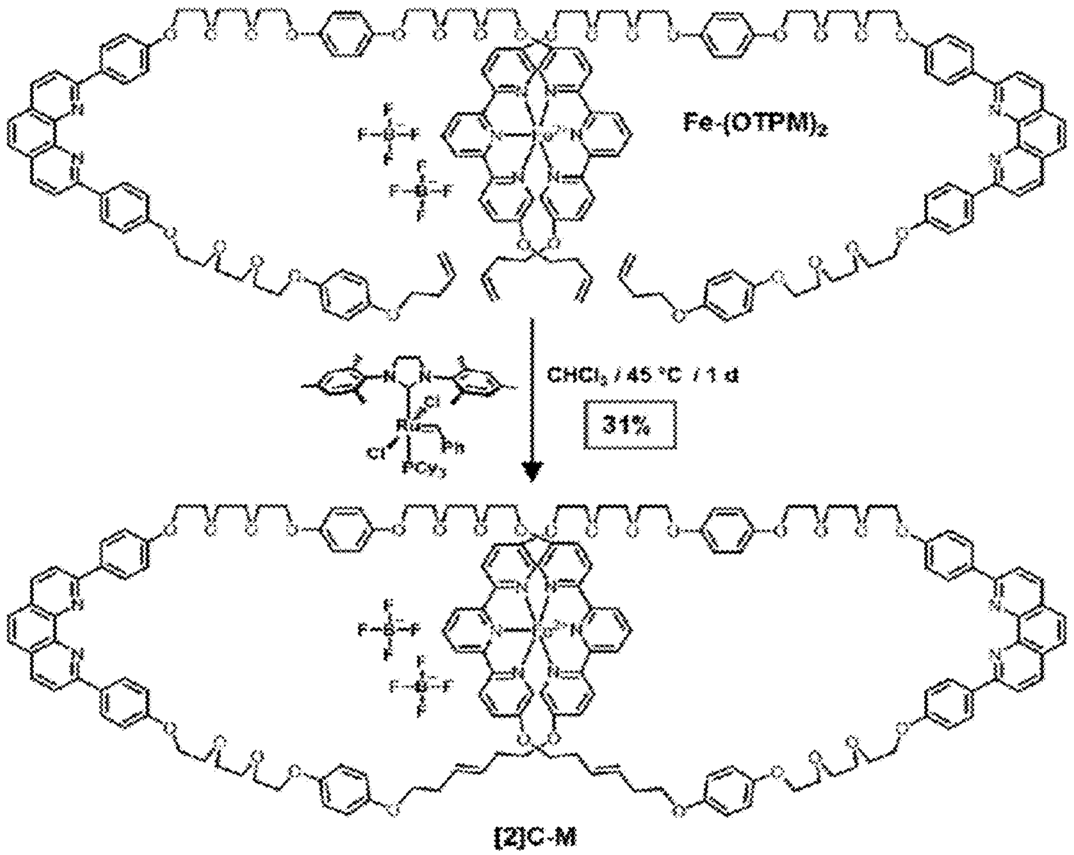
FIG. 11 depicts a detailed scheme for the synthesis of [2]catenate ([2]C-M).

A scheme of this synthesis is shown in FIG. 11. A solution of Fe-$(OTPM)_2$ (0.062 g, 0.0219 mmol, 1 eq.) and Grubbs' $2^{nd}$ generation catalyst (0.0038 g, 0.0046 mmol, 0.2 eq.) was prepared in 75 mL $CHCl_3$. The flask was fitted with a reflux condenser and the solution was heated to 45° C. for 16 h while stirring under $N_2$. An additional 0.2 eq. of catalyst was added and the reaction was heated for an additional 4 h. The solvent was then removed and the crude was purified via column chromatography with basic alumnia ($CHCl_3$ to 5% MeOH/$CHCl_3$) to afford the product as a deep red solid (0.019 g, 31%).

$^1H$ NMR (500 MHz, $CDCl_3$): $\delta_H$ 8.63 (s, 2H), 8.42 (dd, J=33.8, 25.1 Hz, 12H), 8.31-8.19 (m, 6H), 8.03 (dd, J=24.5, 8.3 Hz, 5H), 7.74 (d, J=5.7 Hz, 4H), 7.20 (d, J=20.6 Hz, 4H), 7.07 (dd, J=17.3, 8.8 Hz, 8H), 6.97 (d, J=14.7 Hz, 2H), 6.89-6.62 (m, 16H), 6.41 (d, J=39.6 Hz, 6H), 5.35 (d, J=53.7 Hz, 8H), 4.22 (s, 6H), 4.15-3.42 (m, 67H), 2.32-2.21 (m, 8H). $^{13}C$ NMR (125 MHz, $CDCl_3$): $\delta_C$ 160.3, 159.5, 157.4, 156.4, 153.3, 149.9, 146.1, 137.1, 135.1, 132.4, 130.3, 129.1, 127.7, 125.8, 122.1, 119.5, 115.7, 115.1, 71.1, 70.7, 70.1, 69.9, 68.3, 68.2, 67.7, 29.8. HRMS-ESI calculated for $C_{150}H_{154}FeN_{10}O_{28}$: m/z=1300.0160 $[M]^{2+}$, 867.0132 $[M+H]^{3+}$; Found: 1300.0459 $[M]^{2+}$, 867.0344 $[M+H]^{3+}$.

Example 7. Detailed One-Pot Synthesis of [4]Catenate ([4]C-M)

Figure 12:
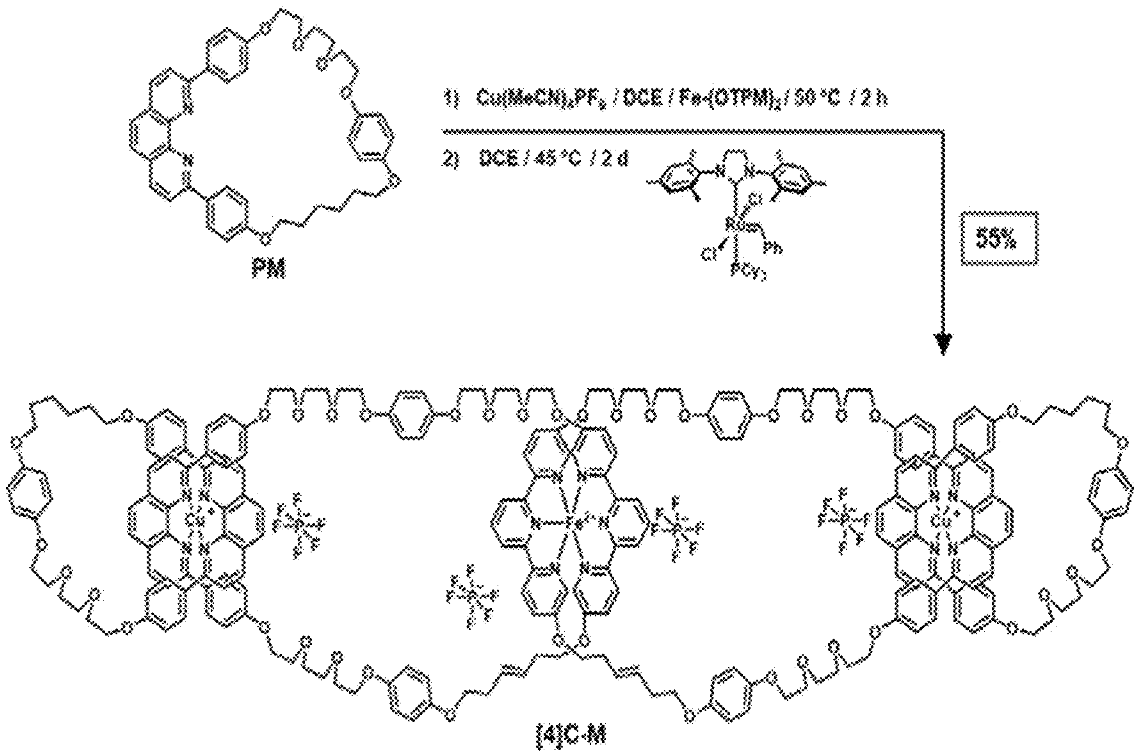
FIG. 12 depicts a detailed scheme for the one-pot synthesis of [4]catenate ([4]C-M).

A scheme of this synthesis is shown in FIG. 12. A solution of PM (0.0177 g, 0.02639 mmol, 5.0 eq.) was prepared in 5 mL $N_2$-purged dichloroethane (DCE) in an oven dried 25 mL RB flask under $N_2$. To this was added a solution of $Cu(MeCN)_4PF_6$ (0.0098 g, 0.02639 mmol, 5.0 eq.) in 1 mL $N_2$-purged anhydrous MeCN, which instantaneously resulted in a color change of the solution from light yellow to orange, indicative of the formation of the air sensitive mono-metalated copper-phenanthroline species. The solution was kept under intense $N_2$ air flow while stirring for 15 min before adding a solution of Fe-$(OTPM)_2$ (0.0176 g, 0.00622 mmol, 1.0 eq.) in 5 mL $N_2$-purged DCE via syringe. The dark red solution was then heated to 50° C. for 2 h. The solvent was then removed in order to remove the coordinating solvent MeCN. The crude mixture was re-dissolved in 10 mL DCE and Grubbs' $2^{nd}$ generation catalyst (0.0016 g, 0.00018 mmol, 0.3 eq.) in 1 mL DCE was added via syringe. The reaction mixture was then heated to 45° C. and the reaction progress was monitored via LRMS-ESI. After 24 h, an additional 0.3 eq. of Grubbs' $2^{nd}$ generation catalyst was added and the solution was heated for an additional 24 h. The reaction was then quenched with 1 mL EVE and 5 mL MeCN.

The solvent was removed via rotary evaporator and the crude mixture was redissolved in a minimal amount of $CH_2Cl_2$. The red solution was then precipitated with $Et_2O$, followed by centrifugation. The red solid was redissolved in a minimal amount of $CH_2Cl_2$ and the process was repeated. The crude red mixture was then purified via HPLC with 20 to 100% MeOH in $H_2O$/0.1% HCOOH in 15 min and then 100% MeOH up to 25 min at 15 mL·min$^{-1}$. The solvent was removed from the purified fractions and the red solid was redissolved in 5 mL MeCN. To this was added 5 mL saturated $KPF_6$ in water. The solution was stirred at room temperature for 0.5 h. The precipitated red solid was collected via vacuum filtration on celite. The cake was washed with 50 mL DI water and 50 mL $Et_2O$. The solid was then redissolved in MeCN and the solvent was removed to afford the product as a deep red solid (0.0161 g, 55%). The average yield for three reactions at this scale purified via HPLC is 50%.

$^1H$ NMR (500 MHz, DMSO-$d_6$): $\delta_H$ 8.94-8.83 (m, 4H), 8.63 (bs, 4H), 8.49 (d, J=5.3 Hz, 8H), 8.31 (bs, 2H), 8.11 (m, 4H), 8.01-7.89 (m, 8H), 7.76 (s, 4H), 7.58 (m, 4H), 7.50-7.33 (m, 16H), 7.04 (dd, J=24.2, 8.9 Hz), 6.96-6.43 (m), 6.12-5.93 (m, 16H), 5.35 (m, 4H), 4.28-3.12 (m), 2.18 (bs), 2.09 (s), 1.86-1.39 (m), 1.34 (m). $^{13}C$ NMR (125 MHz, DMSO-$d_6$): $\delta_C$ 159.5, 159.3, 156.1, 153.3, 153.2, 153.1, 152.9, 143.2, 137.6, 131.4, 129.1, 128.1, 127.9, 126.2, 124.6, 116.1, 116.0, 115.8, 115.7, 115.6, 115.2, 113.1, 113.0, 70.8, 70.6, 70.5, 70.4, 70.2, 70.1, 69.68, 69.65, 69.58, 69.4, 69.3, 69.2, 69.1, 68.7, 68.5, 68.1, 68.0, 67.8, 67.7, 67.6, 67.64, 67.57, 67.4, 30.9, 30.2, 29.0, 28.63, 28.58, 28.52, 25.7, 25.6, 25.5, 25.3. $^{19}F$ NMR (471 MHz, DMSO-$d_6$): $\delta_F$ −69.4, −70.9. LRMS-ESI: calculated for $C_{234}H_{238}Cu_2FeN_{14}O_{40}$: m/z=1016.4 $[M]^{4+}$, 1052.9 $[M+H+PF_6]^{4+}$; Found: 1017.2 $[M]^{4+}$, 1052.7 $[M+H+PF_6]^{4+}$. MALDI-TOF: calculated for $C_{234}H_{238}Cu_2FeN_{14}O_{40}$: m/z=3950.7 $[M-Fe-Cu]^+$, 2006.8 $[M-Fe]^{2+}$; Found: 3950.2 $[M-Fe-Cu]^+$, 2006.3 $[M-Fe]^{2+}$.

The mixture of diastereomers is a result of the asymmetric central rings and asymmetric endcap macrocycles. Since the macrocyclic ligands are asymmetric, there are two possible orientations that the ligand can bind to the metal center, leading to a total of six possible diastereomers. The directionality of each macrocycle was assigned by comparing the oxygen atoms on the hydroquinone linker. Oxygen A has higher priority in both macrocycles, which is represented in cartoon format by an arrow pointed towards oxygen A. No attempt was made to separate the possible diastereomers or confirm which diastereomers were synthesized in this study (see FIG. 8A).

Example 8. Detailed Synthesis of De-Metalation of [4]Catenate ([4]Q

Figure 13:
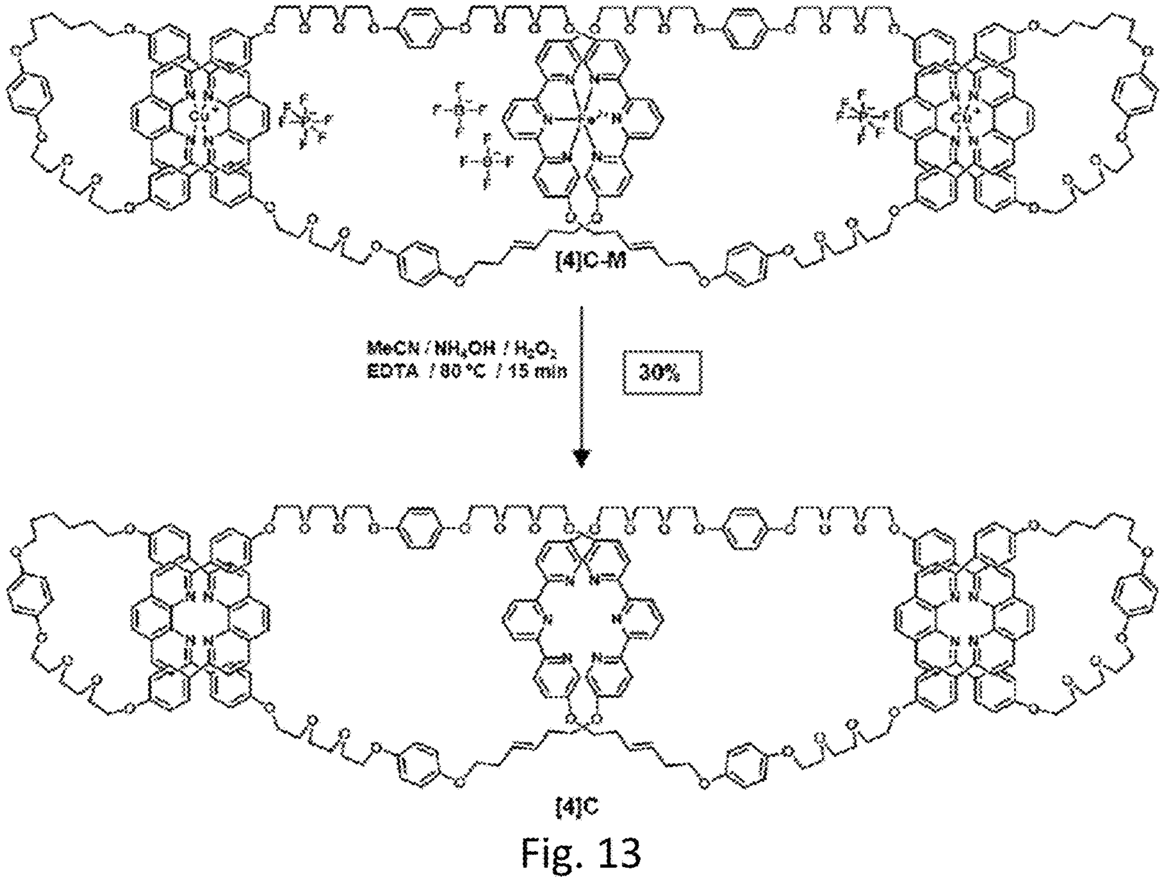
FIG. 13 depicts a detailed scheme for the de-metaliation of [4]catenate ([4]C).

A scheme of this synthesis is shown in FIG. 13. To a solution of [4]C-M (0.0051 g, 0.00113 mmol 1 eq.) in 10 mL MeCN was added 10 mL saturated sodium ethylenediaminetetraacetic acid (EDTA) dibasic, 2 mL saturated $NH_4OH$, and 2 mL 30% $H_2O_2$. The solution was heated to 80° C. for 15 minutes, at which point the color of the solution changed from red to colorless. The mixture was diluted with 50 mL $H_2O$ and extracted with 3×25 mL $CHCl_3$. The organic layer was dried over $Na_2SO_4$ and was filtered. The solvent was removed via rotary evaporator to afford an orange film, which was washed with 50 mL MeOH and 50 mL MeCN to remove any remaining metalated species, leaving the product behind as a faint orange-pink film (0.0013 g, 30%).

$^1H$ NMR (500 MHz, DMSO-$d_6$): $\delta_H$ 8.55-8.34 (m), 8.31 (s), 8.27-8.12 (m), 8.04-7.77 (m), 7.57-7.28 (m), 7.15 (d, J=8.5 Hz), 7.04 (bs), 7.01 (d, J=7.9 Hz), 6.93-6.57 (m), 6.08-4.40 (m), 4.31-3.33 (m), 1.35 (s), 1.24 (s). $^{13}C$ NMR (125 MHz, DMSO-$d_6$): $\delta_C$ 167.0, 160.1, 159.8, 159.7, 159.5, 154.9, 154.8, 154.5, 152.6, 152.5, 152.4, 147.8, 147.7, 145.3, 137.1, 137.0, 136.9, 131.7, 131.6, 131.4, 131.3, 131.2, 131.1, 128.7, 128.5, 127.3, 125.7, 121.3, 119.1, 118.9, 115.6, 115.3, 115.2, 115.1, 114.8, 114.7, 114.6, 114.5, 114.3, 69.9, 69.0, 68.8, 67.4, 38.1, 31.3, 29.8, 29.0, 28.7, 28.5, 28.4, 28.1, 25.1, 25.0, 23.2, 22.4, 14.9, 10.8. LRMS-ESI: calculated for $C_{234}H_{238}N_{14}O_{40}$: m/z=649.1 $[M+6H]^{6+}$, 660.5 $[M+Na(HCOO)+6H]^{6+}$, 778.8 $[M+5H]^{5+}$, 792.4 $[M+Na(HCOO)+5H]^{5+}$, 972.9 $[M+4H]^{4+}$, 989.9 $[M+Na(HCOO)+4H]^{4+}$, 1006.9 $[M+2Na(HCOO)+4H]^{4+}$; Found: m/z=648.4 $[M+6H]^{6+}$, 659.3 $[M+Na(HCOO)+6H]^{6-}$, 778.0 $[M+5H]^{5+}$, 790.5 $[M+Na(HCOO)+5H]^{5+}$, 972.4 $[M+4H]^{4+}$, 987.4 $[M+Na(HCOO)+4H]^{4-}$, 1003.7 $[M+2Na(HCOO)+4H]^{4+}$. MALDI-TOF: calculated for $C_{234}H_{238}N_{14}O_{40}$: m/z=3885.7, $[M+H]^+$, 1942.9 $[M+2H]^{2+}$, 1964.8 $[M+2Na]^{2+}$; Found: 3885.7 $[M+H]^+$, 1944.2 $[M+2H]^{2-}$, 1966.2 $[M+2Na]^{2+}$.

Upon removal of the metal ion templates, the macrocycles are able to move and rotate freely. However, the directionality of each macrocycle is preserved by the mechanical bonds. Therefore, six possible diastereomers remain after the demetallation of [4]C-M. No attempt was made to separate the possible diastereomers or confirm which diastereomers were synthesized in this study (see FIG. 8B).

Example 9. Detailed Stepwise Synthesis of Unsaturated [4]Catenate ([4]C-M-U)

Figure 14:
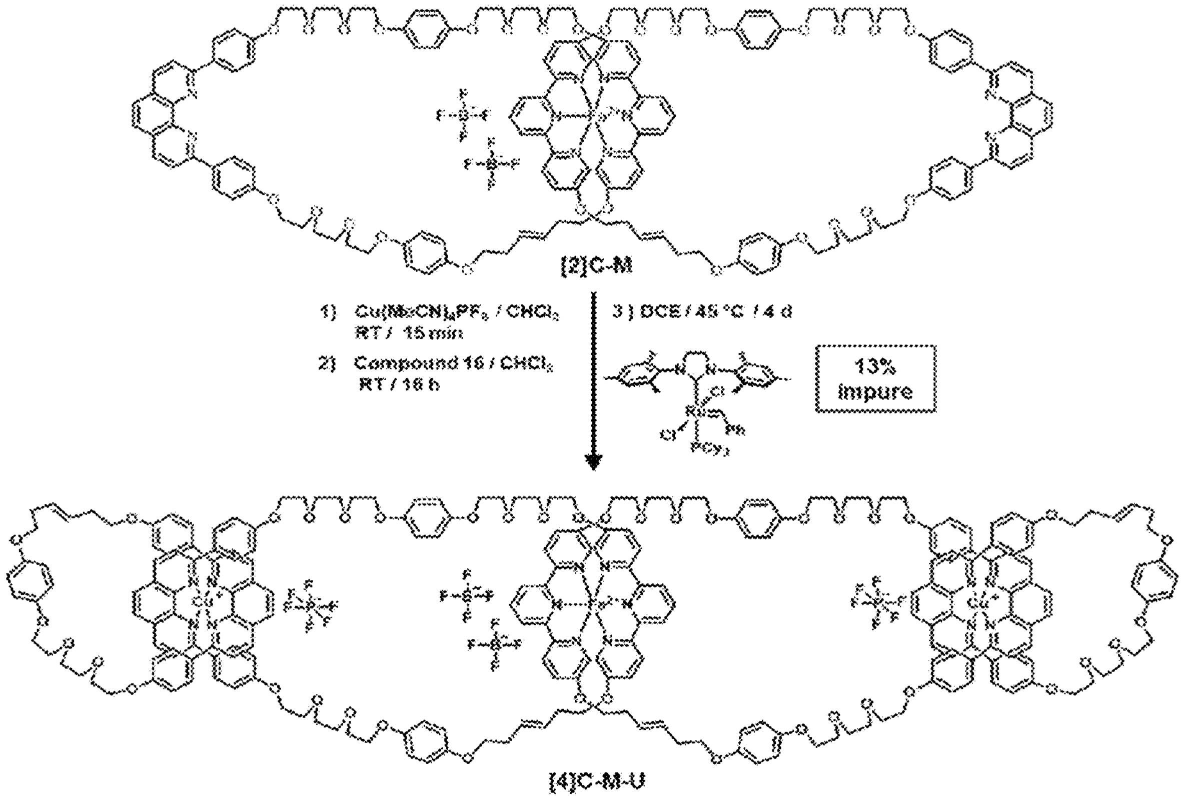
FIG. 14 depicts a detailed scheme for the stepwise synthesis of unsaturated catenate ([4]C-M-U).

A scheme of this synthesis is shown in FIG. 14. A solution of [2]C-M (0.0190 g, 0.00685 mmol, 1 eq.) was prepared in 5 mL $CHCl_3$. To this was added a solution of $Cu(MeCN)_4PF_6$ (0.0059 g, 0.0158 mmol, 2.3 eq.) in 1 mL anhydrous MeCN. The reaction was stirred under $N_2$ at RT for 20 min. A solution of 16 (0.0109 g, 0.0158 mmol, 2.3 eq.) in 1 mL $CHCl_3$ was added via syringe and the solution was continued to stir at RT under $N_2$ for 16 h. The solution was then diluted with 100 mL $CHCl_3$ and was washed with 50 mL DI $H_2O$. The organic layer was dried over $Na_2SO_4$ and was filtered. The solvent was removed to afford the pre-catenate complex as a red solid, which was re-dissolved in 25 mL DCE. A solution of Grubbs' 2nd catalyst (0.0006 g, 0.00069 mmol, 0.1 eq.) in 1 mL DCE was then added and the solution was heated to 45° C. while stirring under $N_2$. The reaction progress was monitored via LRMS-ESI and additional catalyst was added in 0.1 eq. increments every 12 to 16 h up to 0.5 eq. After 4 d of total heating, the reaction was quenched with 1 mL EVE and the solvent removed to afford the crude mixture as a red solid. The crude was purified via preparative TLC on silica (5% MeOH/$CH_2Cl_2$) and two subsequent silica columns ($CH_2$C12 to 8% MeOH/$CH_2Cl_2$). After exhaustive purification attempts, [4]C-M-U (0.004 g, 13%) was collected as a dark red solid; a large impurity remained, as evidenced by LRMS-ESI. Further characterization of this mixture was not attempted. LRMS-ESI: calculated for $C_{234}H_{238}Cu_2FeN_{14}O_{40}$: m/z=1015.9 $[M]^{4+}$; Found: 1016.1 $[M]^{4+}$.

The low yield and difficult purification for this "sequential" route to a linear catenate was the motivation to develop the one-pot approach of [4]C-M. The unsaturated internal olefins of [2]C-M may participate in an unwanted ring-opening metathesis polymerization (ROMP) during ring-closing metathesis to form unwanted oligomeric or branched products. Although the potential for ROMP could be avoided if [2]C-M was hydrogenated prior to forming the $Cu^+$ intermediate with 16, this would require an additional reaction and purification on an already synthetically challenging target, [2]C-M. Additionally, a smaller byproduct [2]catenate based on PM was also observed, which may contribute to the lower yield of [4]C-M-U relative to [4]C-M. These obstacles inherent to the sequential route of [4]C-M-U led us to develop a simpler one-pot approach requiring fewer synthetic steps for the synthesis of a very similar linear [4]catenate, [4]C-M.

Example 10. Molecular Modeling of [4]C-M

It can be seen in FIG. 9A, FIG. 9B, and Table 1 below that the terminal olefins on the same OTPM are relatively close to one another (less than 4.7 Å), while the shortest distance between olefins on adjacent OTPMs (2-3) is 6.08 Å.

TABLE 1

Distances between terminal carbons of terminal olefin groups.

| Interaction Between Olefins | Distance (Å) |
|---|---|
| 1-2 | 4.688 |
| 1-3 | 9.556 |
| 1-4 | 12.935 |
| 2-3 | 6.087 |
| 2-4 | 9.947 |
| 3-4 | 4.422 |

Figure 9C:
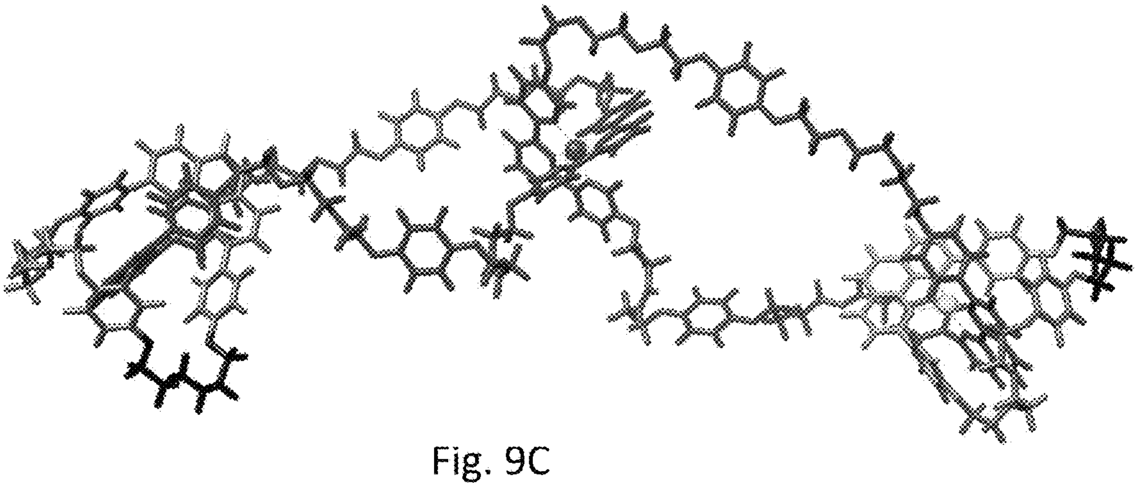
FIG. 9C depicts a molecular model (Spartan'18, MMFF) of the of [4]C-M.

The close proximity between olefins 1-2 and 3-4 favors the formation of the desired linear [4]catenate product, [4]C-M. In order to make the hypothetical figure-of-eight like [3]catenate, olefins 1-3 and 2-4 would both have to undergo RCM. This is unlikely to happen since these distances are more than twice as far away as compared to the olefin distances required for the linear [4]catenate product. Although the distance between 2-3 is relatively short, RCM of 1-4 would also be required to generate the figure-of-eight like [3]catenate. Additionally, no partially ring-closed products were observed by mass spectrometry (FIG. 3B) and the terminal olefins were consumed as evidenced by $^1H$ NMR (FIG. 6). Therefore, it is very likely that the linear [4]catenate was isolated, which is consistent with the lack of shifting in the GPC traces (FIG. 5D) and the fragmentation patterns observed by MALDI (FIG. 7A-7B). A molecular model (Spartan'18, MMFF) of the [4]C-M is also shown (FIG. 9C).

Example 11. Materials and Methods [6]Catenane/ate

The materials and methods of this Example were used in Examples 11-15.

All reagents were purchased from commercial suppliers and used without further purification unless stated otherwise. Metal sources $Fe(BF_4)_2 \cdot 6\ H_2O$ and $Cu(MeCN)_4PF_6$ were purchased from Sigma-Aldrich. Modified literature procedures were employed in the synthesis of compounds 4-6 and 9 (Colley, et al., 2020). All reactions were performed under $N_2$ using common Schlenk techniques. Column chromatography was carried with silica gel (Sorbtech, 0.040-0.063 mm) or neutral alumina (Sorbtech, Act. 1, 0.050-0.2 mm) or basic alumina (Sorbtech, Act. 1, 0.050-0.2 mm). All ring-closing reactions were done using Grubb's 2nd generation catalyst (Chem Scene).

Recycling preparative gel permeation chromatography (prep-GPC) was performed on a Japan Analytical Industry LaboACE instrument with one JAIGEL-2HR column and one JIAGEL-2.5HR column in sequence, running with dimethylformamide (DMF) at 8 $mL \cdot min^{-1}$ as the mobile phase. All nuclear magnetic resonance (NMR) spectra were recorded on Varian Inova-500 spectrometer at 25° C., with working frequencies of 500 (1H) and 125 (13C) MHz. Chemical shifts are reported in ppm relative to the signals corresponding to the residual non-deuterated solvents: $CDCl_3$: $\delta_H$=7.26 ppm and $\delta_C$=77.16 ppm.

Ultraviolet-Visible (UV-Vis) absorbance spectra were recorded on an Agilent Cary 5000 spectrophotometer with a quartz cuvette (1.0 cm pathlength). Analytical GPC analyses were performed on an Agilent 1260 Infinity setup with two Shodex GPC KD-806M columns in sequence in DMF mobile phase (0.025 M LiBr) running at 60° C. at 1.0 mL·min-1. The differential refractive index (dRI) of each compound was monitored using a Wyatt Optilab T-rEX detector. Analytical HPLC analyses were performed on an Avant 2000 HPLC with a Shodex Asahipak ODP-50-2D reverse-phase column with a gradient mobile phase of $H_2O$ with 0.1% trifluoracetic acid (TFA) and acetonitrile (MeCN) with 0.1% TFA running at 40° C. at 0.2 $mL \cdot min^{-1}$, which was in series with an Advion Expression-L Compact Mass Spectrometer; UV-vis absorbance was recorded at 254 nm.

Low-resolution mass spectrometry electrospray ionization (LRMS-ESI) was recorded on an Advion Expression-L Compact Mass Spectrometer. High-resolution mass spectrometry electrospray ionization (HRMS-ESI) was recorded on a Waters Synapt G2 HDMS or a Bruker maXis 4G UHR-TOF mass spectrometer. Tandem high-resolution mass spectrometry electrospray ionization (THRMS-ESI) was recorded on a Bruker maXis 4G Q-TOF mass spectrometer. Matrix-assisted laser desorption/ionization time-of-flight mass spectrometry (MALDI-TOF-MS) was recorded on a Bruker Solaris 12T FT-MS; samples were prepared using 2,5-dihydroxybenzoic or α-cyano-4-hydroxycinnamic acid matrices.

Example 12. Methods Summary [6]Catenane/ate

Synthesis of Linear [6]Catenane [6]C

A solution of endcap [2]catenate 15 (0.0601 g, 0.0284 mmol, 4.0 eq.) was prepared in 10 mL $N_2$-purged anhydrous MeCN in an oven dried 50 mL round bottom (RB) flask. To this was added a solution of $Cu(MeCN)_4PF_6$ (0.0105 g, 0.028 mmol, 4.0 eq.) in 3 mL $N_2$-purged anhydrous MeCN. The solution was stirred at room temperature for 0.5 h under $N_2$ atmosphere before the addition of a solution of 9 (0.022 g, 0.0077 mmol, 1.0 eq.) in 7 mL $N_2$-purged anhydrous MeCN via syringe. The dark red solution was continued to stir under $N_2$ atmosphere for 2.5 d. The solvent was removed via rotary evaporator and the crude was taken up in 100 mL $CH_2Cl_2$. The organics were washed with 3×50 mL DI $H_2O$ and was dried over $Na_2SO_4$. The dark red solution was filtered, and the filtrate was concentrated via rotary evaporator to afford the pre-[6]catenate complex as a dark red film, which was used without further purification. The crude pre-[6]catenate complex was redissolved in 25 mL anhydrous $CH_2Cl_2$ in a 100 mL RB flask and a solution of Grubbs' $2^{nd}$ generation catalyst (0.0013 g, 0.0015 mmol, 0.2 eq.) in 1 mL $CH_2Cl_2$ was added. The flask was fitted with a Vigreux column and was heated to 35° C. while stirring under $N_2$ atmosphere. After 18 h, an aliquot was taken and quenched with ethyl vinyl ether. The reaction was deemed complete by $^1H$ NMR and the remaining reaction mixture was quenched with 1 mL ethyl vinyl ether and 5 mL MeCN. The solvent was then removed via rotary evaporator to afford the crude [6]catenate mixture as a dark red film. In order to remove non-interlocked structures and simplify the purification process, the $Fe^{2+}$ and $Cu^+$ templates were removed. The $Fe^{2+}$ ion was removed from the crude mixture with addition of a weak inorganic base and moderate heating, while Cu-ion was removed in a second step by the addition of a strongly competing ligand. The crude film was redissolved in 25 mL in a 100 mL RB flask. Solid $K_2CO_3$ (1.0 g, 7.23 mmol, 1000 eq.) was added and the suspension was heated to 75° C. for 1 d while stirring open to air. The solvent was removed via rotary evaporator and 50 mL MeCN was added to the reaction mixture. A solution of KCN (0.2 g, 3.07 mmol, 400 eq.) in 10 mL $H_2O$ was added via syringe. The suspension was stirred open to air at room temperature for 0.5 h. The suspension was diluted with 300 mL $CH_2Cl_2$. The organics were washed with 3×100 mL DI $H_2O$, dried over $Na_2SO_4$, and filtered. The solvent was removed via rotary evaporator and the crude was redissolved in 4 mL GPC grade DMF. The solution was filtered via syringe filter and was purified via recycling preparative GPC with DMF mobile phase. The mixed fractions were also collected and repurified. The linear [6]catenane [6]C was isolated as a yellow/orange film (0.0122 g, 25% based on 9).

GPC

Recycling preparative gel permeation chromatography (prep-GPC) was performed on a Japan Analytical Industry LaboAce instrument with one JAIGEL-2HR column and one JIAGEL-2.5HR column in sequence, running with DMF at 8 $mL \cdot min^{-1}$ as the mobile phase. Analytical GPC analyses were performed on an Agilent 1260 Infinity setup with two Shodex GPC KD-8060 columns in sequence, running with DMF (0.025 M LiBr) at 1 $mL \cdot min^{-1}$ as the mobile phase. The differential refractive index (dRI) of each compound was monitored using a Wyatt Optilab T-rEX detector.

HPLC

Analytical HPLC analyses were performed on an Avant 2000 HPLC with a Shodex Asahipak ODP-50-2D reverse phase column with a gradient mobile phase of $H_2O$ with 0.1% trifluoracetic acid (TFA) and MeCN with 0.1% TFA running at 0.2 $mL \cdot min^{-1}$, which was in series with an Advion Expression-L Compact Mass Spectrometer. UV-vis absorbance was recorded at 254 nm.

Tandem High-Resolution Mass Spectrometry Electrospray Ionization (THRMS-ESI)

THRMS-ESI mass spectra were recorded on a Bruker maXis 4G Q-TOF mass spectrometer.

MALDI-Time-of-Flight (MALDI-TOF)

MALDI-TOF mass spectra were recorded on a Bruker Solaris 12T FT-MS; samples were prepared using 2,5-dihydroxybenzoic or α-cyano-4-hydroxycinnamic acid matrices.

Example 13. [6]Catenane/ate Synthesis and Characterization

Herein is described a molecular "zip-tie" synthetic strategy (FIG. 15), a series of sequential, orthogonal metal templation steps, where dual-ligand macrocyclic precursors were complexed with two transition metal ions (iron(II) and copper(I)) and pre-formed macrocycles or [2]catenanes. In the final step, two simultaneous RCM reactions on the pre-catenate metal complexes yielded well-defined, [2n+2] oligo[n]catenanes. The sequential metal-coordinated assembly of the precursors prevented the formation of unwanted figure-of-eight topologies that often arise during intermolecular RCM reactions, a critical outcome that was shown by comparing the products generated from [2]- and [4]catenane syntheses. The full utility of the "zip-tie" strategy was demonstrated by synthesizing a linear [6]catenane. This represents the highest number of interlocked macrocycles ever reported for a linear, unimolecular catenane.

Figure 15:
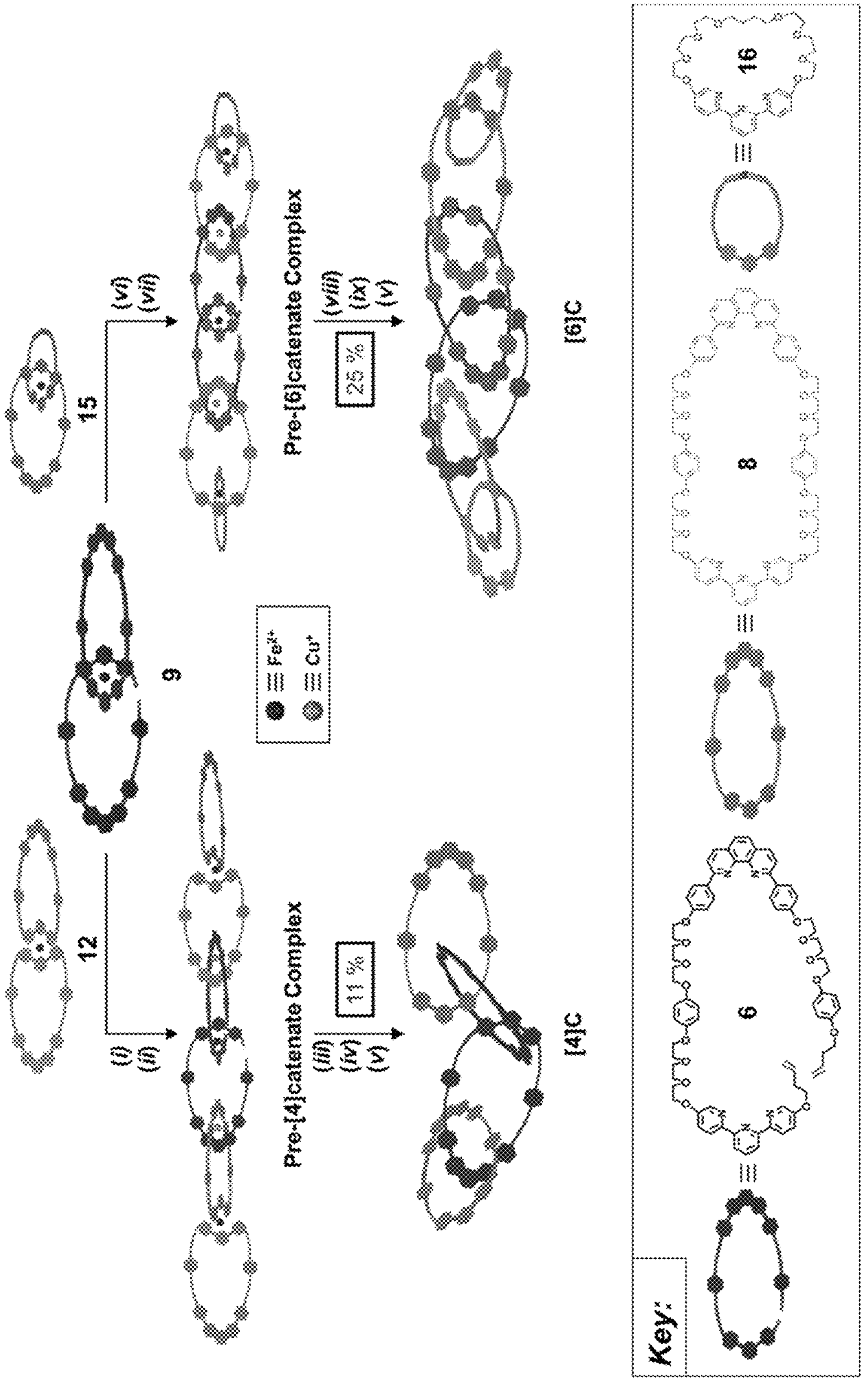
FIG. 15 depicts an overview of the "zip-tie" strategy to synthesize linear [2n+2]catenanes. (n is the number of interlocked macrocycles). (i) 12, $Cu(MeCN)_4PF_6$, MeCN, 25° C., 30 min; (ii) $Cu^+$-12, 50% $MeCN/CH_2Cl_2$, 25° C., 1 d; (iii) Grubbs' $2^{nd}$ generation catalyst, $CH_2Cl_2$, 35° C., 2 d; (iv) $Cs_2CO_3$, DMF, 75° C., 1 d; (v) KCN, $MeCN/H_2O$, 25° C., 30 min; (vi) 15, $Cu(MeCN)_4PF_6$, MeCN, 25° C., 30 min; (vii) $Cu^+$-15, MeCN, 25° C., 2.5 d (viii) Grubbs' $2^{nd}$ generation catalyst, $CH_2Cl_2$, 35° C., 18 h; (ix) $K_2CO_3$, DMF, 75° C., 1 d.
Figure 16A:
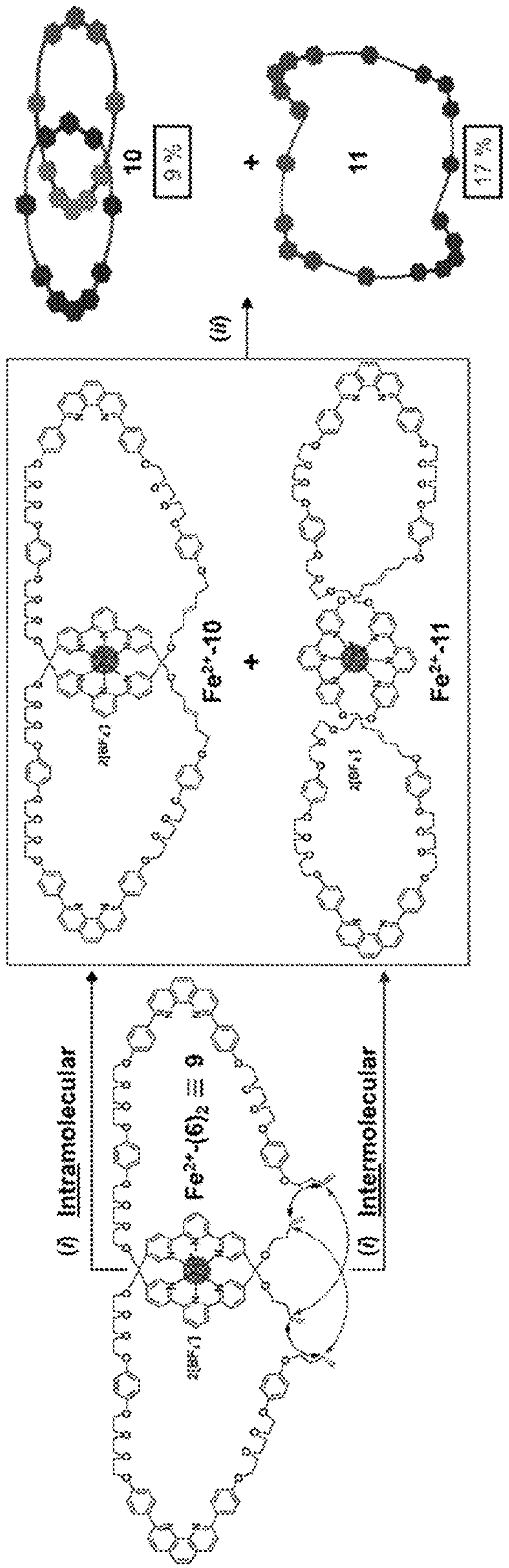
FIG. 16A depicts synthesis of topological isomers 10 and 11. (i) Grubbs' $2^{nd}$ generation catalyst, $CH_2Cl_2$, 35° C., 1 d; (ii) $Cs_2CO_3$, DMF, 75° C., 1 d.
Figure 16B:
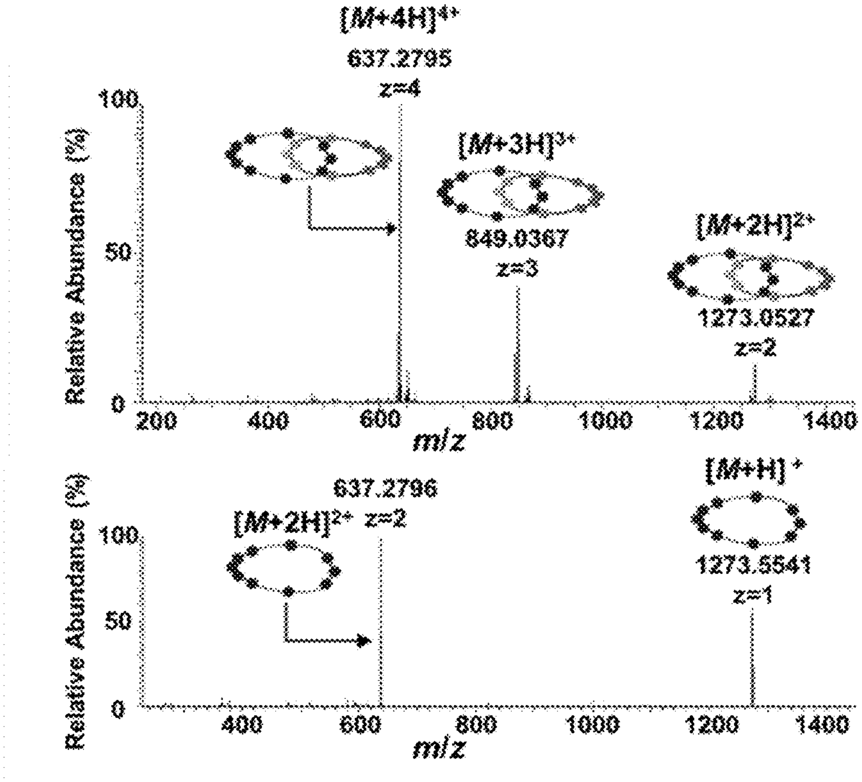
FIG. 16B depicts tandem high-resolution mass spectrometry-electrospray ionization (THRMS-ESI, i.e., MS/MS) of 10. The $[M+3H]^{3+}$ peak was isolated, and its fragmentation data is shown in the bottom spectrum.
Figure 16C:
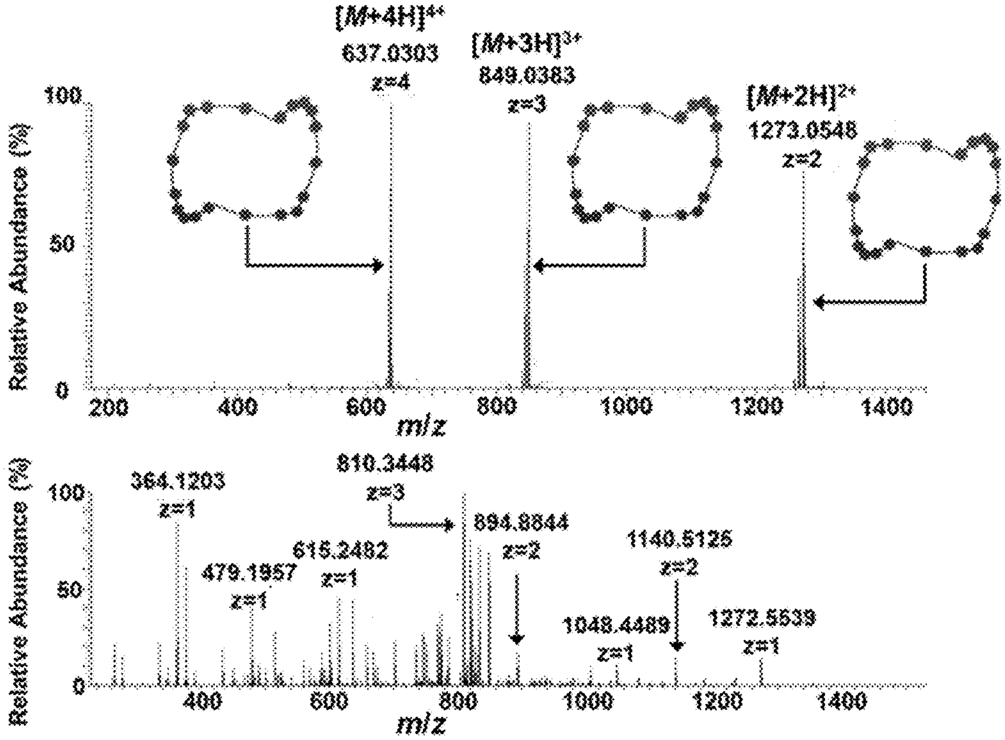
FIG. 16C depicts THRMS-ESI of 11; the $[M+3H]^{3+}$ peak was isolated, and its fragmentation data is shown in the bottom spectrum.

A process to achieve higher-order linear catenanes by using a preformed catenane building block that can undergo further catenation was envisioned. The synthesis of dual-ligand open macrocycle 6 (FIG. 15) and its iron(II) complex 9 (FIG. 16A) is also described above (Examples 1-10). The synthesis and spectroscopic characterization of all precursors and catenanes is described in full detail in Examples 1-10. Open macrocycle 6 contains tridentate terpy and bidentate phen ligands, which preferentially bind bivalent and monovalent metals, respectively. Asymmetric short and long olefin-functionalized linkers were also implemented in an attempt to mitigate the intermolecular metathesis reaction that leads to topologically trivial figure-of-eights, while still promoting intramolecular ring-closing to afford the desired [2]catenane topology. Despite these efforts, the double-RCM reactions of 9 with second-generation Grubbs' catalyst (FIG. 16A) afforded the figure-of-eight product 11 and the [2]catenane 10 in a nearly 2:1 ratio. Moreover, due to the asymmetric nature of 6, both 10 and 11 were isolated as a racemic mixture. To simplify the purification process, the mixture of ring-closed products was demetalated with a suspension of $Cs_2CO_3$ in DMF at 75° C. The metal-free topological isomers were separated via recycling preparative-GPC. The identity of the isolated fractions was determined by MS/MS experiments (FIG. 16B-16C), where in each case, the $[M+3H]^{3+}$ adduct was isolated and fragmented until the parent adduct was consumed. The cleavage of any bond in one of the macrocycles that make up 10 should produce an intact macrocycle, which is what was observed (FIG. 16B, lower spectrum) as the major species in the MS/MS experiment. However, the fragmentation of 11 generated a complex mass spectrum with a wide range of fragments (FIG. 16C, lower spectrum). These fragmentation patterns are consistent with those observed previously (Yee et al., 2019), where differentiated linear oligo[n]catenanes were also differentiated from their figure-of-eight counterparts.

The predominate isolation of 11 over 10 led to the hypothesis that the flexible glycol-based linkers in 9 favored intermolecular ring-closings instead of the desired intramolecular reaction (FIG. 16A), ultimately yielding the figure-of-eight product as the major topological isomer. It was hypothesized that if the flexible linkers could be 'rigidified' (FIG. 16D), the intermolecular RCM reaction would become less favorable. Instead of making chemical modifications to 6 to achieve this goal, it was envisaged complex 9 could be 'rigidified' by non-covalently threading on the macrocycle dimer $Cu^+$-12 before ring closing to afford (FIG. 16D) a pre-[4]catenate complex. Thus, under topological control, the resultant pre-[4]catenate complex (FIG. 16D) can spatially arrange the olefin linkers to favor intramolecular RCM reactions over unproductive intermolecular pathways.

Figure 16D:
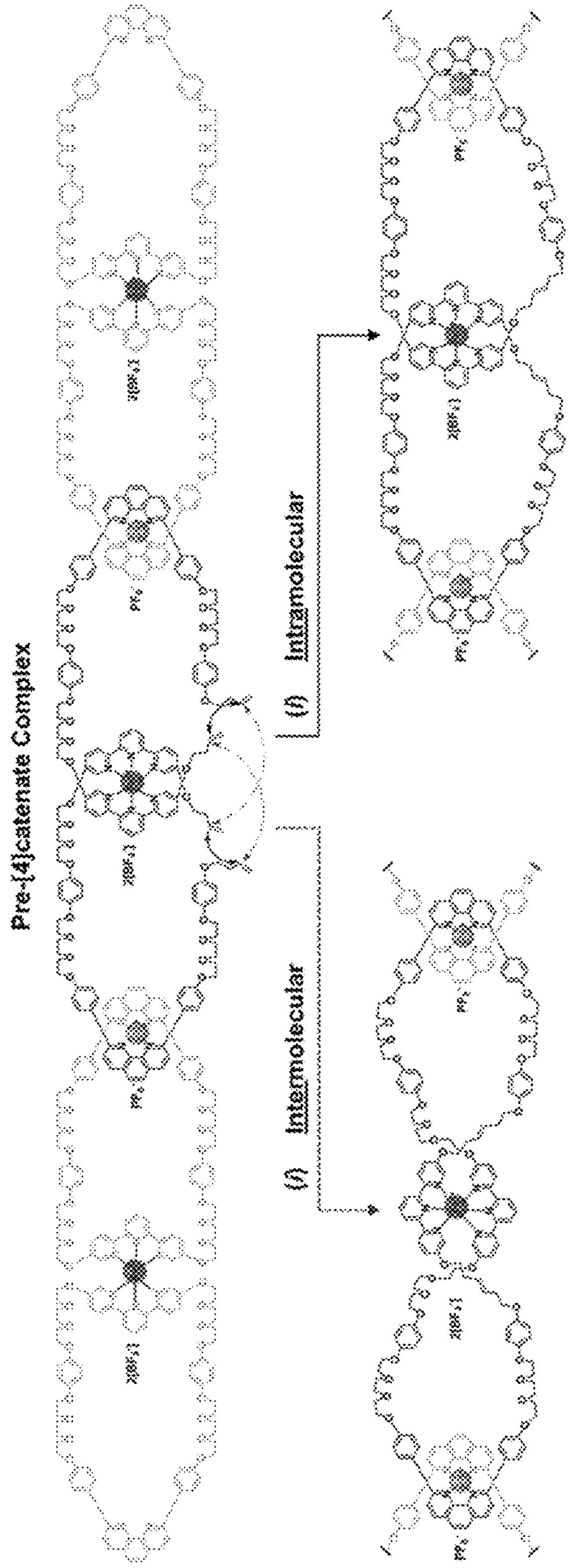
FIG. 16D depicts "zip-tie" synthesis of [4]C through self-assembly of iron complex 9 and macrocycle dimer $Cu^+$-12 under topological control favors intramolecular ring closing and thus the preferred catenane topology.
Figure 17A:
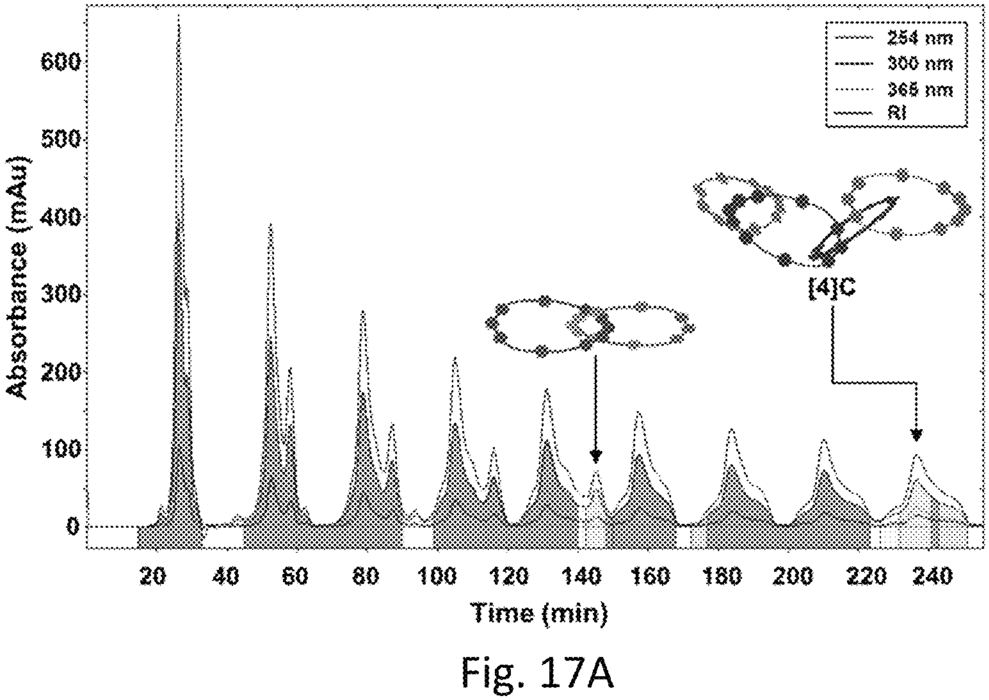
FIG. 17A depicts the preparative GPC data for [4]C (second injection) was collected in a DMF mobile phase at 8 $mL \cdot min^{-1}$. Pure [4]C was isolated in the blue fraction at 235 min.

The "zip-tie" strategy has been demonstrated to synthesize four mechanically bonded molecular rings after two one-pot RCM reactions; however, in that case the smaller, mono-functionalized phen-based macrocycles at each termini prevented further syntheses of higher order catenanes. In order to alleviate this issue, the "zip-tie" approach was adapted using macrocycle 8 (FIG. 15) to synthesize the linear [4]catenane [4]C composed of four large terpy-phen-containing macrocycles (FIG. 15). Initial efforts to directly complex macrocycle 8 with 9 were unsuccessful because 8 collapses during mono-metalation, producing a heteroleptic $Cu^+$-phen-terpy complex[25]. This unwanted complexation was circumvented by first "blocking" the terpy ligands with $Fe^{2+}$ to give the dimeric macrocycle complex 12 (FIG. 15). With the terpy ligands occupied, the phen ligands of 12 were readily mono-metalated with $Cu(MeCN)_4PF_6$ to give $Cu^+$-12. The air-sensitive complex was stirred under $N_2$ atmosphere at 25° C. for 15 minutes before adding a solution of 9 to form the pre-[4]catenate complex (FIG. 15 and FIG. 16D). Following RCM reactions with Grubbs' catalyst, conversion to [4]C was confirmed by $^1H$ NMR. The crude ring-closed products were demetalated in a two-step process (FIG. 15) using $Cs_2CO_3$ in DMF to remove $Fe^{2+}$, followed by KCN in $MeCN/H_2O$ to remove $Cu^+$. After an aqueous workup, the demetalated mixture was purified via recycling preparative GPC (FIG. 17A) to afford [4]C, which was isolated in an 11% yield over the final three steps (i.e., complexation, ring-closing, and demetallation).

Figure 17B:
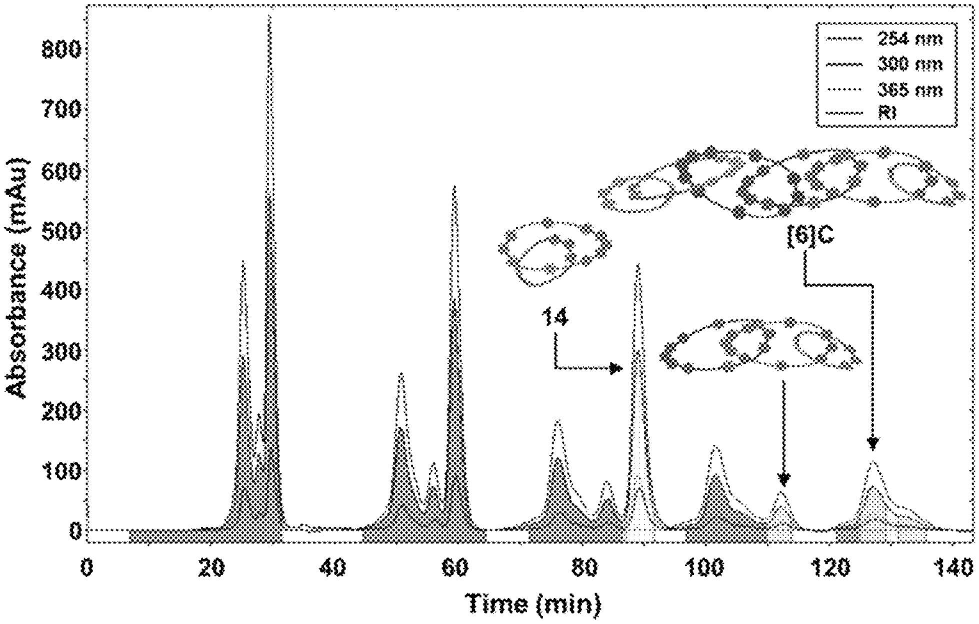
FIG. 17B depicts the preparative GPC data for [6]C (b) was collected in a DMF mobile phase at 8 $mL \cdot min^{-1}$. Pure [6]C was isolated in the green fraction at 125 min.
Figure 17C:
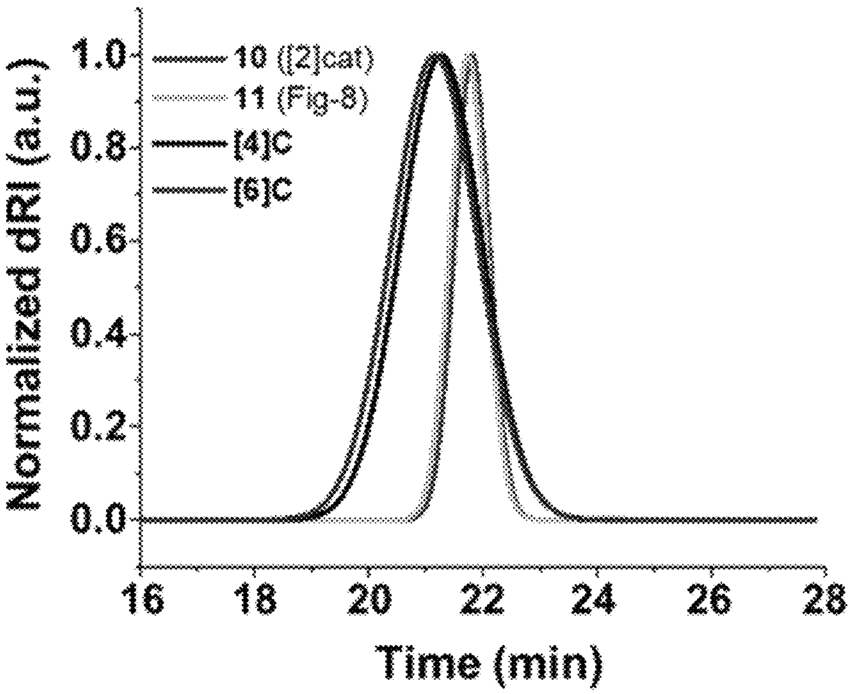
FIG. 17C depicts an overlay of analytical GPC traces (normalized dRI) of [4]C and [6]C in DMF with 0.025 M LiBr at 60° C.
Figure 17D:
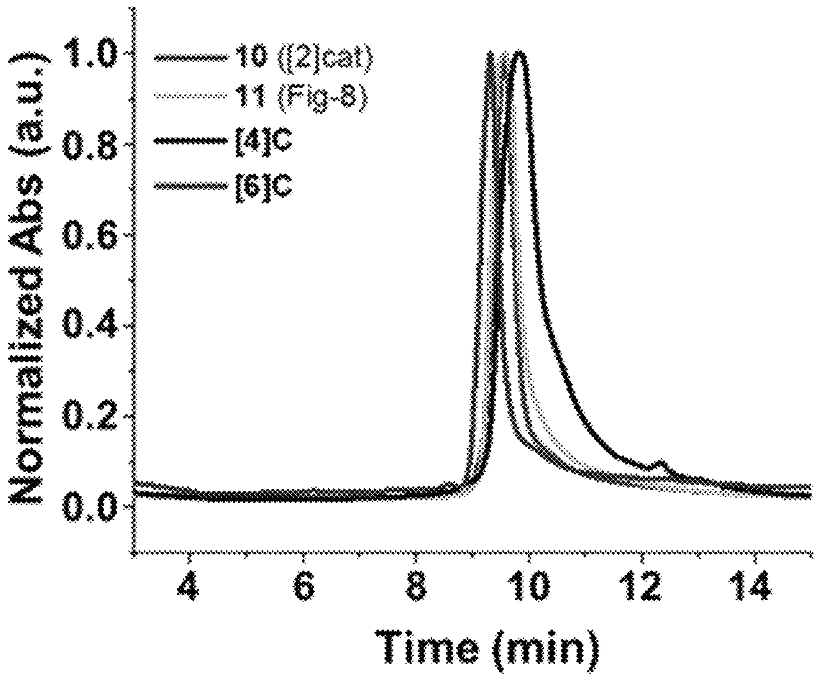
FIG. 17D depicts verlay of analytical HPLC traces (normalized absorbance at 254 nm) with a gradient mobile phase of $MeCN/H_2O$ (0.1% TFA): 5 to 100% in 10 min and 100% for 15 min at 40° C.
Figure 18A:
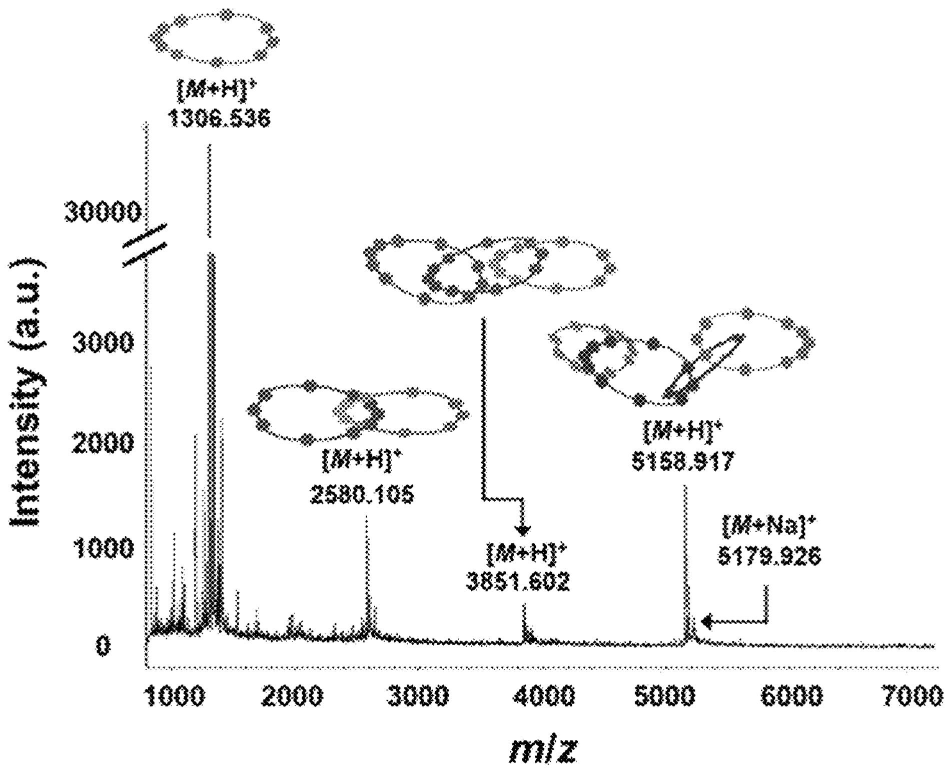
FIG. 18A depicts MALDI-TOF-MS of [4]C with α-cyano-4-hydroxycinnamic acid matrix.
Figure 18B:
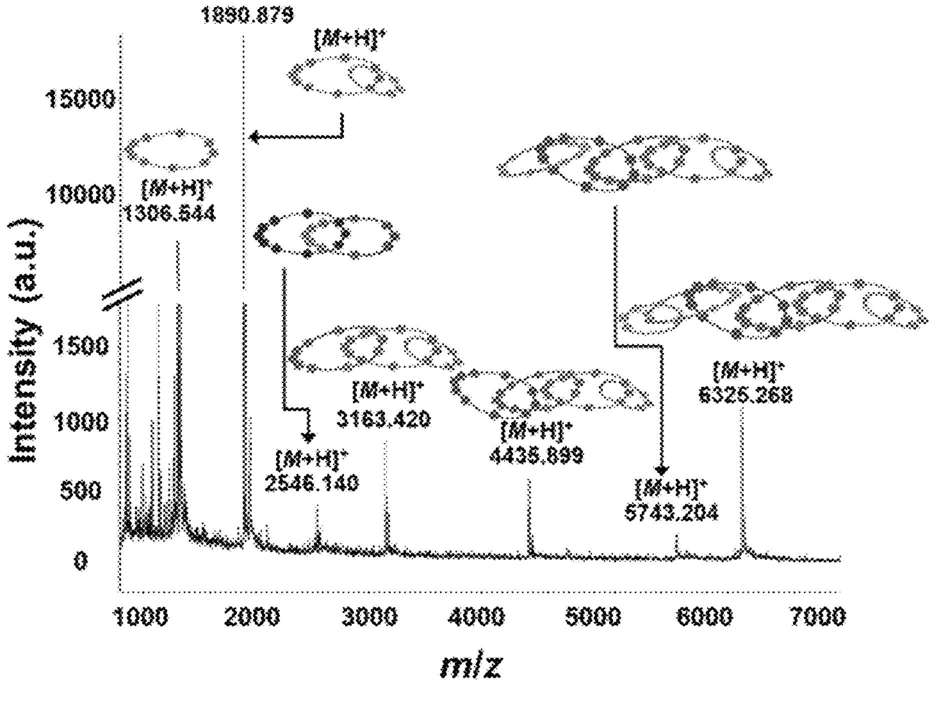
FIG. 18B depicts MALDI-TOF-MS of [6]C with α-cyano-4-hydroxycinnamic acid matrix.
Figure 18C:
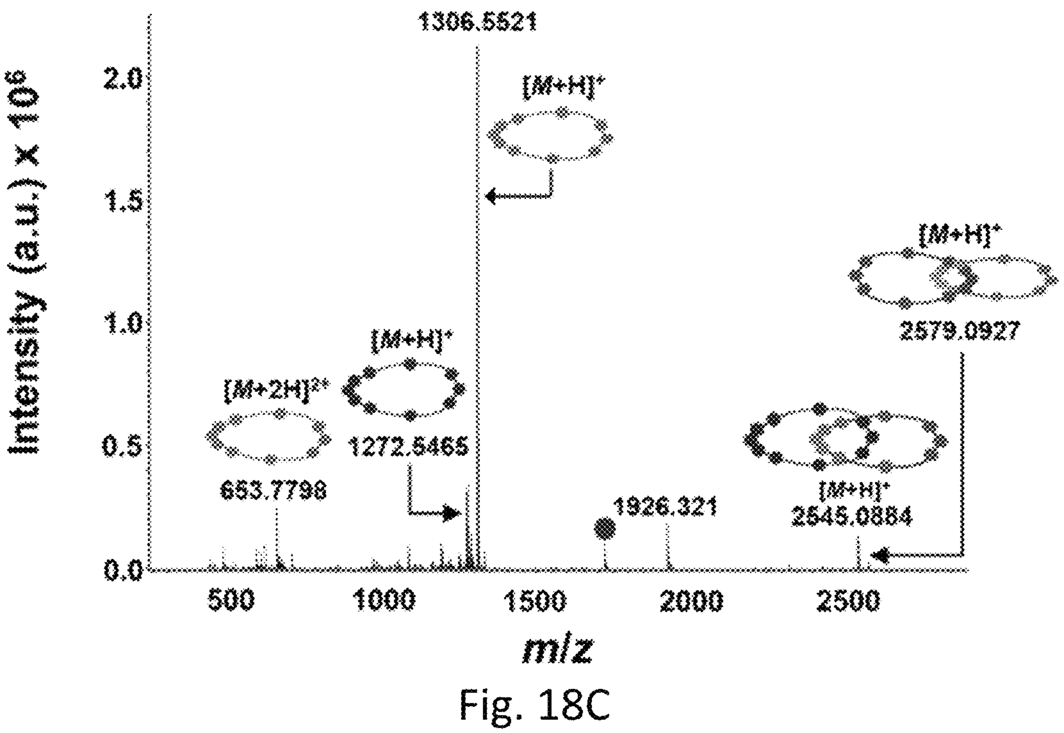
FIG. 18C depicts THRMS-ESI (i.e., MS/MS) of [4]C; the $[M+3H]^{3+}$=1720 Da peak (red dot) was isolated and fragmented.

The purity of [4]C was confirmed by the narrow and unimodal analytical GPC traces (FIG. 17C) and HPLC traces (FIG. 17D), as well as by $^1H$ NMR. The topology of [4]C was confirmed using spectrometric methods, whereby MALDI-TOF-MS of [4]C (FIG. 18A) showed a prominent peak for the corresponding parent molecular ion $[M+H]^+$, as well as the macrocycle and catenane fragments. The asymmetric [2]catenane fragment at m/z=2579 Da could have only originated from the linear [4]catenane, as opposed to the hypothetical [3]catenane derived from the figure-of-eight topological isomer. A similar fragmentation pattern was observed during MS/MS of [4]C (FIG. 18C), in which the $[M+3H]^{3+}$ adduct was isolated and fragmented. In addition to the asymmetric [2]catenane, the ring-closed product of 6 was also observed, both of which can only originate from the pathway to [4]C. In contrast with the RCM reaction of complex 9, in which intramolecular and intermolecular pathways occur concurrently to produce a 2:1 ratio of figure-of-eight to catenane products, the "zip-tie" approach involving two $Cu^+$-12's threaded onto 9 exclusively produced only the catenane product [4]C and no figure-of-eights.

Figure 18D:
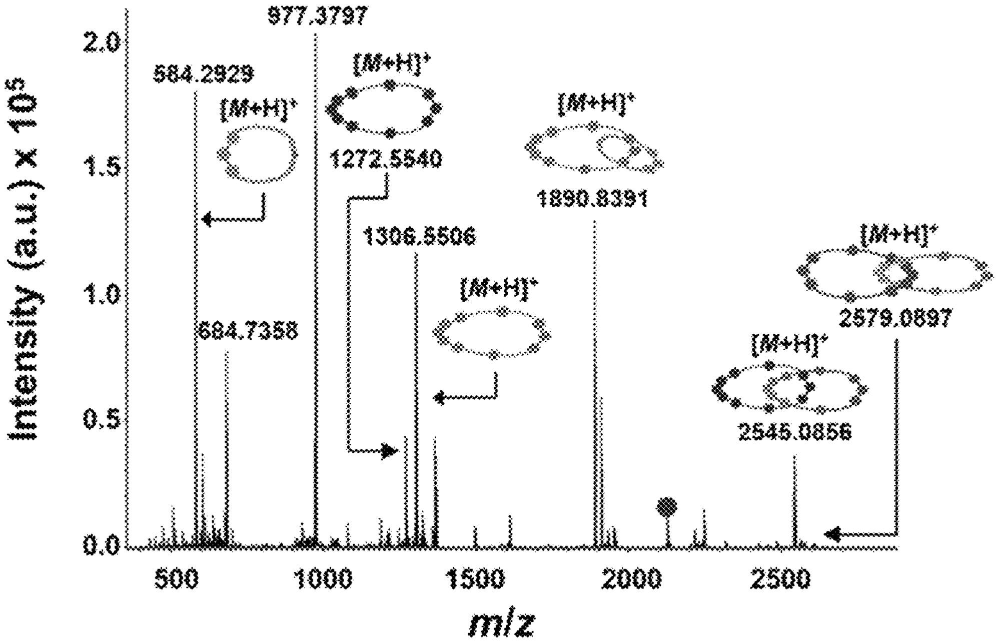
FIG. 18D depicts THRMS-ESI of [6]C; the $[M+3Na]^{3+}$ =2130 Da peak (red dot) was isolated and fragmented.

The full versality of the "zip-tie" approach was demonstrated by substituting the endcap macrocycles (8) in [4]C with pre-formed [2]catenanes (15) to synthesize a linear [6]catenane [6]C (FIG. 15). Compound 15, bearing an open phen-coordination site, was synthesized and mono-metalated with $Cu^+$, analogous to the synthesis of [4]C. A solution of 9 was added to $Cu^+$-15 via syringe, and the dark red solution was allowed to stir under $N_2$ atmosphere for 2.5 days to ensure formation of the pre-[6]catenate complex consisting of two $Cu^+$-15 catenates threaded onto complex 9. Next, RCM with Grubbs' catalyst was carried out on the pre-[6]catenate complex in anhydrous $CH_2Cl_2$ under mild heating. The crude ring-closed products were demetalated (FIG. 15) and purified via recycling preparative GPC (FIG. 17B) to afford [6]C, which was isolated in a 25% yield over the final three steps. The purity of [6]C was verified using analytical GPC (FIG. 17C) and HPLC (FIG. 17D), as well as $^1H$ NMR. Due to its higher molecular weight, [6]C exhibited a shorter retention time by GPC compared to [4]C, 10, and 11. MALDI-TOF-MS of [6]C (FIG. 18B) displayed clear peaks for the parent molecular ion $[M+H]^+$ and the various [n]catenane fragments. The [3]catenane fragment at m/z=3163 Da is distinctive to the linear [6]catenane topology because a hypothetical [5]catenane derived from the figure-of-eight topological isomer could not fragment in this manner. Further evidence for the topology of [6]C was obtained via MS/MS experiments (FIG. 18D), in which the $[M+3H]^{3+}$ adduct was isolated and fragmented. The asymmetric [2]catenane fragment at m/z=2579 Da and the ring-closed macrocycle from 6 at m/z=1272 Da could only be observed by fragmentation of [6]C. The detection of these fragmented species by MALDI-TOF-MS and MS/MS, combined with analytical chromatography methods, provide definitive evidence for the successful synthesis and isolation of the unimolecular, linear [6]catenane. As observed with the synthesis of [4]C, the topological control afforded by the "zip-tie" method again prevented intermolecular ring-closing and yielded only the expected catenane product [6]C and no figure-of-eights.

Example 14. Detailed Synthesis of Open and Closed Macrocyclic Ligands for Catenane/ate a) Mono-Allyl Triethylene Glycol (1)

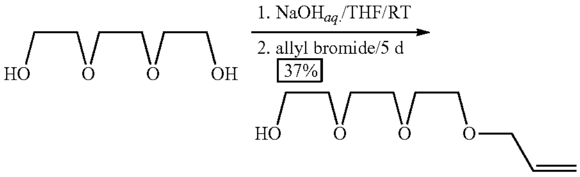

1

A solution of triethylene glycol (25.00 g, 150.2 mmol, 1.0 eq.) was prepared in 300 mL tetrahydrofuran (THF) in a 1 L round-bottom (RB) flask with a stir bar. While stirring, a solution of NaOH (4.66 g, 116.5 mmol, 0.7 eq.) in 25 mL DI $H_2O$ was added. The solution was cooled using an ice bath before adding a solution of allyl bromide (24.2 g, 17.3 mL, 199.8 mmol, 1.2 eq.) in 200 mL THF via slow addition funnel over the course of several hours. The reaction was allowed to warm up to room temperature while stirring open to air for 5 d. The solvent was then removed via rotary evaporator and the crude yellow sludge was taken up in 500 mL dichloromethane ($CH_2Cl_2$). The organic layer was washed with 2×200 mL DI $H_2O$ and 2×200 mL brine. The organics were dried over $Na_2SO_4$ and filtered. The solvent was removed via rotary evaporator to afford the product as a light yellow oil (10.5 g, 37%).

$^1H$ NMR (500 MHz, $CDCl_3$): $\delta_H$ 5.97-5.87 (m, 1H), 5.31-5.15 (m, 2H), 4.03 (d, J=5.7 Hz, 2H), 3.75-3.71 (m, 2H), 3.71-3.65 (m, 6H), 3.64-3.59 (m, 4H). $^{13}C$ NMR (125 MHz, $CDCl_3$): $\delta_C$ 134.7, 117.1, 72.5, 72.3, 70.7, 70.6, 70.4, 69.4, 61.7.

b) Mono-Allyl Triethylene Glyco Mesyl (2)

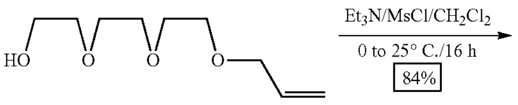

1

-continued

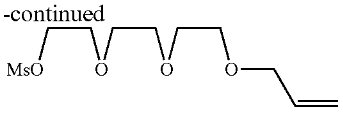

2

A solution of 1 (10.47 g, 55.1 mmol, 1.0 eq.) and triethylamine ($Et_3N$) (29.2 g, 40.0 mL, 288.6 mmol, 5.2 eq.) was prepared in 500 mL $CH_2Cl_2$ in a 2 L RB flask fitted with a slow addition funnel and containing a stir bar. The solution was cooled using an ice bath before adding a solution of mesyl chloride (MsCl) (19.2 g, 13.0 mL, 167.9 mmol, 3.0 eq.) in 300 mL $CH_2Cl_2$ via slow addition funnel over the course of 2 h. The reaction was allowed to warm up to room temperature while stirring overnight. After 16 h, the crude was washed with 5×200 mL 1M HCL. The organics were dried over $Na_2SO_4$ and filtered. The solvent was removed via rotary evaporator to afford the crude as an orange oil. Silica column chromatography ($CH_2Cl_2$ to 3% MeOH/$CH_2Cl_2$) of the crude material afforded the product as a yellow oil (12.4 g, 84%).

$^1H$ NMR (500 MHz, $CDCl_3$): $\delta_H$ 5.87-5.78 (m, 1H), 5.23-5.07 (m, 2H), 4.32-4.27 (m, 2H), 3.93 (dt, J=5.6, 1.4 Hz, 2H), 3.73-3.67 (m, 2H), 3.63-3.49 (m, 8H), 3.00 (s, 3H). $^{13}C$ NMR (125 MHz, $CDCl_3$): $\delta_C$ 134.6, 116.8, 71.9, 70.39, 70.37, 70.32, 69.3, 69.2, 68.8, 37.5. LR-ESI: calculated for $C_{10}H_{20}O_6S$: m/z=291.1 $[M+Na]^+$; Found: 291.2 $[M+Na]^+$.

c) Di-Allyl Triethylene Glycol Terpy (3)

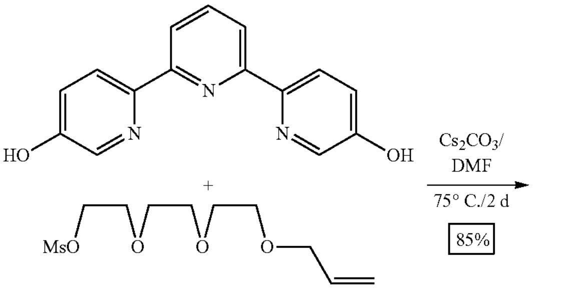

2

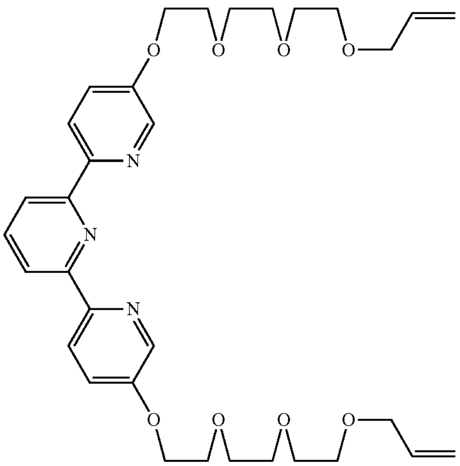

3

A suspension of terpyridine diol (1.50 g, 5.65 mmol, 1.0 eq.) and $Cs_2CO_3$ (9.2 g, 28.3 mmol, 5 eq.) was prepared in 200 mL DMF in a 1 L RB flask with a stir bar. While stirring under $N_2$, the suspension was heated to 75° C. before adding a solution of 2 (4.6 g, 16.95 mmol, 3 eq.) in 300 mL DMF via slow addition funnel over the course of 1 h. The reaction temperature was kept at 75° C. while stirring under $N_2$ for 2 d. The reaction mixture was allowed to cool to room temperature and was filtered via gravity filtration to remove insoluble inorganic salts. The filtrate was concentrated via rotary evaporator. The crude was resuspended in 300 mL $CH_2Cl_2$ and was washed with 3×100 mL brine. The organics were dried over $Na_2SO_4$ and filtered. The solvent was removed via rotary evaporator to afford the crude as a yellow oil. Basic alumina column chromatography (50% hexanes/$CH_2Cl_2$ to 1% MeOH/$CH_2Cl_2$) of the crude material afforded the product as a bright yellow oil (2.9 g, 85%).

$^1$H NMR (500 MHz, $CDCl_3$): $\delta_H$ 8.54 (d, J=8.8 Hz, 2H), 8.40 (d, J=2.8 Hz, 2H), 8.30 (d, J=7.8 Hz, 2H), 7.88 (t, J=7.8 Hz, 1H), 7.38 (dd, J=8.8, 2.9 Hz, 2H), 5.96-5.87 (m, 2H), 5.30-5.14 (m, 5H), 4.29-4.23 (m, 4H), 4.02 (dt, J=5.7, 1.3 Hz, 4H), 3.95-3.90 (m, 4H), 3.76 (dd, J=4.6, 2.0 Hz, 4H), 3.73-3.66 (m, 8H), 3.61 (dd, J=6.0, 3.6 Hz, 4H). $^{13}$C NMR (125 MHz, $CDCl_3$): $\delta_C$ 155.5, 155.1, 149.5, 137.8, 137.2, 134.9, 122.0, 121.8, 119.7, 117.20, 72.4, 71.1, 70.8, 69.8, 69.6, 68.1. MALDI-TOF: calculated for $C_{33}H_{43}N_3O_8$: m/z=610.3 $[M+H]^+$; Found: 610.5 $[M+H]^+$ (2,5-dihydroxybenzoic acid matrix).

d) Terpy HQ Phenol (4)

An alternative synthesis of compound 4 is described above. Herein is reported an improved synthetic method; terpyridine diol and mono tosylated bis(triethylene glycol) hydroquinone were prepared according to the above in Examples 1-10. A suspension of terpyridine diol (1.51 g, 5.68 mmol, 3.0 eq.) and $Cs_2CO_3$ (9.3 g, 28.4 mmol, 15.0 eq.) was prepared in 250 mL DMF in a 500 mL RB flask. The suspension was heated to 100° C. while stirring under $N_2$ for 1 h. The reaction mixture was then cooled to 75° C. before adding a solution of mono tosylated bis(triethylene glycol) hydroquinone (1.00 g, 1.91 mmol, 1.0 eq.) in 150 mL DMF via slow addition over several hours. The reaction temperature was kept at 75° C. while stirring under $N_2$ for a total of 4 d. The reaction mixture was then allowed to cool to room temperature and the suspension was filtered via gravity filtration to remove solid inorganic salts. The solvent was then removed via rotary evaporator to afford the crude as a black oily mixture. To the crude was added 300 mL 1M $CH_3COOH$. The suspension was sonicated and then stirred at room temperature for 1 day before dilution with 300 mL $CH_2Cl_2$. The aqueous layer was then extracted with 3×100 mL $CH_2Cl_2$. The organics were dried over $Na_2SO_4$ and were filtered. The solvent was then removed via rotary evaporator to afford the crude product as a brown oil. The crude oil was redissolved in 18 mL GPC grade DMF and was purified via recycling prep-GPC with DMF over 5 injections to afford the asymmetric product as a brown oil (0.57 g, 49%). $^1$H NMR is consistent with the results described above.

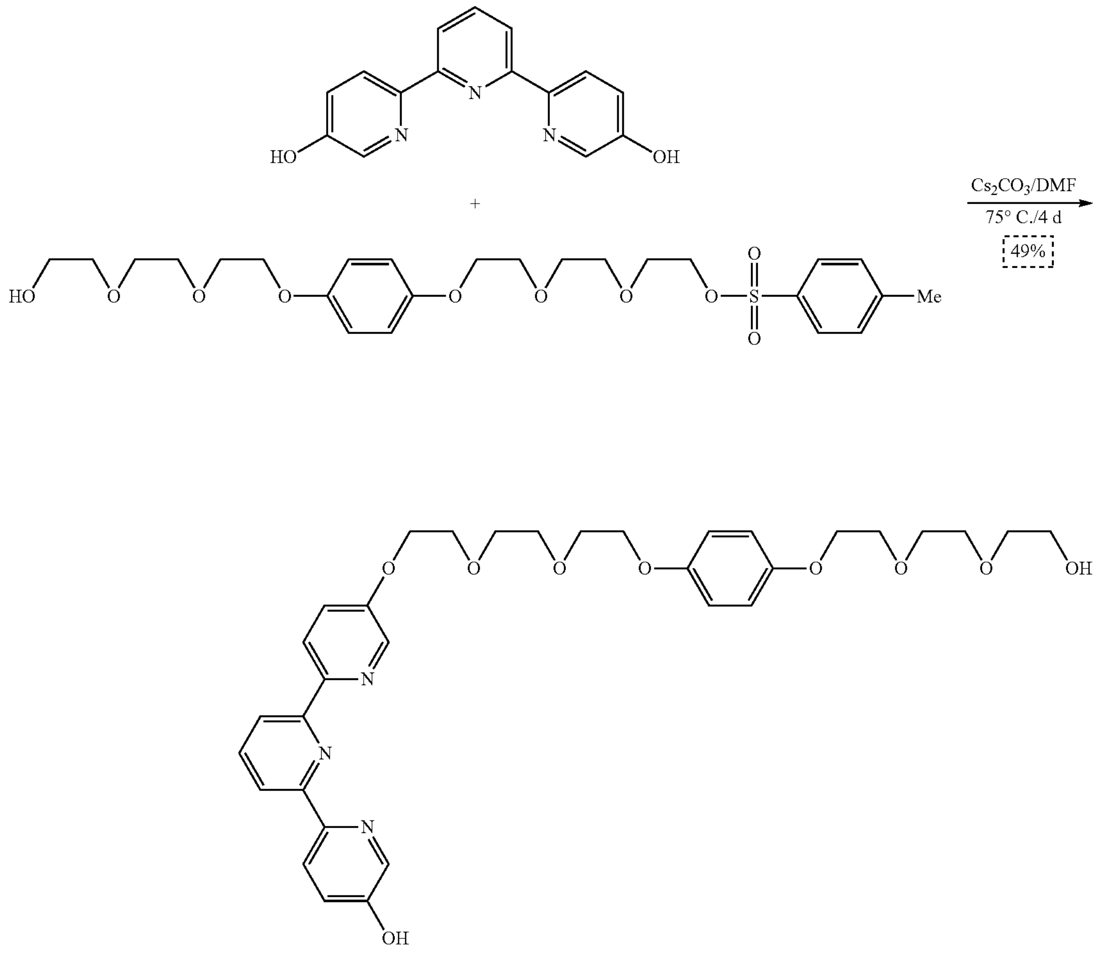

4 e) Phen HQ Olefin (5)

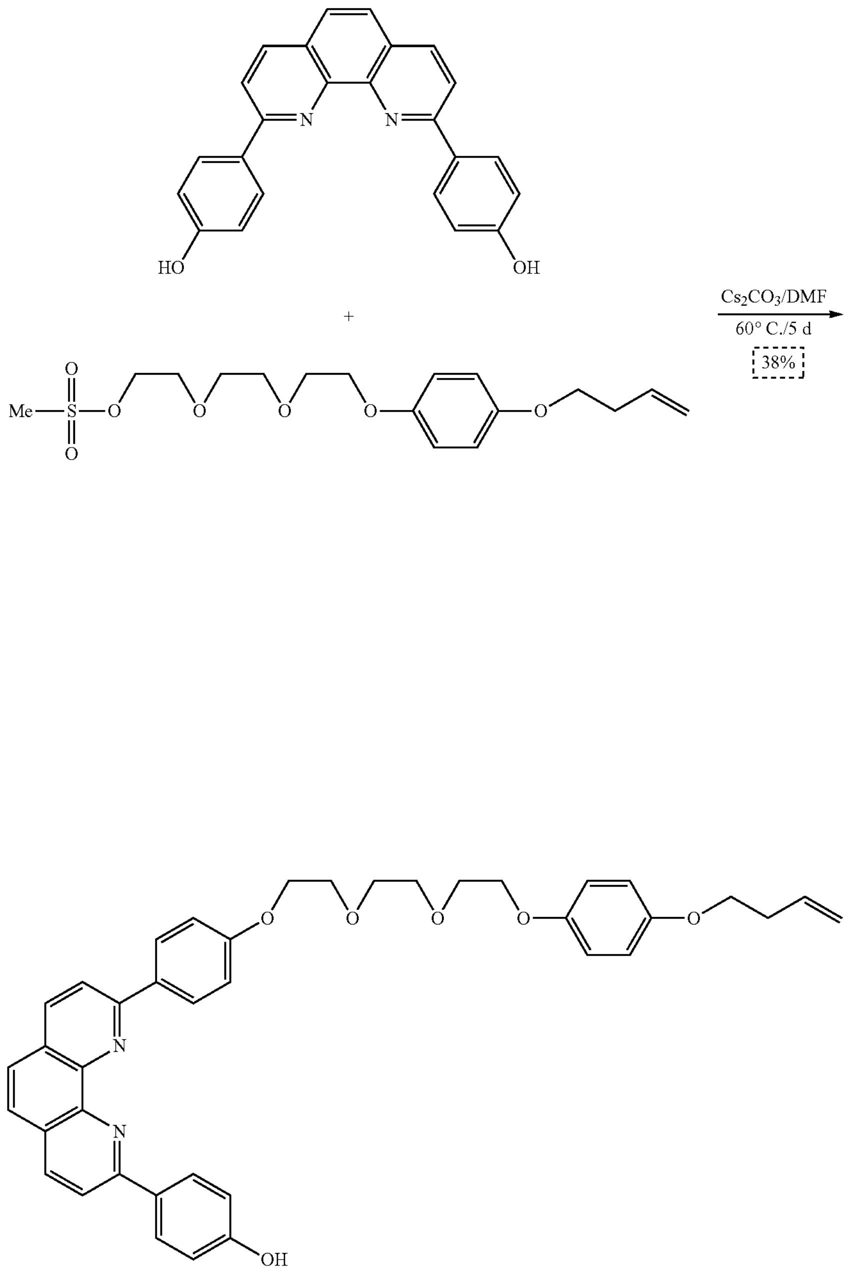

5

An alternative synthesis of compound 5 is described above. Herein is reported an improved synthetic protocol; phenanthroline (phen) diol and mesylated triethylene glycol hydroquinone olefin were prepared according to the above in Examples 1-10. A suspension of phen diol (3.30 g, 9.05 mmol, 2.5 eq.) and $Cs_2CO_3$ (1.73 g, 5.30 mmol, 1.5 eq.) was prepared in 250 mL DMF in a 500 mL RB flask and was heated to 60° C. while stirring under $N_2$. A solution of mono mesylated triethylene glycol hydroquinone olefin (1.33 g, 3.56 mmol, 1.0 eq.) in 50 mL anhydrous DMF was added via syringe pump at 3 $mL{\cdot}h^{-1}$. After heating for a total of 5 d, the reaction solvent was removed via rotary evaporator. To the crude was added 400 mL 10% $MeOH/CH_2Cl_2$. The suspension was stirred at room temperature overnight. The suspension was then filtered via vacuum filtration over a 150 mL fritted funnel with medium porosity. The filtrate was concentrated via rotary evaporator. The crude sludge was taken up in 300 mL $CH_2Cl_2$, which caused unreacted phenanthroline diol starting material to precipitate as an orange solid. The starting material was collected via vacuum filtration. The filtrate was concentrated and was purified via silica column chromatography with a very slow gradient ($CH_2Cl_2$ to 2% $MeOH/CH_2Cl_2$). The product was recovered as a sticky orange solid (0.87 g, 38%). $^1H$ NMR is consistent with the results described above.

f) Open Terpy-Phen Macrocycle (6)

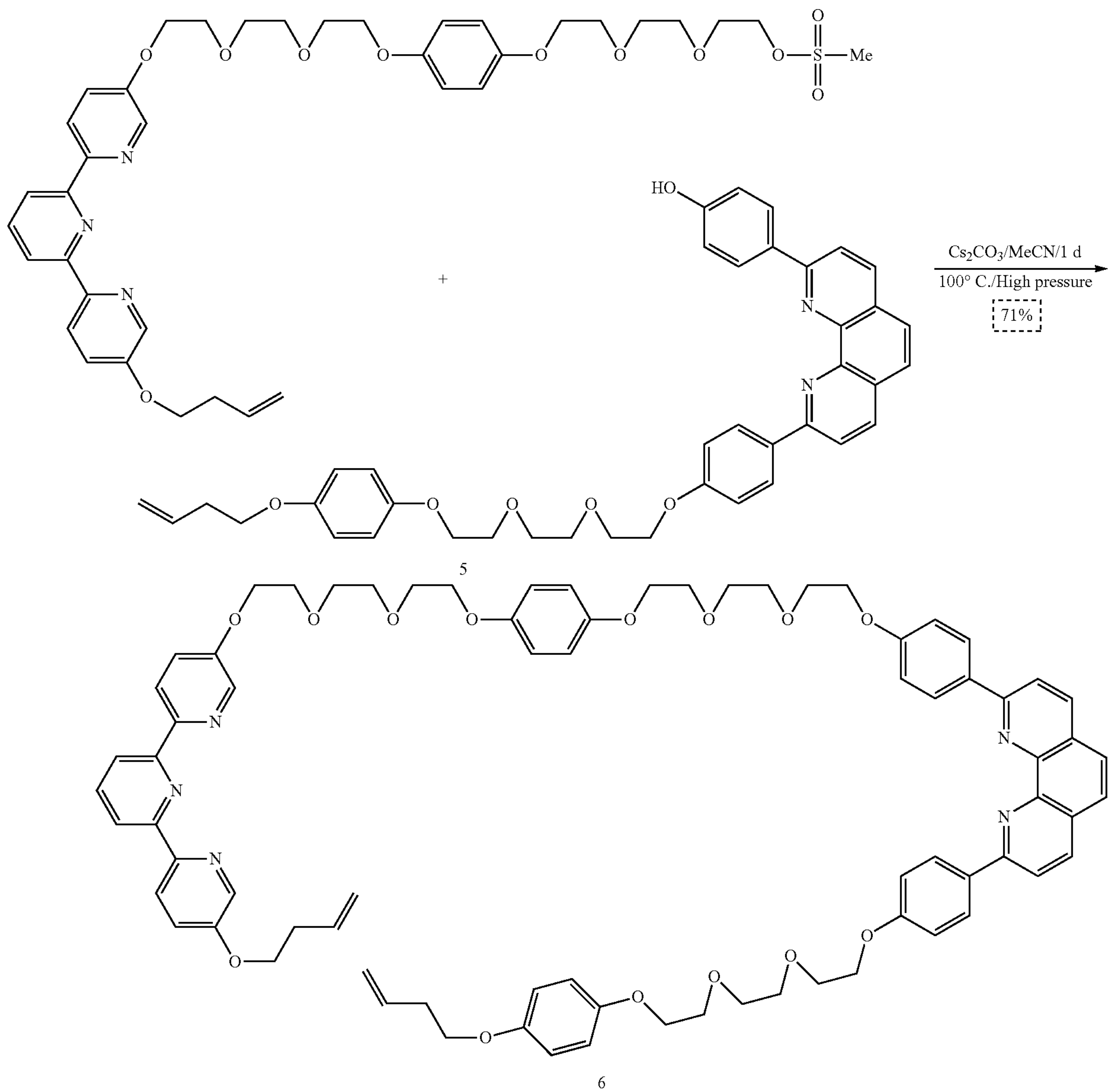

5

6

An alternative synthesis of 6 is described above in Examples 1-10. Herein is reported an improved and scaled synthetic protocol; mesylated terpyridine olefin was prepared according to the above.

Compound 5 (0.55 g, 0.86 mmol, 1.2 eq.) and mesylated terpyridine olefin (0.54 g, 0.715 mmol, 1.0 eq.) was transferred to a 100 mL high-pressure flask (Kemtech) using a minimal amount of $CH_2Cl_2$. The solvent was removed via rotary evaporator and the resulting foam was dried on high vacuum for 2 h. Solid $Cs_2CO_3$ (1.16 g, 3.56 mmol, 5.0 eq.) was added to the vessel, followed by the addition of 40 mL anhydrous MeCN and a stir bar. The vessel was sealed with a Teflon screw cap and was heated to 100° C. for 1 d. After 1 d, the reaction was allowed to cool to room temperature. The crude suspension was diluted with 400 mL $CH_2Cl_2$ and was washed with 3×100 mL brine. The organics were dried over $Na_2SO_4$ and were filtered. The solvent was removed via rotary evaporator to afford crude product as an orange film. Basic alumina column chromatography ($CH_2Cl_2$ to 3% MeOH/$CH_2Cl_2$) of the crude material afforded the product as a sticky orange solid (0.66 g, 71%). $^1$H NMR is consistent with the results described above.

g) Terpy HQ Triethylene Glycol Mesyl (7)

Figure 19:
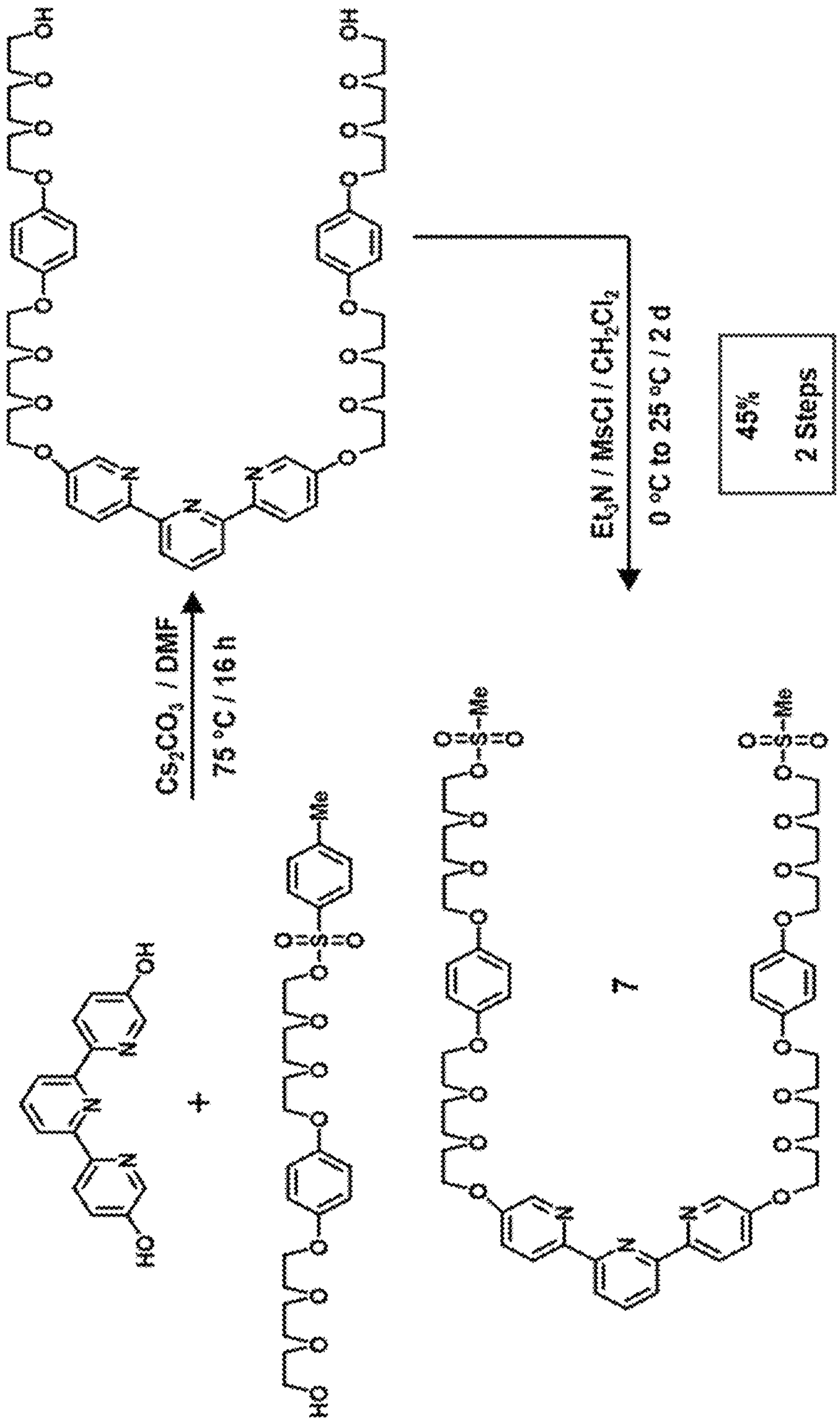
FIG. 19 depicts a detailed scheme for the synthesis of terpy HQ triethylene glycol mesyl.

This synthetic scheme is shown in FIG. 19.

Step 1: A suspension of terpyridine diol (0.50 g, 1.87 mmol, 1.0 eq.) and $Cs_2CO_3$ (3.71 g, 11.38 mmol, 6.0 eq.) was prepared in 400 mL DMF in a 1 L RB flask fitted with a slow addition funnel. A solution of mono tosylated bis (triethylene glycol) hydroquinone (2.98 g, 5.65 mmol, 3.0 eq.) in 200 mL DMF was added via slow addition over 2 h. The reaction was heated to 75° C. while stirring under $N_2$. After 16 h, the solvent was removed by rotary evaporator and the crude product was taken up in 300 mL $CH_2Cl_2$. The organics were washed with 3×100 mL brine, dried over $Na_2SO_4$, and filtered. The filtrate was concentrated via rotary evaporator and was transferred to a 50 mL centrifuge tube. $Et_2O$ was added to precipitate the product out of solution as a white solid and the product was collected via centrifugation. The supernatant was decanted off and the white solid pellet was redissolved in a minimal amount of $CH_2Cl_2$. The precipitation and centrifugation processes were repeated a second time. The pellet was then dried on high vacuum and was taken forward to mesylation without further purification.

Step 2: Stoichiometry assumes full conversion for previous step. A solution of crude terpyridine hydroquinone triethylene glycol (1.87 mmol, 1.0 eq.) and $Et_3N$ (2.85 g, 3.9 mL, 28.2 mmol, 15 eq.) was prepared in 150 mL $CH_2Cl_2$ in a 500 mL RB flask fitted with a stir bar. The solution was cooled using an ice bath under $N_2$ before adding a solution of mesyl chloride (MsCl) (2.15 g, 1.45 mL, 18.76 mmol, 10 eq.) in 100 mL $CH_2Cl_2$ via slow addition funnel. The reaction was allowed to warm up to room temperature while stirring under $N_2$ for 2 d. The solution was then diluted with 300 mL $CH_2Cl_2$ and was washed with 3×100 mL 1 M $CH_3COOH$ and 2×100 mL aqueous saturated $NaHCO_3$. The organics were dried over $Na_2SO_4$ and were filtered. The solvent was removed via rotary evaporator. The crude was redissolved in 25 mL GPC grade DMF and was filtered. It was then purified via recycling prep-GPC with DMF over 5 injections to afford the product as a white solid (0.97 g, 45% over two steps).

$^1H$ NMR (500 MHz, $CDCl_3$): $\delta_H$ 8.53 (d, J=8.8 Hz, 2H), 8.39 (d, J=2.9 Hz, 2H), 8.29 (d, J=7.8 Hz, 2H), 7.88 (t, J=7.8 Hz, 1H), 7.37 (dd, J=8.8, 2.9 Hz, 2H), 6.88-6.77 (m, 8H), 4.38-4.34 (m, 4H), 4.27-4.23 (m, 4H), 4.10-4.05 (m, 4H), 4.05-4.00 (m, 4H), 3.94-3.90 (m, 4H), 3.87-3.82 (m, 4H), 3.81-3.73 (m, 16H), 3.72-3.64 (m, 8H), 3.03 (s, 6H). $^{13}C$ NMR (125 MHz, $CDCl_3$): $\delta_C$ 155.6, 155.1, 153.3, 153.1, 149.3, 137.9, 137.2, 122.2, 121.9, 119.7, 115.7, 115.6, 71.1, 71.0, 70.8, 70.8, 70.1, 70.0, 69.8, 69.4, 69.2, 68.2, 68.1, 37.8. MALDI-TOF: calculated for $C_{53}H_{71}N_3O_{20}S_2$: m/z=1134.4 $[M+H]^+$; Found: 1134.7 $[M+H]^+$ (2,5-dihydroxybenzoic acid matrix).

h) Symmetric Terpy-Phen Macrocycle (8)

Figure 20:
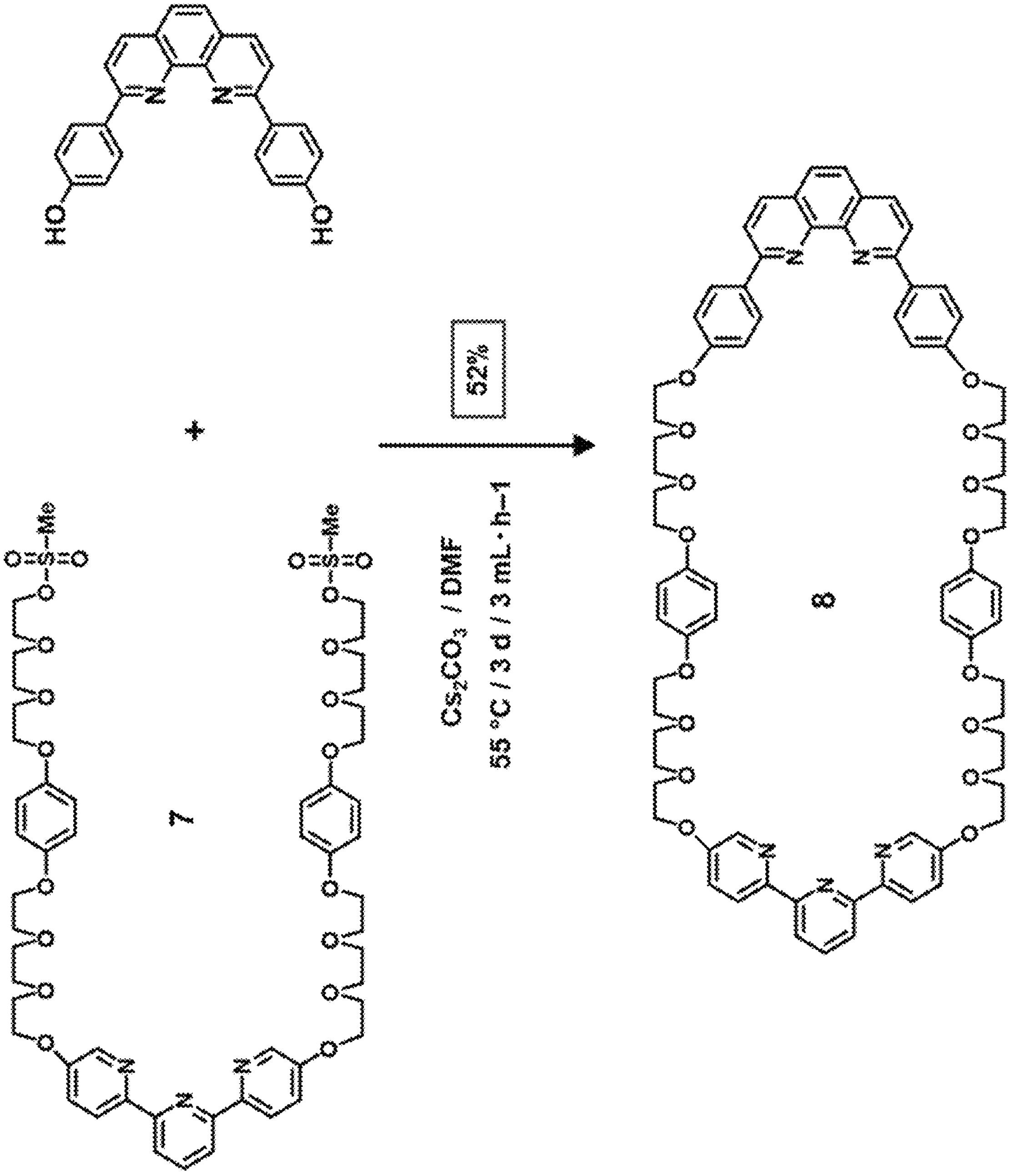
FIG. 20 depicts a detailed scheme for the synthesis of symmetric terpy-phen macrocycle.

This synthetic scheme is shown in FIG. 20.

A suspension of phenanthroline diol (0.312 g, 0.85 mmol, 1.0 eq.) and 7 (0.966 g, 0.85 mmol, 1.0 eq.) was prepared in 50 mL DMF and was added via syringe at 3 $mL\cdot h^{-1}$ using a syringe pump to a suspension of $Cs_2CO_3$ (2.80 g, 8.5 mmol, 10 eq.) in 300 mL DMF in a 500 mL RB flask. The reaction was heated to 55° C. for a total of 3 d. After 3 d, the suspension was filtered via gravity filtration to remove insoluble salts. The filtrate was concentrated via rotary evaporator and the crude was taken up in 300 mL $CH_2Cl_2$. The organics were washed with 3×100 mL DI $H_2O$ and the aqueous layer was back-extracted with 3×50 mL $CH_2Cl_2$. The combined organics were dried over $Na_2SO_4$ and were filtered. The solvent was removed to afford the crude product as a sticky brown film. This was redissolved in 20 mL GPC grade DMF and was filtered via syringe filter. It was then purified via recycling preparative GPC with DMF over 4 injections to afford the product as a sticky orange solid (0.57 g, 52%).

$^1H$ NMR (500 MHz, $CDCl_3$): $\delta_H$ 8.49 (d, J=8.8 Hz, 2H), 8.40 (d, J=8.8 Hz, 4H), 8.37 (d, J=2.9 Hz, 2H), 8.28 (d, J=7.8 Hz, 2H), 8.21 (d, J=8.4 Hz, 2H), 8.03 (d, J=8.4 Hz, 2H), 7.86 (t, J=7.8 Hz, 1H), 7.69 (s, 2H), 7.32 (dd, J=8.8, 2.9 Hz, 2H), 7.09 (d, J=8.8 Hz, 4H), 6.78 (s, 8H), 4.24-4.16 (m, 8H), 4.03-3.97 (m, 8H), 3.91-3.84 (m, 8H), 3.81-3.67 (m, 24H). $^{13}C$ NMR (125 MHz, $CDCl_3$): $\delta_C$ 160.2, 156.3, 155.5, 155.1, 153.2, 153.1, 149.3, 146.1, 137.8, 137.4, 136.8, 132.3, 129.0, 127.6, 125.7, 121.9, 121.8, 119.5, 119.32, 115.66, 115.66, 115.0, 71.04, 71.00, 70.96, 70.93, 69.97, 69.8, 69.7, 68.13, 68.06, 67.6. MALDI-TOF: calculated for $C_{75}H_{79}N_5O_{16}$: m/z=1328.5 $[M+Na]^+$; Found: 1329.5 $[M+Na]^+$ (2,5-dihydroxybenzoic acid matrix).

Example 15. Detailed Synthesis of Linear Catenanes for [6]Catenane/ate a) $Fe^{2+}$-Open Terpy-Phen Macrocycle Dimer (9)

Figure 21:
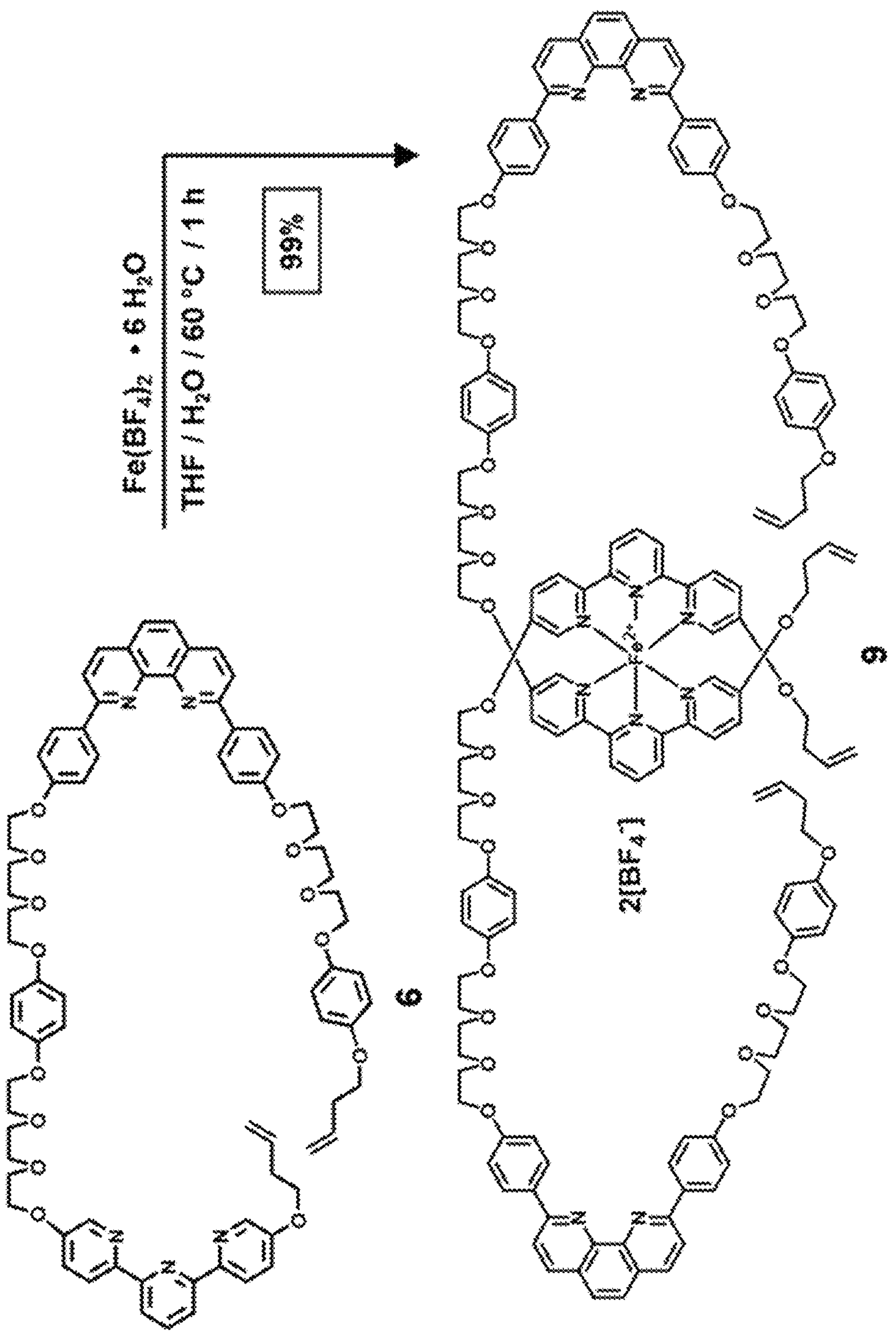
FIG. 21 depicts a detailed scheme for the synthesis of $Fe^{2+}$-open terpy-phen macrocycle dimer.

This synthetic scheme is shown in FIG. 21.

An alternative synthesis of compound 9 is described above in Examples 1-10. Herein is reported an improved and scaled synthetic protocol. A solution of 6 (0.500 g, 0.385 mmol, 1 eq.) was prepared in 150 mL THF in a 250 mL RB flask. The flask was purged with $N_2$ and a solution of $Fe(BF_4)_2\cdot 6\ H_2O$ (0.169 g, 0.499 mmol, 1.3 eq.) in 25 mL DI $H_2O$ was added via syringe. The dark red solution was heated at 60° C. for 1 h while stirring under $N_2$. The solution was then allowed to cool to room temperature before diluting with 300 mL $CH_2Cl_2$. The dark red solution was washed with 3×100 mL brine. The aqueous layer was back-extracted with 2×100 mL $CH_2Cl_2$. The combined organics were dried over $Na_2SO_4$ and were filtered. The solvent was removed via rotary evaporator to afford the product as a dark red sticky solid (0.542 g, 99%). $^1H$ NMR is consistent with the above.

b) [2]Catenane-TPM (10) and Figure-Eight TPM (11)

Figure 22:
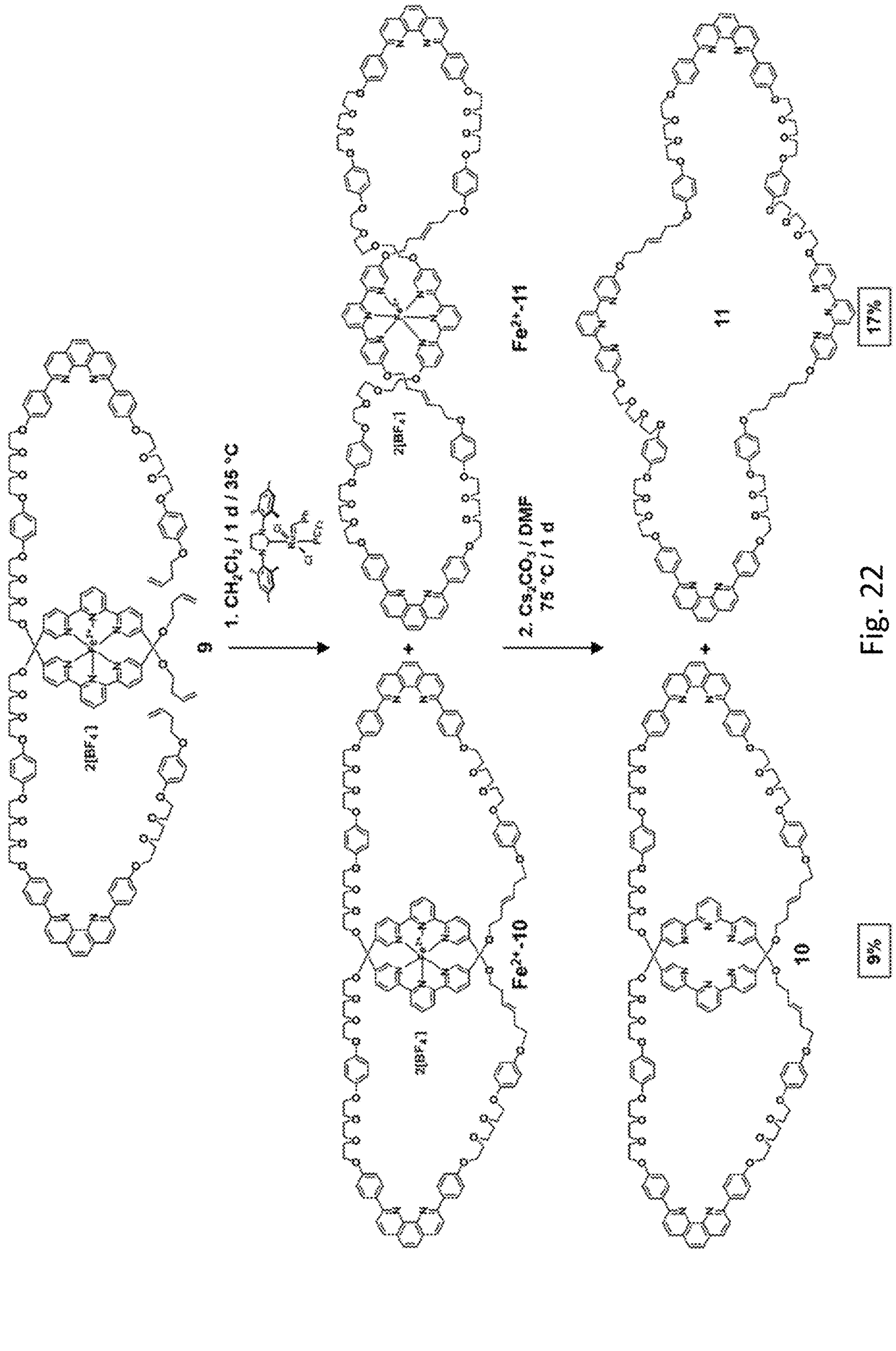
FIG. 22 depicts a detailed scheme for the synthesis of [2]catenane-TPM (10) and figure-eight TPM.

This synthetic scheme is shown in FIG. 22.

Step 1: A solution of 9 (0.209 g, 0.074 mmol, 1 eq.) and Grubbs' $2^{nd}$ generation catalyst (0.012 g, 0.014 mmol, 0.2 eq.) was prepared in 200 mL $CH_2Cl_2$ in a 500 mL RB fitted with a Vigreux column. The dark red solution was then heated to 35° C. while stirring under $N_2$. The reaction progress was monitored by LR-ESI. After 1 d, the reaction was complete and was quenched with 1 mL ethyl vinyl ether and 5 mL MeCN. The solvent was removed to afford the crude product as a dark red film. The crude material was purified via column chromatography with basic alumina ($CHCl_3$ to 5% MeOH/$CHCl_3$). All fractions, including mixed fractions, containing the desired product were collected to be demetalated prior to purification via recycling preparative GPC.

Step 2: The mixed fractions were redissolved in 25 mL DMF in a 50 mL RB flask with a stir bar. Solid $Cs_2CO_3$ (1.0 g, 3.07 mmol, 40 eq.) was added to the dark red solution and the suspension was heated at 75° C. while stirring open to air. After 1 d, the solvent was removed via rotary evaporator and the crude product was taken up in 200 mL $CH_2Cl_2$. The organics were washed with 3×50 mL brine. The aqueous layer was back-extracted with 2×100 mL $CH_2Cl_2$. The combined organics were dried over $Na_2SO_4$ and were filtered. The solvent was removed via rotary evaporator to afford the crude product as an orange film. It was redissolved in 5 mL GPC grade DMF and was filtered via syringe filter, followed by purification via recycling prep-GPC with DMF over 1 injection to separate the desired [2]catenane product 10 (0.0163 g, 9%) from the large macrocycle 11 (0.0327 g, 17%). The identity of these species was determined by HR-ESI-MS/MS.

10: $^1H$ NMR (500 MHz, $CDCl_3$): δ 8.47 (d, J=8.7 Hz, 4H), 8.43-8.29 (m, 12H), 8.25 (d, J=7.9 Hz, 4H), 8.19 (d, J=8.4 Hz, 4H), 8.01 (d, J=8.4 Hz, 4H), 7.83 (t, J=7.8 Hz, 2H), 7.71-7.64 (m, 4H), 7.27 (dd, J=8.2, 2.3 Hz, 2H), 7.23 (dd, J=8.8, 2.9 Hz, 2H), 7.12-7.01 (m, 8H), 6.85-6.71 (m, 16H), 5.65-5.53 (m, 4H), 4.28-4.10 (m, 7H), 4.08-3.94 (m, 8H), 3.92-3.59 (m, 27H), 2.56-2.38 (m, 4H). $^{13}C$ NMR (125 MHz, $CDCl_3$): $\delta_C$ 160.2, 158.5, 156.3, 155.54, 155.48, 155.2, 155.1, 153.3, 153.2, 153.14, 153.08, 149.3, 149.2, 149.1, 146.1, 137.8, 137.6, 137.4, 136.9, 132.4, 129.2, 129.1, 127.8, 127.6, 125.7, 121.9, 121.8, 121.4, 119.5, 119.4, 115.7, 115.6, 115.5, 115.0, 114.9, 71.06, 71.00, 70.95, 70.92, 70.88, 70.03, 69.99, 69.97, 69.85, 69.74, 68.15, 68.10, 68.07, 67.99, 67.9, 67.7, 67.6, 32.7, 32.5. HRMS-ESI: calculated for $C_{150}H_{154}N_{10}O_{28}$: m/z=1273.0557 $[M+2H]^{2+}$, 849.0395 $[M+H]^{3+}$, 637.0315 $[M+4H]^{4+}$; Found: 1273.0527 $[M+2H]^{2+}$, 849.0367 $[M+H]^{3+}$, 637.0292 $[M+4H]^{4+}$.

11: $^1$H NMR (500 Hz, $CDCl_3$): δ 8.49 (dd, J=8.7, 4.1 Hz, 4H), 8.41 (d, J=8.6 Hz, 8H), 8.37 (d, J=2.9 Hz, 2H), 8.33 (d, J=2.8 Hz, 2H), 8.28 (d, J=7.8 Hz, 4H), 8.21 (d, J=8.4 Hz, 4H), 8.04 (d, J=8.4 Hz, 4H), 7.86 (t, J=7.8 Hz, 2H), 7.70 (s, 4H), 7.35-7.26 (m, 4H), 7.10 (dd, J=8.7, 1.5 Hz, 8H), 6.88-6.73 (m, 16H), 5.62 (d, J=5.4 Hz, 4H), 4.26-4.17 (m, 12H), 4.04 (ddd, J=13.1, 9.6, 5.1 Hz, 16H), 3.94-3.66 (m, 50H), 2.63-2.39 (m, 8H). $^{13}$C NMR (125 MHz, $CDCl_3$): $\delta_C$ 160.2, 156.4, 155.54, 155.49, 155.22, 155.15, 153.3, 153.22, 153.17, 153.1, 149.4, 149.3, 149.2, 146.1, 137.8, 137.3, 136.9, 132.4, 129.3, 129.1, 128.4, 127.9, 127.6, 127.1, 125.7, 121.9, 121.83, 121.81, 121.7, 119.6, 119.4, 71.1, 71.00, 70.99, 70.96, 70.06, 70.03, 69.9, 69.8, 68.24, 68.21, 68.18, 68.15, 68.05, 67.9, 67.7, 32.8, 32.6. HRMS-ESI: calculated for $C_{150}H_{154}N_{10}O_{28}$: m/z=1273.0557 $[M+2H]^{2+}$, 849.0395 $[M+H]^{3+}$, 637.0315 $[M+4H]^{4+}$; Found: 1273.0548 $[M+2H]^{2+}$, 849.0383 $[M+H]^{3+}$, 637.0303 $[M+4H]^{4+}$.

When 6 is metalated to form the bis-complex 9, the directionality of the asymmetric open macrocycle is maintained, which results in a pair of enantiomeric coordination complexes. The orientation of the macrocycles is preserved during ring-closing and after demetallation, resulting in enantiomers of 10 and 11.

c) $Fe^{2+}$-Symmetric Terpy-Phen Macrocycle (12)

Figure 23:
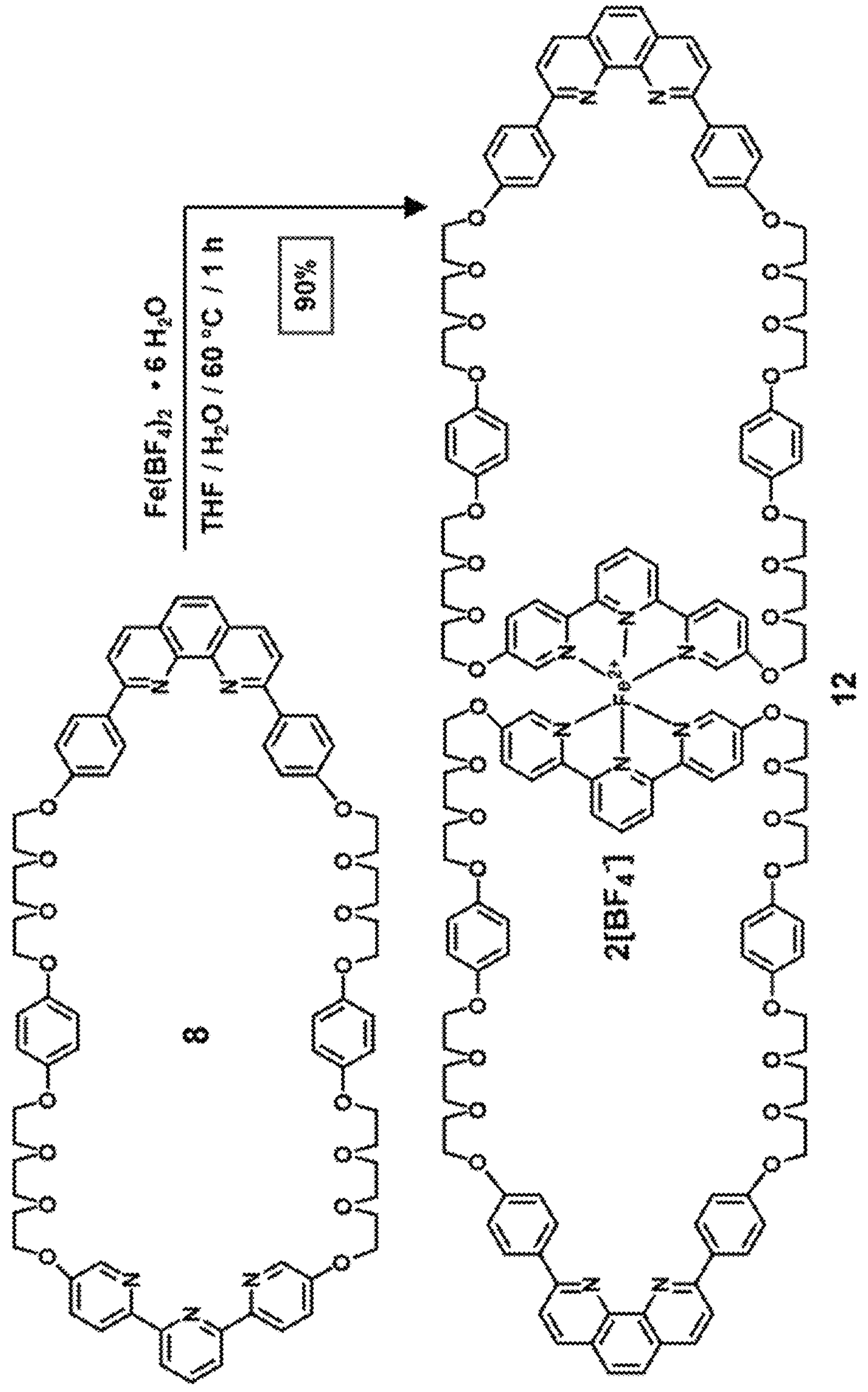
FIG. 23 depicts a detailed scheme for the synthesis of $Fe^{2+}$-symmetric terpy-phen macrocycle.

This synthetic scheme is shown in FIG. 23.

A solution of 8 (0.257 g, 0.197 mmol, 1 eq.) was prepared in 130 mL THF in a 250 mL RB flask. The flask was purged with $N_2$ and a solution of $Fe(BF_4)_2 \cdot 6\ H_2O$ (0.099 g, 0.264 mmol, 1.5 eq.) in 20 mL DI $H_2O$ was added via syringe. The dark red solution was heated at 60° C. for 1 h while stirring under $N_2$. The solution was then allowed to cool to room temperature. The solvent was then removed via rotary evaporator and the crude was taken up in 300 mL $CH_2Cl_2$. The dark red solution was washed with 3×100 mL DI $H_2O$. The organics were dried over $Na_2SO_4$ and were filtered. The solvent was then removed via rotary evaporator to afford the product as a dark red film. The film was then washed with 2×50 mL diethyl ether ($Et_2O$) and 2×50 mL hexanes. The crude product was isolated as a dark red solid (0.253 g, 90%) and was used in the next step without further purification.

$^1$H NMR (500 MHz, $CDCl_3$): δ 8.45-8.40 (m, 2H), 8.36-8.30 (m, 8H), 8.25 (d, J=8.4 Hz, 4H), 8.20 (d, J=7.9 Hz, 4H), 7.98 (d, J=8.5 Hz, 4H), 7.93 (d, J=8.8 Hz, 4H), 7.73 (s, 4H), 7.20 (dd, J=9.0, 2.4 Hz, 4H), 7.09 (d, J=8.8 Hz, 8H), 6.73 (dd, J=62.4, 9.0 Hz, 16H), 6.35 (d, J=2.5 Hz, 4H), 5.00 (s, 2H), 4.27-4.21 (m, 8H), 4.10-4.05 (m, 8H), 3.96-3.91 (m, 8H), 3.90-3.85 (m, 8H), 3.85-3.74 (m, 32H), 3.61-3.56 (m, 8H), 3.51 (s, 8H), 3.44 (dd, J=11.3, 5.4 Hz, 14H). $^{13}$C NMR (125 MHz, $CDCl_3$): $\delta_C$ 160.3, 159.2, 157.4, 156.0, 153.14, 153.05, 151.5, 149.4, 145.9, 142.1, 138.8, 137.1, 135.8, 132.1, 129.0, 128.3, 127.7, 125.8, 125.5, 124.7, 122.1, 120.9, 119.3, 115.7, 115.6, 115.5, 115.0, 70.93, 70.87, 70.46, 70.42, 70.0, 69.8, 69.6, 69.1, 68.8, 68.2, 68.1, 68.0, 67.8, 67.7, 34.3, 30.3. HRMS-ESI: calculated for $C_{150}H_{158}FeN_{10}O_{32}$: m/z=1334.0209 $[M-2BF_4]^{2+}$, 889.6830 $[M-2BF_4+H]^{3+}$, 667.5141 $[M-2BF_4+2H]^{4+}$; Found: 1334.0167 $[M-2BF_4]^{2-}$, 889.6805 $[M-2BF_4+H]^{3+}$, 667.5126 $[M-2BF_4+2H]^{4+}$.

d) [2]Catenane-Endcap Unsaturated (13)

Figure 24:
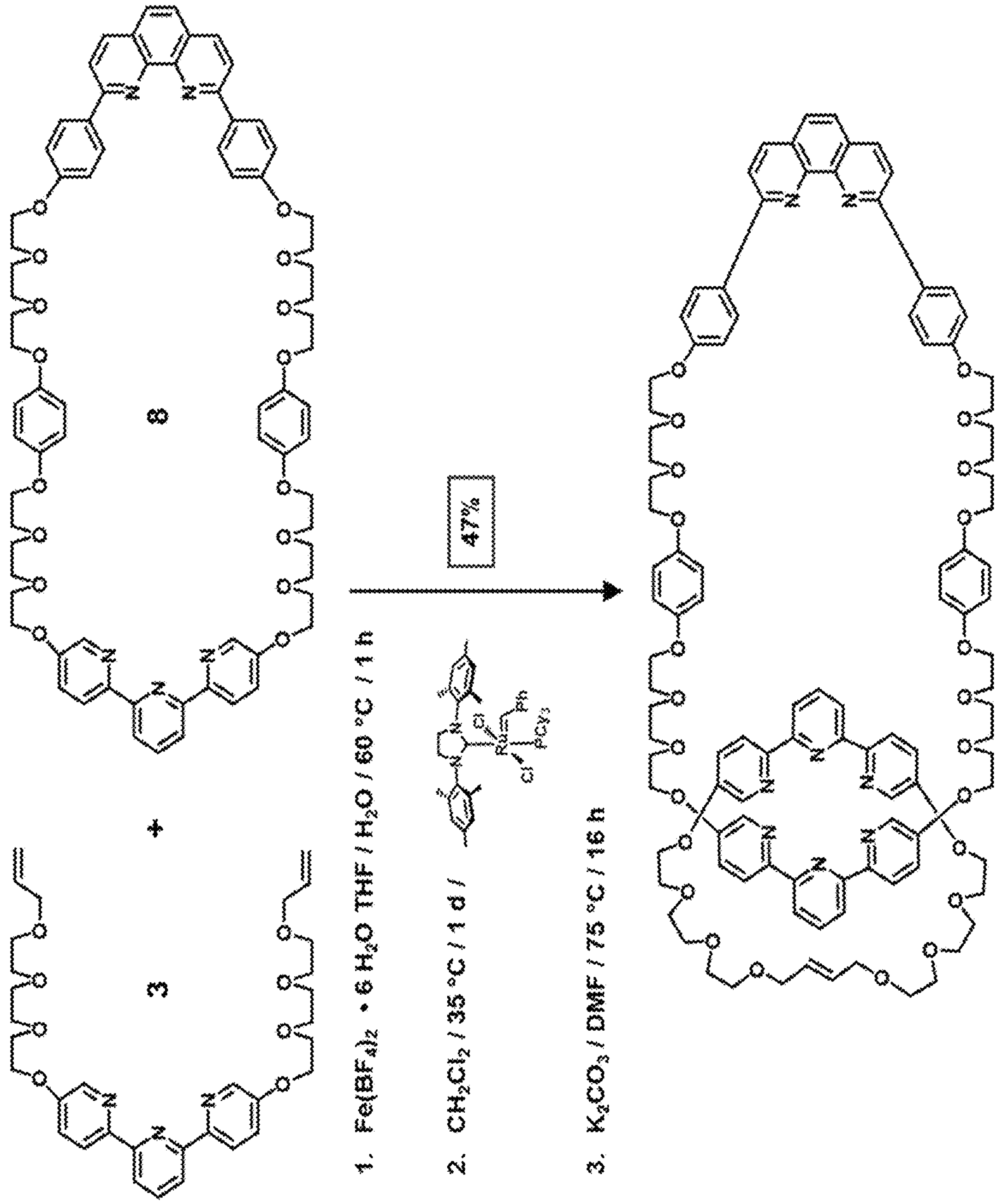
FIG. 24 depicts a detailed scheme for the synthesis of [2]catenane-endcap unsaturated.

This synthetic scheme is shown in FIG. 24.

Step 1: A solution of diallyl terpyridine 3 (0.271 g, 0.444 mmol, 2.0 eq.) and 8 (0.2817 g, 0.216 mmol. 1.0 eq.) was prepared in 300 mL THF in a 500 mL RB flask. While stirring under $N_2$, a solution of $Fe(BF_4)_2 \cdot 6\ H_2O$ (0.220 g, 0.65 mmol, 3.0 eq.) in 50 mL DI $H_2O$ was added via syringe. The dark red solution was then heated to 60° C. for 1 h while stirring under $N_2$. The solution was then allowed to cool to room temperature while stirring for 2 d. The solvent was removed via rotary evaporator and crude material was taken up in 300 mL $CH_2Cl_2$. The dark red solution was washed with 3×100 mL DI $H_2O$. The organics were dried over $Na_2SO_4$ and were filtered. The solvent was removed via rotary evaporator and the crude product was isolated as a dark red film, which was taken forward to the next step without any further purification.

Step 2: The crude red film was redissolved in 500 mL $CH_2Cl_2$ in a 1 L RB flask. A solution of Grubbs' $2^{nd}$ generation catalyst (0.018 g, 0.0216 mmol, 0.1 eq.) in 5 mL $CH_2Cl_2$ was added. The reaction was fitted with a Vigreux column and was heated to 35° C. while stirring under $N_2$. The reaction progress was monitored by LR-ESI. After 8 h, an additional 0.05 eq. Grubbs' $2^{nd}$ generation catalyst was added, and the reaction temperature was maintained at 35° C. while stirring under $N_2$. After 1 d of total heating, the reaction was complete and was quenched with 5 mL ethyl vinyl ether and 5 mL MeCN. The solvent was removed via rotary evaporator and the crude was transferred to a 100 mL RB flask.

Step 3: The crude red film was redissolved in 50 mL DMF, followed by the addition of solid $K_2CO_3$ (3.0 g, 21.7 mmol, 100 eq.). The suspension was then heated to 75° C. for 16 h while stirring open to air. The solvent was then removed via rotary evaporator and the crude product was taken up in 300 mL $CH_2Cl_2$. The solution was washed with 2×100 mL DI $H_2O$ and 2×100 mL brine. The organics were dried over $Na_2SO_4$ and were filtered. The solvent was removed via rotary evaporator to afford the crude demetalated mixture as a sticky brown solid. It was redissolved in 12 mL GPC grade DMF and was filtered via syringe filter, followed by purification via recycling prep-GPC with DMF over 3 injections to afford to afford the asymmetric [2]catenane product as a sticky orange solid (0.189 g, 47%).

$^1$H NMR (500 MHz, $CDCl_3$): δ 8.57-8.48 (m, 4H), 8.40 (d, J=8.8 Hz, 4H), 8.35 (d, J=2.9 Hz, 2H), 8.29-8.25 (m, 4H), 8.23 (d, J=8.4 Hz, 2H), 8.17 (d, J=7.8 Hz, 2H), 8.05 (d, J=8.4 Hz, 2H), 7.84 (t, J=7.8 Hz, 1H), 7.80 (t, J=7.8 Hz, 1H), 7.72 (s, 2H), 7.36 (dd, J=8.9, 2.9 Hz, 2H), 7.30 (dd, J=8.8, 2.9 Hz, 2H), 7.07 (d, J=8.8 Hz, 4H), 6.78 (s, J=2.3 Hz, 8H), 5.57-5.53 (m, 2H), 4.24-4.20 (m, 4H), 4.17 (dd, J=9.8, 6.3 Hz, 8H), 4.04-3.99 (m, 8H), 3.85 (dd, J=10.9, 7.1 Hz, 8H), 3.81-3.67 (m, 32H), 3.64-3.60 (m, 4H), 3.60-3.55 (m, 4H), 3.54 (dd, J=5.9, 4.2 Hz, 4H), 3.47-3.41 (m, 4H). $^{13}$C NMR (125 MHz, $CDCl_3$): $\delta_C$ 160.2, 156.3, 155.7, 155.5, 155.08, 155.06, 153.14, 153.11, 149.30, 149.26, 146.1, 138.6, 137.8, 137.7, 137.4, 136.9, 132.3, 129.6, 129.1, 127.6, 125.7, 122.5, 121.9, 121.83, 121.76, 119.5, 119.4, 119.1, 115.6, 114.9, 71.3, 71.03, 70.96, 70.7, 70.00, 69.96, 69.8, 69.7, 69.4, 68.3, 68.1, 68.0, 67.5. MALDI-TOF: calculated for $C_{106}H_{118}N_8O_{24}$: m/z=1888.8 $[M+H]^+$; Found: 1889.0 $[M+H]^+$ (2,5-dihydroxybenzoic acid matrix).

e) [2]Catenane-Endcap (14)

Figure 25:
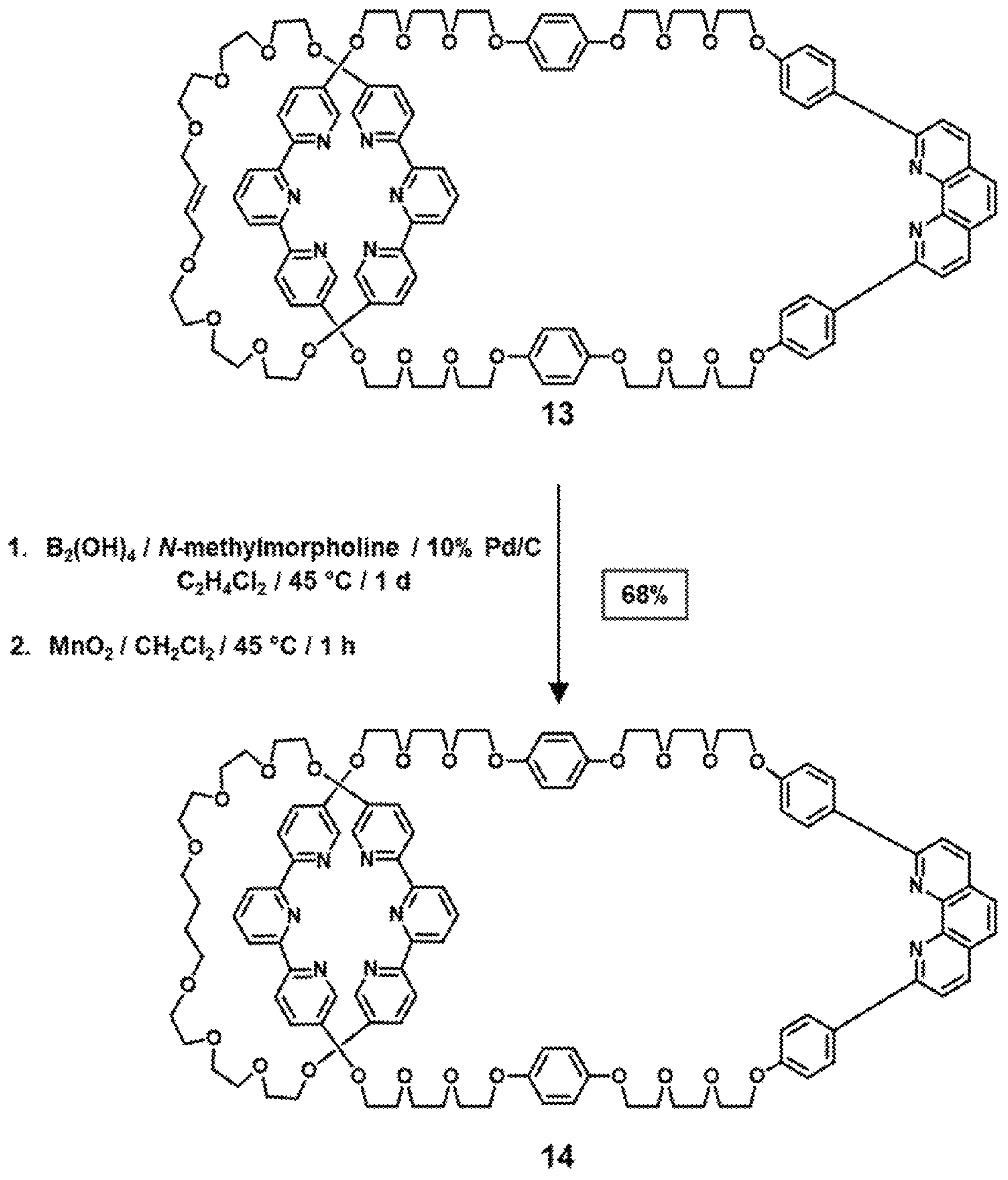
FIG. 25 depicts a detailed scheme for the synthesis of [2]catenane-endcap.

This synthetic scheme is shown in FIG. 25.

Step 1: A solution of 13 (0.0701 g, 0.0371 mmol, 1 eq.) was prepared in 5 mL 1,2-dichloroethane ($C_2H_4Cl_2$) in a 10 mL high-pressure vessel with a stir bar. The vessel was then charged with $B_2(OH)_4$ (0.341 g, 3.80 mmol, 100 eq.), N-methylmorpholine (0.75 g, 0.82 mL, 7.43 mmol, 200 eq.) and 10% Pd/C (0.035 g, 0.5 eq. wt/wt)[2]. It was quickly sealed and was heated to 45° C. while stirring for 1 d. The reaction was then allowed to cool to room temperature. The catalyst was removed via gravity filtration and the black solid was washed with 100 mL 10% $MeOH/CH_2Cl_2$. The filtrate was washed with 3×50 mL brine. The organics were dried over $Na_2SO_4$ and were filtered. The solvent was removed rotary evaporator and the crude yellow film was taken forward to the rearomatization step without further purification.

Step 2: The crude yellow film was redissolved in 25 mL $CH_2Cl_2$ in a 100 mL RB flask. Solid $MnO_2$ (1.4 g, 20 eq. wt/wt) was added, and the flask was fitted with a Vigreux column. The suspension was heated to 45° C. while stirring under $N_2$ for 1 h. The crude material was then filtered over celite by vacuum filtration and the cake was washed with 200 mL 10% $MeOH/CH_2Cl_2$. The filtrate was concentrated and was then purified via a short basic alumina column ($CH_2Cl_2$ to 5% $MeOH/CH_2Cl_2$), which afforded the product as a as a yellow film (0.048 g, 68%).

$^1$H NMR (500 MHz, $CDCl_3$): δ 8.53-8.47 (m, 4H), 8.40 (d, J=8.8 Hz, 4H), 8.35 (d, J=2.9 Hz, 2H), 8.30-8.22 (m, 6H), 8.16 (d, J=7.8 Hz, 2H), 8.06 (d, J=8.5 Hz, 2H), 7.84 (t, J=7.8 Hz, 1H), 7.79 (t, J=7.8 Hz, 1H), 7.73 (s, 2H), 7.35 (dd, J=8.9, 3.0 Hz, 2H), 7.31 (dd, J=8.8, 2.9 Hz, 2H), 7.07 (d, J=8.8 Hz, 4H), 6.79 (s, 8H), 4.27-4.14 (m, 12H), 4.05-3.99 (m, 8H), 3.89-3.83 (m, 8H), 3.82-3.67 (m, 28H), 3.66-3.57 (m, 8H), 3.53 (t, J=5.2 Hz, 4H), 3.47-3.41 (m, 4H), 3.15 (d, J=15.0 Hz, 4H). $^{13}$C NMR (125 MHz, $CDCl_3$): $\delta_C$ 160.2, 156.4, 155.7, 155.5, 155.1, 155.0, 153.2, 153.1, 149.31, 149.27, 146.1, 138.4, 137.8, 137.7, 137.4, 136.9, 132.3, 129.1, 127.6, 125.7, 122.5, 122.0, 121.84, 121.79, 119.53, 119.47, 119.1, 115.64, 115.62, 114.9, 71.3, 71.1, 71.04, 70.97, 70.95, 70.90, 70.65, 70.63, 70.01, 69.98, 69.92, 69.86, 69.7, 68.2, 68.1, 68.0, 67.6, 26.2. MALDI-TOF: calculated for $C_{106}H_{120}N_8O_{24}$: m/z=1889.9 $[M+H]^+$; Found: 1889.09 $[M+H]^-$ (α-cyano-4-hydroxycinnamic acid matrix).

j) $Fe^{2+}$-[2]C-Endcap (15)

Figure 26:
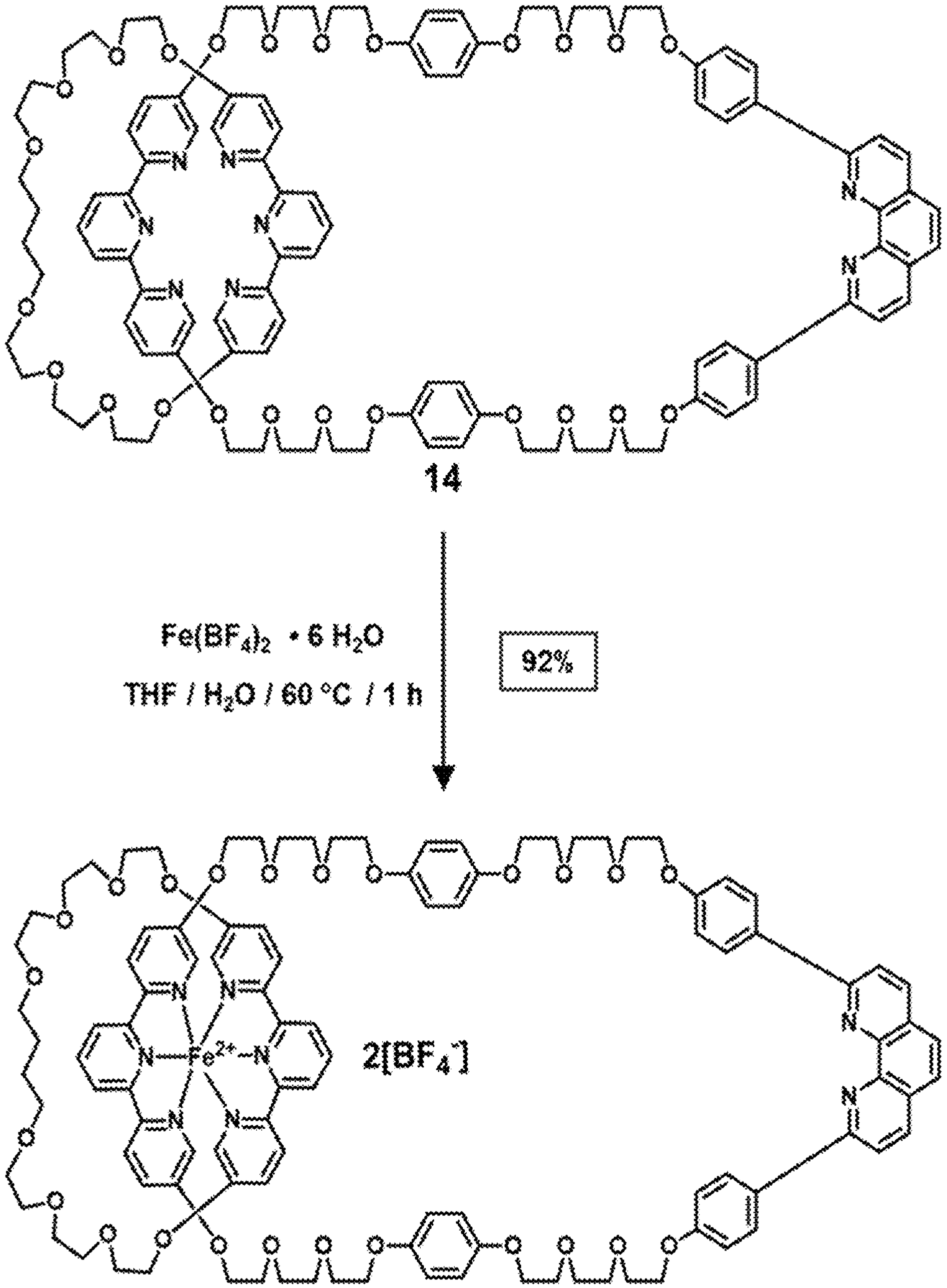
FIG. 26 depicts a detailed scheme for the synthesis of $Fe^{2+}$-[2]C-endcap.

This synthetic scheme is shown in FIG. 26.

A solution of 14 (0.183 g, 0.0968 mmol, 1 eq.) was prepared in 100 mL 25% MeOH/THF in a 100 mL RB flask. The flask was purged with $N_2$ and a solution of $Fe(BF_4)_2 \cdot 6H_2O$ (0.0507 g, 0.1501 mmol, 1.5 eq.) in 10 mL DI $H_2O$ was added via syringe. The dark red solution was heated to 60° C. for 1 h while stirring under $N_2$. The solution was then allowed to cool to room temperature and the solvent was removed via rotary evaporator. The crude product was taken up in 300 mL $CH_2Cl_2$ and was washed with 3×100 mL DI $H_2O$. The aqueous layer was back-extracted with 3×100 mL $CH_2Cl_2$. The combined organics were dried over $Na_2SO_4$ and were filtered. The solvent was removed via rotary evaporator to afford a dark red film. The crude product was redissolved in a minimal amount of $CH_2Cl_2$ and was transferred to a 50 mL centrifuge tube. The product was precipitated out of solution by the addition of hexanes. The red suspension was centrifuged, and the supernatant was discarded. The dark red pellet was redissolved in $CH_2Cl_2$ and was again precipitated out of solution by the addition of hexanes. The red suspension was centrifuged, and the supernatant was discarded. The dark red pellet was redissolved in $CH_2Cl_2$ and was transferred to a vial. The solvent was removed via rotary evaporator to afford the product as a dark red solid (0.1881 g, 92%) and was used in the next step without further purification.

$^1$H NMR (500 MHz, $CDCl_3$): δ 8.81 (d, J=8.1 Hz, 2H), 8.62-8.54 (m, 1H), 8.49 (d, J=9.0 Hz, 2H), 8.44-8.36 (m, 6H), 8.30-8.22 (m, 3H), 8.18 (d, J=8.9 Hz, 2H), 8.07 (d, J=8.5 Hz, 2H), 7.76 (s, 2H), 7.36 (dd, J=9.0, 2.6 Hz, 2H), 7.22 (dd, J=8.9, 2.6 Hz, 2H), 7.09 (d, J=8.8 Hz, 4H), 6.89-6.75 (m, 8H), 6.61 (d, J=2.6 Hz, 2H), 6.50 (d, J=2.6 Hz, 2H), 4.27-4.20 (m, 4H), 4.15-4.10 (m, 4H), 4.02-3.50 (m, 58H), 3.46 (dd, J=5.7, 3.5 Hz, 4H), 3.36 (dd, J=5.6, 3.6 Hz, 4H), 1.84-1.73 (m, 4H). $^{13}$C NMR (125 MHz, $CDCl_3$): $\delta_C$ 160.3, 159.59, 159.56, 157.6, 157.5, 153.3, 153.2, 149.96, 149.94, 146.1, 141.8, 140.9, 138.9, 138.4, 137.1, 132.3, 129.0, 127.7, 125.9, 125.3, 124.9, 124.1, 122.3, 121.9, 121.2, 119.4, 115.86, 115.80, 115.1, 71.5, 71.1, 71.0, 70.9, 70.69, 70.64, 70.56, 70.47, 70.06, 69.93, 69.87, 69.80, 69.0, 68.9, 68.7, 68.3, 68.1, 67.7, 26.9. HRMS-ESI: calculated for $C_{106}H_{120}FeN_8O_{24}$: m/z=972.8894 $[M-2BF_4]^{2+}$, 648.9287 $[M-2BF_4+H]^{3+}$; Found: 972.8888 $[M-2BF_4]^{2+}$, 648.9285 $[M-2BF_4+H]^{3+}$.

g) $Ru^{2+}$-[2]C-Endcap (16)

Figure 27:
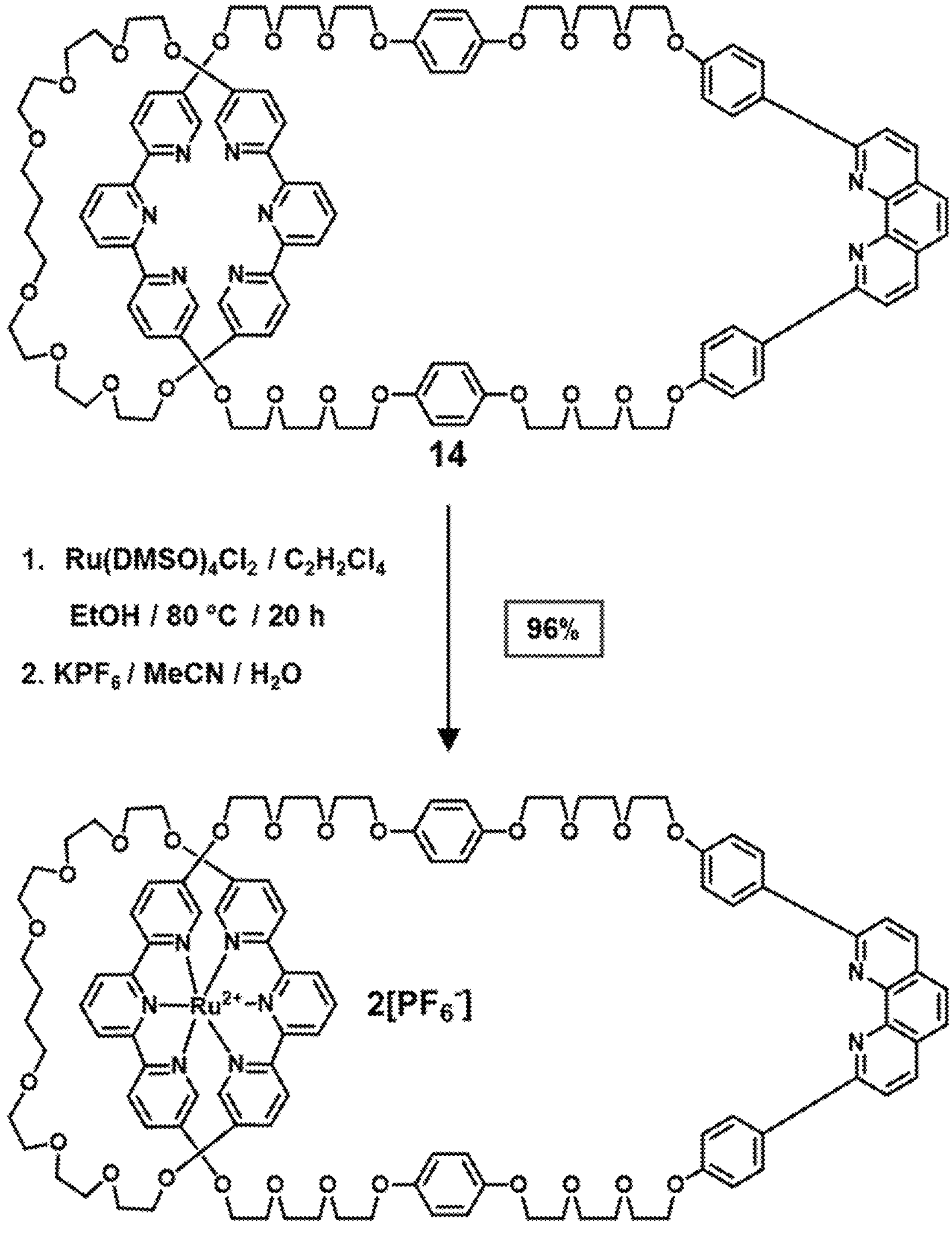
FIG. 27 depicts a detailed scheme for the synthesis of $Ru^{2+}$-[2]C-endcap.

This synthetic scheme is shown in FIG. 27.

A solution of 14 (0.100 g, 0.0529 mmol, 1 eq.) was prepared in mixed solvent solution of 20 mL tetrachloroethane and 10 mL ethanol (EtOH) in a 50 mL RB flask with a stir bar. Solid $Ru(DMSO)_4Cl_2$ (0.0293 g, 0.0605 mmol, 1.1 eq.) was added to the yellow solution and the flask was fitted with a Vigreux column. The suspension was heated to 80° C. while stirring under $N_2$. The solution gradually changed color from yellow to orange to red. After 20 h of heating, the solvent was removed via rotary evaporator. The crude was redissolved in a minimal amount of MeCN and was precipitated with saturated aqueous $KPF_6$. The suspension was diluted with 200 mL DI $H_2O$ and the aqueous layer was extracted with 5×100 mL $CH_2Cl_2$. The organics were dried over $Na_2SO_4$ and were filtered over celite via vacuum filtration. The solvent was removed via rotary evaporator to afford a reddish orange film. The film was washed with 3×25 toluene (MePh). The film was redissolved in $CH_2Cl_2$ and was transferred to a vial. The solvent was removed via rotary evaporator to afford the product reddish orange solid (0.116 g, 96%).

h) [4]Catenane ([4]C)

Figure 28:
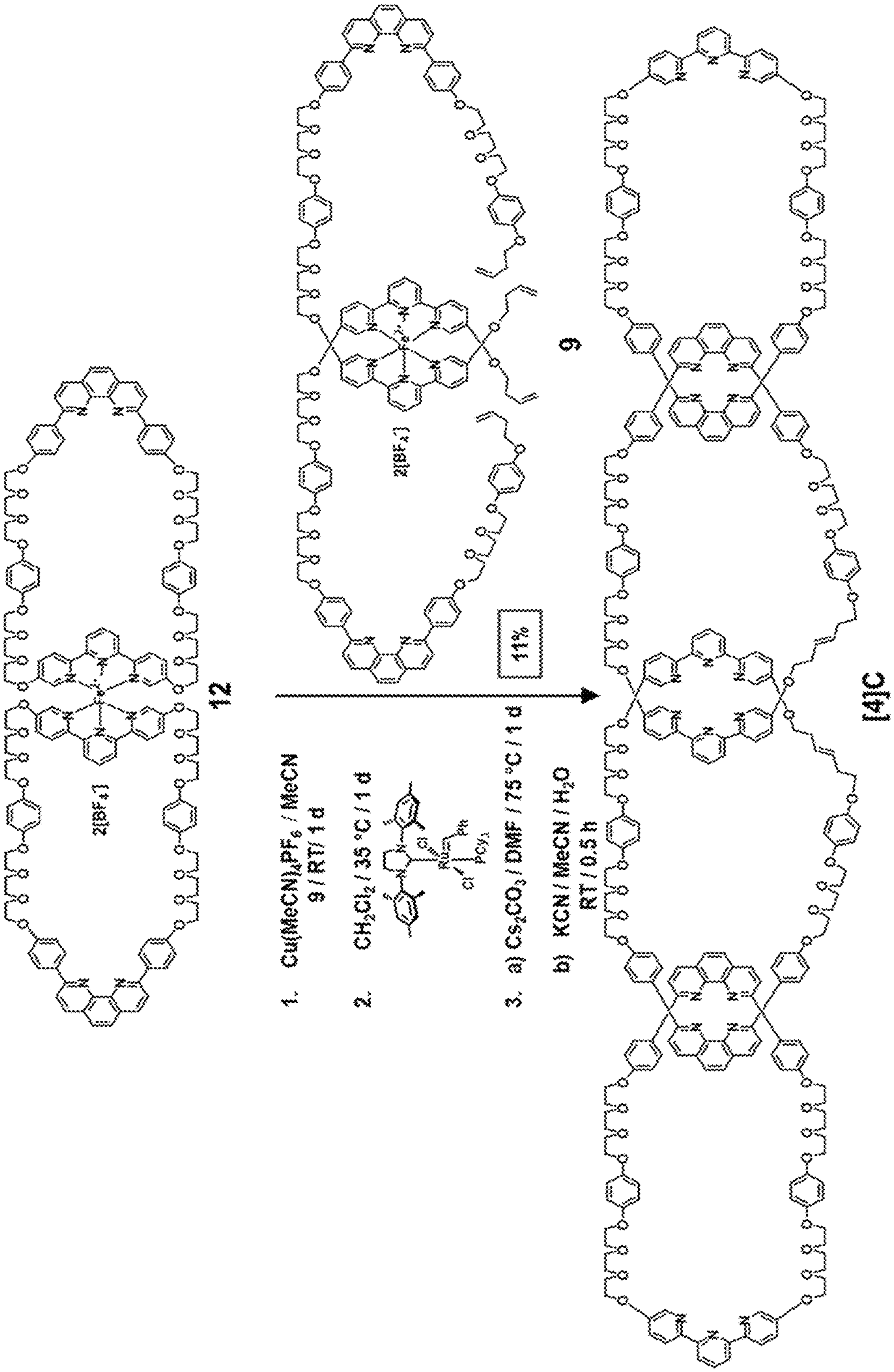
FIG. 28 depicts a detailed scheme for the synthesis of [4]Catenane ([4]C).

This synthetic scheme is shown in FIG. 28.

Step 1: A solution of 12 (0.247 g, 0.0868 mmol, 4.0 eq.) in 25 mL $N_2$-purged anhydrous MeCN was added via syringe to solid $Cu(MeCN)_4PF_6$ (0.0616 g, 0.165 mmol, 7.5 eq.) in an oven-dried 100 mL RB flask. The dark red solution was stirred at room temperature under $N_2$. After 30 min, a solution of 9 (0.0643 g, 0.0227 mmol, 1.0 eq.) in 20 mL 50% $MeCN/CH_2Cl_2$ was added via syringe. The dark red solution was stirred at room temperature under $N_2$ for 1 d. The solvent was then removed via rotary evaporator, and the crude product was taken up in 100 mL $CH_2Cl_2$. The dark red solution was washed with 3×25 mL DI $H_2O$. The organics were dried over $Na_2SO_4$ and were filtered. The solvent was removed via rotary evaporator to afford the pre-[4]catenate complex as a foamy red solid, which was taken forward to the next step without further purification.

Step 2: The crude foamy red solid was redissolved in 60 mL anhydrous $CH_2C2$ in a 250 mL RB flask with a stir bar. A solution of Grubbs' 2$^{nd}$ generation catalyst (0.004 g, 0.0045 mmol, 0.2 eq.) in 1 mL $CH_2Cl_2$ was added. The flask was fitted with a Vigreux column, and the dark red solution was heated to 35° C. while stirring under $N_2$. After 1 d, an additional 0.2 eq. Grubbs' 2$^{nd}$ generation catalyst was added. The reaction was heated at 35° C. while stirring under $N_2$ for an additional 1 d. After 2 d of total heating, the reaction was quenched with 1 mL ethyl vinyl ether and 5 mL MeCN. The solvent was removed via rotary evaporator to afford the crude [4]catenate mixture as a dark red film.

Step 3: a) The $Fe^{2+}$ ion was first removed from the crude mixture with the addition of a weak inorganic base and moderate heating. The crude red film was redissolved in 50 mL DMF in a 250 mL RB flask. Solid $Cs_2CO_3$ (1.0 g, 3.07 mmol, 135 eq.) was added and the suspension was heated to 75° C. for 1 d while stirring open to air. b) The $Cu^-$ then removed by addition of an excess of strongly competing ligand, namely potassium cyanide (KCN). The solvent was then removed via rotary evaporator and 50 mL MeCN was added to the crude suspension. A solution of KCN (0.2 g, 3.07 mmol, 135 eq.) in 10 mL $H_2O$ was added via syringe. The suspension was stirred at room temperature for 30 min before dilution with 300 mL $CH_2Cl_2$. The organics were washed with 3×50 mL brine. The aqueous layer was back-extracted with 2×100 mL $CH_2Cl_2$. The combined organics were dried over $Na_2SO_4$ and were filtered. The filtrate was concentrated via rotary evaporator to afford the crude product as a yellow/orange film. The crude was redissolved in 5 mL GPC grade DMF and the solution was centrifuged to remove any remaining insoluble salts. The supernatant was filtered via syringe filter and was purified via recycling prep-GPC with DMF to afford only mixed [4]catenane product. The mixed fractions were then purified a second time via recycling prep-GPC with DMF to afford [4]C as a sticky orange film (0.0133 g, 11%) as a racemic mixture.

$^1H$ NMR (500 MHz, $CDCl_3$): δ 8.54-8.40 (m), 8.38 (d, J=8.6 Hz), 8.33 (d, J=2.8 Hz), 8.30 (d, J=2.9 Hz), 8.25 (dd, J=7.7, 3.5 Hz), 8.18 (dd, J=8.4, 2.5 Hz), 8.16-8.03 (m), 8.00 (dd, J=8.5, 2.0 Hz), 7.98-7.86 (m), 7.83 (td, J=7.8, 1.6 Hz), 7.74-7.69 (m), 7.67 (d, J=2.7 Hz), 7.64 (d, J=10.7 Hz), 7.37-7.21 (m), 7.11 (d, J=7.5 Hz), 7.08-6.97 (m), 6.96 (s), 6.87-6.68 (m), 5.67-5.52 (m), 5.38-5.32 (m), 4.27-4.17 (m), 4.16-4.09 (m), 4.09-4.03 (m), 4.03-3.94 (m), 3.94-3.57 (m), 2.56-2.27 (m). $^{13}C$ NMR (125 MHz, $CDCl_3$): $\delta_C$ 160.3, 160.2, 156.3, 155.55, 155.51, 155.48, 155.14, 155.12, 153.3, 153.20, 153.16, 153.10, 149.34, 149.30, 146.1, 137.84, 137.78, 137.4, 137.3, 136.9, 132.4, 129.9, 129.2, 129.09, 129.06, 129.0, 127.9, 127.68, 127.64, 126.8, 126.5, 125.7, 121.89, 121.86, 121.8, 119.56, 119.54, 119.4, 115.72, 115.65, 115.60, 115.03, 114.98, 114.96, 71.08, 71.06, 71.00, 70.97, 70.93, 70.91, 70.89, 70.07, 70.03, 70.02, 69.97, 69.87, 69.86, 69.75, 69.73, 68.2, 68.1, 68.01, 67.98, 67.7, 67.59, 67.57, 32.1, 30.1. HRMS-ESI: calculated for $C_{300}H_{312}N_{20}O_{60}$: m/z=2579.6110 $[M+2H]^{2-}$, 1720.0764 $[M+3H]^{3+}$; Found: m/z=2579.5995 $[M+2H]^{2+}$, 1720.0672 $[M+3H]^{3+}$. MALDI-TOF: calculated for $C_{300}H_{312}N_{20}O_{60}$: m/z=5158.2 $[M+H]^+$; Found: 5158.9 $[M+H]^+$ (α-cyano-4-hydroxycinnamic acid matrix).

i) [6]Catenane ([6]C)

Figure 29:
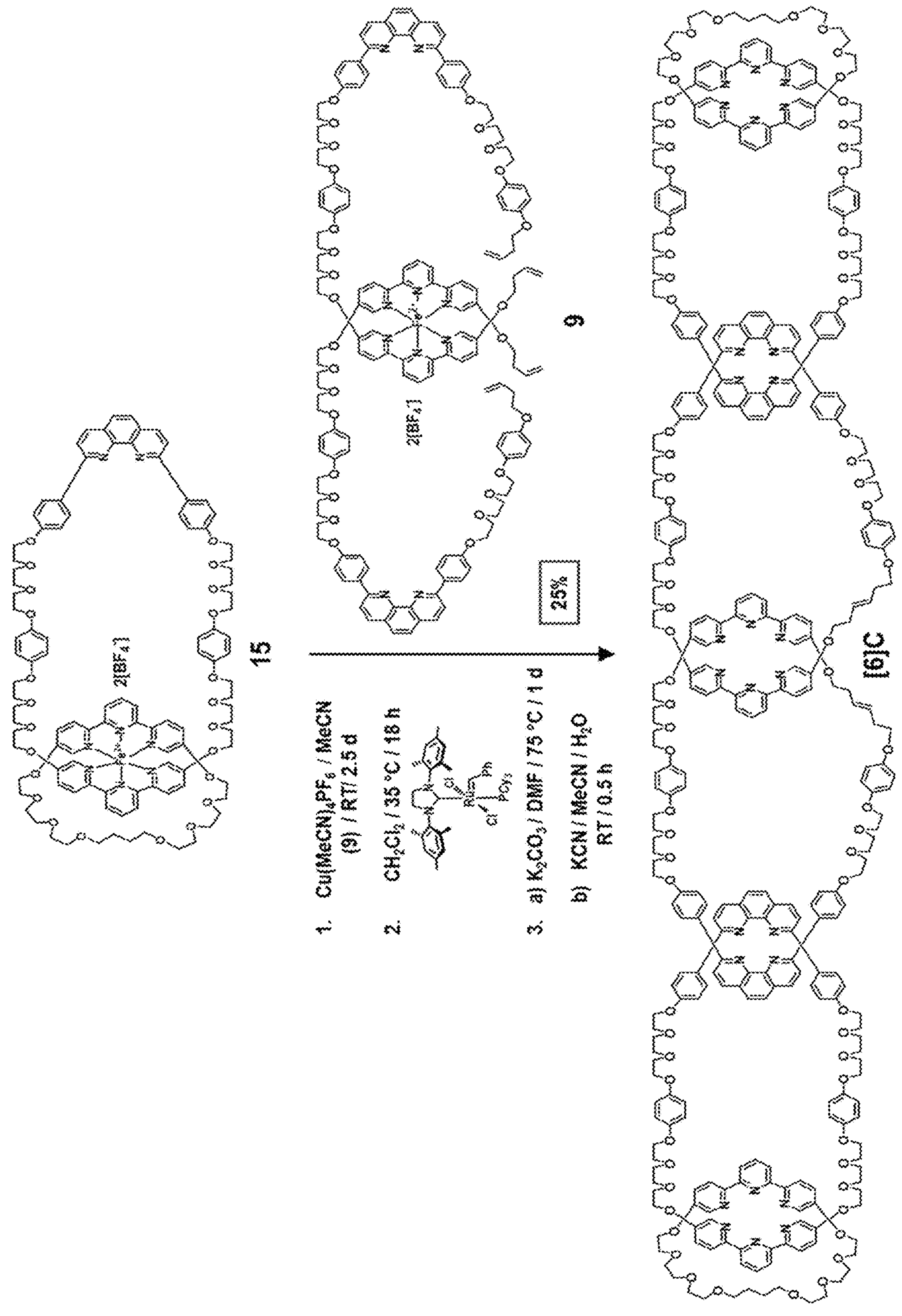
FIG. 29 depicts a detailed scheme for the synthesis of [6]Catenane ([6]C).

This synthetic scheme is shown in FIG. 29.

Step 1: A solution of $Cu(MeCN)_4PF_6$ (0.0105 g, 0.028 mmol, 4.0 eq.) in 3 mL $N_2$-purged anhydrous MeCN was added via syringe to a solution of 15 (0.0601 g, 0.0284 mmol, 4.0 eq.) in 10 mL $N_2$-purged anhydrous MeCN in an oven dried 50 mL RB flask. The dark red solution was stirred at room temperature under $N_2$. After 30 min, a solution of 9 (0.022 g, 0.0077 mmol, 1.0 eq.) in 7 mL $N_2$-purged anhydrous MeCN was added via syringe. The dark red solution continued to stir at room temperature under $N_2$ for 2.5 d. The solvent was then removed via rotary evaporator to afford the crude product as a foamy red solid, which was taken up in 100 mL CH2C12. The organic layer was washed with 3×50 mL DI $H_2O$ and was dried over $Na_2SO_4$. The dark red solution was filtered, and the solvent was removed via rotary evaporator to afford the pre-[6]catenate complex as a dark red film, which was used in the next step without further purification.

Step 2: The crude foamy red solid was redissolved in 25 mL anhydrous $CH_2Cl_2$ in a 100 mL RB flask with a stir bar. A solution of Grubbs' $2^{nd}$ generation catalyst (0.0013 g, 0.0015 mmol, 0.2 eq.) in 1 mL $CH_2Cl_2$ was added. The flask was fitted with a Vigreux column, and the dark red solution was heated to 35° C. while stirring under $N_2$. After 18 h, an aliquot was quenched with ethyl vinyl ethe and the reaction was deemed complete by $^1H$ NMR. The remaining solution was quenched with 1 mL ethyl vinyl ether and 5 mL MeCN. The solvent was removed via rotary evaporator to afford the crude [6]catenate mixture as a dark red film.

Step 3: a) The $Fe^{2+}$ ion was first removed from the crude mixture with the addition of a weak inorganic base and moderate heating. The crude red film was redissolved in 25 mL DMF in a 100 mL RB flask. Solid $K_2CO_3$ (1.0 g, 7.23 mmol, 1000 eq.) was added and the suspension heated to 75° C. for 1 d while stirring open to air. The solvent then removed via rotary evaporator and 50 mL MeCN was added to the crude suspension. b) The $Cu^+$ then removed by addition of an excess of strongly competing ligand, namely KCN. A solution of KCN (0.2 g, 3.07 mmol, 400 eq.) in 10 mL $H_2O$ was added via syringe. The suspension was stirred at room temperature for 0.5 h before dilution with 300 mL $CH_2Cl_2$. The organics were washed with 3×100 mL DI $H_2O$. The organics were dried over $Na_2SO_4$ and were filtered. The solvent was removed via rotary evaporator and the crude was redissolved in 4 mL GPC grade DMF. The solution was filtered via syringe filter and was purified via recycling preparative GPC with DMF. The mixed fractions were repurified via recycling preparative GPC with DMF. The linear [6]catenane [6]C was isolated as a yellow/orange film (0.0122 g, 25%) as a racemic mixture.

$^1H$ NMR (500 MHz, $CDCl_3$): δ 8.50-8.44 (in), 8.36 (dd, J=11.6, 8.7 Hz), 8.30 (ddd, J=8.6, 6.8, 3.3 Hz), 8.27-8.22 (m), 8.18 (dd, J=8.4, 2.8 Hz), 8.16-8.13 (m), 8.03-7.98 (m), 7.96 (d, J=8.5 Hz), 7.85-7.73 (m), 7.67 (d, J=2.8 Hz), 7.64 (d, J=15.7 Hz), 7.33-7.27 (m), 7.26-7.17 (m), 7.11 (d, J=8.2 Hz), 7.07-6.97 (m), 5.66-5.46 (m), 4.23 (s), 4.18 (t, J=4.9 Hz), 4.16-4.03 (m), 4.03-3.88 (m), 3.87-3.53 (m), 3.50 (t, J=5.2 Hz), 3.41 (dd, J=5.6, 4.6 Hz), 3.14 (s), 2.55-2.34 (m). $^{13}C$ NMR (125 MHz, $CDCl_3$): $\delta_C$ 160.21, 160.19, 156.33, 156.31, 156.26, 155.7, 155.54, 155.49, 155.46, 155.19, 155.16, 155.12, 155.08, 155.04, 153.18, 153.15, 153.13, 153.12, 149.3, 149.20, 149.19, 146.14, 146.12, 138.5 137.8, 137.7, 137.4, 137.3, 136.9, 132.34, 132.30, 132.26, 129.2, 129.08, 129.05, 127.9, 127.6, 125.7, 122.5, 122.0, 121.86, 121.85, 121.7, 119.51, 119.46, 119.41, 119.1, 115.68, 115.63, 115.59, 115.58, 114.96, 114.91, 71.3, 71.1, 71.00, 70.96, 70.89, 70.83, 70.80, 70.66, 70.63, 70.01, 69.94, 69.91, 69.85, 69.80, 69.7, 68.21, 68.16, 68.07, 68.03, 67.99, 67.94, 67.91, 67.6, 67.5, 32.8, 32.6, 29.8, 26.3. HRMS-ESI: calculated for $C_{362}H_{394}N_{26}O_{76}$: m/z=2109.2704 $[M+3H]^{3}$~, 2130.2523 $[M+3Na]^{3+}$; Found: m/z=2109.2655 $[M+3H]^{3+}$, 2130.2374 $[M+3Na]^{3+}$. MALDI-TOF: calculated for $C_{362}H_{394}N_{26}O_{76}$: m/z=6325.8 $[M+H]^+$; Found: 6325.3 $[M+H]^+$ (α-cyano-4-hydroxycinnamic acid matrix).

Example 16. Materials and Methods [2]Catenane/ate Polymer

The materials and methods of this Example were used in Examples 16-22.

All reagents were purchased from commercial suppliers and used without further purification unless stated otherwise. $[Cu(MeCN)_4]\cdot PF_6$ was purchased from Sigma-Aldrich. Modified literature procedures were employed in the synthesis of compounds 4 and 5. All reactions were performed under $N_2$ using common Schlenk techniques. All reactions that were performed under high-pressure, were done, so in heavy-walled, glass, high-pressure vessels with Teflon screw caps from Kemtech America.

Column chromatography was carried with silica gel (Sorbtech, 0.040-0.063 mm). All ring closing reactions were done using Grubb's $2^{nd}$ generation catalyst (Chem Scene). Preparative gel permeation chromatography (GPC) was preformed on a Japan Analytical Industry LaboACE instrument with one JAIGEL-2HR column and one JIAGEL-2.5HR column in sequence, running with either dimethylformamide (DMF) at 8 $mL\cdot min^{-1}$ or chloroform ($CHCl_3$) at 10 $mL\cdot min^{-1}$ as the mobile phase. Preparative high-pressure liquid chromatography (HPLC) was performed on an Agilent 1260 Infinity instrument with a Zorbax 300SB-C18 column (21.2×250 mm) with a gradient mobile phase of water ($H_2O$) with 0.1% acetic acid ($CH_3COOH$) and acetonitrile (MeCN) with 0.1% $CH_3COOH$.

All nuclear magnetic resonance (NMR) spectra were recorded on Varian Inova-500 spectrometer at 25° C., with working frequencies of 500 ($^1H$) and 125 ($^{13}C$) MHz. Chemical shifts are reported in ppm relative to the signals corresponding to the residual non-deuterated solvents: $CDCl_3$: $\delta_H$=7.26 ppm and $\delta_C$=77.16 ppm; $(CD_3)_2SO$: $\delta_H$=2.50 ppm and $\delta_C$=39.52 ppm; $CD_3CN$: $\delta_H$=1.94 ppm and $\delta_C$=118.26, 1.32 ppm.

Ultraviolet-Visible (UV-Vis) absorbance spectra were recorded on an Agilent Cary 5000 spectrophotometer. Analytical GPC analyses were performed on an Agilent 1260 Infinity setup with two Shodex GPC KD-806M columns in sequence in DMF mobile phase (0.025 M LiBr) running at 60° C. at 1.0 $mL\cdot min^{-1}$. The differential refractive index (dRI) of each compound was monitored using a Wyatt Optilab T-rEX detector.

Low-res mass spectrometry electrospray ionization (LRMS-ESI) was recorded on an Advion Expression-L Compact Mass Spectrometer. High-res mass spectrometry electrospray ionization (HRMS-ESI) was recorded on a Waters Synapt G2 HDMS or a Bruker maXis 4G UHR-TOF mass spectrometer. Matrix assisted laser desorption/ionization time-of-flight mass spectrometry (MALDI-TOF-MS) was recorded on a Bruker Solaris 12T FT-MS; samples were prepared using 3,5-Dimethoxy-4-hydroxycinnamic acid, α-Cyano-4-hydroxycinnamic acid matrices, 3,5-Dihydroxybenzoic acid, or trans-2-[3-(4-tert-Butylphenyl)-2-methyl-2-propenylidene]malononitrile (DCTB).

Gels were synthesized using ratios in Table 2 below, which lists the reagents used for the synthesis of one Acryl[2]catenane crosslinked gel and one poly(ethylene glycol) diacrylate crosslinked control gel (PEGDA). 2-Methoxyethyl acrylate (MEA), ammonium persulfate (APS).

TABLE 2

| Crosslinker mol % | Acryl[2]cat 0.27 mol % | PEGDA 0.27 mole % |
|---|---|---|
| MEA (mg) | 262.4 | 269.7 |
| Crosslinker (mg) | 11.0 | 3.6 |
| APS (mg) | 1.7 | 1.7 |
| MEA (mol %) | 99.4 | 99.4 |
| Total Mass (mg) | 275.0 | 275.0 |
| DMSO (mL) | 550.0 | 550.0 |

The reagents were dissolved in DMSO and pipetted into 2.5 cm silicon molds. Reagents were vortexed in a vial before pipetting into molds to ensure even mixing. Gels were then cured in an oven at 80° C. for 25 min. Gels were removed carefully with a spatula and then swelled in MeOH for 48 h, changing solvent every 24 h. Then gels were swelled in a 0.010 M solution of either LiCN or KCN in MeOH. After 2 h, the gels were swelled in fresh MeOH for 48 h, changing solvent every 12 h. Metal was incorporated into the gels by swelling the gel in a 0.010 M solution of $[Cu(CH_3CN)_4]\cdot PF_6$ and 0.010 M sodium ascorbate in MeOH for 2 h. MeOH used in this step was purged with $N_2$ gas for 2 h prior to use to help minimize oxidation of the copper source. Then gels were swelled in a 0.010 M solution of ethylenediaminetetraacetic acid disodium salt dihydrate (EDTA) in a 50:50 mixture of MeOH:$H_2O$. After 2 h, the gels were swelled in fresh MeOH for 48 h, changing solvent every 12 h, to remove any excess metal and remaining EDTA from the system. Metals were removed from the catenates by soaking the gels in a 0.010 M solution of either KCN or LiCN in MeOH. After 1 h, the gels were swelled in fresh MeOH for 48 h, changing solvent every 12 h. Metallation was repeated once for each set of gels for a total of two complete cycles. A third cycle was completed on the rheology samples of the acryl[2]catenane gels as the testing method was non-destructive.

All rheological data was obtained on a TA HR-20 Rheometer using an 8 mm smooth geometry. All samples tested were 8 mm circular punches cut from larger gels, synthesized as described above. All tests were performed at 15° C. to minimize the evaporation of the methanol swollen into the gels; however, minor solvent evaporation was still evident. Gels were subjected to a squeeze pull off test until a normal force of 0.1500 N was reached, at which point a strain sweep test ranging from 0.1-10% strain was performed. Angular frequency was kept constant at 1 rad/s throughout the test.

All tensile testing data obtained on a TA ElectroForce 3200 using standard clamp fixtures to grip the dogbone punches. Dogbones were punched from larger gels, synthesized as described above, using a PLA 3-D printed punch—purchased from Bobbiscutters on Etsy—with a height of 1.0 cm and an outer gauge of 0.39 cm. Starting distance between the clamps was 1.57 mm, and gels were stretched at a rate of 0.0500 mm/sec until break.

Calculations of crosslinking density, swelling ratio, and Mc of acryl[2]catenane crosslinked organogels were performed as follows. The volumetric swelling ratio, Q, was calculated as follows:

$$Q = 1 + \left(\frac{\rho \mathrm{MEA}}{\rho \mathrm{MeOH}}\right) \times \left(\frac{Ms}{Md} - 1\right),$$

where ρMEA is the density of poly(2-methoxyethyl acrylate) at 298 K (1.20 g/mL, average calculated data), ρMeOH is the density of MeOH at 298 K (0.792 g/mL), $M_s$ is the mass of the swollen gel in MeOH, and $M_d$ is the mass of the dried gel. The crosslinking density was calculated as follows:

$$\text{Crosslinking Density} = \frac{G^3\sqrt{Q}}{RT},$$

where G is the complex shear modulus, $(\sqrt{(G')^{2+}(G'')^2}$, from oscillatory shear rheology at 1 rad $s^{-1}$ and 1% strain), R is the gas constant $$\left(8.31449848\frac{m^3\text{Pa}}{MolK}\right), \text{ and } T = 298K, \text{ in units of } \frac{mol}{mol^3}.$$

The average molecular weight between crosslinks[5] ($M_c$) was calculated as follows:

$$M_c\frac{\rho gelRT}{G}$$

where ρgel is the density of the gel ( $$\left(\left(\frac{M_D}{M_s - M_D}\right)\times \rho\text{MeOH}\right),$$

R is the gas constant $$\left(8.31449848\times 10^6\frac{\text{cm}^3\text{Pa}}{MolK}\right),$$

and T=298 K, in units of $$\frac{g}{mol}.$$

For acryl[2]catenane crosslinked organogels as synthesized, Q (swelling ratio)=5.52±0.08, G*=5069±446 Pa, crosslinking density=3.61±0.02 mol/$m^3$, and $M_c$=130±2 KDa.

Example 17. [2]Catenane/ate Polymer Synthesis and Characterization

Figure 30A:
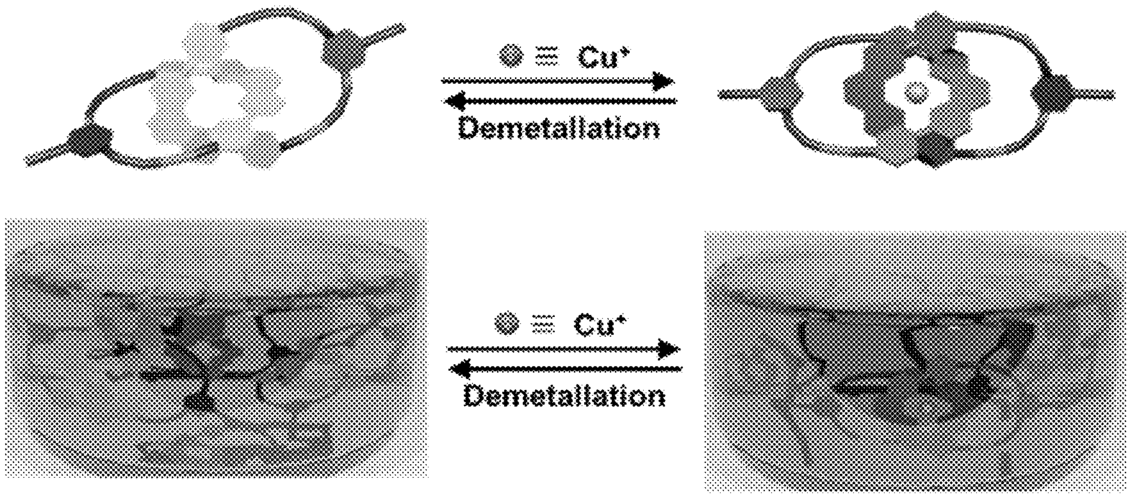
FIG. 30A depicts the metal response from small molecule crosslinker and synthesized hydrogel.
Figure 30B:
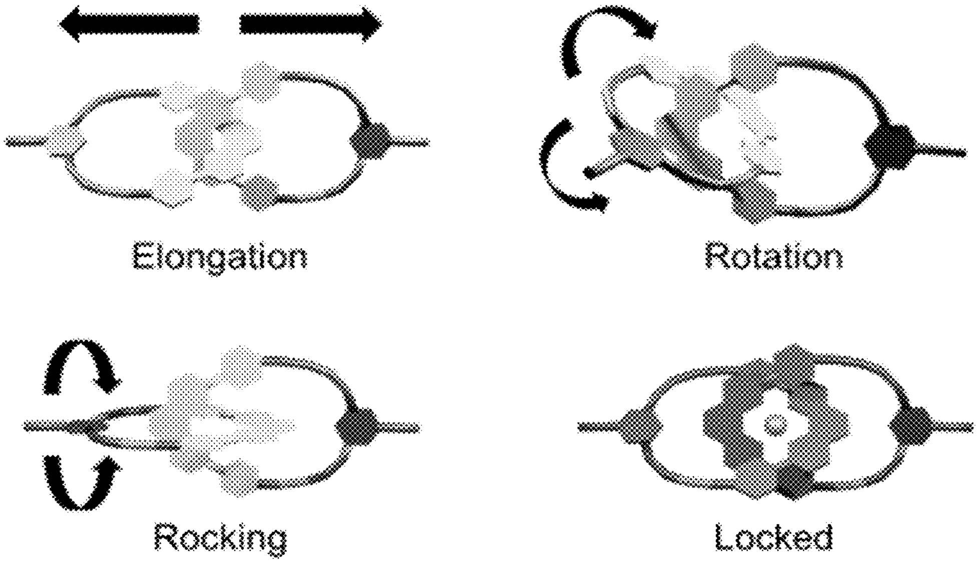
FIG. 30B depicts motions granted by catenane that increase degrees of freedom vs locked catenate.

Catenanes are mechanically interlocked rings that are particularly interesting within this field as a result of their increased degrees of freedom, inherent to the ability of the rings to access motions such as elongation, rocking, and circumrotation (FIG. 30).

Herein the synthesis of a metal responsive [2]catenane crosslinker, via a copper metal-templated strategy is described. Its incorporation into an organogel network and its subsequent mechanical testing are also discussed. Addition of copper to the crosslinker allowed for study of a rigidified system, while removing the metal allowed the mechanical bonds to freely rotate once again. The result was a metal responsive system with an ability to affect the elasticity of the material by controlling its molecular topology (see FIGS. 30A-30B).

The [2]catenane crosslinker allows for an adaptable system in which the metallated catenate (15) behaves like a linear molecule, yet the demetallated [2]catenane (14) shows increased flexibility due to the free rotation of the rings about one another. A macrocycle was designed to take advantage of known methodologies of synthesizing [2]catenanes, while adding functionality in the form of amines. Phenanthroline moieties were chosen for their quick and selective coordination with Cu(I) and olefin ring closing metathesis (RCM) was chosen for its high efficiency and compatibility with many molecules. The choice of Cu(I) phenanthroline chemistry also allowed for easy removal of the metal center using cyanide salts, which was vital in creating an adaptable system. The amines were later transformed into acrylamides for incorporation into organogel networks.

Figure 31A:
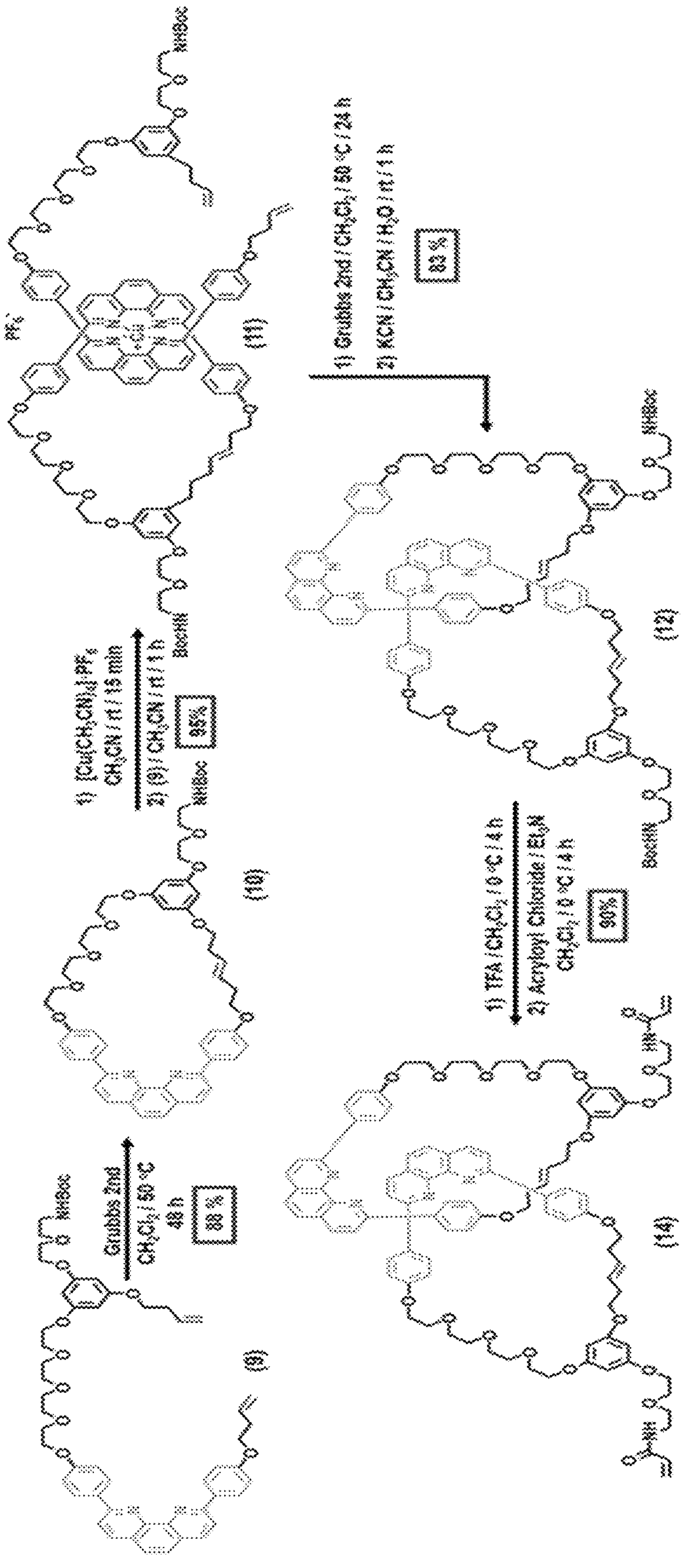
FIG. 31A depicts a scheme describing the synthesis of [2]catenane crosslinker 14.

Synthesis of the [2]catenane 14 began through convergent synthesis of compound 9 from two asymmetric pieces (FIG. 31A). Phloroglucinol and phen diol (5) were each functionalized to compounds 3 and 7 respectively. After mesylation of compound 7, compound 8 was obtained and subsequently coupled to compound 3 using a high pressure assisted Williamson ether synthesis to yield open macrocycle 9. Grubbs $2^{nd}$ generation catalyst was then employed to achieve the desired RCM and yield 10. Copper was added to 10 as $[Cu(CH_3CN)_4]\cdot PF_6$ to form the air-sensitive metallated species. This orange solution turned dark red immediately upon addition of open macrocycle 9, indicative of the air stable ternary complex 12. This was converted to [2]catenane 13 though another RCM, followed by removal of the metal center and purification.

Figure 31B:
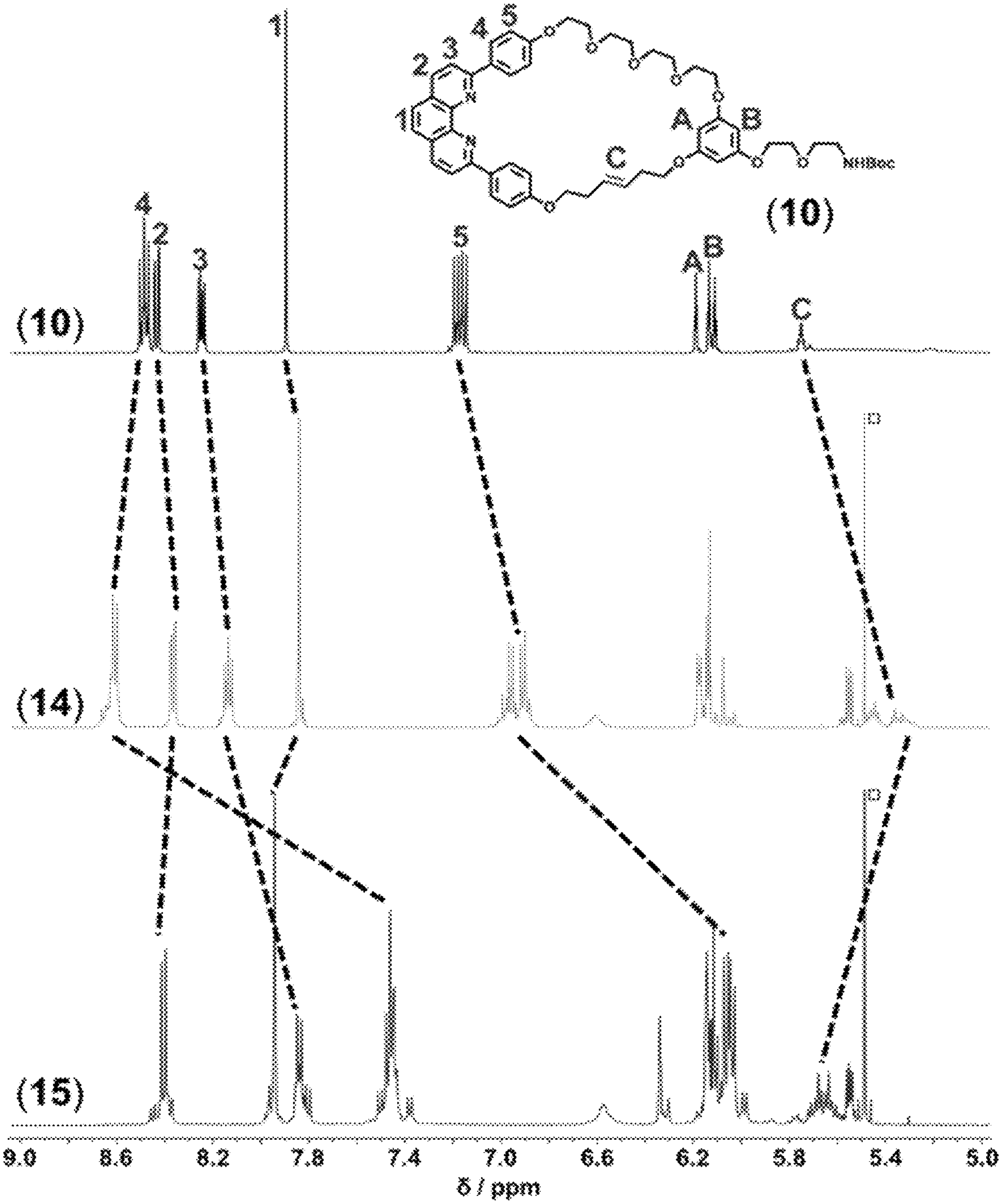
FIG. 31B depicts $^1$HNMR of Boc Protected Macrocycle (10), [2]catenane (14), and Cu Acryl [2]catenate (15). □ indicates $CH_2Cl_2$
Figure 31C:
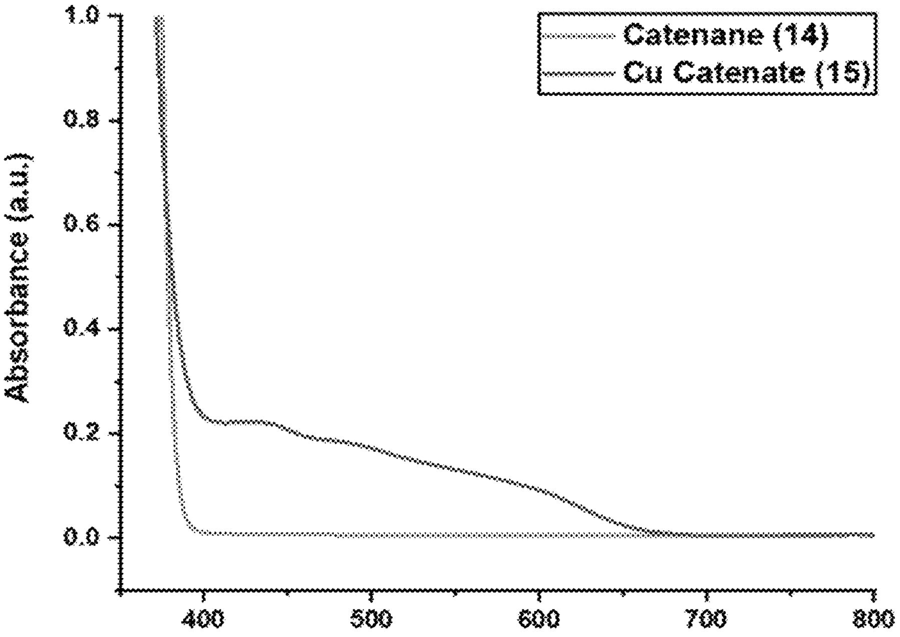
FIG. 31C depicts UV-Vis spectroscopy of 14 and 15.
Figure 31D:
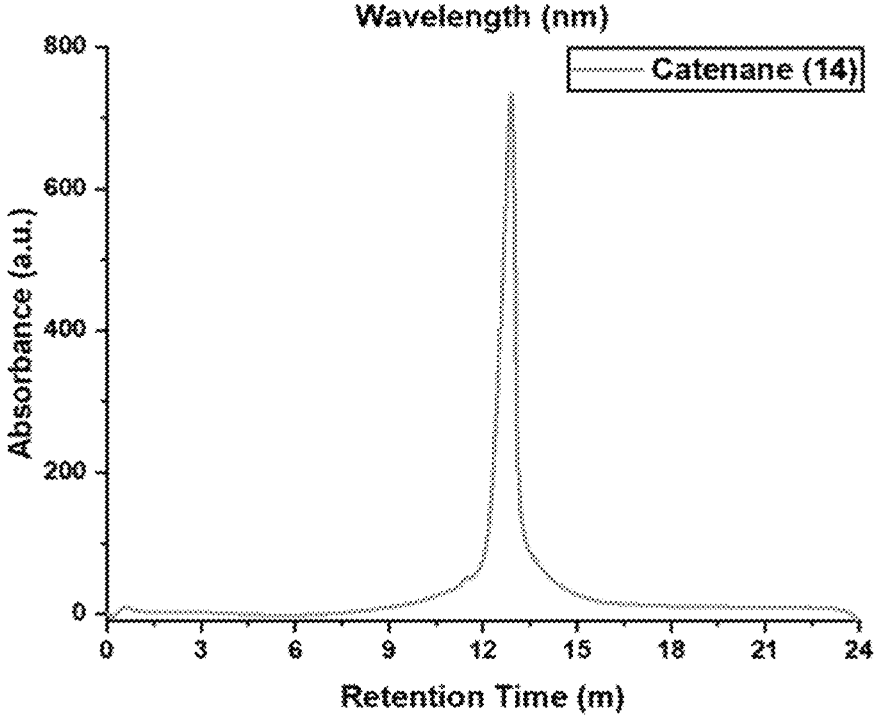
FIG. 31D depicts HPLC trace of [2]catenane crosslinker 14 to show purity.

Although the internal olefin of compound 11 could theoretically react in the RCM step used to form the [2]catenane, hydrogenation was deemed unnecessary as it was often low yielding. This is attributed to the susceptibility of the N to C double bonds in the phenanthroline moiety to hydrogenation. Impurities resulting from interaction of the internal olefin and the external olefins during RCM were easily separated via column chromatography. Conversion of catenane 12 to a usable crosslinker was achieved through deprotection of the Boc-protected amines (13) using trifluoroacetic acid (TFA), followed addition of acryloyl chloride to obtain catenane 14 in 90% yield. Purity of crosslinker 14 was confirmed by $^1$H NMR and HPLC (FIG. 31B-31D).

Catenane 14 shows small changes in the NMR spectra when compared to macrocycle 10. While splitting patterns of the diagnostic phenanthroline peaks change subtly—as the molecule is symmetric—significant upfield shifting can be observed because of the interlocked nature of the molecule. Peaks shift further upfield upon formation of the ternary Cu complex, catenate 15. Formation of the Cu complex was further corroborated by UV-Vis spectroscopy, as diagnostic peaks from 450-600 nm indicate the ligand to metal charge transfer of the Cu to the phenanthroline moieties. Formation of the dative bonds between the phenanthroline ligands and the Cu metal are crucial for utilizing the responsive topology of the crosslinker.

A small subpopulation of [2]catenate with a mass of 1786.80 Da was observed, approximately 14 Da less than the desired product. This is attributed to isomerization of the terminal alkene during the RCM, leading to the loss of a methylene unit. This has been observed previously in RCM and is common place in the synthesis of small and oligocatenanes. After complete characterization, catenane 14 was incorporated into organo-gels to test the extent to which the mechanical bond impacted the gel's properties.

Figure 32A:
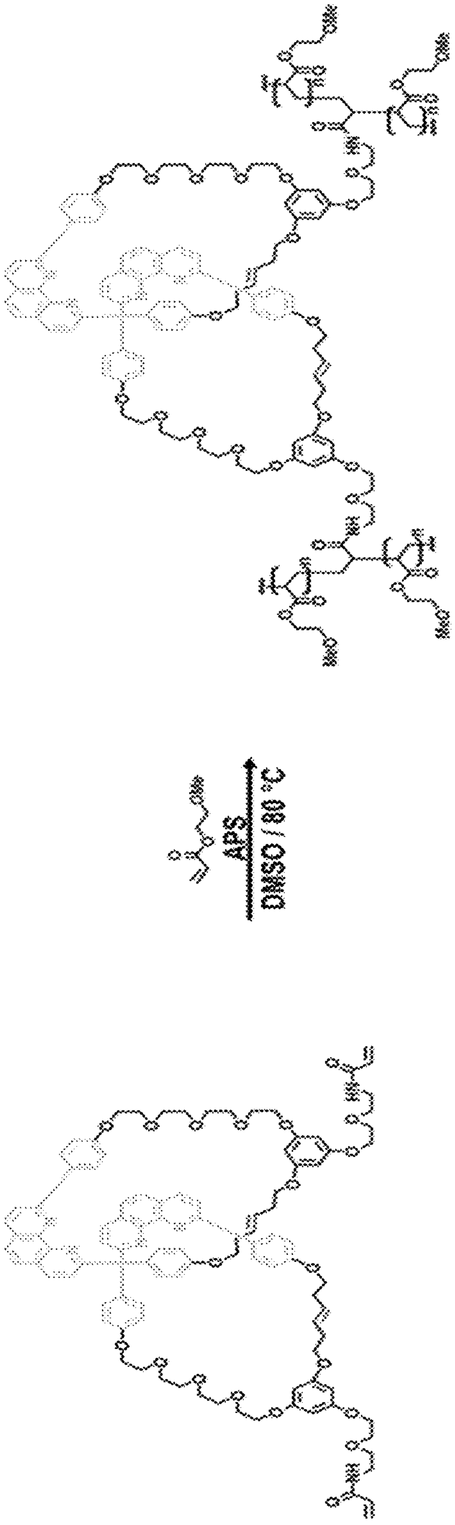
FIG. 32A depicts a scheme describing the incorporation of [2]catenane crosslinker 14 into an organogel.
Figure 32B:
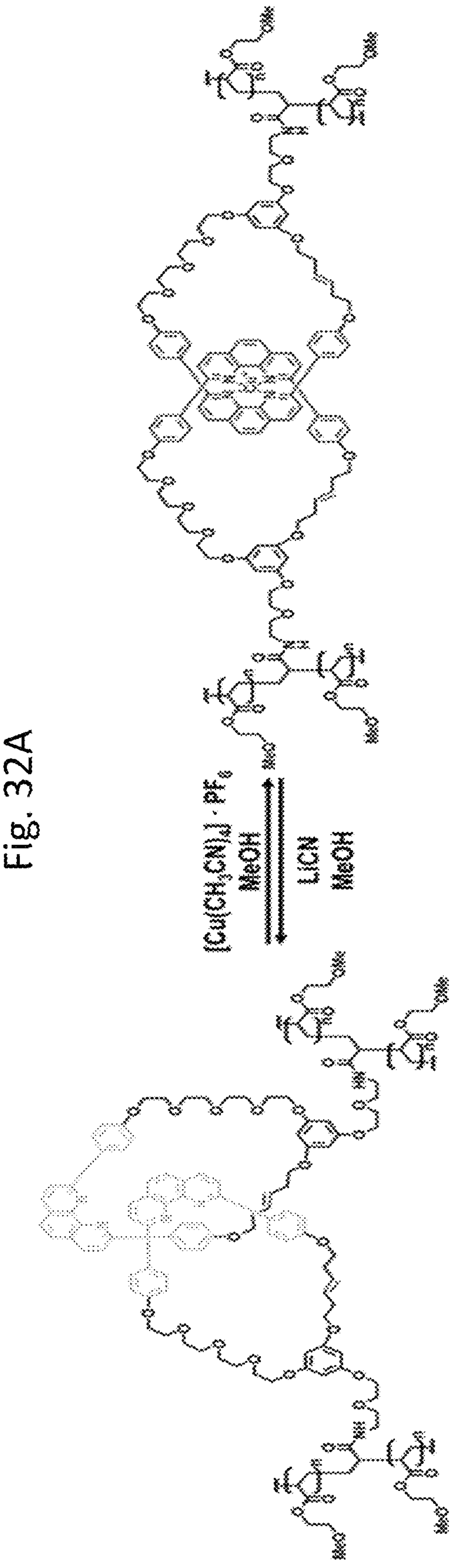
FIG. 32B depicts a scheme describing cyclability of catenane crosslinker between non-metal and metal forms.
Figure 32C:
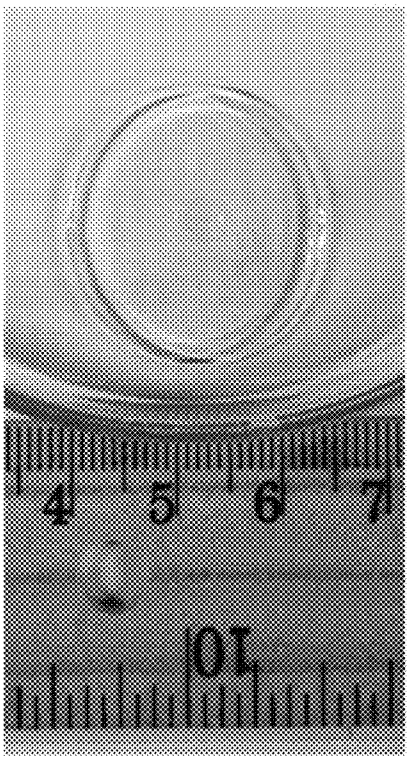
FIG. 32C depicts pictures of gels cycled as synthesized (non-metal).
Figure 32D:
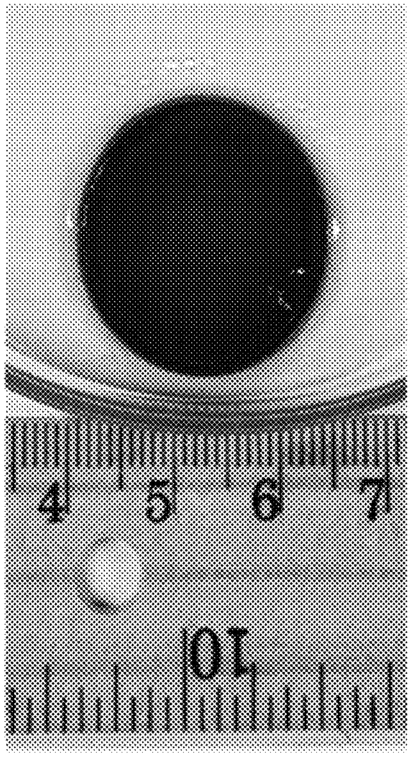
FIG. 32D depicts pictures of gels cycled as Cu treated.
Figure 32E:
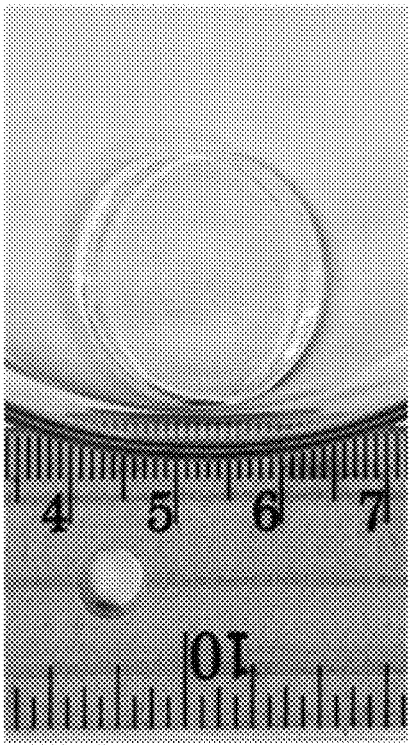
FIG. 32E depicts pictures of gels cycled as KCN treated.
Figure 32F:
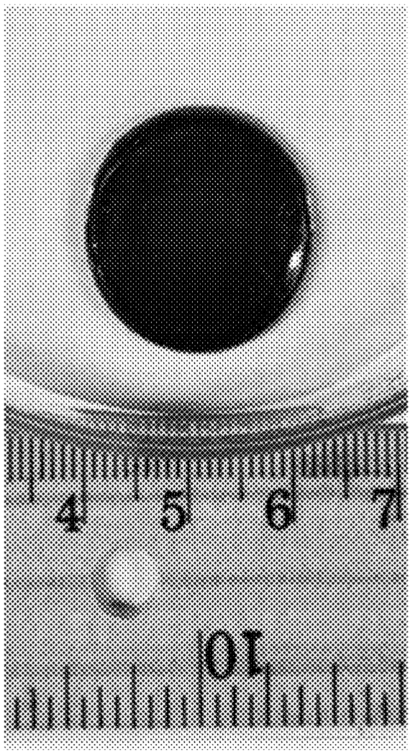
FIG. 32F depicts pictures of gels cycled as Cu treated again.

Gels were synthesized using 2-Methoxyehtylacrylate (MEA) as the bulk material, catenane 14 as the crosslinker and ammonium persulfate (APS) as the heat-based initiator. (FIG. 32A-32B) These reagents were each dissolved in DMSO, vortexed to ensure compete mixing, and pipetted into molds and cured at 80° C. for 25 min. After removing from the molds, gels were swelled in MeOH prior to testing. Swollen gels were then tested using rheology and tensile strength measurements. Gels could not be synthesized with metal crosslinker 15 as oxidation reactions of copper competed with homolytic formation of radicals necessary to initiate the polymerization.

Copper metal was easily incorporated into gels by soaking the gels in a solution of $[Cu(CH_3CN)_4]PF_6$ and sodium ascorbate in MeOH, that had been purged with $N_2$. Gels were then soaked in an ethylenediaminetetraacetic acid (EDTA) solution to remove any excess metal that may be coordinated by the bulk monomer. Removal of copper from gels containing Cu-catenate crosslinker was tested by soaking the gels in a LiCN or KCN solution of MeOH for 2 h. A visible color change was observed, as the red color from the metal ligand interaction was slowly disrupted. (FIG. 32C-32F) The use of LiCN was necessary, as using more readily available KCN lead to issues in the tensile testing. However, the result was not observed to a significant degree during rheological testing. It was hypothesized that crosslinker 14 can coordinate the larger $K^-$ cations, resulting in unwanted increase in elongation at break and diminished tensile strength of organogels. Testing of MEA oligomers with KCN shows that the bulk polymer is resistant to the caustic treatment—at least during limited soak times of the experiments—and that all changes in physical properties are directly resultant from the changes to the conformation of the crosslinker.

Adaptability of the materials synthesized from these crosslinkers is dependent on the ability of the metal to be introduced and removed. The dative covalent bonds between the copper metal and the phenanthroline nitrogens significantly hinders the ability of the rings to circumrotate about one another. This locked catenate structure results in stiffer gels with higher complex modulus, Young's modulus and higher yield strength. Similar gels synthesized using MEA as the bulk material and polyethylene glycol diacrylate (PEGDA) as a crosslinker. No changes in material properties were observed upon treatment of the PEGDA gels with Cu solution, further confirming that the physical changes in the [2]catenane gels is due entirely to the inherent topology of the crosslinker.

Oscillatory rheology was performed using a strain sweep at 15° C. to assess the extent to which the topology of the crosslinker impacted the material, through analysis of the storage (G'), loss (G") and complex (G*) moduli. Circular punches, 8 mm in diameter, were taken from the organogels for each experiment. Dynamic tensile testing was used to assess the Young's modulus (E), tensile strength, and elongation at break of dog bone punches taken from the organogels. Each gel was swollen in a solution of KCN or LiCN in methanol, then treated with in a solution of $[Cu(CH_3CN)_4]PF_6$, then cyanide again, testing between each treatment. This allowed for a complete cycle from free rotating catenanes, to a locked catenate structure and back to freely rotating. Although gels were large enough for four punches, after three experiments physical degradation of the gels became evident and results became less reliable.

Figure 33A:
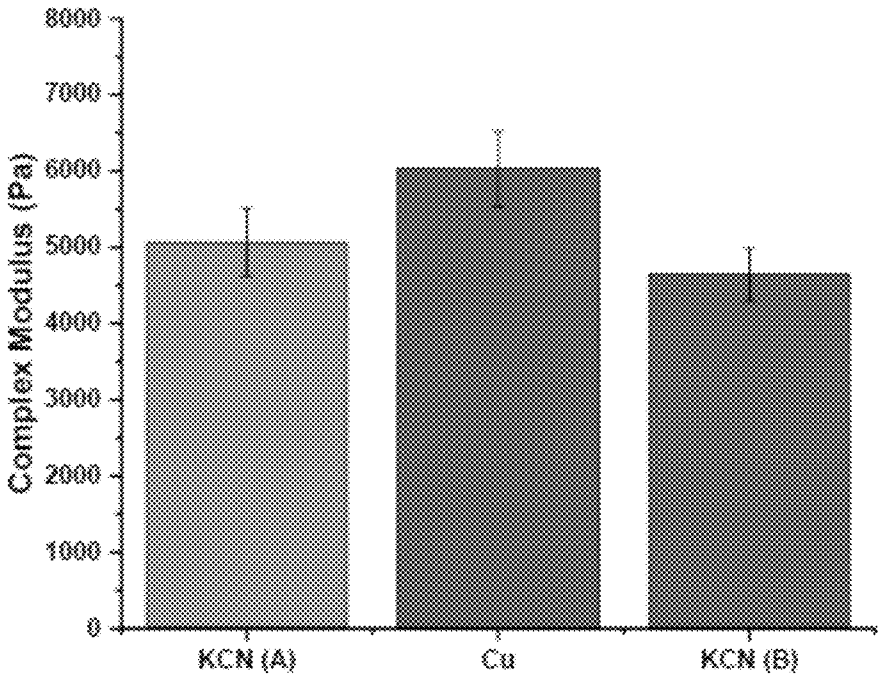
FIG. 33A depicts complex modulus trends for [2]catenane crosslinked organogels.

Dramatic changes in G* could be observed (FIG. 33A) when comparing the gels containing metals to as synthesized gels, or gels treated with KCN. Comparing the ratios of G' to G" for each gel reveals that gels with a locked catenate confirmation behaved more like ideal elastic materials compared to their free moving catenane counterparts. Although a true increase in loss modulus was not observed for free moving catenane gels, the decreased storage modulus in these samples suggests that they are more viscous than the metal containing, conformationally locked samples. The result was a 19% change in G* before and after addition of Cu, with the ability to return the material to its base value, at least once.

Figure 33B:
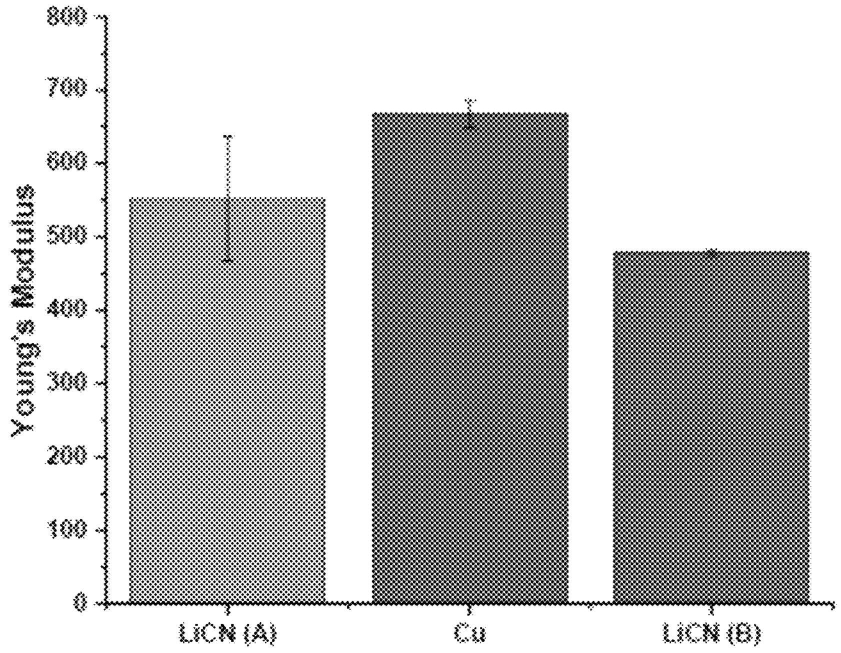
FIG. 33B depicts Young's modulus trends for [2]catenane crosslinked organogels.
Figure 33C:
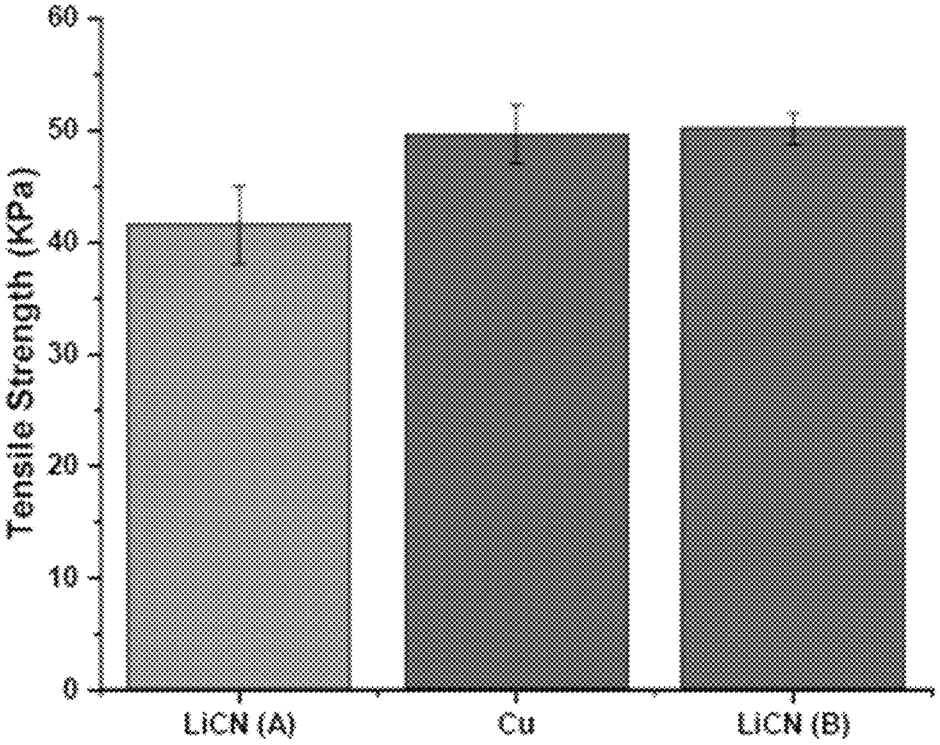
FIG. 33C depicts tensile strength trends for [2]catenane crosslinked organogels.
Figure 33D:
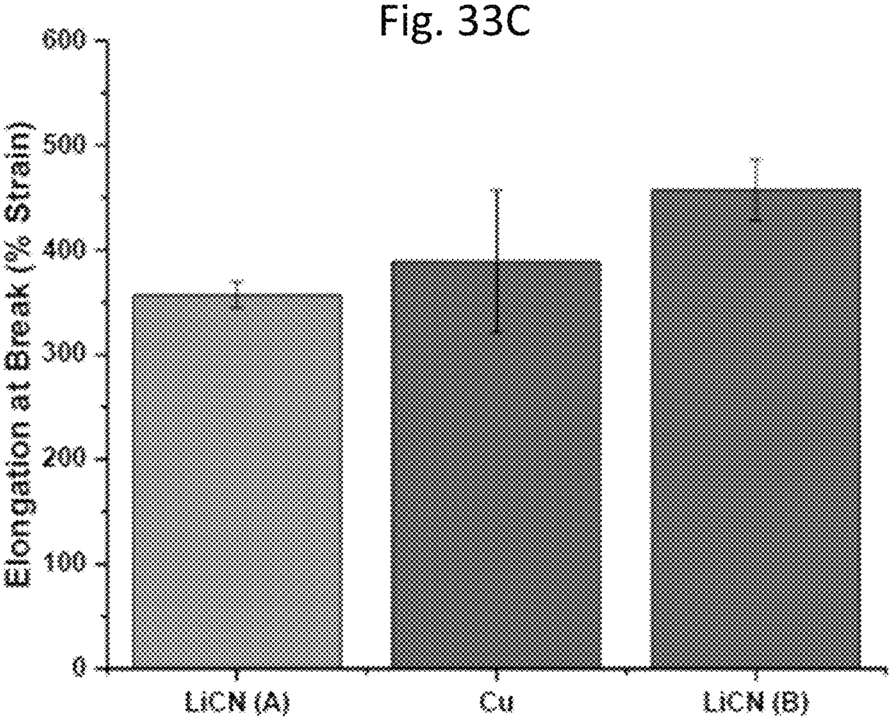
FIG. 33D depicts elongation at break trends for [2]catenane crosslinked organogels.

Very similarly, E was shown to change in a near identical fashion upon addition and removal of Cu ions to the crosslinker (FIG. 33B). Locking the topology of the catenane crosslinker increased E by nearly 21%, which was then decreased slightly below starting levels after removal of the Cu ions. This result corresponds incredibly well to the changes observed in G*, as both G* and E are measurements of the stiffness of the material. While an expected, and desired, increase in tensile strength of the material was also observed upon addition of Cu ions to the system, this parameter was not reversible upon removal of Cu (FIG. 33C). Similarly, the elongation at break of the material trended upward after each subsequent treatment (FIG. 33D). This is attributed to the softness of the bulk material, which showed signs of toughening and eventually degradation after subsequent treatments and removal of material with each experiment.

A summary of physical characteristics of Acryl[2]catenane gels is in Table 3, shown below.

TABLE 3

| Acryl[2]catenane | $E^a$ (Kpa) | $G^{*b}$ (Pa) | $TS^c$(KPa) | $\varepsilon_B{}^d$ |
|---|---|---|---|---|
| Li or KCN (A) | 55.2 ± 8.5 | 5069 ± 446 | 41.6 ± 3.5 | 357.0 ± 12.0 |
| Cu (A) | 66.7 ± 1.9 | 6029 ± 492 | 49.7 ± 2.6 | 389.2 ± 67.8 |
| Li or KCN (B) | 0.4 | 4642 ± 350 | 50.2 ± 1.4 | 505.9 ± 29.1 |

A summary of physical characteristics of control PEGDA gels is in Table 4, shown below.

TABLE 4

| PEGDA | $E^a$ (Kpa) | $G^{*b}$ (Pa) | $TS^c$(KPa) | $\varepsilon_B{}^d$ |
|---|---|---|---|---|
| As Synthesized | 25.5 ± 3.5 | 5968 ± 361 | 33.9 ± 1.7 | 299.2 ± 1.7 |
| Cu (A) | 24.0 ± 6.6 | 5259 ± 166 | 27.9 ± 4.1 | 295.8 ± 4.1 |
| KCN | 26.8 ± 7.2 | 5605 ± 368 | 25.0 ± 5.1 | 195.5 ± 5.1 |
| Cu (B) | 24.7 ± 4.2 | 5815 ± 313 | 23.5 ± 1.4 | 186.9 ± 1.4 |

Therefore, a Cu responsive [2]catenane based crosslinker was synthesized, incorporated into MEA based organogels, and tested using oscillatory shear rheology and dynamic tensile testing. The result was an organogel, in which an atomic level change to only 4 wt % (0.27 mol %) of the total material was able to affect a 19% change in G* and a 21% change in E, reversibly. This is due to the effectiveness of catenanes as topologically elastic linkers in materials, and their incredible responsiveness to stimuli. Future works will include incorporation of the catenane into other more robust materials, as well as investigations into improving the cyclability of the system on whole.

Example 18. Detailed Synthesis of Open Macrocycle for [2]Catenane/ate Polymer a) Mono Olefin Phloroglucinol (Chloro) (1)

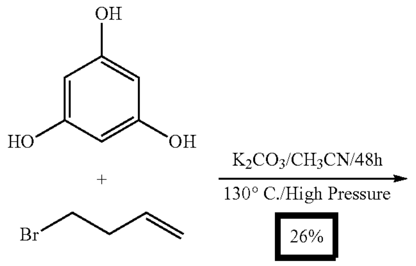

-continued

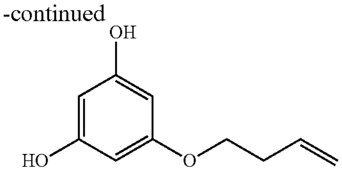

(1)

To a 350 mL high-pressure vessel (Kemtech) with Teflon screw cap and a stir bar, was added a solution of phloroglucinol (15.00 g, 188.94 mmol, 4.0 eq.) in 100 mL of $CH_3CN$, followed by $K_2CO_3$ (12.33 g, 89.21 mmol, 3.0 eq), and 4-bromo-1-butene (4.02 g, 29.74 mmol, 1.0 eq) sequentially. The vessel was then sealed, and the reaction mixture was heated to 130° C. while stirring for 48 h. The reaction mixture was then allowed to cool to room temperature over 2 h. The reaction mixture was then transferred to a round bottom flask and the solvent was removed. The crude was dissolved in 1 M HCl (400 mL) and $CHCl_3$ (300 mL). The aqueous layer was then back extracted with $CHCl_3$ (3×300 mL). The organic layers were combined, dried over $Na_2SO_4$ and filtered. Solvent was removed to yield a brown oil with solid particles suspended within it. Silica column chromatography (0.5% $MeOH/CH_2Cl_2$ to 5% $MeOH/CH_2Cl_2$) of the crude afforded the product as a brown oil (1.4 g, 25%).

$^1H$ NMR (500 MHz, $CDCl_3$): $\delta_H$ 6.00 (bs, 2H), 5.95 (d, J=2 Hz, 1H), 5.92-5.84 (m, 1H), 5.17-5.09 (dd, J=31, 10 Hz, 2H), 4.70 (bs, 2H), 3.96-3.93 (t, J=6.5 Hz, 2H), 2.53-2.49 (q, J=6.5 Hz, 2H). $^{13}C$ NMR (125 MHz, $CDCl_3$): $\delta_C$ 160.9, 157.3, 134.2, 117.1, 96.0, 95.1, 67.4, 33.4. MALDI: calculated for $C_{10}H_{12}O_3$: m/z=181.0864 $[M+H]^+$; Found: 181.0860 $[M+H]^+$.

b) Boc Tos (2)

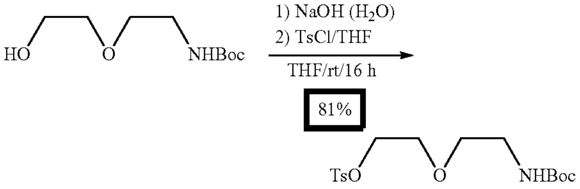

(2)

To a solution of 2-[2-(Boc-amino)ethoxy]ethanol (4.52 g, 22.08 mmol, 1.0 eq) in THF stirring at room temperature, was added a solution of NaOH (1.32 g, 33.12 mmol, 1.5 eq) in $H_2O$ (10 mL). After 1 h the round bottom flask was fitted with a slow addition funnel, to which a solution of TsCl (10.52 g, 55.20 mmol, 2.5 eq) in THF. This solution was added dropwise over the course of 1 h. After 16 h the reaction mixture was dilute with $CH_2Cl_2$ (300 mL) and washed with brine (250 mL). The aqueous layer was then extracted with $CH_2Cl_2$ (3×250 mL). Organics were combined, dried over $Na_2SO_4$ and filtered. Solvent was removed by rotary evaporation to yield a yellow oil. Crude was purified by silica column chromatography (10:90, Hexanes: Ethyl Acetate to Ethyl Acetate) to afford the product as a white solid (6.46 g, 81%).

$^1H$ NMR (500 MHz, $CDCl_3$): $\delta_H$ 7.81-7.80 (d, J=8.5 Hz, 2H), 7.36-7.34 (d, J=8.5 Hz, 2H), 4.79 (bs, 1H), 4.17-4.15 (dd, J=6, 3.5 Hz, 2H), 3.64-3.62 (dd, J=6, 3.5 Hz, 2H), 3.46-3.44 (t, J=5 Hz, 2H), 3.25-3.22 (q, J=5.5 Hz, 2H), 2.45 (s, 3H), 1.45 (s, 9H)$^{13}C$ NMR (125 MHz, $CDCl_3$): $\delta_C$ 156.0, 145.0, 133.2, 129.9, 128.1, 79.5, 70.5, 69.2, 68.5, 40.4, 28.5, 21.8 MALDI: calculated for $C_{16}H_{25}NO_6S$: m/z=382.1300 $[M+Na]^+$; Found: 382.1295 $[M+Na]^+$.

c) Boc Olefin Phloro (3)

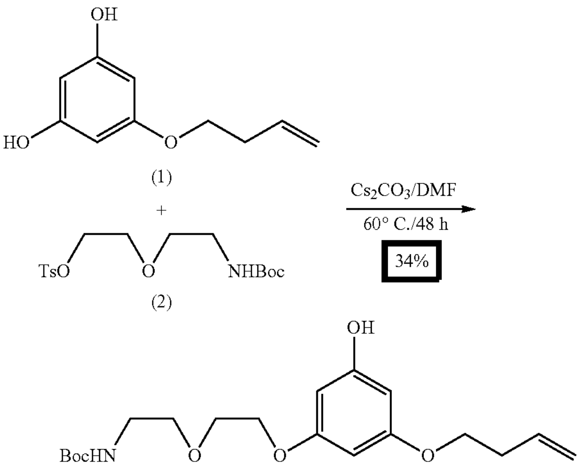

(3)

A solution of 1 (8.91 g, 49.43 mmol, 3.0 eq.) and $Cs_2CO_3$ (16.10 g, 49.43 mmol, 3.0 eq) in 400 mL of DMF was heated to 60° C. for 1 h while stirring under $N_2$. A solution of 2 (5.92 g, 16.48 mmol, 1.0 eq) in 50 mL of DMF was added via syringe pump at 1.5 $mL \cdot h^{-1}$. After 48 h the solvent was removed via rotary evaporation, and the solid was resuspended in ethyl acetate. This suspension was filtered through a sintered funnel. The precipitate was dissolved, transferred to another flask using methanol before drying via rotary evaporation. The supernatant was concentrated via rotary evaporation to yield a brown oil. The precipitate was taken up in water (150 mL), brine (150 mL) and glacial acetic acid (1 mL). This dark colored aqueous layer was extracted with ethyl acetate (3×250 mL). Organic layers were combined and washed with saturated aqueous $NaHCO_3$. Organics were then dried over $Na_2SO_4$ and filtered. Solvent was removed by rotary evaporation to yield a tacky brown oil. Both crudes were combined, the purified by silica column chromatography (60:40, Hexane:Ethyl Acetate to Ethyl Acetate) to afford the product as a tacky brown oil (2.08 g, 34%).

$^1H$ NMR (500 MHz, $CDCl_3$): $\delta_H$ 6.12 (t, J=2 Hz, 1H), 6.09 (t, J=2 Hz, 1H), 6.06 (t, J=2 Hz, 1H), 5.93-5.85 (m, 1H), 5.60 (bs, 1H), 5.19-5.09 (qq, J=17.5, 2 Hz, 2H), 4.98 (bs, 1H), 4.09-4.07 (dd, J=6.5, 1.5 Hz, 2H), 3.98-3.95 (t, J=7 Hz, 2H), 3.79-3.77 (t, J=4.5 Hz, 2H), 3.60-3.58 (t, J=5 Hz, 2H), 3.36-3.35 (q, J=5 Hz, 2H), 2.54-2.50 (qt, J=6.5, 1 Hz, 2H), 1.46 (s, 9H). $^{13}C$ NMR (125 MHz, $CDCl_3$): $\delta_C$ 160.9, 160.6, 158.2, 156.5, 134.5, 117.0, 95.3, 95.1, 94.1, 79.82, 70.3, 69.5, 67.4, 67.3, 40.5, 33.6, 28.5 MALDI: calculated for $C_{19}H_{29}NO_6$: m/z=390.1892 $[M+Na]^+$; Found: 390.1888 $[M+Na]^+$.

d) Methoxy Phen (4)

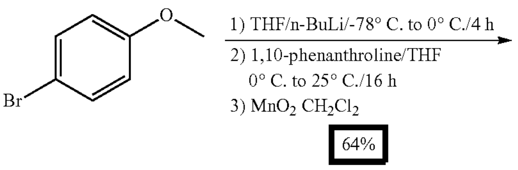

-continued

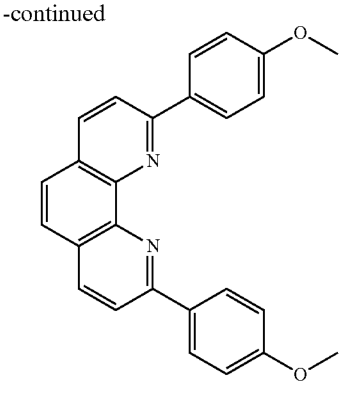

(4)

Compound 3 was prepared following a modified prep from Dietrich-Buchecker et al., 1990. To an oven-dried 250 mL RB flask was added 4-bromoanisole (20.76 g, 110.9 mmol, 4.0 eq.) and 100 mL anhydrous THF. The solution was cooled on Hexane/dry ice bath and 75 mL n-BuLi (2.5 M hexanes, 188.6 mmol, 6.8 eq.) was cannulated into a slow addition funnel, then added dropwise while stirring under $N_2$. The solution was stirred at −78° C. for 2 h, transferred to ice bath and stirred for an additional 2 h. The ice bath was removed, and the reaction was stirred for 2 h, slowly coming to room temperature. The resulting yellow solution was transferred via cannula to an oven-dried 300 mL RB flask containing a solution of 1,10-phenanthroline (5.00 g, 27.7 mmol, 1.0 eq.) in 50 mL anhydrous THF cooled on an ice bath. The resulting dark red solution was stirred in ice bath for 1 h and was then allowed to warm up to room temperature while stirring over 16 h. The reaction was quenched by adding $H_2O$ (40 mL) that had been cooled on an ice bath and the solvent was removed via rotary evaporator. The aqueous residue was extracted with $CH_2Cl_2$ (3×100 mL). The organic layers were combined, dried ($Nas_2SO_4$) and filtered. The filtrate was evaporated under reduced vacuum and the residue was re-dissolved in 200 mL $CH_2Cl_2$. To this solution was added $MnO_2$ (50 g, 583 mmol, 21 eq.) and the suspension was stirred at reflux for 1 h. The suspension was dried over $Na_2SO_4$, then the solids were filtered off and the filtrate was concentrated by rotary evaporation. The resulting solid was then recrystallized in hot toluene to afford the product as yellow crystals (6.96 g, 64%).

$^1H$ NMR (500 MHz, $CDCl_3$): $\delta_H$ 8.44 (d, J=8.8 Hz, 4H), 8.26 (d, J=8.4 Hz, 2H), 8.09 (d, J=8.4 Hz, 2H), 7.74 (s, 2H), 7.12 (d, J=8.8 Hz, 4H), 3.93 (s, 6H). BC NMR (125 MHz, $CDCl_3$): $\delta_C$ 161.0, 156.4, 146.1, 136.9, 132.3, 129.1, 127.6, 125.7, 119.4, 114.3, 55.5. LRMS-ESI: calculated for $C_{26}H_{20}N_2O_2$: m/z=393.2 $[M+H]^+$; Found: 393.2 $[M+H]^+$.

e) Phen Diol (5)

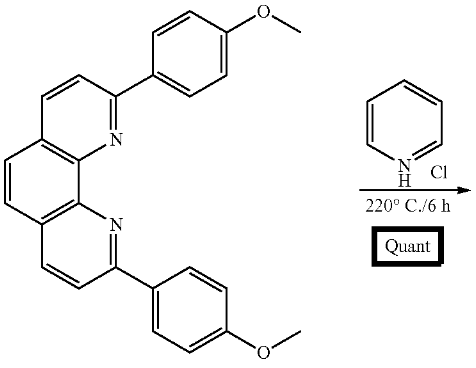

(4)

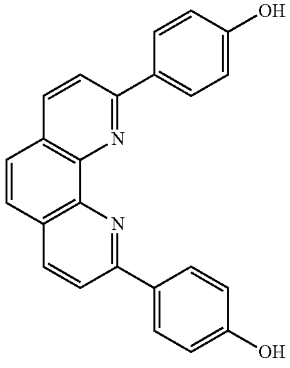

(5)

Compound 5 was prepared following a modified prep from Dietrich-Buchecker et. al.[1] To a 500 mL RB flask was added 4 (2.9 g, 7.4 mmol, 1.0 eq.) and pyridine hydrochloride (55 g, 480 mmol, 65 eq.). The mixture was stirred at 220° C. for 6 h. After cooling to 180° C., 120 mL hot $H_2O$ was added slowly. A mixed solvent of 250 mL EtOH:$H_2O$ (40:60) was added at room temperature. The suspension was stirred for 1 h and was allowed to sit at 4° C. for overnight. The suspension was neutralized to pH=7.4 with 1 M NaOH solution in $H_2O$. The solid was filtered and dried under vacuum to afford the product as a dark brown solid with a quantitative yield.

$^1H$ NMR (500 MHz, DMSO-$d_6$): $\delta_H$ 10.20 (s, 2H), 8.72 (d, J=7.7 Hz, 2H), 8.42 (d, J=8.4 Hz, 2H), 8.35 (d, J=8.4 Hz, 4H), 8.08 (s, 2H), 7.06 (d, J=8.5 Hz, 4H). $^{13}C$ NMR (125 MHz, DMSO-$d_6$): $\delta_C$ 159.9, 155.1, 138.6, 129.8, 129.5, 127.3, 125.7, 120.4, 115.8, 115.7. HRMS-ESI: calculated for $C_{24}H_{16}N_2O_2$: m/z=365.1285 $[M+H]^+$; Found: 365.1319 $[M+H]^+$.

f) Mono Tos TEG (6)

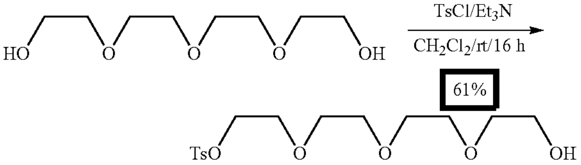

(6)

To a solution of tetraethylene glycol (77.69 g, 400 mmol, 4.0 eq) and $Et_3N$ (20.24 g, 200 mmol, 2.0 eq) in $CH_2Cl_2$ (500 mL) was added TsCl (19.07 g, 100 mmol, 1.0 eq) slowly as a solid while stirring at room temperature. After 72 h the reaction was diluted with $CH_2Cl_2$ (200 mL) and washed with aqueous 10% $K_2CO_3$ (2×200 mL), brine (2×200 mL) and 0.1 M HCl (2×200 mL). Organic layer was dried over $Na_2SO_4$ and filtered. Solvent was removed via rotary evaporation to yield a yellow oil. Purification of the crude by silica column chromatography ($CH_2Cl_2$ to 5% Acetone/$CH_2Cl_2$ to 5% MeOH/$CH_2Cl_2$) afforded the product as a clear pale-yellow oil (21.25 g, 61%).

$^1$H NMR (500 MHz, $CDCl_3$): $\delta_H$ 7.81-7.79 (d, J=8 Hz, 2H), 7.35-7.33 (d, J=8.5 Hz, 2H), 4.18-4.16 (dd, J=5, 5 Hz, 2H), 3.73-3.68 (m, 4H), 3.67-3.62 (m, 4H), 3.61-3.59 (m, 6H), 2.45 (s, 3H). $^{13}$C NMR (125 MHz, $CDCl_3$): $\delta_C$ 144.8, 132.9, 129.8, 127.9, 72.4, 70.6, 70.5, 70.4, 70.2, 69.2, 68.6, 61.6, 21.5. MALDI: calculated for $C_{15}H_{24}O_7S$: 371.1140 $[M+Na]^+$; Found: 371.1135 $[M+Na]^+$.

g) Phen Tetraethylene Glycol Olefin (7)

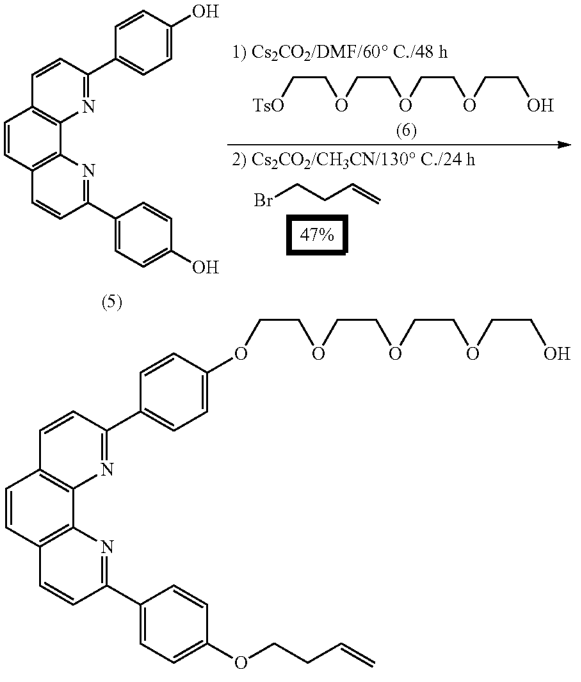

(5)

(7)

A solution of 5 (2.00 g, 5.49 mmol, 2.0 eq) and $Cs_2CO_3$ (1.34 g, 4.12 mmol, 1.5 eq) in 100 mL of DMF was heated to 60° C. for 1 h while stirring under $N_2$. A solution of 6 (0.96 g, 2.75 mmol, 1.0 eq) in 20 mL of DMF was added via syringe pump at 1.5 mL·h$^{-1}$. After complete addition of 6 the reaction mixture stirred at 60° C. for 48 h. The reaction mixture was filtered, and the precipitate was washed with $CH_2Cl_2$:MeOH (50:50). The supernatants were combined, then concentrated by rotary evaporation and the resulting orange solid was transferred to a high-pressure vessel (Kemtech) with Teflon screw cap and a stir bar. To the high-pressure vessel was added $CH_3CN$ (40 mL), $Cs_2CO_3$ (4.47 g, 13.73 mmol, 5.0 eq), and 4-bromo-1-butene (1.85 g, 13.73 mmol, 5.0 eq). The vessel was then sealed, and the reaction mixture was heated to 130° C. while stirring for 24 h. The reaction mixture was then allowed to cool to room temperature over 2 h. The reaction mixture was then transferred to a round bottom flask and the solvent was removed. The resulting solid was taken up in $H_2O$ (250 mL), brine (250 mL) and $CH_2Cl_2$ (250 mL). Organic layer was further extracted with $CH_2Cl_2$ (2×250 mL). Organic layers were combined, dried over $Na_2SO_4$ and filtered. Solvent was removed by rotary evaporation to yield an orange solid. Purification of the crude by silica column chromatography (2% MeOH/$CH_2Cl_2$) to afford the product as a pale yellow-orange waxy solid (0.76, 47%).

$^1$H NMR (500 MHz, $CDCl_3$): $\delta_H$ 8.46-8.43 (dd, J=14.5 Hz, 4H), 8.28-8.26 (dd, J=8.5, 0.5 Hz, 2H), 8.11-8.09 (d, J=8.5 Hz, 2H), 7.76 (s, 2H), 7.15-7.12 (dd, J=9, 8 Hz, 4H), 6.02-5.94 (m, 1H), 5.25-5.15 (qq, J=17.5, 1.5 Hz, 2H), 4.29-4.27 (t, J=4.5 Hz, 2H), 4.18-4.15 (t, J=7 Hz, 2H), 3.95-3.93 (t, J=5 Hz, 2H), 3.81-3.78 (m, 2H), 3.75-3.72 (m, 4H), 3.71 (s, 4H), 3.64-3.62 (m, 2H), 2.65-2.61 (qt, J=7, 1.5 Hz, 2H). ($^{13}$C NMR (125 MHz, $CDCl_3$): $\delta_C$ 160.2, 160.1, 156.4, 156.3, 146.0, 136.8, 136.7, 134.4, 132.3, 132.2, 129.0, 129.0, 127.5, 127.5, 125.6, 125.6, 119.3, 119.3, 117.1, 114.9, 114.8, 72.5, 70.9, 70.7, 70.6, 70.4, 69.8, 67.5, 67.3, 61.8, 50.7, 33.7. MALDI: calculated for $C_{36}H_{38}N_2O_6$: 585.2808 $[M+H]^+$; Found: 595.2803 $[M+H]^+$.

h) Phen Mesyl Olefin (8)

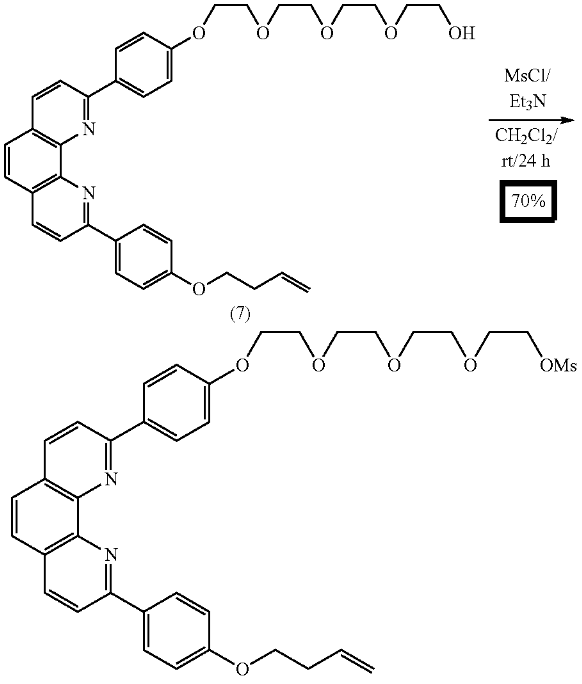

(7)

(8)

To a solution of 7 (0.45 g, 0.75 mmol, 1.0 eq) in 100 mL of dry $CH_2Cl_2$ was added MsCl (0.43 g, 3.76 mmol, 5.0 eq) via syringe, then $Et_3N$ (0.38 g 3.76 mmol, 5.0 eq) via syringe, while stirring at room temperature under $N_2$. After 24 h the reaction mixture was dilute with $CH_2Cl_2$ (150 mL) and washed with 1 M acetic acid (2×100 mL), saturated aqueous $NaHCO_3$ (2×100 mL), and brine (2×100 mL). Organic layer was then dried over $Na_2SO_4$ and filtered. Solvent was removed by rotary evaporation to yield a yellow-orange solid. Purification of the crude by silica column chromatography (50:50 Hexanes:Ethyl Acetate to Ethyl Acetate) afforded the product as a tacky pale orange liquid (0.35 g, 70%).

$^1$H NMR (500 MHz, $CDCl_3$): $\delta_H$ 8.45-8.43 (dd, J=8.5, 3 Hz, 4H), 8.28-8.26 (dd, J=8.5, 1.5 Hz, 2H), 8.11-8.09 (dd, J=8.5, 1 Hz, 2H), 7.75 (s, 2H), 7.14-7.11, (dd, J=8.5, 6.5 Hz, 4H), 6.03-5.92 (m, 1H), 5.25-5.15 (qq, J=17, 1.5 Hz, 2H), 4.39-4.37 (m, 2H), 4.28-4.26 (t, J=4.5 Hz, 2H), 4.17-4.15 (t, J=5 Hz, 2H), 3.79-3.77 (m, 4H), 3.72-3.70 (m, 2H), 3.69 (s, 3H), 3.07 (s, 3H), 2.65-2.61 (qt, J=7, 1.5 Hz, 2H). $^{13}$C NMR (125 MHz, $CDCl_3$): $\delta_C$ 160.4, 160.2, 156.5, 156.4, 146.2, 136.9, 136.9, 134.5, 132.5, 132.3, 129.1, 127.7, 127.7, 125.8, 125.7, 119.5, 119.4, 117.3, 115.0, 114.9, 71.1, 70.8, 70.8, 70.0, 69.4, 69.2, 67.7, 67.5, 37.9, 33.8. MALDI: calculated for $C_{37}H_{40}N_2O_8S$: 673.2583 $[M+H]^+$; Found: 673.2579 $[M+H]^+$.

i) Boc Protected Open Macrocycle (9)

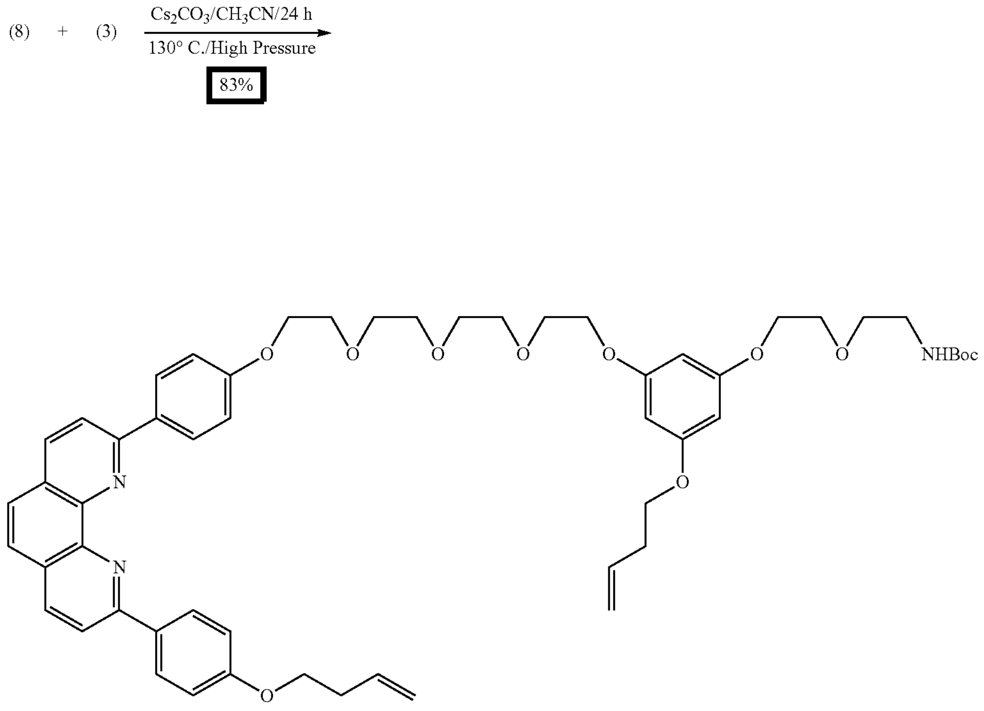

(9)

To a 100 mL high pressure vessel (Kemtech) with Teflon screw cap and a stir bar was added a solution of 8 (0.353 g, 0.524 mmol, 1.0 eq.) and 3 (0.193 g, 0.524 mmol, 1.0 eq) in 30 mL of $CH_3CN$, followed by $Cs_2CO_3$ (0.854 g, 2.62 mmol, 5.0 eq). The vessel was then sealed and the reaction mixture was heated to 130° C. while stirring for 24 h. The reaction mixture was then allowed to cool to room temperature over 2 h. The reaction mixture was then filtered into a round bottom flask and the solvent was removed en vacuo. The crude solid was then taken up in $CH_2C12$ (200 mL) and washed with $H_2O$ (150 mL) and brine (3×150 mL). The organic layer was then dried over $Na_2SO_4$ and filtered. Solvent was removed by rotary evaporation to yield a tacky orange solid. Purification of the crude by silica column chromatography (50:50 Hexanes:Ethyl Acetate to Ethyl Acetate) afforded the product as a waxy pale yellow-orange solid (0.410 g, 83%).

$^1$H NMR (500 MHz, $CDCl_3$): $\delta_H$ 8.44-8.41 (dd, J=8.5, 3 Hz, 4H), 8.27-8.25 (dd, J=8.5, 1.5 Hz, 2H), 8.09-8.07 (dd, J=8.5, 1 Hz, 2H), 7.74 (s, 2H), 7.12-7.10 (dd, J=8.5, 6.5 Hz, 4H), 6.10 (s, 3H), 6.00-5.83 (m, 2H), 5.24-5.07 (m, 4H), 4.93 (bs, 1H), 4.26-4.24 (t, J=4.5 Hz, 2H), 4.16-4.13 (t, J=6.5 Hz, 2H), 4.08-4.06 (t, J=4.5 Hz, 2H), 4.05-4.03 (t, J=4.5 Hz, 2H), 3.96-3.91 (m, 4H), 3.85-3.83 (t, J=5 Hz, 2H), 3.78-3.67 (m, 10H), 3.58-3.56 (t, J=5 Hz, 2H), 3.33-3.32 (q, J=5.5 Hz, 2H), 2.64-2.59 (qt, J=6.5, 1 Hz, 2H), 2.52-2.48 (qt, J=7, 1.5 Hz, 2H), 1.43 (s, 9H). $^{13}$C NMR (125 MHz, $CDCl_3$): 160.7, 160.7, 160.5, 160.3, 160.2, 156.3, 156.3, 146.1, 136.8, 134.5, 134.4, 13.4, 132.2, 129.0, 129.0, 127.6, 127.6, 125.7, 125.6, 119.3, 119.3, 117.2, 117.1, 114.9, 114.9, 94.4, 94.3, 71.0, 70.9, 70.8, 70.8, 70.4, 69.8, 69.7, 69.4, 67.6, 67.5, 67.4, 67.3, 67.3, 33.7, 33.6, 28.5 MALDI: calculated for $C_{55}H_{65}N_3O_{11}$: 966.4516 $[M+Na]^+$; Found: 966.4512 $[M+Na]^+$.

j) Roc Protected Closed Macrocycle (10)

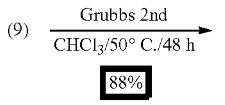

-continued

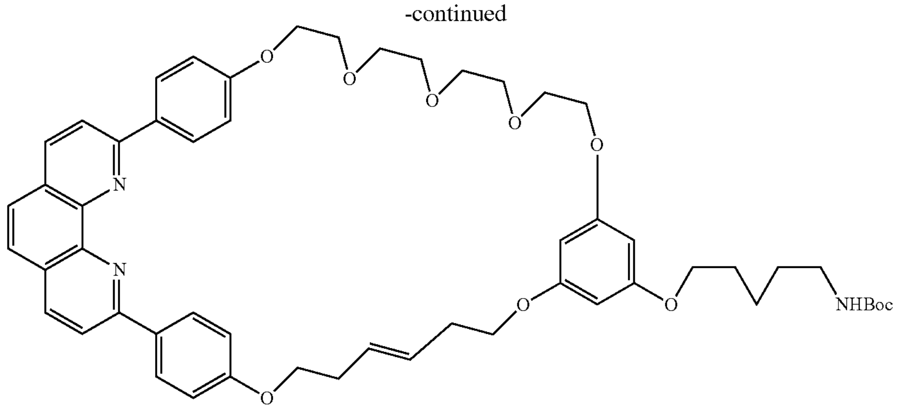

(10)

To a solution of 9 (0.550 g, 0.583 mmol, 1 eq.) in 600 mL of dry $CH_2Cl_2$ was added a solution of Grubbs' 2$^{nd}$ generation catalyst (0.050 g, 0.058 mmol, 0.1 eq.) in CH2C12 (2 mL) via pipette. The solution was then heated to 50° C. while stirring under $N_2$. The reaction was periodically checked via low-res ESI for the consumption of the starting material. After 24 h the reaction had reached completion based on disappearance of the starting material and was quenched with ethyl vinyl ether (EVE) (25 mL) and $CH_3CN$ (10 mL) then allowed to cool to room temperature for 1 h. Solvent was removed via rotary evaporation to yield the crude product as a brown solid. The crude was purified via silica gel column chromatography (EtOAc) to afford the product as a pale orange-yellow solid (0.472 g, 88%).

$^1$H NMR (500 MHz, $CDCl_3$): $\delta_H$ 8.46-8.44 (dd, J=8.5, 4 Hz, 4H), 8.28-8.26 (d, J=8.5 Hz, 2H), 8.11-8.09 (d, J=8 Hz, 2H), 7.76 (s, 2H), 7.14-7.11 (m, 4H), 6.18 (t, J=2 Hz, 1H), 6.15-6.13 (dt, J=7.5, 1.5 Hz, 2H), 5.76-5.67 (m, 2H), 4.92 (bs, 1H), 4.26-4.24 (t, J=4.5 Hz, 2H), 4.16-4.13 (t, J=4.5 Hz, 2H), 4.08-4.06 (t, J=4.5 Hz, 2H), 4.05-4.03 (t, J=4.5 Hz, 2H), 3.96-3.91 (m, 4H), 3.85-3.83 (t, J=4.5 Hz, 2H), 3.78-3.67 (m, 10H), 3.58-3.56 (t, J=5.5 Hz, 2H), 3.33-3.32 (q, J=5 Hz, 2H), 2.64-2.59 (qt, J=6.5 Hz, 2H), 2.52-2.48 (qt, J=6.5 Hz, 21H), 1.43 (s, 9H). $^{13}$C NMR (125 MHz, $CDCl_3$): $\delta_C$ 160.86, 160.80, 160.7, 160.6, 160.5, 160.3, 160.2, 156.3, 156.28, 156.23, 156.0, 146.0, 136.8, 132.3, 132.1, 129.02, 129.00, 128.6, 128.2, 128.0, 127.9, 127.58, 127.56, 125.67, 125.64, 119.28, 119.23, 114.95, 114.91, 94.9, 94.5, 94.48, 94.40, 94.1, 71.1, 71.06, 71.03, 71.00, 70.95, 70.91, 70.7, 70.4, 70.3, 69.82, 69.80, 69.7, 69.4, 67.7, 67.6, 67.5, 67.49, 67.41, 40.39, 32.6, 32.5, 29.7, 28.4, 27.8, 27.6 MALDI: calculated for $C_{53}H_{61}N_3O_{11}$: 916.4384 $[M+H]^+$, 928.4203 $[M+Na]^+$, 954.3943 $[M+K]^+$; Found: 916.4379 [M+H], 938.4275 $[M+Na]^+$, 954.3938 $[M+K]^+$.

Example 19: Detailed Synthesis of [2]Catenate for [2]Catenane/ate Polymer a) Pre-Catenate Complex (11)

Figure 34:
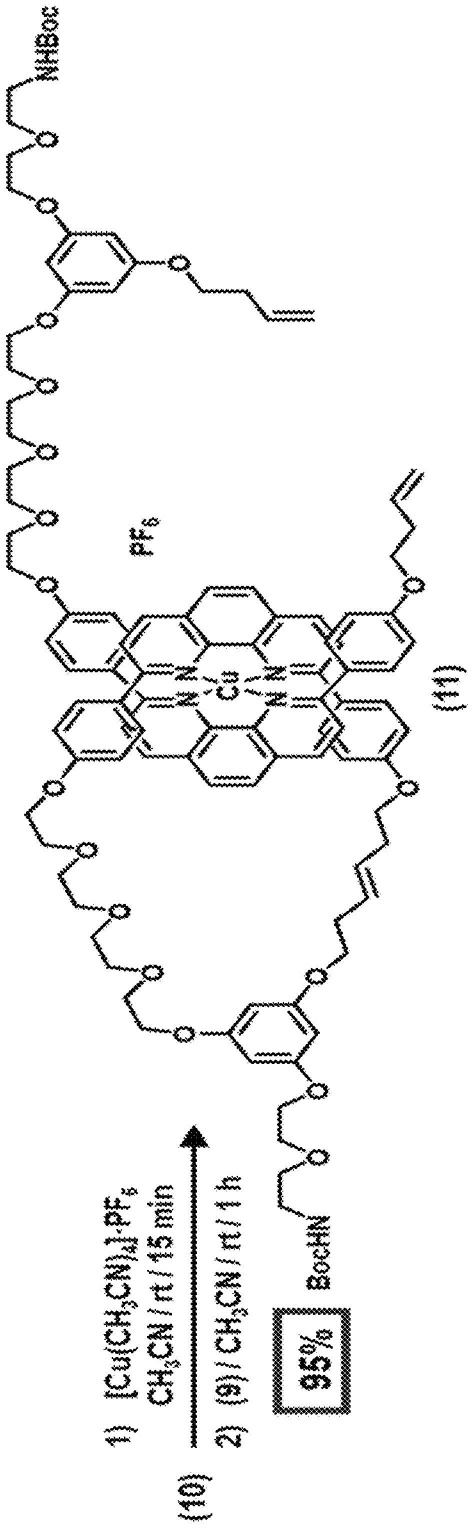
FIG. 34 depicts a detailed scheme for the synthesis of pre-catenate complex.

This synthetic scheme is shown in FIG. 34.

To a 25-mL round bottom flask charged with a stir bar, was added a solution of 10 (0.351 g, 0.383 mmol, 1.0 eq) in dry, degassed $CH_3CN$. The flask was thoroughly flushed with $N_2$ gas before a solution of $[Cu(CH_3CN)_4—PF_6]$(0.157 g, 0.421 mmol, 1.1 eq) in dry, degassed $CH_3CN$ was added dropwise. The formation of the air-sensitive metal complex could be observed as the color changed from pale yellow to orange. This solution was allowed to stir at room temperature for 15 minutes before a solution of 9 (0.362 g, 0.383 mmol, 1.0 eq) in dry, degassed $CH_3CN$ was added dropwise. Formation of 11 could be followed as the color rapidly changed from orange to dark red. The solution stirred for 1 h at room temperature, then was concentrated by rotary evaporation to yield a red film. This film was dissolved in $CH_2Cl_2$ then washed with DI water (3x35 mL). The organic layer was dried ($Na_2SO_4$), filtered and concentrated via rotary evaporation to yield the product as a solid red foam (0.755 g, 95%).

$^1$H NMR 6H (500 MHz, $CD_3CN$) 8.55-8.54 (d, J=9 Hz, 2H), 8.42-8.40 (d, J=8 Hz, 2H), 8.08 (s, 2H), 7.95 (s, 2H), 7.90-7.80 (m, 6H), 7.53-7.38 (m, 10H), 6.34 (t, J=1 Hz, 2H), 6.14 (t, J=1 Hz, 2H), 6.11-5.98 (m, 12H), 5.94-5.82 (m, 4H), 5.72-5.59 (m, 4H), 5.40 (bs, 1H), 5.24 (bs, 1H), 5.21-5.04 (m, 8H), 4.16-4.13 (m, 4H), 4.05-4.03 (m, 4H), 4.00-3.91 (m, 8H), 3.87-3.83 (m, 4H), 3.79-3.55 (m, 38H), 3.49-3.47 (t, J=4.5 Hz, 2H), 3.20-3.16 (m, 6H), 3.12-3.09 (q, J=6.5 Hz, 2H), 2.61-2.57 (q, J=7 Hz, 2H), 2.45-2.36 (q, J=6.5 Hz, 2H), 2.31-2.27 (q, J=7 Hz, 2H), 1.40 (s, 9H), 1.37 (s, 9H). $^{13}$C NMR (125 MHz, $CDCl_3$): $\delta_C$ 207.0, 160.89, 160.81, 160.7, 160.65, 160.61, 160.4, 159.5, 159.4, 159.3, 156.0, 137.2, 134.4, 134.3, 129.1, 129.0, 128.8, 127.9, 126.2, 117.1, 117.0, 113.1, 113.0, 112.9, 94.7, 94.46, 94.42, 94.2, 79.2, 70.89, 70.86, 70.82, 70.78, 70.71, 70.6, 70.5, 70.35, 70.34, 70.30, 69.7, 69.6, 69.4, 69.3, 67.8, 67.7, 67.5, 67.37, 67.31, 67.2, 67.1, 40.3, 33.5, 33.2, 32.4, 32.0, 30.9, 29.7, 29.2, 28.43, 28.42, 27.5, 22.7, 14.1. MALDI: calculated for $C_{108}H_{126}CuN_6O_{22}$ 1921.8221 $[M]^+$; Found: 1921.8216 $[M]^+$.

b) Boc [2]Catenane (12)

Figure 35:
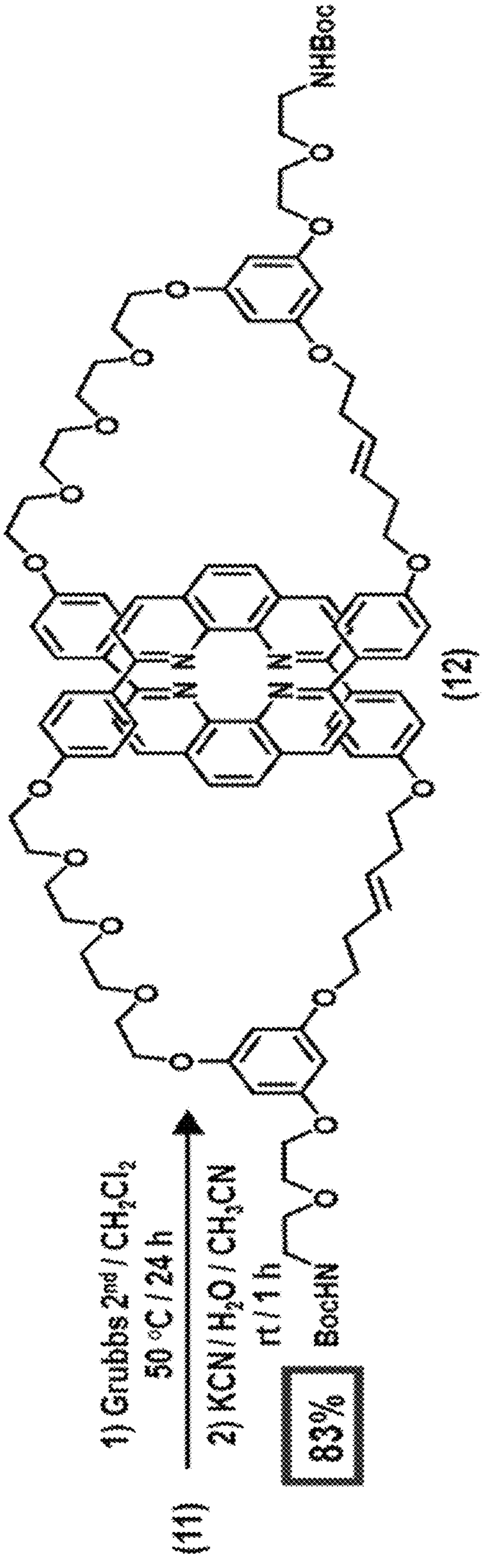
FIG. 35 depicts a detailed scheme for the synthesis of boc [2]catenane.

This synthetic scheme is shown in FIG. 35.

Compound 11 (0.400 g, 0.193 mmol, 1.0 eq) was added to an oven-dried round bottom flask. The solid red foam was then dissolved in dry $CH_2Cl_2$ (400 mL), resulting in a dark red solution. To the solution was added a solution of Grubbs 2$^{nd}$ generation catalyst (8.2 mg, 0.0193 mmol, 10 mol %) in $CH_2Cl_2$ via pipette. Addition of the catalyst turned the solution red brown. The round bottom flask was fitted with a reflux condenser, purged with $N_2$ (s) and stirred at 50° C. Progress of the reaction was monitored via TLC-MS. After 24 h the reaction had reached completion by disappearance of the starting material. The catalyst was quenched by adding EVE (25 mL) and $CH_3CN$ (15 mL) and stirring open to air for 1 h. The reaction mixture was concentrated by rotary evaporation to yield a red film. The red film was resuspended in acetonitrile (50 mL) and a solution of KCN (0.252 g, 3.868 mmol, 20 eq) in $H_2O$ was added via pipette. The reaction stirred open to air for 1 h, as the color rapidly changed from dark red to faint orange. The reaction mixture was concentrated via rotary evaporation to yield a white and orange solid. This solid was resuspended in $CH_2Cl_2$ (200 mL) and brine (100 mL) and then further washed with brine (3×150 mL). Aqueous layers were combined and back extracted with $CH_2Cl_2$ (3×100 mL). Organic layers were combined, dried ($Na_2SO_4$), filtered, and concentrated via rotary evaporation to yield an orange film. This film was purified via silica gel column chromatography (1:99 MeOH: $CH_2Cl_2$ to 5:95 MeOH:$CH_2Cl_2$) to yield the product as a yellow-orange solid foam (0.293 g, 83%).

$^1H$ NMR (500 MHz, $CD_3CN$): $\delta_H$ 8.58-8.56 (d, J=8 Hz, 8H), 8.34-8.31 (dd, J=8.5, 3 Hz, 4H), 8.11-8.08 (m, 4H), 7.80 (s, 4), 6.95-6.83 (m, 8H), 6.14 (t, J=2.5 Hz, 2H), 6.09-5.99 (m, 4H), 5.43-5.38 (m, 2H), 5.33-5.23 (m, 4H), 4.12-4.10 (m, 4H), 4.01-3.99 (m, 3H), 3.94-3.93 (m, 1H), 3.80-3.77 (m, 6H), 3.75-3.72 (m, 2H), 3.67-3.53 (m, 20H), 3.46-3.38 (m, 16H), 3.16-3.13 (q, J=5.5 Hz, 4H), 2.27-2.23 (m, 4H), 1.34 (s, 18H). $^{13}C$ NMR (125 MHz, $CD_3CN$): $\delta_C$ 161.85, 161.80, 161.7, 160.9, 160.8, 156.7, 156.3, 156.2, 146.8, 137.8, 132.6, 129.9, 129.3, 128.8, 128.5, 126.6, 119.9, 115.6, 115.4, 95.3, 94.9, 94.6, 79.1, 71.4, 71.25, 71.20, 71.1, 70.6, 70.3, 69.9, 68.59, 68.53, 68.3, 68.09, 68.01, 40.9, 33.0, 32.9, 28.5, 28.0. MALDI: calculated for $C_{106}H_{122}N_6O_{22}$: 1831.86904 $[M+H]^+$, 916.4384 $[M+2H]^{2+}$; Found: 1832.0577 $[M+H]^+$, 916.5383 $[M+2H]^{2+}$.

c) Amine [2]Catenate (13)

Figure 36:
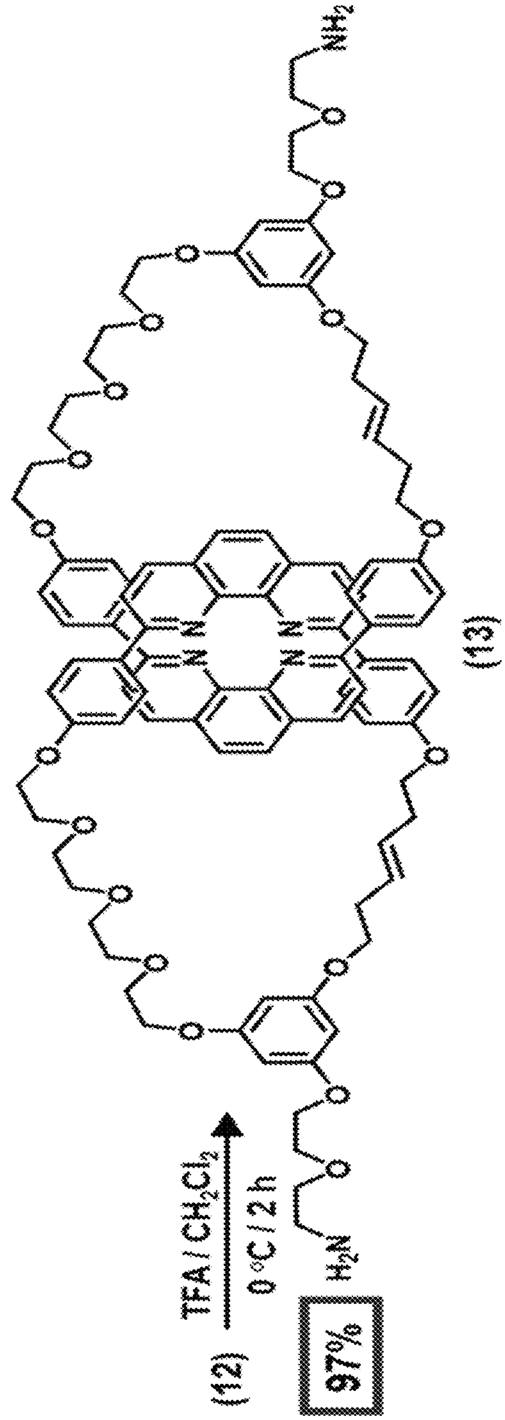
FIG. 36 depicts a detailed scheme for the synthesis of amine [2]catenate.

This synthetic scheme is shown in FIG. 36.

A solution of compound 12 (0.274 g, 0.150 mmol) in $CH_2Cl_2$ (10 mL) was stirred under $N_2$ at 0° C. as trifluoroacetic acid (TFA, 10 mL) was added. The reaction mixture immediately turned from yellow to a orange. The reaction mixture stirred at 0° C. at which point the reaction mixture was diluted with $CH_2Cl_2$ (150 mL) and carefully washed with 0.1 M NaOH (3×100 mL) until the resulting aqueous layer was no longer acidic. The aqueous layers were combined and back extracted with $CH_2Cl_2$ (3×200 mL). The organic layers were combined, dried ($Na_2SO_4$), filtered and concentrated via rotary evaporation to yield a solid white foam. (0.237 g, 97%).

$^1H$ NMR (500 MHz, $CD_3CN$): $\delta_H$ 8.59-8.50 (d, J=8.5 Hz, 8H), 8.34-8.31 (d, J=7.5 Hz, 4H), 8.13-8.08 (m, 4H), 7.80 (s, 4H), 6.97-6.82 (dd, J=27, 8.5 Hz, 8H), 6.13-6.11 (d, J=48 Hz, 2H), 6.07-5.97 (m, 4H), 5.46-5.39 (m, 2H), 5.35-5.28 (m, 2H), 4.10-4.09 (m, 4H), 4.01-3.99 (m, 4H), 3.80-3.73 (m, 8H), 3.68-3.52 (m, 20H), 3.48-3.33 (m, 16H), 2.71-2.62 (t, J=5 Hz, 4H), 2.33-2.16 (m, 8H)$^{13}C$ NMR (125 MHz, $CDCl_3$): $\delta_C$ 160.8, 160.7, 160.6, 160.0, 159.9, 145.7, 137.0, 131.78, 131.73, 131.2, 129.8, 128.9, 128.5, 128.0, 127.65, 127.64, 127.62, 125.77, 125.74, 125.71, 119.2, 119.1, 114.7, 114.5, 94.3, 93.9, 93.7, 71.2, 70.4, 70.2, 69.3, 68.9, 67.6, 67.5, 67.3, 67.2, 67.1, 39.6, 35.1, 32.0, 31.9, 31.6, 30.2, 29.4, 29.3, 29.2, 28.9, 26.8, 22.6, 22.4, 13.4. MALDI: calculated for $C_{96}H_{106}N_6O_{18}$: 1631.76419 $[M+H]^+$, 816.3860 $[M+2H]^{2+}$; Found: 1631.9115 $[M+H]^+$, 816.4732 $[M+2H]^2$.

d) Acryl [2]Catenane (14)

Figure 37:
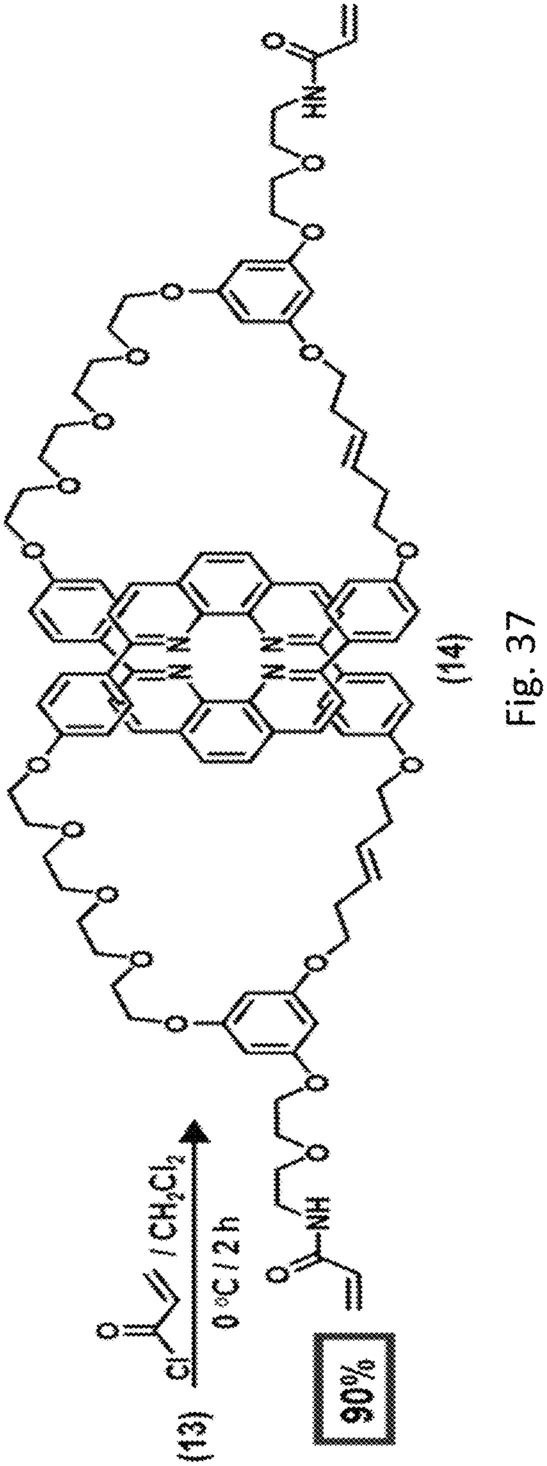
FIG. 37 depicts a detailed scheme for the synthesis of acryl [2]catenane.

This synthetic scheme is shown in FIG. 37.

A solution of 13 (0.237 g, 0.145 mmol, 1 eq) in dry $CH_2Cl_2$ was stirred at 0° C. as a solution acryloyl chloride (0.028 g, 0.305 mmol, 2.1 eq) in $CH_2Cl_2$ (1 mL) was added via syringe. The reaction was monitored via LR-TLC-MS, and a bright yellow color was observed. After 4 h the reaction had reached completion and a solution of triethylamine (0.073 g, 0.725 mmol, 5 eq) in $CH_2Cl_2$ (1 mL) was added, eliminating the yellow color. After an additional 30 min the reaction was diluted with $CH_2Cl_2$ (50 mL) and washed with sat $NaHCO_3$ (3×50 mL) and brine (2×25 mL). The aqueous layers were combined and back extracted with $CH_2Cl_2$ (2×50 mL). The organic layers were combined, dried ($Na_2SO_4$), filtered and concentrated via rotary evaporation at 0° C. to yield an orange film. This film was purified via silica gel column chromatography ($CH_2Cl_2$ to 5:95 MeOH:$CH_2Cl_2$) to yield the product as a yellow orange foam. (0.227 g, 90%).

$^1H$ NMR (500 MHz, $CD_3CN$): $\delta_H$ 8.62-8.56 (d, J=8 Hz, 8H), 8.34-8.31 (dd, J=8.5, 2.5 Hz, 4H), 8.11-8.08 (m, 4H), 7.80 (s, 4H), 6.95-6.84 (dq, J=25.5, 13 Hz, 8H), 6.56 (bs, 2H), 6.14-6.13 (dt, J=6.5, 2 Hz, 2H), 6.11-6.09 (m, 3H), 6.07-5.99 (m, 3H), 5.52-5.50 (dd, J=7.5, 5 Hz, 2H), 5.43-5.38 (m, 2H), 5.33-5.25 (m, 2H), 4.14-4.10 (m, 4H), 4.02-4.00 (m, 4H), 3.81-3.78 (m, 8H), 3.71-3.31 (m, 36H), 2.27-2.23 (m, 4H)$^{13}C$ NMR (125 MHz, $CDCl_3$): $\delta_C$ 166.0, 161.88, 161.83, 161.78, 161.74, 161.0, 160.89, 160.85, 156.4, 156.29, 156.27, 146.8, 137.9, 132.6, 132.3, 130.0, 129.99, 129.96, 129.4, 128.8, 128.5, 126.69, 126.67, 125.9, 119.99, 119.93, 115.6, 115.4, 95.3, 94.9, 94.7, 71.5, 71.27, 71.22, 71.1, 70.4, 70.2, 69.97, 69.92, 68.6, 68.5, 68.4, 68.3, 68.1, 68.0, 39.8, 33.0, 32.9, 28.0. MALDI: calculated for $C_{102}H_{110}N_6O_{20}$: 1739.78531 $[M+H]^+$, 870.3965 $[M+2H]^{2+}$; Found: 1739.9667 $[M+H]^+$, 870.496 $[M+2H]^{2+}$.

Example 20: Detailed Synthesis of Metalation of [2]Catenane for [2]Catenane/ate Polymer a) Cu Acryl [2]Catenate (15)

Figure 38:
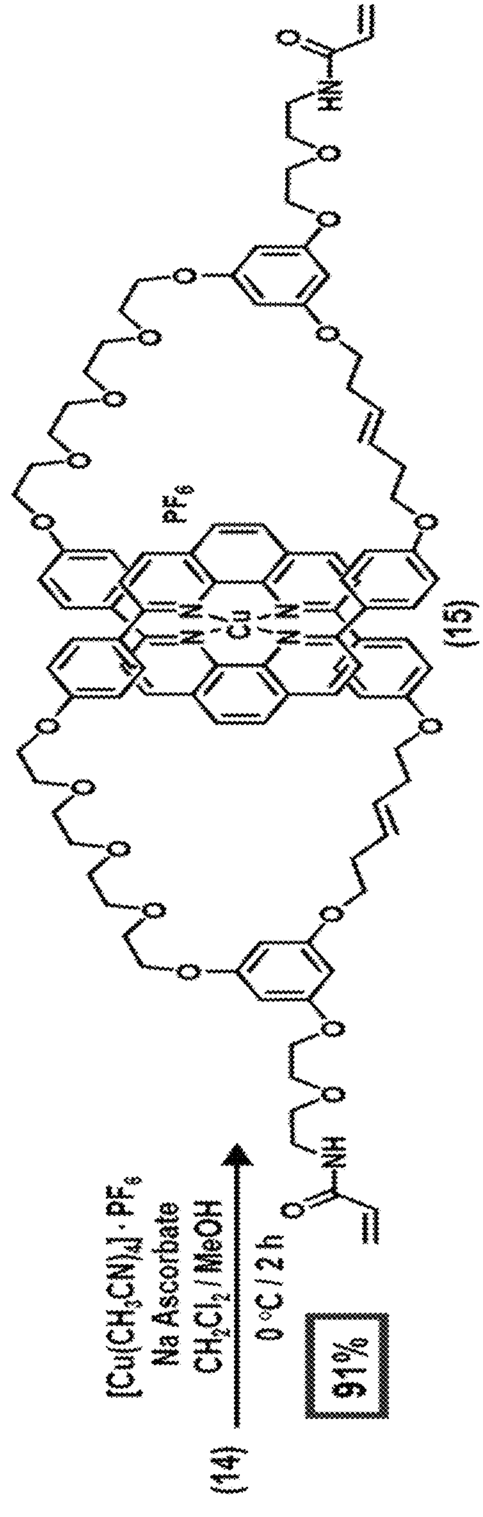
FIG. 38 depicts a detailed scheme for the synthesis of Cu acryl [2]catenate.

This synthetic scheme is shown in FIG. 38.

A mixture of sodium ascorbate (0.0112 g, 0.0567 mmol, 3 eq in MeOH (2 mL) and $CH_2Cl_2$ (2 mL) was vortexed to ensure mixing. To this mixture was added $[Cu(CH_3CN)_4]\cdot PF_6$ (0.0106 g, 0.0284 mmol, 1.5 eq). The solution remained colorless suggesting minimal oxidation of the of the copper source. This mixture was transferred to a vial of acryl[2]catenane (14), simultaneously dissolving the compound and changing the color to a dark red. This mixture stirred at 0° C. for 2 h, at which point it was diluted with $CH_2Cl_2$ (50 mL). The organic layer was washed with brine (2×30 mL). The aqueous layers were combined and back extracted with $CH_2Cl_2$ (2×30 mL). The organic layers were combined, dried ($Na_2SO_4$), filtered and concentrated via rotary evaporation at 0° C. to yield the product as a red foam (0.0334 g, 91%). Formation of the metal complex was confirmed by NMR and UV-Vis.

$^1H$ NMR (500 MHz, $CD_3CN$): $\delta_H$ 8.37-8.36 (d, J=8.5 Hz, 4H), 7.90 (s, 4H), 7.81-7.79 (m, 4H), 7.44-7.40 (m, 8H), 6.53 (bs, 2H), 6.30-6.26 (t, J=2 Hz, 2H), 6.11-6.06 (m, 6H), 6.03-5.99 (m, 8H), 5.68-5.57 (m, 4H), 5.52-5.50 (dd, J=7.5, 5 Hz, 2H), 4.12-4.09 (m, 8H), 4.02-3.92 (t, J=5.5 Hz, 4H), 3.84-3.79 (m, 4H), 3.72-3.57 (m, 24H), 3.54-3.49 (m, 4H), 3.44-3.42 (q, J=7 Hz, 2H), 3.39-3.32 (m, 2H), 3.29-3.21 (dq, J=23.5, 6 Hz, 4H), 2.57-2.53 (q, J=6 Hz, 4H), 2.42-2.38 (q, J=5.5 Hz, 1H), 2.26-2.22 (q, J=6.5 Hz, 3H). $^{13}C$ NMR (125 MHz, $CDCl_3$): $\delta_C$ 166.0, 162.11, 162.11, 161.96, 161.92, 161.8, 160.24, 160.20, 160.1, 157.2, 157.1, 157.06, 157.02, 156.99, 156.91, 144.2, 138.0, 132.3, 132.29, 132.27, 130.54, 130.51, 130.4, 129.8, 129.0, 128.9, 128.0, 127.0, 126.0, 125.06, 125.04, 113.8, 113.7, 95.3, 94.9, 94.8, 71.57, 71.51, 71.49, 71.46, 71.35, 70.34, 70.19, 70.15, 70.0, 69.88, 69.81, 68.7, 68.5, 68.37, 68.34, 68.2, 68.0, 67.9, 39.78, 39.72, 39.6, 33.2, 32.6, 28.2, 28.0 MALDI: calculated for $C_{102}H_{110}N_6O_{20}$ 1801.7070 $[M]^+$; Found: 1801.7066 $[M]^+$.

b) EDTA Demetallation Control

Figure 39:
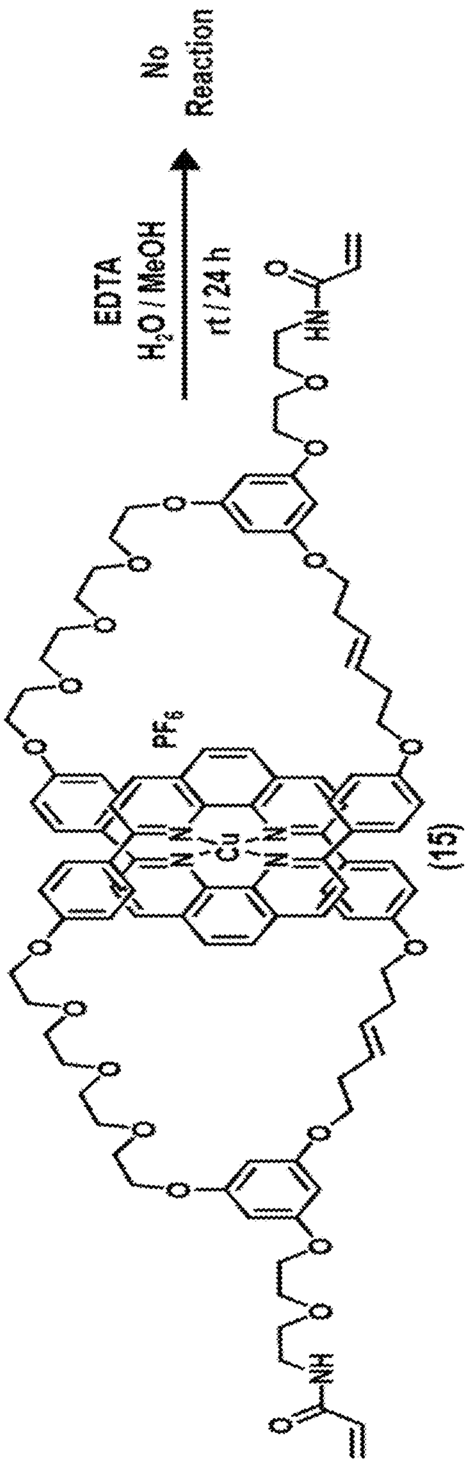
FIG. 39 depicts a detailed scheme for the synthesis of EDTA demetallation control.

This synthetic scheme is shown in FIG. 39.

A solution of EDTA (0.115 g, 0.308 mmol, 20 eq) in $H_2O$ (10 mL) was added to a solution of 15 (0.030 g, 0.0154 mmol, 1 eq) in MeOH (20 mL) via pipette. The reaction mixture stirred at room temperature, open to air for 24 h. These reaction conditions-were chosen as they best mimic the reaction condition of soaking gels in solution. After 24 h the reaction was filtered and concentrated via rotary evaporation to yield a red film. This film was resuspended in $CH_2Cl_2$ (50 mL) and washed with brine (3×50 mL). The aqueous layers were combined and back extracted with $CH_2Cl_2$ (3×25 mL). The organic layers were combined, dried ($Na_2SO_4$), filtered, and concentrated via rotary evaporation at 0° C. to yield a red film. Products were analyzed via $^1$H NMR and UV-Vis, to ensure that the metal complex had not been disrupted. No yield was taken.

Example 21: Bulk Polymer Testing for [2]Catenane/ate Polymer a) Synthesis of Oligo MEA

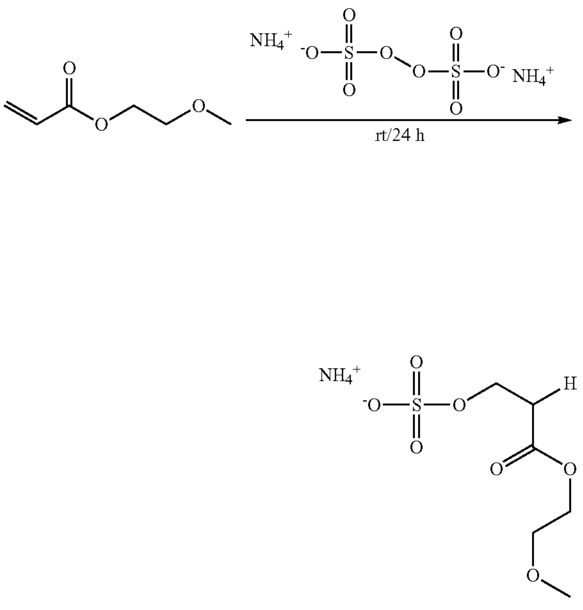

A solution of 2-methoxyethyl acrylate (0.100 g, 0.768 mmol, 20 eq) and ammonium persulfate (0.009 g, 0.038 mmol, 1 eq) in MeOH (0.5 mL) and water (0.5 mL) was stirred at 80° C. for 24 h. The reaction mixture was dilute in EtOAC (150 mL) and washed with brine (3×150 mL). The organic layer was dried ($Na_2SO_4$), filtered, and concentrated via rotary evaporation to yield a white solid. The product was analyzed via $^1$H and $^{13}$C NMR. No yield was taken, and no end group analysis was performed. Full conversion of the monomer to the polymer was assumed for the following reaction.

$^1$H NMR (500 MHz, $CD_3CN$): $\delta_H$ 4.20-4.09 (m, 4H), 3.53 (s, 4H), 3.31 (s, 6H), 2.40-2.31 (m, 2H), 1.90-1.82 (m, 1H), 1.64-1.43 (m, 3H). $^{13}$C NMR (125 MHz, $CDCl_3$): $\delta_C$ 174.4, 70.0, 63.5, 63.38, 63.34, 63.28, 58.0, 41.3.

b) KCN Treatment

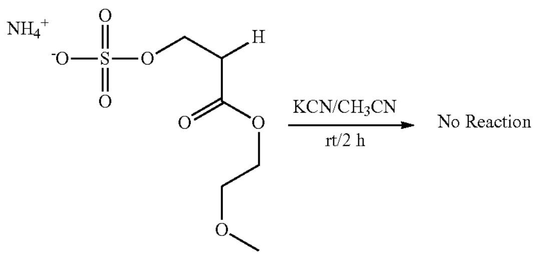

A solution of Poly 2-methoxyethyl acrylate (0.100 g, 0.038 mmol, 1 eq) in MeOH (3 mL) and water (3 mL) was stirred at rt as KCN (0.0024 g, 0.038 mmol, 1 eq). The reaction mixture was dilute with EtOAC (150 mL) and washed with brine (3×150 mL). The organic layer was dried ($Na_2SO_4$), filtered, and concentrated via rotary evaporation to yield a white solid. The product was analyzed via $^1$H and $^{13}$C NMR to ensure no reaction had occurred.

$^1$H NMR (500 MHz, $CD_3CN$): $\delta_H$ 4.20-4.09 (m, 4H), 3.53 (s, 4H), 3.31 (s, 6H), 2.40-2.31 (m, 2H), 1.90-1.82 (m, 1H), 1.64-1.43 (m, 3H). $^{13}$C NMR (125 MHz, $CDCl_3$): $\delta_C$ 174.4, 70.0, 63.5, 63.38, 63.34, 63.28, 58.0, 41.3.

Example 22: Polymerization of [3]Catenane

Figure 40:
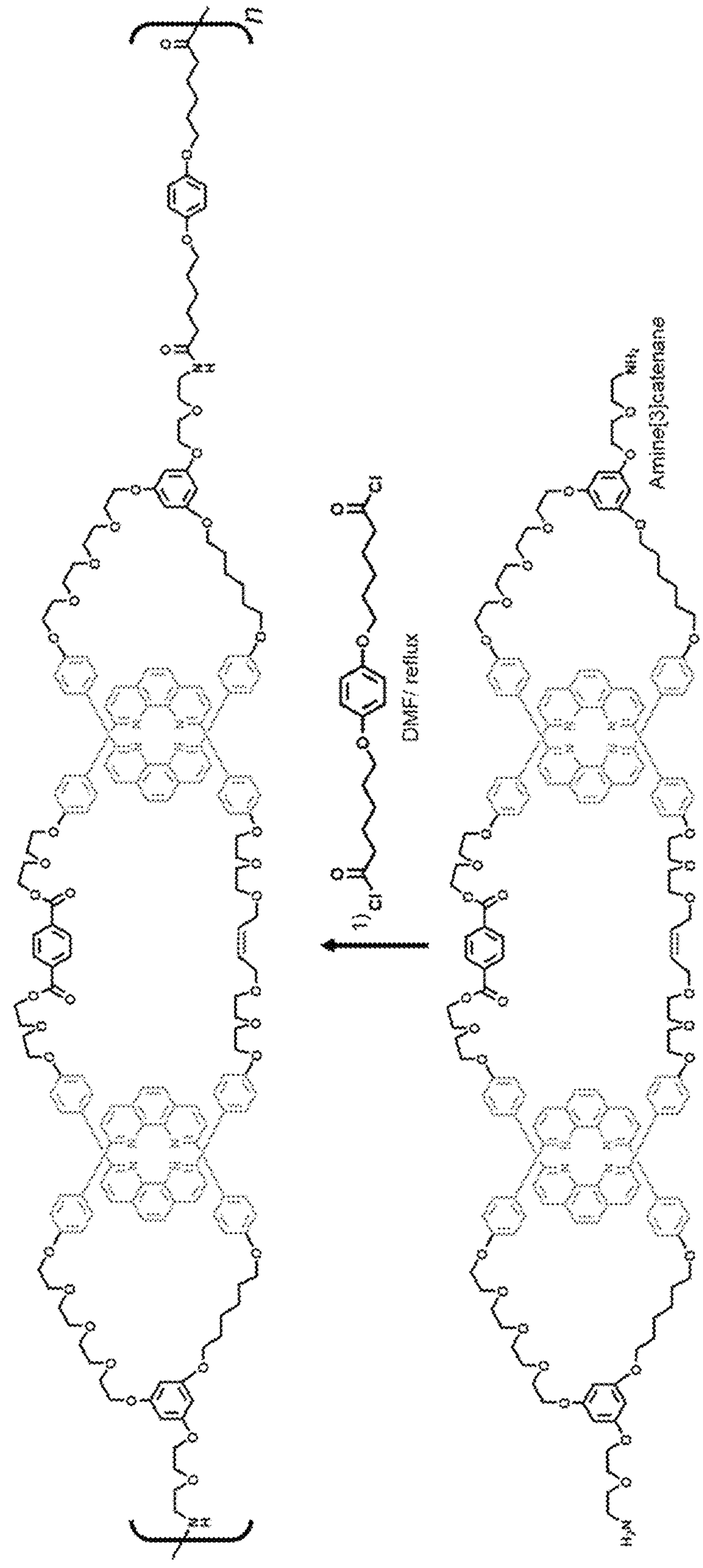
FIG. 40 depicts a detailed scheme for the synthesis of a polymer of catenane.

This synthetic scheme is shown in FIG. 40.

In this scheme, amine[3]catenane building blocks are polymerized into a linear chain of [3]catenanes.

Example 23: Advantages of Topologically Elastic Linkers (TELs) for the Incorporation of Mechanical Bonds into Polymeric Materials This example describes the development of a synthetic protocol for well-defined unimolecular linear [n]catenane crosslinkers, termed Topologically Elastic Linker (TELs), that are composed of mechanically interlocked macrocycles, where the terminal rings can be functionalized with polymerizable handles that allow for the precise incorporation of topological features into polymeric materials. The terminal macrocycles can each bear a primary amine that can be readily functionalized with a variety of polymerizable groups, which allows for this technology to be compatible with a multitude of monomers, such as those commercially available, to form hydrogels, organogels, elastomers, or thermosets.

Unlike typical crosslinkers that influence topology as a result of branching during polymerization, the topological features afforded by TELs arise from the preformed catenane architecture, which is preserved during polymerization. Once incorporated into a crosslinked polymer network, the conformational motions of the catenane-based TEL lead to macroscopic changes in the properties of a bulk material—even when the TEL makes up less than 5% of the network.

The macroscopic properties can be altered by the addition of metal ions into TELs, resulting in the rigidification of the macrocycles while stiffening the bulk material; this process can be reversed via the removal of the metal ions under mild conditions.

The extent of changes to these material properties can also be varied via the use of higher order (i.e., [3]-, [4]-, [5]-, [6]-) linear [n]catenane-based TELs, which possess greater conformational mobility relative to the [2]catenane-based TEL.

The synthesis of higher order linear [n]catenane TELs is highly plausible using our recently published orthogonal metal templation approach for the synthesis of a discrete linear [4]catenane.

Although there are two recent examples in the literature that use pH-responsive functional [2]catenane-based crosslinkers to synthesize hydrogels, well-defined crosslinkers that utilize higher order linear [n]catenanes (e.g., more than two interlocking molecular rings) are non-existent in the field of polymer networks and network topology. The improvement of the TEL design is that 1) it uses catenanes that are responsive to specific metal ions to cause changes in the properties of the bulk material, 2) it is the first example of higher order well-defined catenane crosslinkers for the synthesis of polymeric materials, and 3) its versatile monomer compatibility allows the introduction of well-defined mechanical bonds into hydrogels, organogels, elastomers, and thermosets.

Additionally, higher order TELs could be polymerized in a linear fashion to create poly[n]catenane thermoplastics—namely poly[3]-, poly[4]-, poly[5]-, and poly[6]catenates—where every n mechanical bonds are separated by rigid covalent linkages. For perspective, there are many examples of poly[2]catenanes, but there are no poly[3]catenane systems or larger that have been reported. These previously unreported topological polymers are expected to be strong, yet flexible materials due to the high concentration of unrestricted mechanical bonds.

The orthogonal metal templation method used to synthesize the linear catenanes that was developed to make TELs able to also be utilized to synthesize linear main chain poly[n]catenanes—reminiscent of real-world chains—possessing the highest concentration of mechanical bonds and the greatest conformational mobility.

The disclosed "zip-tie" strategy has been developed to link metalated catenanes and/or [4]catenanes together via a symmetric bis-phenanthroline open macrocycle, which will, after subsequent ring closing, form a polydisperse mixture of linear poly[n]catenanes, where all macrocycles are mechanically bonded. To date, there have been two reports of poly[n]catenanes. However, both of these reports had branched and cyclic topologies that were mixed in with the desired linear poly[n]catenane product. Additionally, the known methodologies are currently not scalable. One reported only 10's of milligrams of impure poly[n]catenanes, while the other did not even report a yield. Unlike these previously reported poly[n]catenanes, this orthogonal metal templation strategy and rational spacing of ring closing events provided from preformed mechanical bonds can facilitate the formation of solely linear poly[n]catenanes.

REFERENCES

Amabilino, D. B.; Ashton, P. R.; Reder, A. S.; Spencer, N.; Stoddart, J. F. Olympiadane. Angew. Chem., Int. Ed. Engl. 1994, 33 (12), 1286-1290.

Bunha, A.; Tria, M. C.; Advincula, R. Polymer catenanes via a supramolecularly templated ATRP initiator. Chem. Commun. 2011, 47 (32), 9173-9175.

Chambron, J. C.; Mitchell, D. K.; Sauvage, J. P. Synthesis, characterization, and a proton NIIR study of topologically chiral copper(I) [2]-catenates and achiral analogs. J. Am. Chem. Soc. 1992, 114 (12), 4625-4631.

Colley, N. D., et al. One-Pot Synthesis of a Linear [4]Catenate Using Orthogonal Metal Templation and Ring-Closing Metathesis. Inorg. Chem. 2020, 59(15): 10450-10460.

Dietrich-Buchecker, C.; Sauvage, J.-P., Templated synthesis of interlocked macrocyclic ligands, the catenands. Preparation and characterization of the prototypical bis-30 membered ring system. Tetrahedron 1990, 46 (2), 503-512.

Iwamoto, H.; Tafuku, S.; Sato, Y.; Takizawa, W.; Katagiri, W.; Tayama, E.; Hasegawa, E.; Fukazawa, Y.; Haino, T. Synthesis of linear [5]catenanes via olefin metathesis dimerization of pseudorotaxanes composed of a [2]catenane and a secondary ammonium salt. Chem. Commun. 2016, 52 (2), 319-322.

Forgan, R. S.; Blackburn, A. K.; Boyle, M. M.; Schneebeli, S. T.; Stoddart, J. F. The topological and chemical implications of introducing oriented rings to [3]catenanes. Supramol. Chem. 2014, 26 (3-4), 192-201.

Lam, R. T. S.; Belenguer, A.; Roberts, S. L.; Naumann, C.; Jarrosson, T.; Otto, S.; Sanders, J. K. M. Amplification of Acetylcholine-Binding Catenanes from Dynamic Combinatorial Libraries. Science 2005, 308 (5722), 667-669.

Mitchell, D. K.; Sauvage, J.-P. A Topologically Chiral [2]Catenand. Angew. Chem., Int. Ed. Engl. 1988, 27 (7), 930-931.

Patiny, L.; Borel, A.; ChemCalc: A Building Block for Tomorrow's Chemical Infrastructure. J. Chem. Inf. Model. 2013, 53 (5), 1223-1228

Spartan'18, Wavefunction, Inc. Irvine, CA.

Veliks, J.; Tseng, J.-C.; Arias, K. I.; Weisshar, F.; Linden, A.; Siegel, J. S., Linear bilateral extended 2,2':6',2"-terpyridine ligands, their coordination complexes and heterometallic supramolecular networks. Chem. Sci. 2014, 5 (11), 4317-4327.

Wu, Q.; Rauscher, P. M.; Lang, X.; Wojtecki, R. J.; de Pablo, J. J.; Hore, M. J. A.; Rowan, S. J. Poly[n]catenanes: Synthesis of molecular interlocked chains. Science 2017, 358 (6369), 1434-1439.

Yee, C.-C.; Ng, A. W. H.; Au-Yeung, H. Y. Control over the macrocyclisation pathway and product topology in a copper-templated catenane synthesis. Chem. Commun. 2019, 55 (44), 6169-6172.

What is claimed is:

1. A [n]catenane-based product comprising a polymer building block represented by formula (II-A), (II-B), (III-A), or (III-B):

A1|||||M1|||||C1|||||D1|||||C2|||||M2|||||A2 (II-A)

A1|||D2|||C3|||M1|||C1|||D1|||C2|||M2|||C4|||D3|||$A_2$ (II-B)

(A1)(C1)(C2)(A2) (III-A)

(A1)(C3)(C1)(C2)(C4)(A2) (III-B)

where:

A1 and A2 each independently comprise a closed ring macrocyclic compound comprising a monovalent or divalent ligand or a [n]catenane/ate;

C1, C2, C3, and C4 each independently comprise a closed ring macrocycle molecule comprising a monovalent ligand and a divalent ligand;

D1, D2, and D3 are each a divalent metal ion;

M1 and M2 are each a monovalent metal ion; and wherein "|||||||" represents one or more bonds between a metal ion and a ligand, wherein A1 and C1, C1 and C2, and C2 and A2 are mechanically interlocked or A1 and C3, C3 and C1, C1 and C2, C2 and C4, and C4 and A2 are mechanically interlocked.

2. The product of claim 1, wherein A1 and A2 each independently comprise a compound represented by formula (VI-A), (VI-B), or an ion thereof:

(VI-A)

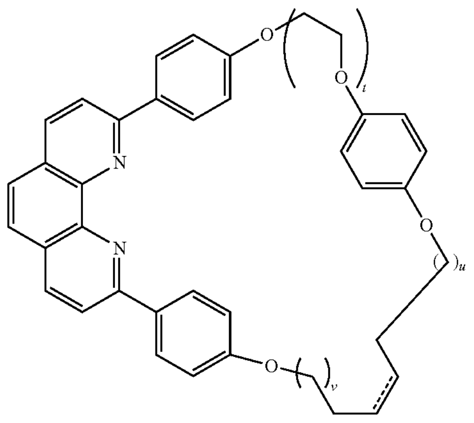

(VI-B)

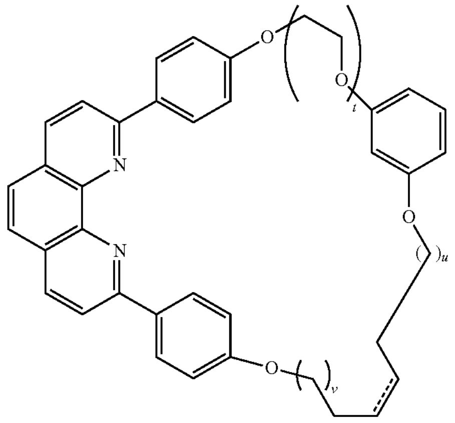

where:

t is an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and u and v are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

3. The product of claim 1, wherein A1 and A2 each independently comprise a compound of the following structure, or an ion thereof:

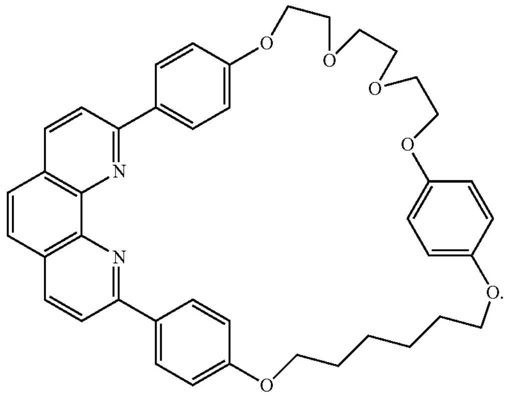 [SMILES: c1cc2ccc1OCCCCCCOc1ccc(cc1)-c1ccc3ccc4ccc(nc4c3n1)-c1ccc(cc1)OCCOCCOCCO2]

4. The product of claim 1, wherein C1, C2, C3, and C4 each independently comprise a compound represented by formula (V), or an ion thereof:

(V)

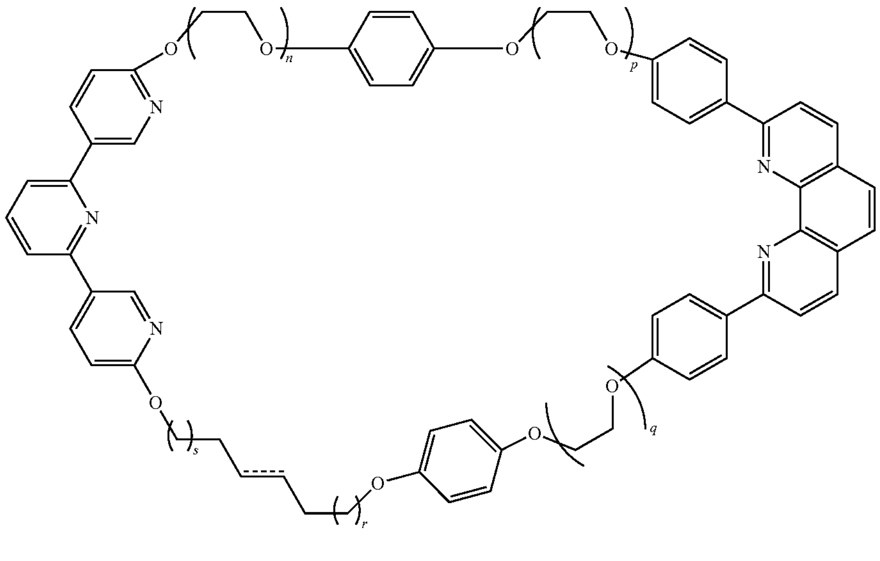

where:

n, p, and q are each independently an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and r and s are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

5. The product of claim 1, wherein C1, C2, C3, and C4 each independently comprise a compound of the following structure, or an ion thereof:

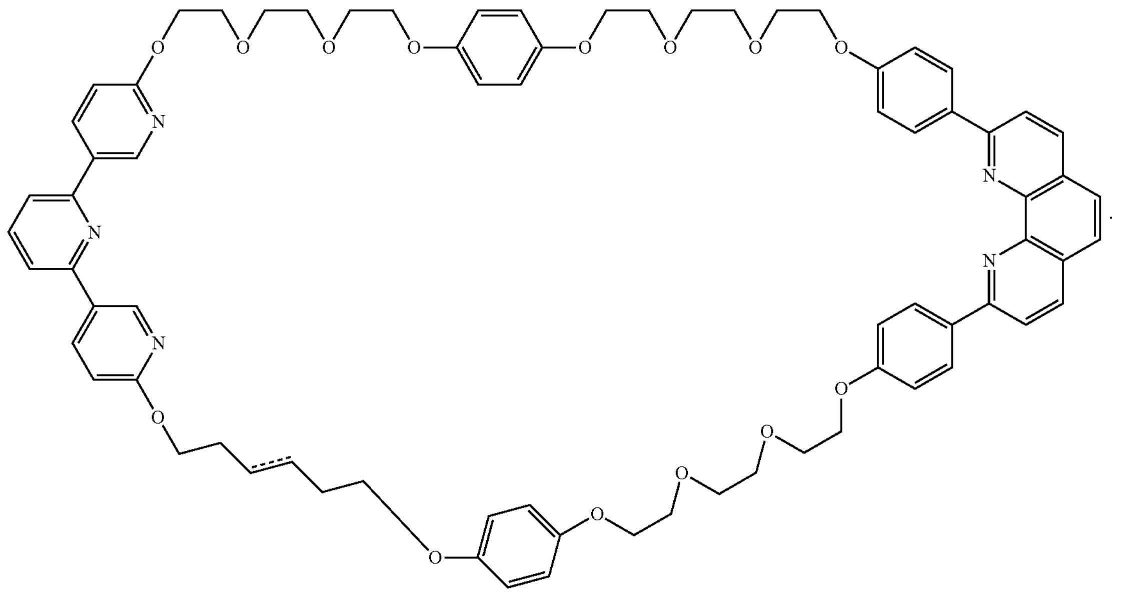

6. The product of claim 1, wherein D1, D2, and D3 are each $Fe^{2+}$.

7. The product of claim 1, wherein M1 and M2 are each $Cu^{+}$.

8. The product of claim 1, wherein the polymer building block of formula (II-A) comprises the following structure:

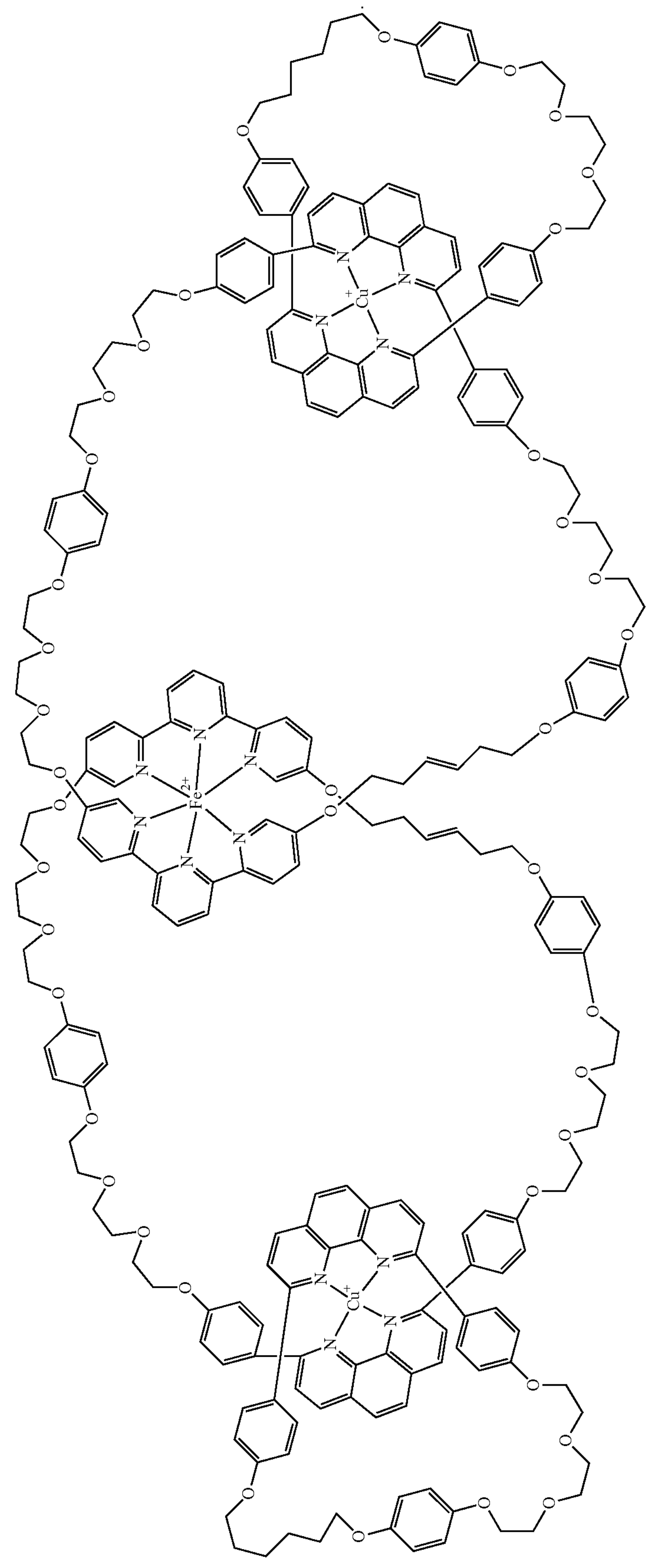

9. The product of claim 1, wherein the composition of formula (III-A) comprises the following structure, or an ion thereof:

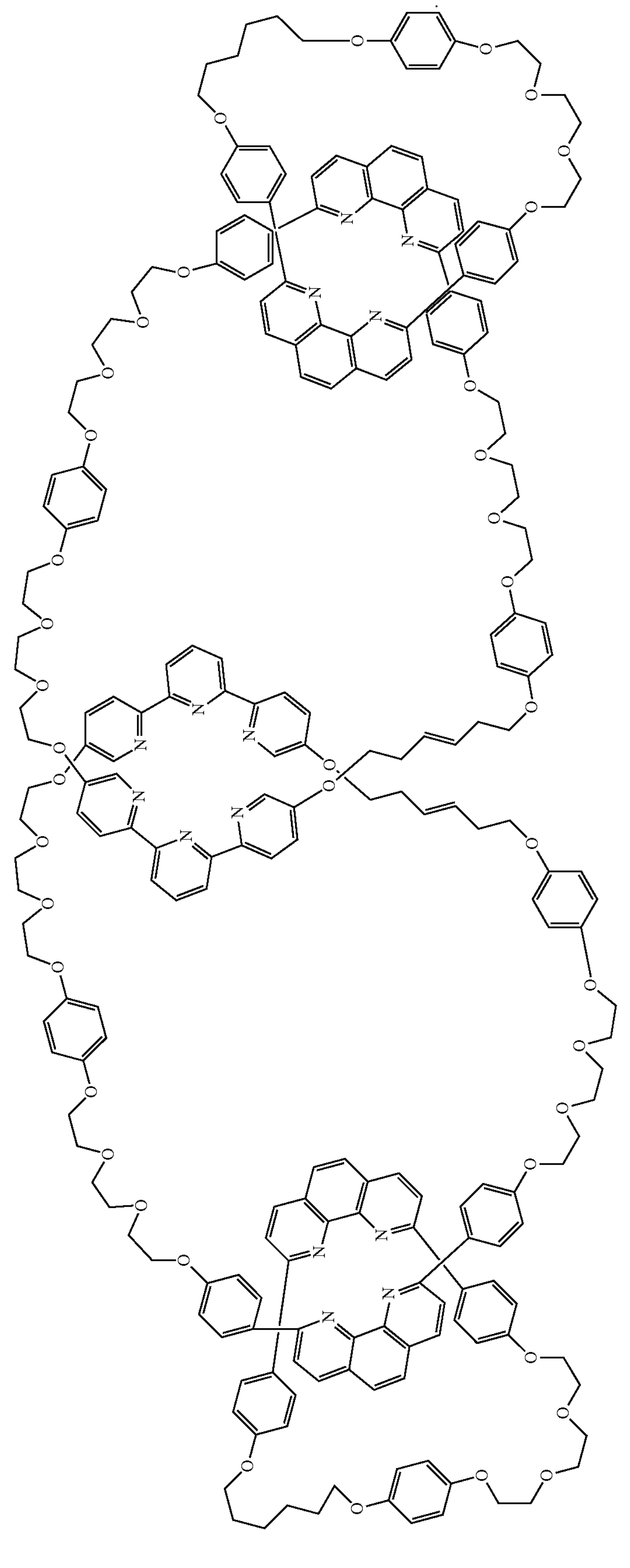

10. The product of claim 1, wherein at least one or at least two of A1, A2, C1, C2, C3, and C4 is functionalized with at least one polymerizable group each.

11. The product of claim 10, wherein A1 and/or A2 is functionalized with at least one polymerizable group and each independently comprises a compound represented by formula (VI-B), (VI-C), or an ion thereof:

(VI-C)

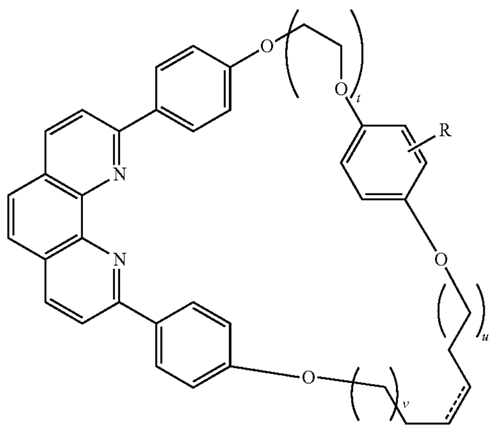

-continued (VI-D)

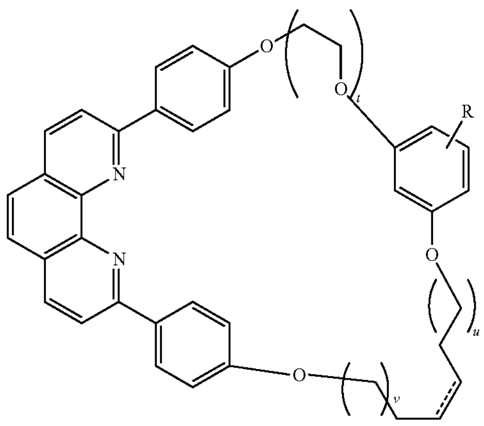

where:

R is a polymerizable group;

t is an integer of from 1 to 20, 1 to 15, 1 to 10, 1 to 5, 1 to 4, 1 to 3, 2 to 20, 2 to 15, 2 to 10, 2 to 5, 2 to 4, or 2, 3, or 4; and u and v are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.

12. The product of claim 11, wherein A1 and/or A2 each independently comprises a compound of the following structures, or ion or salt thereof:

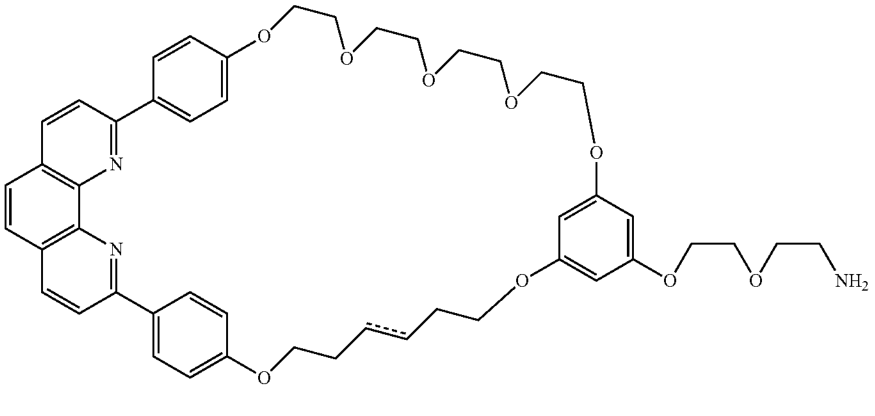

or

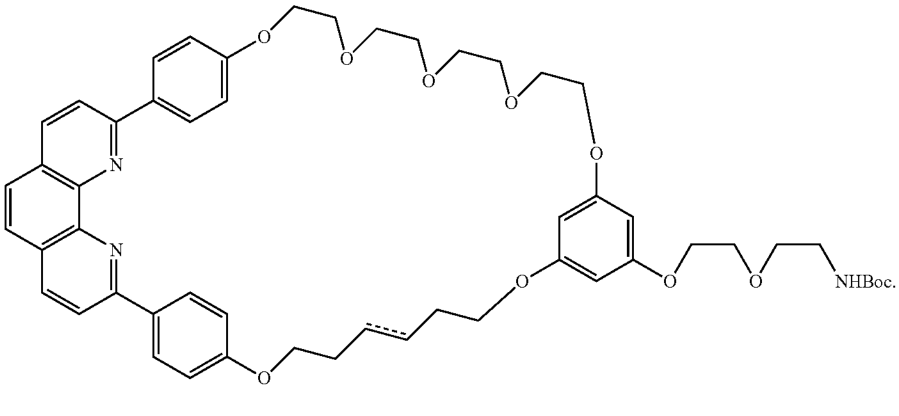

13. The product of claim 10, wherein the at least one polymerizable group comprises a styrene, acrylate, acrylamide, cycloalkene, amine, alcohol, thiol, or combinations thereof.

14. A polymeric composition comprising:

a plurality of the [n]catenane-based product of claim 10, wherein the at least one polymerizable group of the plurality of [n]catenane-based product are polymerized into a polymer network.

15. A polymeric composition comprising:

a plurality of the [n]catenane-based product of claim 1; and at least one or more monomers in an amount sufficient to form a polymer network;

wherein the [n]catenane-based product are cross-linked with the monomers of the polymer network.

16. A method of preparing a [n]catenane-based product comprising a polymer building block, the method comprising:

contacting in a reaction mixture:

(i) a metal loaded-catenane precursor complex represented by formula (I):

P1||||||D1||||||P2 (I)

where:

P1 and P2 are each an open ring macrocycle precursor molecule, wherein P1 and P2 each independently comprise a monovalent ligand and a divalent ligand;

D1 is a divalent metal ion; and (ii) a closed ring macrocyclic compound comprising a monovalent or divalent ligand and/or a metal-loaded [2]catenane comprising two mechanically interlocked macrocycles and a divalent ligand; and, (iii) a monovalent metal compound comprising a monovalent metal ion, to form the polymer building block, wherein the polymer building block is represented by formula (II-A) or (II-B):

A1||||||M1||||||C1||||||D1||||||C2||||||M2||||||A2 (II-A)

A1||||D2||||C3|||M1||||C1||||D1||||C2|||M2|||C4|||D3|||$A_2$ (II-B)

where:

C1 is a closed ring form of P1;

C2 is a closed ring form of P2;

A1 and A2 each independently comprise a closed ring macrocyclic compound comprising a monovalent or divalent ligand or a [n]catenane/ate;

C3 and C4 each independently comprise a closed ring macrocycle molecule comprising a monovalent ligand and a divalent ligand;

D2 and D3 are each a divalent metal ion;

M1 and M2 are each a monovalent metal ion; and wherein "||||||" represents one or more bonds between a metal ion and a ligand, wherein A1 and C1, C1 and C2, and C2 and A2 are mechanically interlocked or A1 and C3, C3 and C1, C1 and C2, C2 and C4, and C4 and A2 are mechanically interlocked.

17. A method of preparing a [n]catenane-based product, the method comprising:

contacting the metal loaded-[n]catenane-based product prepared by the method of claim 16 with a chelating agent to remove the monovalent and divalent metal ions from the product and form the [n]catenane-based product.

18. A compound comprising the structure of formula (IV) or (V):

(IV)

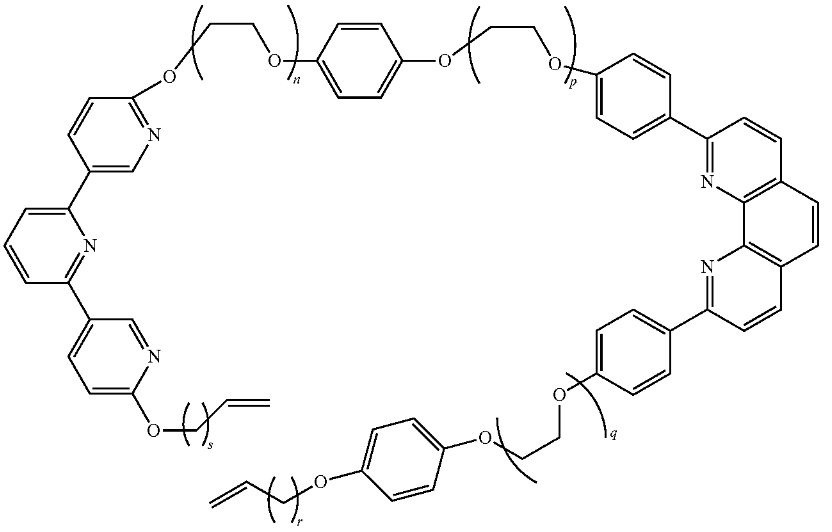

(V)
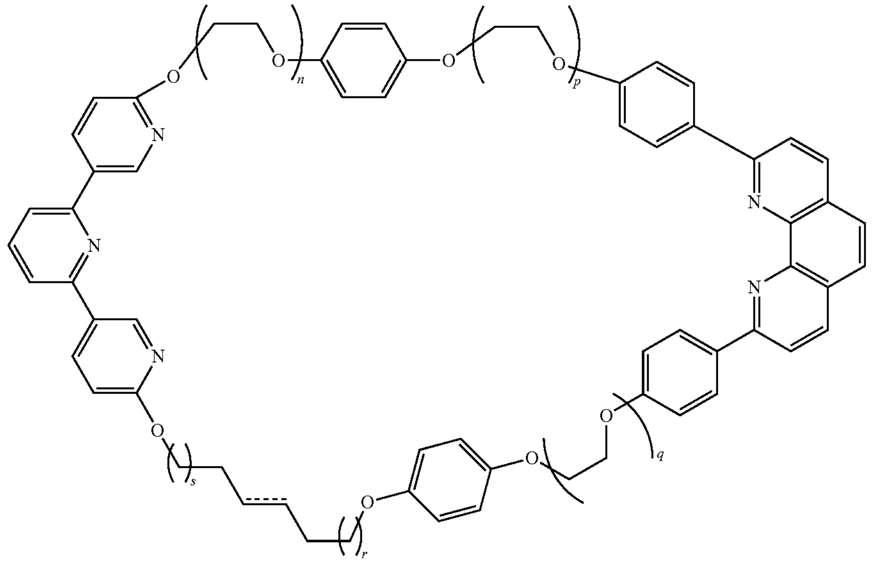
where:
n, p, and q are each independently an integer of from 1 to 20, 1 to 15, 1 to 10, 1 to 5, 1 to 4, 1 to 3, 2 to 20, 2 to 15, 2 to 10, 2 to 5, 2 to 4, or 2, 3, 4, 5, or 6; and
r and s are each independently an integer of from 0 to 20, 0 to 15, 0 to 10, 0 to 5, 0 to 4, 0 to 3, 1 to 20, 1 to 15, 1 to 10, 1 to 5, 1 to 4, 1 to 3, 2 to 20, 2 to 15, 2 to 10, 2 to 5, 2 to 4, or 2, 3, or 4.
19. The compound of claim 18, wherein the compound comprises the following structure:
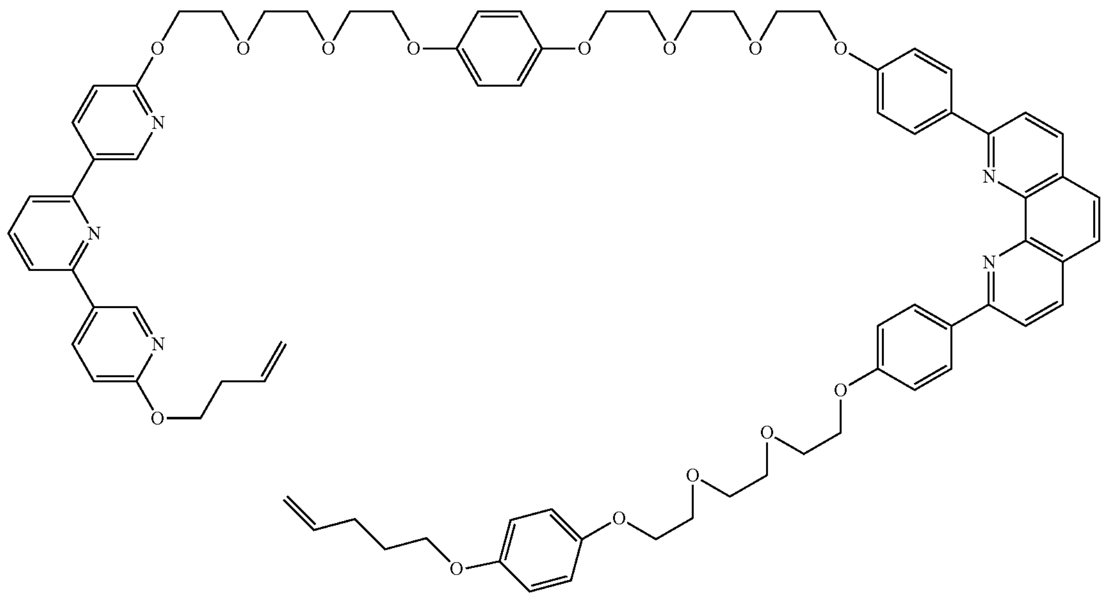
.

20. The compound of claim 18, wherein the compound comprises the following structure:
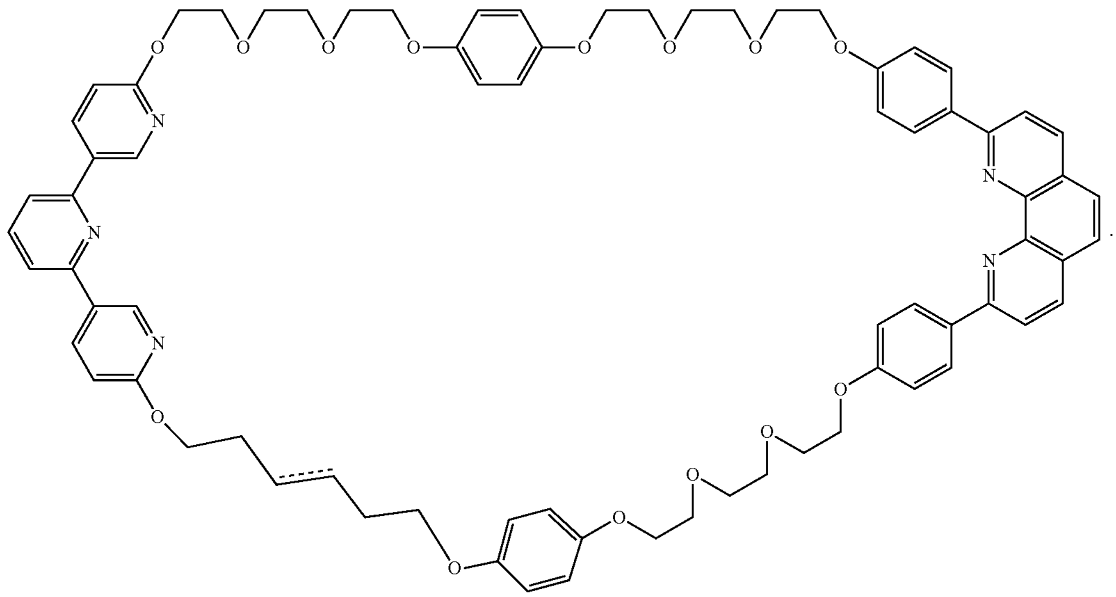
.
* * * * *